(12) United States Patent
Olson

(10) Patent No.: US 7,053,084 B1
(45) Date of Patent: *May 30, 2006

(54) SUCCINOYLAMINO BENZODIAZEPINES AS INHIBITORS OF Aβ PROTEIN PRODUCTION

(75) Inventor: Richard E. Olson, Wilmington, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/505,788

(22) Filed: Feb. 17, 2000

Related U.S. Application Data

(63) Continuation-in-part of application No. 09/469,939, filed on Dec. 24, 1999.

(60) Provisional application No. 60/113,588, filed on Dec. 24, 1998.

(51) Int. Cl.
  *A61P 25/28* (2006.01)
  *A61K 31/55* (2006.01)
  *C07D 243/00* (2006.01)

(52) U.S. Cl. .................. 514/221; 540/504; 540/505; 540/506; 540/509; 540/517; 540/518

(58) Field of Classification Search ................ 514/221; 540/504, 505, 506, 509, 517, 518
See application file for complete search history.

(56) References Cited

U.S. PATENT DOCUMENTS

| | | | |
|---|---|---|---|
| 3,651,023 A | 3/1972 | Ottenheym et al. | 260/784 |
| 4,929,614 A | 5/1990 | Calvet et al. | 514/214 |
| 5,283,241 A | 2/1994 | Bochis et al. | 514/183 |
| 5,532,359 A | 7/1996 | Marsters et al. | 540/522 |
| 5,550,126 A | 8/1996 | Horwell et al. | 514/237.5 |
| 5,578,629 A | 11/1996 | Ciccarone et al. | 514/397 |
| 5,595,990 A | 1/1997 | Baldwin et al. | 514/221 |
| 5,602,145 A | 2/1997 | Samanen | 514/309 |
| 5,602,156 A | 2/1997 | Kohn et al. | 514/359 |
| 5,618,812 A | 4/1997 | Castro Pineiro et al. | 514/221 |
| 5,672,596 A | 9/1997 | Wyvratt et al. | 514/183 |
| 5,672,598 A | 9/1997 | De et al. | 514/212 |
| 5,703,129 A | 12/1997 | Felsenstein et al. | 514/613 |
| 5,710,153 A | 1/1998 | Ohmoto et al. | 514/236.2 |
| 5,710,171 A | 1/1998 | Dinsmore et al. | 514/396 |
| 5,756,528 A | 5/1998 | Anthony et al. | 514/399 |
| 5,763,437 A | 6/1998 | Sato et al. | 514/221 |
| 5,770,573 A | 6/1998 | Arrhenius et al. | 514/18 |
| 5,852,010 A | 12/1998 | Graham et al. | 514/221 |
| 5,856,326 A | 1/1999 | Anthony et al. | 514/252 |
| 5,859,012 A | 1/1999 | Dinsmore et al. | 514/252 |
| 5,869,682 A | 2/1999 | DeSolms | 548/335.5 |
| 5,872,135 A | 2/1999 | DeSolms | 514/326 |
| 5,885,995 A | 3/1999 | Dinsmore | 514/252 |
| 5,891,889 A | 4/1999 | Anthony et al. | 514/326 |
| 5,905,077 A | 5/1999 | Jungheim et al. | 514/222.2 |
| 5,919,785 A | 7/1999 | Dinsmore et al. | 514/255 |
| 5,936,089 A | 8/1999 | Carpino et al. | 546/143 |
| 5,965,578 A | 10/1999 | Graham et al. | 514/326 |
| 5,985,900 A | 11/1999 | Bender et al. | 514/336 |
| 5,998,407 A * | 12/1999 | Graham et al. | 514/221 |
| 2003/0134841 A1* | 7/2003 | Olson et al. | 514/212.08 |

FOREIGN PATENT DOCUMENTS

| | | |
|---|---|---|
| EP | 0421802 | 4/1991 |
| EP | 0434360 | 6/1991 |
| EP | 0842944 | 5/1998 |
| WO | WO 9217460 | 10/1992 |
| WO | WO 9403437 | 2/1994 |
| WO | WO 9405634 | 3/1994 |
| WO | WO 9414776 | 7/1994 |
| WO | WO 9509633 | 4/1995 |
| WO | WO 9617833 | 6/1996 |
| WO | WO 9618602 | 6/1996 |
| WO | WO 9620918 | 7/1996 |
| WO | WO 9629313 | 9/1996 |
| WO | WO 9633165 | 10/1996 |
| WO | WO 9639137 | 12/1996 |
| WO | WO 9712861 | 4/1997 |
| WO | WO 9719053 | 5/1997 |
| WO | WO 9727852 | 8/1997 |
| WO | WO 9736877 | 10/1997 |
| WO | WO 9736879 | 10/1997 |

(Continued)

OTHER PUBLICATIONS

Dingwall; J. Clinical Invest., 108, Nov. 2001, 1243-1246.

(Continued)

*Primary Examiner*—Brenda Coleman
(74) *Attorney, Agent, or Firm*—Aldo A. Algieri; Kelly, Drye & Warren LLP

(57) ABSTRACT

This invention relates to novel lactams having the formula (I):

(I)

to their pharmaceutical compositions and to their methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

56 Claims, No Drawings

FOREIGN PATENT DOCUMENTS

| | | |
|---|---|---|
| WO | WO 9736900 | 10/1997 |
| WO | WO 9738664 | 10/1997 |
| WO | WO 9745412 | 12/1997 |
| WO | WO 9816523 | 4/1998 |
| WO | WO 9822430 | 5/1998 |
| WO | WO 9822433 | 5/1998 |
| WO | WO 9822441 | 5/1998 |
| WO | WO 9822493 | 5/1998 |
| WO | WO 9827053 | 6/1998 |
| WO | WO 9828268 | 7/1998 |
| WO | WO 9828980 | 7/1998 |
| WO | WO 9835941 | 8/1998 |
| WO | WO 9837079 | 8/1998 |
| WO | WO 9841510 | 9/1998 |
| WO | WO 9844797 | 10/1998 |
| WO | WO 9858915 | 12/1998 |
| WO | WO 9900654 | 1/1999 |
| WO | WO 9903826 | 1/1999 |
| WO | WO 9907730 | 2/1999 |
| WO | WO 9907731 | 2/1999 |
| WO | WO 9917777 | 4/1999 |
| WO | WO 9918951 | 4/1999 |
| WO | WO 9919305 | 4/1999 |
| WO | WO 9932453 | 7/1999 |
| WO | WO 9966934 | 12/1999 |
| WO | WO 9967219 | 12/1999 |
| WO | WO 9967220 | 12/1999 |
| WO | WO 9967221 | 12/1999 |
| WO | WO 0002903 | 1/2000 |
| WO | WO 0007995 | 2/2000 |
| WO | WO 0028331 | 5/2000 |
| WO | WO 0038618 | 7/2000 |
| WO | WO 0160826 | 8/2001 |

OTHER PUBLICATIONS

Selkoe; J. Alzheimer's Disease, 3, 2001, p. 75-81.

Olson et al., Current Opinion in Drug Discovery and Development, 4, 2001, p. 390-401.

Su San Mok et al, A Novel Metalloprotease in Rat rain cleaves . . . Biochemistry, vol. 36, No. 1, 1997, pp. 156-163 XP002177252.

Database WPI, Section Ch, Week 199839, Derwent Pub. Ltd., London GB; Class B02, AN 1998-457046 XP002203452, 1998.

Patani et al, Bioisosterism: A Rational Approach in Drug Design, Chem. Rev., 1996, 96, 3147-3176 XP000652176.

Natchus et al, Design and Synthesis of Conformationally-Constrained MMP Inhibitors, Bioorganic & Medicinal Chem. Letters 8 (1998) 2077-2080 XP004137222.

Yong et al, Matrix Metalloproteinases and Diseases of the CNS, TINS vol. 21, No. 2, 1998 75-80 XP000942162.

International Search Report PCT/US99/30815 dated Apr. 17, 2000.

* cited by examiner

SUCCINOYLAMINO BENZODIAZEPINES AS INHIBITORS OF Aβ PROTEIN PRODUCTION

This application is a continuation-in-part of application Ser. No. 09/469,939, filed Dec. 24, 1999, which claims the benefit of U.S. Provisional Application No. 60/113,588, filed Dec. 24, 1998.

FIELD OF THE INVENTION

This invention relates to novel lactams having drug and bio-affecting properties, their pharmaceutical compositions and methods of use. These novel compounds inhibit the processing of amyloid precursor protein and, more specifically, inhibit the production of Aβ-peptide, thereby acting to prevent the formation of neurological deposits of amyloid protein. More particularly, the present invention relates to the treatment of neurological disorders related to β-amyloid production such as Alzheimer's disease and Down's Syndrome.

BACKGROUND OF THE INVENTION

Alzheimer's disease (AD) is a degenerative brain disorder characterized clinically by progressive loss of memory, temporal and local orientation, cognition, reasoning, judgment and emotionally stability. AD is a common cause of progressive dementia in humans and is one of the major causes of death in the United States. AD has been observed in all races and ethnic groups worldwide, and is a major present and future health problem. No treatment that effectively prevents AD or reverses the clinical symptoms and underlying pathophysiology is currently available (for review, Selkoe, 1994).

Histopathological examination of brain tissue derived upon autopsy or from neurosurgical specimens in effected individuals revealed the occurrence of amyloid plaques and neurofibrillar tangles in the cerebral cortex of such patients. Similar alterations were observed in patients with Trisomy 21 (Down's syndrome), and hereditary cerebral hemorrhage with amyloidosis of the Dutch-type. Neurofibrillar tangles are nonmembrane-bound bundles of abnormal proteinaceous filaments and biochemical and immunochemical studies led to the conclusion that their principle protein subunit is an altered phosphorylated form of the tau protein (reviewed in Selkoe, 1994).

Biochemical and immunological studies revealed that the dominant proteinaceous component of the amyloid plaque is an approximately 4.2 kilodalton (kD) protein of about 39 to 43 amino acids. This protein was designated Aβ, β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Aβ was first purified and a partial amino acid reported in 1984 (Glenner and Wong, Biochem. Biophys. Res. Commun. 120: 885–890). The isolation and sequence data for the first 28 amino acids are described in U.S. Pat. No. 4,666,829.

Compelling evidence accumulated during the last decade revealed that Aβ is an internal polypeptide derived from a type 1 integral membrane protein, termed β amyloid precursor protein (APP). β APP is normally produced by many cells both in vivo and in cultured cells, derived from various animals and humans. Aβ is derived from cleavage of β APP by as yet unknown enzyme (protease) system(s), collectively termed secretases.

The existence of at least four proteolytic activities has been postulated. They include β secretase(s), generating the N-terminus of Aβ, α secretase(s) cleaving around the 16/17 peptide bond in Aβ, and γ secretases, generating C-terminal Aβ fragments ending at position 38, 39, 40, 42, and 43 or generating C-terminal extended precursors which are subsequently truncated to the above polypeptides.

Several lines of evidence suggest that abnormal accumulation of Aβ plays a key role in the pathogenesis of AD. Firstly, Aβ is the major protein found in amyloid plaques. Secondly, Aβ is neurotoxic and may be causally related to neuronal death observed in AD patients. Thirdly, missense DNA mutations at position 717 in the 770 isoform of β APP can be found in effected members but not unaffected members of several families with a genetically determined (familiar) form of AD. In addition, several other β APP mutations have been described in familiar forms of AD. Fourthly, similar neuropathological changes have been observed in transgenic animals overexpressing mutant forms of human β APP. Fifthly, individuals with Down's syndrome have an increased gene dosage of β APP and develop early-onset AD. Taken together, these observations strongly suggest that Aβ depositions may be causally related to the AD.

It is hypothesized that inhibiting the production of Aβ will prevent and reduce neurological degeneration, by controlling the formation of amyloid plaques, reducing neurotoxicity and, generally, mediating the pathology associated with Aβ production. One method of treatment methods would therefore be based on drugs that inhibit the formation of Aβ in vivo.

Methods of treatment could target the formation of Aβ through the enzymes involved in the proteolytic processing of β amyloid precursor protein. Compounds that inhibit β or γ secretase activity, either directly or indirectly, could control the production of Aβ. Advantageously, compounds that specifically target γ secretases, could control the production of Aβ. Such inhibition of β or γsecretases could thereby reduce production of Aβ, which, thereby, could reduce or prevent the neurological disorders associated with Aβ protein.

PCT publication number WO 96/29313 discloses the general formula:

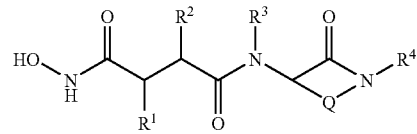

covering metalloprotease inhibiting compounds useful for the treatment of diseases associated with excess and/or unwanted matrix metalloprotease activity, particularly collagenase and or stromelysin activity.

Compounds of general formula:

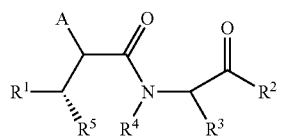

are disclosed in PCT publication number WO 95/22966 relating to matrix metalloprotease inhibitors. The compounds of the invention are useful for the treatment of conditions associated with the destruction of cartilage, including corneal ulceration, osteoporosis, periodontitis and cancer.

European Patent Application number EP 0652009A1 relates to the general formula:

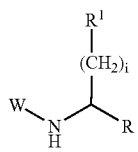

and discloses compounds that are protease inhibitors that inhibit Aβ production.

U.S. Pat. No. 5,703,129 discloses the general formula:

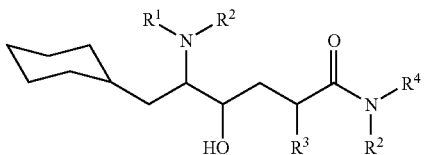

which covers 5-amino-6-cyclohexyl-4-hydroxy-hexanamide derivatives that inhibit Aβ production and are useful in the treatment of Alzheimer's disease.

Copending, commonly assigned U.S. patent application Ser. No. 09/370,089 filed Aug. 7, 1999 (equivalent to international application PCT US99/17717) discloses lactams of general formula:

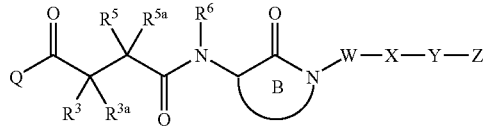

wherein the lactam ring B is substituted by succinamide and a carbocyclic, aryl, or heteroaryl group. These compounds inhibit the processing of amyloid precursor protein and, more specifically, inhibit the production of Aβ-peptide, thereby acting to prevent the formation of neurological deposits of amyloid protein.

None of the above references teaches or suggests the compounds of the present invention which are described in detail below.

SUMMARY OF THE INVENTION

One object of the present invention is to provide novel compounds which are useful as inhibitors of the production of Aβ protein or pharmaceutically acceptable salts or prodrugs thereof.

It is another object of the present invention to provide pharmaceutical compositions comprising a pharmaceutically acceptable carrier and a therapeutically effective amount of at least one of the compounds of the present invention or a pharmaceutically acceptable salt or prodrug form thereof.

It is another object of the present invention to provide a method for treating degenerative neurological disorders comprising administering to a host in need of such treatment a therapeutically effective amount of at least one of the compounds of the present invention or a pharmaceutically acceptable salt or prodrug form thereof.

These and other objects, which will become apparent during the following detailed description, have been achieved by the inventors' discovery that compounds of Formula (I):

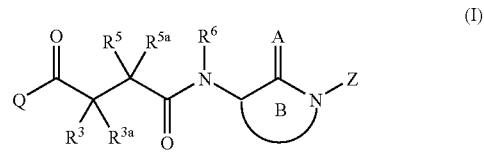

or pharmaceutically acceptable salt or prodrug forms thereof, wherein $R^3$, $R^{3a}$, $R^5$, $R^{5a}$, $R^6$, A, Q, B, and Z are defined below, are effective inhibitors of the production of Aβ.

DETAILED DESCRIPTION OF PREFERRED EMBODIMENTS

Thus, in a first embodiment, the present invention provides a novel compound of Formula (I):

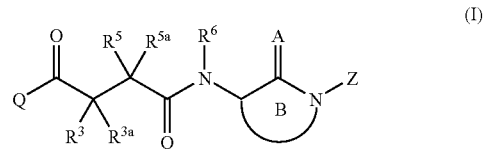

or a pharmaceutically acceptable salt or prodrug thereof, wherein:

A is selected from O and S;
Q is —$NR^1R^2$;
$R^1$, at each occurrence, is independently selected from:
    H;
    $C_1$–$C_6$ alkyl substituted with 0–3 $R^{1a}$;
    $C_3$–$C_{10}$ carbocycle substituted with 0–3 $R^{1b}$;
    $C_6$–$C_{10}$ aryl substituted with 0–3 $R^{1b}$; and
    5 to 10 membered heterocycle containing 1 to 4 heteroatoms selected from nitrogen, oxygen, and sulphur, wherein said 5 to 10 membered heterocycle is substituted with 0–3 $R^{1b}$.

$R^{1a}$, at each occurrence, is independently selected from H, $C_1$–$C_6$ alkyl Cl, F, Br, I, =O, CN, $NO_2$, $NR^{15}R^{16}$, $CF_3$;
    $C_3$–$C_{10}$ carbocycle substituted with 0–3 $R^{1b}$;
    $C_6$–$C_{10}$ aryl substituted with 0–3 $R^{1b}$; and
    5 to 10 membered heterocycle containing 1 to 4 heteroatoms selected from nitrogen, oxygen, and sulphur, wherein said 5 to 10 membered heterocycle is substituted with 0–3 $R^{1b}$;

$R^{1b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_6$ haloalkyl, and $C_1$–$C_4$ haloalkoxy;

$R^2$ is independently selected from H, $C_1$–$C_6$ alkyl, $C_3$–$C_{10}$ carbocycle, $C_6$–$C_{10}$ aryl, and 5 to 10 membered heterocycle containing 1 to 4 heteroatoms selected from nitrogen, oxygen, and sulphur;

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$,
—$(CR^7R^{7a})_n$—$N(R^{7b})$—$(CR^7R^{7a})_m$—$R^4$,
—$(CR^7R^{7a})_n$—S(=O)—$(CR^7R^{7a})_m$—$R^4$,
—$(CR^7R^{7a})_n$—S(=O)$_2$—$(CR^7R^{7a})_m$—$R^4$,
—$(CR^7R^{7a})_n$—C(=O)—$(CR^7R^{7a})_m$—$R^4$,
—$(CR^7R^{7a})_n$—$N(R^{7b})$C(=O)—$(CR^7R^{7a})_m$—$R^4$,
—$(CR^7R^{7a})_n$—C(=O)$N(R^{7b})$—$(CR^7R^{7a})_m$—$R^4$,
—$(CR^7R^{7a})_n$—$N(R^{7b})$S(=O)$_2$—$(CR^7R^{7a})_m$—$R^4$, or
—$(CR^7R^{7a})_n$—S(=O)$_2N(R^{7b})$—$(CR^7R^{7a})_m$—$R^4$;

n is 0, 1, 2, or 3;
m is 0, 1, 2, or 3;
$R^{3a}$ is H, OH, $C_1$–$C_4$ alkyl, $C_1$–$C_4$ alkoxy, $C_2$–$C_4$ alkenyl or $C_2$–$C_4$ alkenyloxy;
$R^4$ is H, OH, $OR^{14a}$,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from is H, F, Cl, Br, I, $CF_3$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkyl-S—;
$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H, OH, $C_1$–$C_4$ alkyl, $C_1$–$C_4$ alkoxy, $C_2$–$C_4$ alkenyl, or $C_2$–$C_4$ alkenyloxy;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R_{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkyl-S—;
$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;
$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;
$R^7$, at each occurrence, is independently selected from H, OH, Cl, F, Br, I, CN, $NO_2$, $CF_3$, phenyl and $C_1$–$C_4$ alkyl;
$R^{7a}$, at each occurrence, is independently selected from H, OH, Cl, F, Br, I, CN, $NO_2$, $CF_3$, and $C_1$–$C_4$ alkyl;
$R_{7b}$ is independently selected from H and $C_1$–$C_4$ alkyl;
Ring B is a 7 membered lactam or thiolactam,
wherein the lactam or thiolactam is saturated, partially saturated or unsaturated;
wherein each additional lactam carbon or thiolactam carbon is substituted with 0–2 $R^{11}$; and,
optionally, the lactam or thiolactam contains a heteroatom selected from —O—, —S—, —S(=O)—, —S(=O)$_2$—, —N=, —NH—, and —$N(R^{10})$—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3$–$C_6$ carbocycle substituted with 0–3 $R^{13}$;
$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$–$C_6$ alkyl optionally substituted with 0–3 $R^{10a}$;
$C_6$–$C_{10}$ aryl substituted with 0–4 $R^{10b}$;
$C_3$–$C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or aryl substituted with 0–4 $R^{10b}$;
$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;
$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;
phenyl substituted with 0–3 $R^{11b}$;
$C_3$–$C_6$ cycloalkyl substituted with 0–3 $R^{11b}$; and 5 to 6 membered heterocycle containing 1 to 3 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkyl-S—;

Z is H;

$C_1$–$C_8$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
$C_1$–$C_8$ alkyl substituted with 0–3 $R^{12a}$;
$C_2$–$C_4$ alkenyl substituted with 0–3 $R^{12a}$;
$C_2$–$C_4$ alkynyl substituted with 0–3 $R^{12a}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4-heteroatoms selected from nitrogen, oxygen, and sulphur, wherein said 5 to 10 membered heterocycle is substituted with 0–3 $R^{12b}$;

$R^{12}$ at each occurrence is independently selected from
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, or $C_1$–$C_4$ halothioalkyl-S—;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl,
aryl substituted by 0–4 $R^{17a}$, or
—$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and $R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

provided, when $R^{13}$ is H,
then Z is H;
$C_4$–$C_8$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
$C_1$–$C_8$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$; and provided, when ring B is a 1,3,4,5-tetrahydro-1-(Z)-5-($R^{10}$)-6,6,7,7-tetra($R^{11}$)-2,4-dioxo-2H-1,5-diazepin-3-yl core, and $R^{13}$ is H; then $R^{10}$ is H, C(=O)$R^{17}$, C(=O)O$R^{17}$, C(=O)$NR^{18}R^{19}$, $S(=O)_2NR^{18}R^{19}$, $S(=O)_2R^{17}$; or
$C_1$–$C_6$ alkyl optionally substituted with 0–3 $R^{10a}$;

$R^{10a}$, at each occurrence, is independently selected from H, $C_1$–$C_6$ alkyl, $OR^{14}$, Cl, F, Br, I, =O, CN, $NO_2$, $NR^{15}R^{16}$, and $CF_3$.

[2] In a preferred embodiment the present invention provides for a compound of Formula (Ia):

(Ia)

or a pharmaceutically acceptable salt or prodrug thereof, wherein:

Z is H;
$C_{1-8}$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$.

[3] In a more preferred embodiment the present invention provides for a compound of Formula (Ia):

wherein:

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—$(CR^7R^{7a})_m$—$R^4$, or
—$(CR^7R^{7a})_n$—N($R^{7b}$)—$(CR^7R^{7a})_m$—$R^4$;

n is 0, 1, or 2;

m is 0, 1, or 2;

$R^{3a}$ is H, OH, methyl, ethyl, propyl, butyl, methoxy, ethoxy, propoxy, butoxy, allyl, or 3-buten-1-yl;

$R^4$ is H, OH, $OR^{14a}$,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{16}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, F, Cl, Br, I, $CF_3$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^5$ is H, $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{60}$ carbocycle substituted with 0–3 $R^{5c}$;
  $C_6$–$C_{10}$ aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H or $C_1$–$C_4$ alkyl;
$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$;
  $C_3$–$C_{10}$ carbocycle substituted with 0–3 $R^{5c}$;
  $C_6$–$C_{10}$ aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^6$ is H, methyl, or ethyl;
$R^7$, at each occurrence, is independently selected from H, OH, Cl, F, Br, I, CN, $NO_2$, $CF_3$, phenyl and $C_1$–$C_4$ alkyl;
$R^{7a}$, at each occurrence, is independently selected from H, OH, Cl, F, Br, I, CN, $NO_2$, $CF_3$, and $C_1$–$C_4$ alkyl;
$R^{7b}$ is independently selected from H, methyl, ethyl, propyl, and butyl;
Ring B is a 7 membered lactam or thiolactam,
  wherein the lactam or thiolactam is saturated, partially saturated or unsaturated;
  wherein each additional lactam carbon or thiolactam carbon is substituted with 0–2 $R^{11}$; and,
  optionally, the lactam or thiolactam contains a heteroatom selected from, —O—, —S—, —S(=O)—, —S(=O)$_2$—, —N=, —NH—, and —N($R^{10}$)—;
additionally, two $R^{11}$ substituents on adjacent atoms may be combined to form a benzo fused radical; wherein said benzo fused radical is substituted with 0–3 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3$–$C_6$ carbocycle substituted with 0–3 $R^{13}$;
$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
  $C_1$–$C_6$ alkyl optionally substituted with 0–2 $R^{10a}$;
  $C_6$–$C_{10}$ aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$ at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–4 $R^{10b}$;
$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;

$R^{11}$, at each occurrence, is independently selected from H, $C_1$–$C_4$ alkoxy, Cl, F, Br, I, =O, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
  $C_1$–$C_6$ alkyl optionally substituted with 0–3 $R^{11a}$;
  $C_6$–$C_{10}$ aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;
$R^{11b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
Z is H;
  $C_1$–$C_6$ alkyl substituted with 0–3 $R^{12a}$;
  $C_2$–$C_4$ alkenyl substituted with 0–3 $R^{12a}$; or
  $C_2$–$C_4$ alkynyl substituted with 0–3 $R^{12a}$;
$R^{12a}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;
$R^{14}$ is H, phenyl, benzyl, $C_1$–$C_6$ alkyl, or $C_2$–$C_6$ alkoxyalkyl;
$R^{14a}$ is H, phenyl, benzyl, methyl, ethyl, propyl, or butyl;
$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{17}$ is H, $C_1$–$C_6$ alkyl, $C_2$–$C_6$ alkoxyalkyl,
  aryl substituted by 0–4 $R^{17a}$, or
  —$CH_2$-aryl substituted by 0–4 $R^{17a}$;
$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;
$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and
$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—.

[4] In a further more preferred embodiment the present invention provides for a compound of Formula (Ia) wherein:
$R^3$ is —$(CHR^7)_n$—$R^4$,
n is 0 or 1;
$R^{3a}$ is H, OH, methyl, ethyl, propyl, butyl, methoxy, ethoxy, propoxy, butoxy, allyl, or 3-buten-1-yl;
$R^4$ is H, OH, $OR^{14a}$,
  $C_1$–$C_4$ alkyl substituted with 0–2 $R^{4a}$,
  $C_2$–$C_4$ alkenyl substituted with 0–2 $R^{4a}$,
  $C_2$–$C_4$ alkynyl substituted with 0–1 $R^{4a}$,
  $C_3$–$C_6$ carbocycle substituted with 0–3 $R^{4b}$,
  $C_6$–$C_{10}$ aryl substituted with 0–3 $R^{4b}$, or
  5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4a}$, at each occurrence, is independently selected from is H, F, Cl, Br, I, $CF_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^5$ is H, $OR^{14}$;
$C_1$–$C_4$ alkyl substituted with 0–3 $R^{5b}$;
$C_2$–$C_4$ alkenyl substituted with 0–3 $R^{5b}$;
$C_2$–$C_4$ alkynyl substituted with 0–3 $R^{5b}$;

$R^{5a}$ is H, methyl, ethyl, propyl, or butyl;

$R^{5b}$, at each occurrence, is independently selected from:
H, methyl, ethyl, propyl, butyl, $CF_3$, $OR^{14}$, Cl, F, Br, I, =O;
$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^6$ is H;

$R^7$, at each occurrence, is independently selected from H, F, $CF_3$, methyl, and ethyl;

Ring B is a 7 membered lactam or thiolactam,
wherein the lactam or thiolactam is saturated, partially saturated or unsaturated;
wherein each additional lactam carbon or thiolactam carbon is substituted with 0–2 $R^{11}$; and,
optionally, the lactam or thiolactam contains a heteroatom selected from —N=, —NH—, and —N($R^{10}$)—;

additionally, two $R^{11}$ substituents on adjacent atoms may be combined to form a benzo fused radical; wherein said benzo fused radical is substituted with 0–2 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–2 $R^{13}$;

additionally, two $R^{11}$ substituents on the same or adjacent carbon atoms may be combined to form a $C_3$–$C_6$ carbocycle substituted with 0–2 $R^{13}$;

$R^{10}$ is H, $C(=O)R^{17}$, $C(=O)OR^{17}$;
$C_1$–$C_4$ alkyl optionally substituted with 0–1 $R^{10a}$;
phenyl substituted with 0–4 $R^{10b}$;
$C_3$–$C_6$ carbocycle substituted with 0–3 $R^{10b}$; or
5 to 6 membered heterocycle containing 1 to 4 heteroatoms selected from nitrogen, oxygen, and sulphur, wherein said 5 to 6 membered heterocycle is substituted with 0–3 $R^{10b}$;

$R^{10a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, or phenyl substituted with 0–4 $R^{10b}$;

$R^{10b}$, at each occurrence, is independently selected from H, OH, $C_1$–$C_4$ alkyl, $C_1$–$C_3$ alkoxy, Cl, F, Br, I, CN, $NO_2$, $NR^{15}R^{16}$, or $CF_3$;

$R^{11}$, at each occurrence, is independently selected from H, $C_1$–$C_4$ alkoxy, Cl, F, =O, $NR^{18}R^{19}$, $C(=O)R^{17}$, $C(=O)OR^{17}$, $CF_3$;
$C_1$–$C_6$ alkyl optionally substituted with 0–3 $R^{11a}$;
$C_6$–$C_{10}$ aryl substituted with 0–3 $R^{11b}$;
$C_3$–$C_6$ carbocycle substituted with 0–3 $R^{11b}$; or
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11a}$, at each occurrence, is independently selected from H, $C_1$–$C_4$ alkyl, $OR^{14}$, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Z is H;
$C_1$–$C_4$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{17}$ is H, methyl, ethyl, propyl, butyl, methoxymethyl, ethoxymethyl, methoxyethyl, ethoxyethyl, phenyl substituted by 0–3 $R^{17a}$, or —$CH_2$-phenyl substituted by 0–3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl;

$R^{19}$, at each occurrence, is independently selected from H, methyl, and ethyl.

[5] In an even more preferred embodiment the present invention provides for a compound of Formula (Ib):

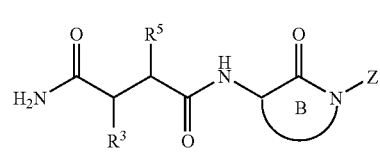

(Ib)

or a pharmaceutically acceptable salt or prodrug thereof wherein:

Ring B is selected from:

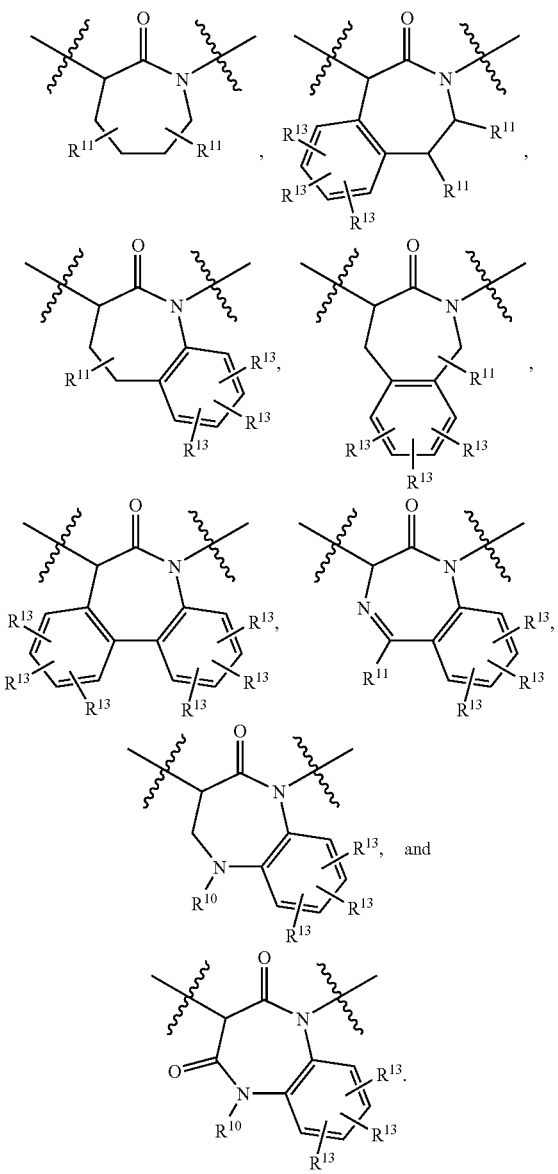

[6] In an even further more preferred embodiment the present invention provides for a compound of Formula (Ic):

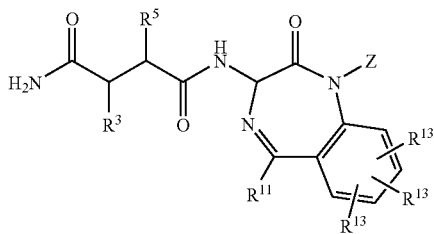

(Ic)

or a pharmaceutically acceptable salt or prodrug thereof wherein $R^3$ is $R^4$, $R^4$ is $C_1$–$C_4$ alkyl substituted with 0–1 $R^{4a}$,
$C_2$–$C_4$ alkenyl substituted with 0–1 $R^{4a}$, or
$C_2$–$C_4$ alkynyl substituted with 0–1 $R^{4a}$;

$R^{4a}$, at each occurrence, is independently selected from
H, F, $CF_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^5$ is $C_1$–$C_4$ alkyl substituted with 0–1 $R^{5b}$;
$C_2$–$C_4$ alkenyl substituted with 0–1 $R^{5b}$;
$C_2$–$C_4$ alkynyl substituted with 0–1 $R^{5b}$;

$R^{5b}$, at each occurrence, is independently selected from:
H, methyl, ethyl, propyl, butyl, $CF_3$, $OR^{14}$, =O;
$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{11}$, at each occurrence, is independently selected from
H, =O, $NR^{18}R^{19}$, $CF_3$;
$C_1$–$C_4$ alkyl optionally substituted with 0–1 $R^{11a}$;
phenyl substituted with 0–3 $R^{11b}$;
$C_3$–$C_6$ carbocycle substituted with 0–3 $R^{11b}$; and
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1$–$C_4$ alkyl, $OR^{14}$, F, Cl, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

Z is H;
$C_1$–$C_4$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2OH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

[7] In another even further more preferred embodiment the present invention provides for a compound of Formula (Id):

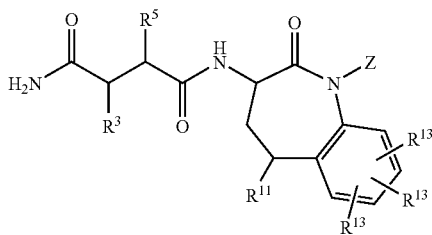

or a pharmaceutically acceptable salt or prodrug thereof wherein:

$R^3$ is $R^4$, $R^4$ is $C_1$–$C_4$ alkyl substituted with 0–1 $R^{4a}$,
$C_2$–$C_4$ alkenyl substituted with 0–1 $R^{4a}$, or
$C_2$–$C_4$ alkynyl substituted with 0–1 $R^{4a}$;

$R^{4a}$, at each occurrence, is independently selected from H, F, CF$_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, $C_1$–$C_2$ haloalkyl, and $C_1$–$C_2$ haloalkoxy;

$R^5$ is $C_1$–$C_4$ alkyl substituted with 0–1 $R^{5b}$;
$C_2$–$C_4$ alkenyl substituted with 0–1 $R^{5b}$;
$C_2$–$C_4$ alkynyl substituted with 0–1 $R^{5b}$;

$R^{5b}$, at each occurrence, is independently selected from:
H, methyl, ethyl, propyl, butyl, CF$_3$, OR$^{14}$, =O;
$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, $C_1$–$C_2$ haloalkyl, and $C_1$–$C_2$ haloalkoxy;

$R^{11}$, at each occurrence, is independently selected from H, =O, NR$^{18}$R$^{19}$, CF$_3$;
$C_1$–$C_4$ alkyl optionally substituted with 0–1 $R^{11a}$;
phenyl substituted with 0–3 $R^{11b}$;
$C_3$–$C_6$ carbocycle substituted with 0–3 $R^{11b}$; or
5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1$–$C_4$ alkyl, OR$^{14}$, F, Cl, =O, NR$^{15}$R$^{16}$, CF$_3$, or phenyl substituted with 0–3 $R^{11b}$;

$R^{11b}$, at each occurrence, is independently selected from H, OH, Cl, F, NR$^{15}$R$^{16}$, CF$_3$, methyl, ethyl, propyl, butyl, methoxy, ethoxy, propoxy, $C_1$–$C_2$ haloalkyl, and $C_1$–$C_2$ haloalkoxy;

Z is H;
$C_1$–$C_4$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl; propyl, butyl, methoxy, ethoxy, Cl, F, Br, CN, NR$^{15}$R$^{16}$, and CF$_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

[8] In another even further more preferred embodiment the present invention provides for a compound of Formula (Ie):

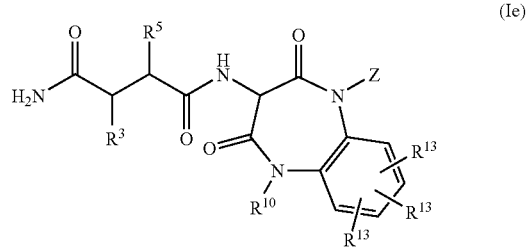

or a pharmaceutically acceptable salt or prodrug thereof wherein:

$R^3$ is $R^4$, $R^4$ is $C_1$–$C_4$ alkyl substituted with 0–1 $R^{4a}$,
$C_2$–$C_4$ alkenyl substituted with 0–1 $R^{4a}$, or
$C_2$–$C_4$ alkynyl substituted with 0–1 $R^{4a}$;

$R^{4a}$, at each occurrence, is independently selected from
H, F, CF$_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^5$ is C$_1$–C$_4$ alkyl substituted with 0–1 $R^{5b}$;
C$_2$–C$_4$ alkenyl substituted with 0–1 $R^{5b}$;
C$_2$–C$_4$ alkynyl substituted with 0–1 $R^{5b}$;

$R^{5b}$, at each occurrence, is independently selected from:
H, methyl, ethyl, propyl, butyl, CF$_3$, OR$^{14}$, =O;
C$_3$–C$_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^{10}$ is H, C(=O)R$^{17}$, C(=O)OR$^{17}$;
C$_1$–C$_4$ alkyl optionally substituted with 0–1 $R^{10a}$;
phenyl substituted with 0–4 $R^{10b}$;
C$_3$–C$_6$ carbocycle substituted with 0–3 $R^{10b}$; or
5 to 6 membered heterocycle containing 1 to 4 heteroatoms selected from nitrogen, oxygen, and sulphur, wherein said 5 to 6 membered heterocycle is substituted with 0–3 $R^{10b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{10a}$, at each occurrence, is independently selected from H, methyl, ethyl, propyl, butyl, OR$^{14}$, Cl, F, =O, NR$^{15}$R$^{16}$, CF$_3$, or phenyl substituted with 0–4 $R^{10b}$;

$R^{10b}$ at each occurrence is independently selected from H, OH, methyl, ethyl, propyl, butyl, methoxy, ethoxy, propoxy, Cl, F, NR$^{15}$R$^{16}$, and CF$_3$;

Z is H;
C$_1$–C$_4$ alkyl substituted with 0–3 $R^{12a}$;
C$_2$–C$_4$ alkenyl substituted with 0–3 $R^{12a}$; or
C$_2$–C$_4$ alkynyl substituted with 0–3 $R^{12a}$;

$R^{12a}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^{13}$, at each occurrence, is independently selected from H, OH, methyl, ethyl, propyl, butyl, methoxy, ethoxy, Cl, F, Br, CN, NR$^{15}$R$^{16}$, and CF$_3$;

$R^{14}$ is H, phenyl, benzyl, methyl, ethyl, propyl, or butyl;
$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{17}$ is H, methyl, ethyl, propyl, butyl, methoxymethyl, ethoxymethyl, methoxyethyl, ethoxyethyl, phenyl substituted by 0–3 $R^{17a}$, or —CH$_2$-phenyl substituted by 0–3 $R^{17a}$;

$R^{17a}$ is H, methyl, methoxy, —OH, F, Cl, CF$_3$, or OCF$_3$;

$R^{18}$ at each occurrence, is independently selected from H, methyl, ethyl, propyl, butyl, phenyl, benzyl, and phenethyl; and $R^{19}$, at each occurrence, is independently selected from H, methyl, and ethyl.

[9] In another even further more preferred embodiment the present invention provides for a compound of Formula (If):

(If)

or a pharmaceutically acceptable salt or prodrug thereof wherein:

$R^3$ is $R^4$,
$R^4$ is C$_1$–C$_4$ alkyl substituted with 0–1 $R^{4a}$,
C$_2$–C$_4$ alkenyl substituted with 0–1 $R^{4a}$, or
C$_2$–C$_4$ alkynyl substituted with 0–1 $R^{4a}$;

$R^{4a}$, at each occurrence, is independently selected from
H, F, CF$_3$,
C$_3$–C$_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^5$ is —C$_4$ alkyl substituted with 0–1 $R^{5b}$;
C$_2$–C$_4$ alkenyl substituted with 0–1 $R^{5b}$;
C$_2$–C$_4$ alkynyl substituted with 0–1 $R^{5b}$;

$R^{5b}$, at each occurrence, is independently selected from:
H, methyl, ethyl, propyl, butyl, CF$_3$, OR$^{14}$, =O;
C$_3$–C$_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

Z is H;
$C_1$–$C_4$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

[10] In another even further more preferred embodiment the present invention provides for a compound of one of Formulas (Ic), (Id), (Ie), or (If), wherein:

$R^3$ is —$CH_3$, —$CH_2CH_3$, —$CH_2CH_2CH_3$, —$CH_2CH_2CH_2CH_3$, —$CH_2(CH_3)_2$, —$CH(CH_3)CH_2CH_3$, —$CH_2CH(CH_3)_2$, —$CH_2C(CH_3)_3$, —$CF_3$, —$CH_2CF_3$, —$CH_2CH_2CF_3$, —$CH_2CH_2CH_2CF_3$, —CH=$CH_2$, —$CH_2CH$=$CH_2$, —$CH_2C(CH_3)$=$CH_2$, —$CH_2CH$=$C(CH_3)_2$, —$CH_2CH_2CH$=$CH_2$, —$CH_2CH_2C(CH_3)$=$CH_2$, —$CH_2CH_2CH$=$C(CH_3)_2$, cis-$CH_2CH$=$CH(CH_3)$, cis-$CH_2CH_2CH$=$CH(CH_3)$, trans-$CH_2CH$=$CH(CH_3)$, trans-$CH_2CH_2CH$=$CH(CH_3)$; —C≡CH, —$CH_2C$≡CH, —$CH_2C$≡$C(CH_3)$, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, or (3-F-5-Cl-phenyl)$CH_2CH_2$—, $R^5$ is —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH(CH_2CH_3)_2$, —$CF_3$, —$CH_2CF_3$, —$CH_2CH_2CF_3$, —$CH_2CH_2CH_2CF_3$, —$CH_2CH_2CH_2CH_2CF_3$, —CH=$CH_2$, —$CH_2CH$=$CH_2$, —CH=$CHCH_3$, cis-$CH_2CH$=$CH(CH_3)$, trans-$CH_2CH$=$CH(CH_3)$, trans-$CH_2CH$=$CH(C_6H_5)$, —$CH_2CH$=$C(CH_3)_2$, cis-$CH_2CH_2CH$=$CHCH_2CH_3$, trans-$CH_2CH$=$CHCH_2CH_3$, cis-$CH_2CH_2CH$=$CH(CH_3)$, trans-$CH_2CH_2CH$=$CH(CH_3)$, trans-$CH_2CH$=$CHCH_2(C_6H_5)$, —C≡CH, —$CH_2C$≡CH, —$CH_2C$≡$C(CH_3)$, —$CH_2C$≡$C(C_6H_5)$ —$CH_2CH_2C$≡CH, —$CH_2CH_2C$≡$C(CH_3)$, —$CH_2CH_2CE$-$C(C_6H_5)$ —$CH_2CH_2CH_2C$≡CH, —$CH_2CH_2CH_2C$≡$C(CH_3)$, —$CH_2CH_2CH_2C$≡$C(C_6H_5)$ cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—, phenyl-$CH_2$—, (2-F-phenyl)$CH_2$—, (3-F-phenyl)$CH_2$—, (4-F-phenyl)$CH_2$—, furanyl-$CH_2$—, thienyl-$CH_2$—, pyridyl-$CH_2$—, 1-imidazolyl-$CH_2$—, oxazolyl-$CH_2$—, isoxazolyl-$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, isoxazolyl-$CH_2CH_2$—, Z is methyl, ethyl, i-propyl, n-propyl, n-butyl, i-butyl, s-butyl, t-butyl, or allyl;

$R^{10}$ is H, methyl, ethyl, phenyl, benzyl, phenethyl, 4-F-phenyl, (4-F-phenyl)$CH_2$—, (4-F-phenyl)$CH_2CH_2$—, 4-Cl-phenyl, (4-Cl-phenyl)$CH_2$—, (4-Cl-phenyl)$CH_2CH_2$—, 4-$CH_3$-phenyl, (4-$CH_3$-phenyl)$CH_2$—, (4-$CH_3$-phenyl)$CH_2CH_2$—, 4-$CF_3$-phenyl, (4-$CF_3$-phenyl)$CH_2$—, or (4-$CF_3$-phenyl)$CH_2CH_2$—;

$R^{11}$, at each occurrence, is independently selected from H, =O, methyl, ethyl, phenyl, benzyl, phenethyl, 4-F-phenyl, (4-F-phenyl)$CH_2$—, (4-F-phenyl)$CH_2CH_2$—, 3-F-phenyl, (3-F-phenyl)$CH_2$—, (3-F-phenyl)$CH_2CH_2$—, 2-F-phenyl, (2-F-phenyl)$CH_2$—, (–2-F-phenyl)$CH_2CH_2$—, 4-Cl-phenyl, (4-Cl-phenyl)$CH_2$—, (4-Cl-phenyl)$CH_2CH_2$—, 3-Cl-phenyl, (3-Cl-phenyl)$CH_2$—, (3-Cl-phenyl)$CH_2CH_2$—, 4-$CH_3$-phenyl, (4-$CH_3$-phenyl)$CH_2$—, (4-$CH_3$-phenyl)$CH_2CH_2$—, 3-$CH_3$-phenyl, (3-$CH_3$-phenyl)$CH_2$—, (3-$CH_3$-phenyl)$CH_2CH_2$—, 4-$CF_3$-phenyl, (4-$CF_3$-phenyl)$CH_2$—, (4-$CF_3$-phenyl)$CH_2CH_2$—, pyrid-2-yl, pyrid-3-yl, or pyrid-4-yl, and $R^{13}$, at each occurrence, is independently selected from H, F, Cl, OH, —$CH_3$, —$CH_2CH_3$, —$OCH_3$, or —$CF_3$.

[11] In another even further more preferred embodiment the present invention provides for a compound selected from:

(2R,3S) N1-[1,3-dihydro-1-methyl-2-oxo-5-phenyl-2H-1,4-benzodiazepin-3-yl]-2-(2-methylpropyl)-3-allyl-butanediamide;

(2R,3S) N1-[1,3-dihydro-1-methyl-2-oxo-5-phenyl-2H-1,4-benzodiazepin-3-yl]-2-(2-methylpropyl)-3-propyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-allyl-butanediamide;

(2R,3S) N1-[(3R)-1,3-dihydro-1-methyl-2-oxo-5-phenyl-2H-1,4-benzodiazepin-3-yl]-2-(2-methylpropyl)-3-allyl-butanediamide;

(2R,3S) N1-[(3R)-1,3-dihydro-1-methyl-2-oxo-5-phenyl-2H-1,4-benzodiazepin-3-yl]-2-(2-methylpropyl)-3-propyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-propyl-butanediamide;

(2R,3S) N1-[1,3-dihydro-1-methyl-2-oxo-5-phenyl-2H-1,4-benzodiazepin-3-yl]-2-methyl-3-allyl-butanediamide;

(2R,3S) N1-[(3S)-1,3-dihydro-1-methyl-2-oxo-5-phenyl-2H-1,4-benzodiazepin-3-yl]-2-methyl-3-allyl-butanediamide;

(2R,3S) N1-[(3S)-1,3-dihydro-1-methyl-2-oxo-5-phenyl-2H-1,4-benzodiazepin-3-yl]-2-methyl-3-propyl-butanediamide;

(2R) N1-[1,3-dihydro-1-methyl-2-oxo-5-phenyl-2H-1,4-benzodiazepin-3-yl]-2-methyl-butanediamide;

(2R,3S) N1-[1,3-dihydro-2-oxo-5-phenyl-2H-1,4-benzodiazepin-3-yl]-2-(2-methylpropyl)-3-allyl-butanediamide;

(2R,3S) N1-[1,3-dihydro-1-methyl-2-oxo-5-phenyl-7-chloro-2H-1,4-benzodiazepin-3-yl]-2-(2-methylpropyl)-3-allyl-butanediamide;

(2R,3S) N1-[(3S)-1,3-dihydro-1-methyl-2-oxo-5-phenyl-7-chloro-2H-1,4-benzodiazepin-3-yl]-2-(2-methylpropyl)-3-allyl-butanediamide;

(2R,3S) N1-[(3R)-1,3-dihydro-1-methyl-2-oxo-5-phenyl-7-chloro-2H-1,4-benzodiazepin-3-yl]-2-(2-methylpropyl)-3-allyl-butanediamide;

(2R,3S) N1-[1,3-dihydro-1-methyl-2-oxo-5-(2-fluorophenyl)-7-chloro-2H-1,4-benzodiazepin-3-yl]-2-(2-methylpropyl)-3-allyl-butanediamide;

(2R,3S) N1-[(3S)-1,3-dihydro-1-methyl-2-oxo-5-(2-fluorophenyl)-7-chloro-2H-1,4-benzodiazepin-3-yl]-2-(2-methylpropyl)-3-allyl-butanediamide;

(2R,3S) N1-[(3R)-1,3-dihydro-1-methyl-2-oxo-5-(2-fluorophenyl)-7-chloro-2H-1,4-benzodiazepin-3-yl]-2-(2-methylpropyl)-3-allyl-butanediamide;

(2S,3S) N1-[1,3-dihydro-1-methyl-2-oxo-5-phenyl-2H-1,4-benzodiazepin-3-yl]-2-(2-methylpropyl)-3-allyl-butanediamide;

(2S,3S) N1-[(3S)-1,3-dihydro-1-methyl-2-oxo-5-phenyl-7-chloro-2H-1,4-benzodiazepin-3-yl])-2-(2-methylpropyl)-3-propyl-butanediamide;

(2R,3S) N1-[(3S)-1,3-dihydro-1-methyl-2-oxo-5-(2-fluorophenyl)-7-chloro-2H-1,4-benzodiazepin-3-yl]-2-(2-methylpropyl)-3-propyl-butanediamide;

(2R,3S) N1-[1,3-dihydro-1-methyl-2-oxo-5-(4-fluorophenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-fluorophenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-fluorophenyl)-2H-1,4-benzodiazepin-3-yl]-2-(2-methylpropyl)-3-allyl-butanediamide;

(2R,3S) N1-[1,3-dihydro-1-methyl-2-oxo-5-(pyrid-2-yl)-2H-1,4-benzodiazepin-3-yl]-2-(2-methylpropyl)-3-allyl-butanediamide;

(2R,3S) N1-[1,3-dihydro-1-methyl-2-oxo-5-(N-morpholino)-2H-1,4-benzodiazepin-3-yl]-2-(2-methylpropyl)-3-allyl-butanediamide;

(2R,3S) N1-[1,3-dihydro-1-methyl-2-oxo-5-(dimethylamino)-2H-1,4-benzodiazepin-3-yl]-2-(2-methylpropyl)-3-allyl-butanediamide;

(2R,3S) N1-[1,3-dihydro-1-methyl-2-oxo-5-(N-methyl-N-phenylamino)-2H-1,4-benzodiazepin-3-yl]-2-(2-methylpropyl)-3-allyl-butanediamide;

(2R,3S) N1-[1,3-dihydro-1-methyl-2-oxo-5-(N-piperidinyl)-2H-1,4-benzodiazepin-3-yl]-2-(2-methylpropyl)-3-allyl-butanediamide;

(2R,3S) N1-[1,3-dihydro-1-methyl-2-oxo-5-(N-homopiperidinyl)-2H-1,4-benzodiazepin-3-yl]-2-(2-methylpropyl)-3-allyl-butanediamide;

(2R,3S) N1-[1,3-dihydro-1-methyl-2-oxo-5-(3-methoxyphenyl)-2H-1,4-benzodiazepin-3-yl]-2-(2-methylpropyl)-3-allyl-butanediamide;

(2R,3S) N1-[1,3-dihydro-1-methyl-2-oxo-5-(pyrid-4-yl)-2H-1,4-benzodiazepin-3-yl]-2-(2-methylpropyl)-3-allyl-butanediamide;

(2R,3S) N1-[1,3-dihydro-1-methyl-2-oxo-5-phenyl-7-methoxy-2H-1,4-benzodiazepin-3-yl]-2-(2-methylpropyl)-3-allyl-butanediamide;

(2R,3S) N1-[1,3-dihydro-1-methyl-2-oxo-5-(pyrid-3-yl)-2H-1,4-benzodiazepin-3-yl]-2-(2-methylpropyl)-3-allyl-butanediamide;

(2R,3S) N1-[1,3-dihydro-1-methyl-2-oxo-5-phenyl-2H-1,4-benzodiazepin-3-yl]-2-(2-methylpropyl)-3-(cyclopropylmethyl)-butanediamide;

(2R,3S) N1-[1,3-dihydro-1-methyl-2-oxo-5-(3-fluorophenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(3-fluorophenyl)-2H-1,4-benzodiazepin-3-yl]-2-(2-methylpropyl)-3-allyl-butanediamide;

(2R,3S) N1-[(3R)-1,3-dihydro-1-methyl-2-oxo-5-(3-fluorophenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-(3-buten-1-yl)-butanediamide;

(2R,3S) N1-[(3S)-1,3-dihydro-1-methyl-2-oxo-5-phenyl-2H-1,4-benzodiazepin-3-yl]-2-(2-methylpropyl)-3-(cyclopentylethyl)-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-(3-buten-1-yl)-butanediamide;

(2R,3S) N1-[(3R)-1,3-dihydro-1-methyl-2-oxo-5-(4-trifluoromethylphenyl)-2H-1,4-benzodiazepin-3-yl]-2-(2-methylpropyl)-3-(3-buten-1-yl)-butanediamide;

(2R,3S) N1-[1,3-dihydro-1-methyl-2-oxo-5-(4-trifluoromethylphenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-allyl-butanediamide;

(2R,3S) N1-[(3R)-1,3-dihydro-1-methyl-2-oxo-5-(4-trifluoromethylphenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-n-butyl-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-propyl-butanediamide;

(2R,3S) N1-[(3S)-1,3-dihydro-1-methyl-2-oxo-5-(4-chlorophenyl)-2H-1,4-benzodiazepin-3-yl]-2-(2-methylpropyl)-3-(3-buten-1-yl)-butanediamide;

(2R,3S) N1-[(3S)-1,3-dihydro-1-methyl-2-oxo-5-(4-chlorophenyl)-2H-1,4-benzodiazepin-3-yl]-2-(2-methylpropyl)-3-n-butyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-allyl-N4-[benzyl]-butanediamide;

(2R,3S) N1-[1,3-dihydro-1-methyl-2-oxo-5-methyl-2H-1,4-benzodiazepin-3-yl]-2-(2-methylpropyl)-3-allyl-butanediamide;

(2R,3S) N1-[1,3-dihydro-1-methyl-2-oxo-5-n-butyl-2H-1,4-benzodiazepin-3-yl]-2-(2-methylpropyl)-3-allyl-butanediamide;

(2R,3S) N1-[1,3-dihydro-1-methyl-2-oxo-5-(2-methylpropyl)$_2$H-1,4-benzodiazepin-3-yl]-2-(2-methylpropyl)-3-allyl-butanediamide;

(2R,3S) N1-[1,3-dihydro-1-methyl-2-oxo-5-(4-chlorophenyl)$_2$H-1,4-benzodiazepin-3-yl]-2-(2-methylpropyl)-3-allyl-butanediamide;

(2R,3S) N1-[1,3-dihydro-1-ethyl-2-oxo-5-phenyl-2H-1,4-benzodiazepin-3-yl]-2-(2-methylpropyl)-3-allyl-butanediamide;

(2R,3S) N1-[1,3-dihydro-1-propyl-2-oxo-5-phenyl-2H-1,4-benzodiazepin-3-yl]-2-(2-methylpropyl)-3-allyl-butanediamide;

(2R,3S) N1-[1,3-dihydro-1-(isopropyl)-2-oxo-5-phenyl-1,4-benzodiazepin-3-yl]-2-(2-methylpropyl)-3-allyl-butanediamide;

(2R,3S) N1-[(3S)-1,3-dihydro-1-methyl-2-oxo-5-phenyl-2H-1,4-benzodiazepin-3-yl]-2-(2-methylpropyl)-3,3-diallyl-butanediamide;

(2R,3S) N1-[6,7-dihydro-5-methyl-6-oxo-5H-dibenz[b,d]azepin-7-yl]-2-(2-methylpropyl)-3-allyl-butanediamide; and (2R,3S) N1-[1,3,4,5-tetrahydro-1,5-dimethyl-2,4-dioxo-2H-1,5-benzodiazepin-3-yl]-2-(2-methylpropyl)-3-allyl butanediamide.

[12] In a preferred embodiment the present invention provides for a compound of Formula (Ia):

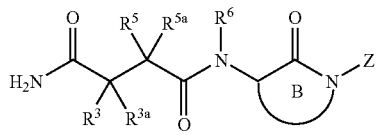

(Ia)

or a pharmaceutically acceptable salt or prodrug thereof, wherein:

Z is $C_1$–$C_8$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

provided, when $R^{13}$ is H,
then Z is $C_4$–$C_8$ alkyl substituted with 1–3 $R^{12}$;
—$C_2$–$C_4$ alkenyl substituted with 1–3 $R^{12}$; or $C_2$–$C_4$ alkynyl substituted with 1–3 $R^{12}$; and provided, when ring B is a 1,3,4,5-tetrahydro-1-(Z)-5-($R^{10}$)-6,6,7,7-tetra($R^{11}$)-2,4-dioxo-2H-1,5-diazepin-3-yl core, and $R^{13}$ is H; then $R^{10}$ is H, C(=O)$R^{17}$, C(=O)O$R^{17}$, C(=O)N$R^{18}R^{19}$, S(=O)$_2$N$R^{18}R^{19}$, S(=O)$_2R^{17}$; or $C_1$–$C_6$ alkyl optionally substituted with 0–3 $R^{10a}$;

$R^{10a}$, at each occurrence, is independently selected from H, $C_1$–$C_6$ alkyl, O$R^{14}$, Cl, F, Br, I, =O, CN, NO$_2$, N$R^{15}R^{16}$, and CF$_3$.

[13] In a more preferred embodiment the present invention provides for a compound of Formula (Ia):
$R^3$ is —(CR$^7$R$^{7a}$), —R$^4$,
—(CR$^7$R$^{7a}$)$_n$—S—(CR$^7$R$^{7a}$)$_m$—R$^4$,
—(CR$^7$R$^{7a}$)$_n$—O—(CR$^7$R$^{7a}$)$_m$—R$^4$, or
—(CR$^7$R$^{7a}$)$_n$—N(R$^{7b}$)—(CR$^7$R$^{7a}$)$_m$—R$^4$;

n is 0, 1, or 2;
m is 0, 1, or 2;
$R^{3a}$ is H, OH, methyl, ethyl, propyl, butyl, methoxy, ethoxy, propoxy, butoxy, allyl, or 3-buten-1-yl;
$R^4$ is H, OH, OR$^{14a}$,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from is H, F, Cl, Br, I, CF$_3$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, and $C_1$–$C_4$ haloalkoxy;

$R^5$ is H, OR$^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H or $C_1$–$C_4$ alkyl;
$R^{5b}$, at each occurrence, is independently selected from:
H, O$_1$–$C_6$ alkyl, CF$_3$, OR$^{14}$, Cl, F, Br, I, =O, CN, NO$_2$, N$R^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, and $C_1$–$C_4$ haloalkoxy;

$R^6$ is H, methyl, or ethyl;
$R^7$, at each occurrence, is independently selected from H, OH, Cl, F, Br, I, CN, NO$_2$, CF$_3$, phenyl, and $C_1$–$C_4$ alkyl;
$R^{7a}$, at each occurrence, is independently selected from H, OH, Cl, F, Br, I, CN, NO$_2$, CF$_3$, and $C_1$–$C_4$ alkyl;
$R^{7b}$ is independently selected from H, methyl, ethyl, propyl, and butyl;
Ring B is a 7 membered lactam,
wherein the lactam is saturated, partially saturated or unsaturated;

wherein each additional lactam carbon is substituted with 0–2 $R^{11}$; and, optionally, the lactam contains a heteroatom selected from —O—, —S—, —S(=O)—, —S(=O)$_2$—, —N=, —NH—, and N($R^{10}$)—;

additionally, two $R^{11}$ substituents on adjacent atoms may be combined to form a benzo fused radical; wherein said benzo fused radical is substituted with 0–3 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;

additionally, two $R^{11}$ substituents on the same or adjacent carbon atoms may be combined to form a $C_3$–$C_6$ carbocycle substituted with 0–3 $R^{13}$;

$R^{10}$ is H, C(=O)$R^{17}$, C(=O)O$R^{17}$, C(=O)N$R^{18}R^{19}$, S(=O)$_2$N$R^{18}R^{19}$, S(=O)$_2R^{17}$;

$C_1$–$C_6$ alkyl optionally substituted with 0–2 $R^{10a}$;
$C_6$–$C_{10}$ aryl substituted with 0–4 $R^{10b}$;
$C_3$–$C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H, $C_1$–$C_6$ alkyl, O$R^{14}$, Cl, F, Br, I, =O, CN, NO$_2$, N$R^{15}R^{16}$, CF$_3$, or phenyl substituted with 0–4 $R^{10b}$;

$R^{10b}$; at each occurrence, is independently selected from H, OH, $C_1$–$C_6$ alkyl, $C_1$–$C_4$ alkoxy, Cl, F, Br, I, CN, NO$_2$, N$R^{15}R^{16}$, or CF$_3$;

$R^{11}$, at each occurrence, is independently selected from H, $C_1$–$C_4$ alkoxy, Cl, F, Br, I, =O, CN, NO$_2$, N$R^{18}R^{19}$, C(=O)$R^{17}$, C(=O)O$R^{17}$, C(=O)N$R^{18}R^{19}$, S(=O)$_2$N$R^{18}R^{19}$, CF$_3$;

$C_1$–$C_6$ alkyl optionally substituted with 0–3 $R^{11a}$;
$C_6$–$C_{10}$ aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, O$R^{14}$, Cl, F, Br, I, =O, CN, NO$_2$, N$R^{15}R^{16}$, CF$_3$, or phenyl substituted with 0–3 $R^{11b}$;

$R^{11b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, and $C_1$–$C_4$ haloalkoxy;

Z is $C_1$–$C_6$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$, at each occurrence, is independently selected from
$C_6$–$C_{10}$ aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, and $C_1$–$C_4$ haloalkoxy;

$R^{13}$, at each occurrence, is independently selected from H, OH, $C_1$–$C_6$ alkyl, $C_1$–$C_4$ alkoxy, Cl, F, Br, I, CN, NO$_2$, N$R^{15}R^{16}$, and CF$_3$;

$R^{14}$ is H, phenyl, benzyl, $C_1$–$C_6$ alkyl, or $C_2$–$C_6$ alkoxyalkyl;

$R^{14a}$ is H, phenyl, benzyl, methyl, ethyl, propyl, or butyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —CH$_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, CF$_3$, OCF$_3$, SCH$_3$, S(O)CH$_3$, SO$_2$CH$_3$, —NH$_2$, —N(CH$_3$)$_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and $R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

provided, when $R^{13}$ is H,
then Z is $C_4$–$C_6$ alkyl substituted with 1–3 $R^{12}$;
$C_2$–$C_4$ alkenyl substituted with 1–3 $R^{12}$; or
$C_2$–$C_4$ alkynyl substituted with 1–3 $R^{12}$.

[14] In a further more preferred embodiment the present invention provides for a compound of Formula (Ia) wherein:
$R^3$ is —(CH$R^7$)$_n$—$R^4$,
n is 0 or 1;
$R^{3a}$ is H, OH, methyl, ethyl, propyl, butyl, methoxy, ethoxy, propoxy, butoxy, allyl, or 3-buten-1-yl;
$R^4$ is H, OH, O$R^{14a}$,
$C_1$–$C_4$ alkyl substituted with 0–2 $R^{4a}$,
$C_2$–$C_4$ alkenyl substituted with 0–2 $R^{4a}$,
$C_2$–$C_4$ alkynyl substituted with 0–1 $R^{4a}$,
$C_3$–$C_6$ carbocycle substituted with 0–3 $R^{4b}$,
$C_6$–$C_{10}$ aryl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4a}$, at each occurrence, is independently selected from is H, F, Cl, Br, I, CF$_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, NO$_2$, N$R^{15}R^{16}$, CF$_3$, acetyl, SCH$_3$, S(=O)CH$_3$, S(=O)$_2$CH$_3$, $C_1$–$C_4$ alkyl, $C_1$–$C_3$ alkoxy, $C_1$–$C_2$ haloalkyl, and $C_1$–$C_2$ haloalkoxy;

$R^5$ is H, O$R^{14}$;
$C_1$–$C_4$ alkyl substituted with 0–3 $R^{5b}$;
$C_2$–$C_4$ alkenyl substituted with 0–3 $R^{5b}$;
$C_2$–$C_4$ alkynyl substituted with 0–3 $R^{5b}$;

$R^{5a}$ is H, methyl, ethyl, propyl, or butyl;

$R^{5b}$, at each occurrence, is independently selected from:
H, methyl, ethyl, propyl, butyl, CF$_3$, O$R^{14}$, Cl, F, Br, I, =O;

$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^6$ is H;

$R^7$, at each occurrence, is independently selected from H, F, $CF_3$, methyl, and ethyl;

Ring B is a 7 membered lactam,
  wherein the lactam is saturated, partially saturated or unsaturated;
  wherein each additional lactam carbon is substituted with 0–2 $R^{11}$; and,
  optionally, the lactam contains a heteroatom selected from —N=, —NH—, and —N($R^{10}$)—;

additionally, two $R^{11}$ substituents on adjacent atoms may be combined to form a benzo fused radical; wherein said benzo fused radical is substituted with 0–2 $R^{13}$;

additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–2 $R^{13}$;

additionally, two $R^{11}$ substituents on the same or adjacent carbon atoms may be combined to form a $C_3$–$C_6$ carbocycle substituted with 0–2 $R^{13}$;

$R^{10}$ is H, $C(=O)R^{17}$, $C(=O)OR^{17}$;
  $C_1$–$C_4$ alkyl optionally substituted with 0–1 $R^{10a}$;
  phenyl substituted with 0–4 $R^{10b}$;
  $C_3$–$C_6$ carbocycle substituted with 0–3 $R^{10b}$; or
  5 to 6 membered heterocycle containing 1 to 4 heteroatoms selected from nitrogen, oxygen, and sulphur, wherein said 5 to 6 membered heterocycle is substituted with 0–3 $R^{10b}$;

$R^{10a}$, at each occurrence, is independently selected from H, $C_1$–$C_4$ alkyl, $OR^{14}$, Cl, F, Br, I, =O, CN, $NO_2$, $NR^{15}R^{16}$, $CF_3$, or phenyl substituted with 0–4 $R^{10b}$;

$R^{10b}$, at each occurrence, is independently selected from H, OH, $C_1$–$C_4$ alkyl, $C_1$–$C_3$ alkoxy, Cl, F, Br, I, CN, $NO_2$, $NR^{15}R^{16}$, or $CF_3$;

$R^{11}$, at each occurrence, is independently selected from
  H, $C_1$–$C_4$ alkoxy, Cl, F, =O, $NR^{18}R^{19}$, $C(=O)R^{17}$, $C(=O)OR^{17}$, $CF_3$;
  $C_1$–$C_6$ alkyl optionally substituted with 0–3 $R^{11a}$;
  $C_6$–$C_{10}$ aryl substituted with 0–3 $R^{11b}$;
  $C_3$–$C_6$ carbocycle substituted with 0–3 $R^{11b}$; or
  5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11a}$, at each occurrence, is independently selected from H, $C_1$–$C_4$ alkyl, $OR^{14}$, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Z is $C_1$–$C_4$ alkyl substituted with 1–3 $R^{12}$;
  $C_2$–$C_4$ alkenyl substituted with 1–3 $R^{12}$;
  $C_2$–$C_4$ alkynyl substituted with 1–3 $R^{12}$;
  $C_6$–$C_{10}$ aryl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 6 membered heterocycle is substituted with 0–3 $R^{12b}$;

$R^{12}$, at each occurrence, is independently selected from
  $C_6$–$C_{10}$ aryl substituted with 0–4 $R^{12b}$;
  $C_3$–$C_6$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, ($C_1$–$C_4$ alkyl)-$C(=O)$—, and ($C_1$–$C_4$ alkyl)-$S(=O)_2$—;

$R^{16}$, at each occurrence, is independently selected from H, OH, $C_1$–$C_4$ alkyl, benzyl, phenethyl, ($C_1$–$C_4$ alkyl)-$C(=O)$—, and ($C_1$–$C_4$ alkyl)-$S(=O)_2$—;

$R^{17}$ is H, methyl, ethyl, propyl, butyl, methoxymethyl, ethoxymethyl, methoxyethyl, ethoxyethyl, phenyl substituted by 0–3 $R^{17a}$, or —$CH_2$-phenyl substituted by 0–3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;

provided, when $R^{13}$ is H,
then Z is butyl substituted with 1–3 $R^{12}$;
  $C_2$–$C_4$ alkenyl substituted with 1–3 $R^{12}$; or
  $C_2$–$C_4$ alkynyl substituted with 1–3 $R^{12}$.

[15] In an even more preferred embodiment the present invention provides for a compound of Formula (Ib):

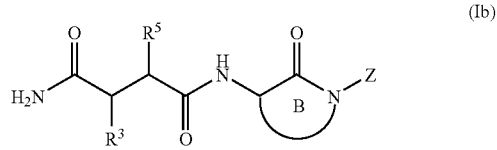

(Ib)

or a pharmaceutically acceptable salt or prodrug thereof wherein:

Ring B is selected from:

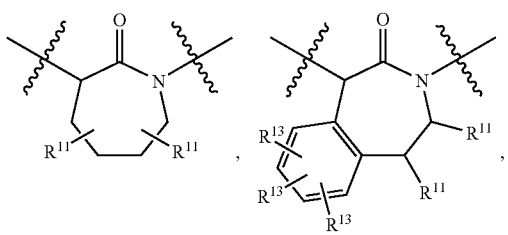

-continued

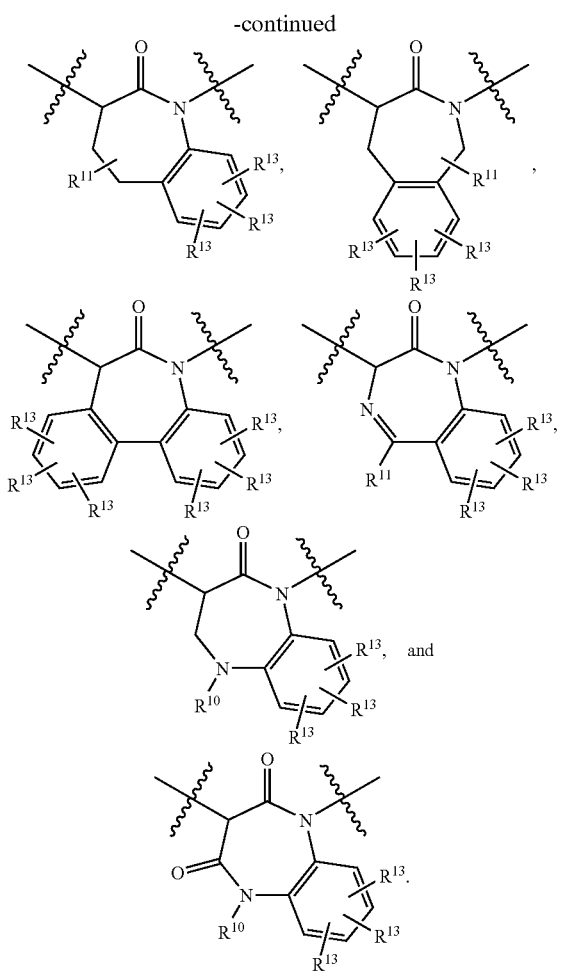

[16] In an even further more preferred embodiment the present invention provides for a compound of Formula (Ic):

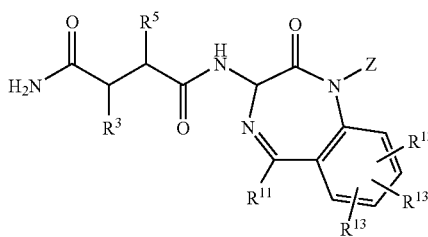

or a pharmaceutically acceptable salt or prodrug thereof wherein
$R^3$ is $R^4$,
$R^4$ is $C_1$–$C_4$ alkyl substituted with 0–1 $R^{4a}$,
  $C_2$–$C_4$ alkenyl substituted with 0–1 $R^{4a}$, or
  $C_2$–$C_4$ alkynyl substituted with 0–1 $R^{4a}$;
$R^{4a}$, at each occurrence, is independently selected from
  H, F, $CF_3$,
  $C_3$–$C_6$ carbocycle substituted with 0–3 $R^{4b}$,
  phenyl substituted with 0–3 $R^{4b}$, or
  5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;
$R^5$ is $C_1$–$C_4$ alkyl substituted with 0–1 $R^{5b}$;
  $C_2$–$C_4$ alkenyl substituted with 0–1 $R^{5b}$;
  $C_2$–$C_4$ alkynyl substituted with 0–1 $R^{5b}$;
$R^{5b}$, at each occurrence, is independently selected from:
  H, methyl, ethyl, propyl, butyl, $CF_3$, $OR^{14}$, =O;
  $C_3$–$C_6$ carbocycle substituted with 0–2 $R^{5c}$;
  phenyl substituted with 0–3 $R^{5c}$; or
  5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;
$R^{11}$, at each occurrence, is independently selected from
  H, =O, $NR^{18}R^{19}$, $CF_3$;
  $C_1$–$C_4$ alkyl optionally substituted with 0–1 $R^{11a}$;
  phenyl substituted with 0–3 $R^{11b}$;
  $C_3$–$C_6$ carbocycle substituted with 0–3 $R^{11b}$; or
  5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{11a}$, at each occurrence, is independently selected from H, $C_1$–$C_4$ alkyl, $OR^{14}$, F, Cl, =O, $NR^{15}R^{16}$, $CF_3$, or phenyl substituted with 0–3 $R^{11b}$;
$R^{11b}$, at each occurrence, is independently selected from H, OH, Cl, F, $NR^{15}R^{16}$, $CF_3$, methyl, ethyl, propyl, butyl, —methoxy, ethoxy, propoxy, $C_1$–$C_2$ haloalkyl, and $C_1$–$C_2$ haloalkoxy;
Z is $C_1$–$C_3$ alkyl substituted with 1–3 $R^{12}$;
  $C_2$–$C_3$ alkenyl substituted with 1–3 $R^{12}$;
  $C_2$–$C_3$ alkynyl substituted with 1–3 $R^{12}$;
  $C_6$–$C_{10}$ aryl substituted with 0–4 $R^{12b}$;
  $C_3$–$C_6$ carbocycle substituted with 0–3 $R^{12b}$; or
  5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{12}$, at each occurrence, is independently selected from
  $C_6$–$C_{10}$ aryl substituted with 0–4 $R^{12b}$;
  $C_3$–$C_6$ carbocycle substituted with 0–3 $R^{12b}$; or
  5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

provided, when $R^{13}$ is H,
then Z is $C_2$–$C_3$ alkenyl substituted with 1–3 $R^{12}$; or
$C_2$–$C_3$ alkynyl substituted with 1–3 $R^{12}$.

[17] In another even further more preferred embodiment the present invention provides for a compound of Formula (Id):

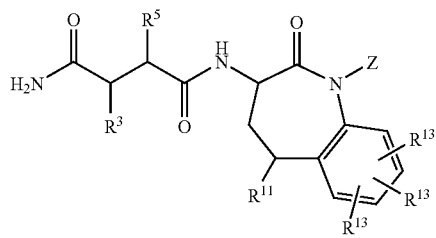

or a pharmaceutically acceptable salt or prodrug thereof wherein:

$R^3$ is $R^4$, $R^4$ is $C_1$–$C_4$ alkyl substituted with 0–1 $R^{4a}$,
$C_2$–$C_4$ alkenyl substituted with 0–1 $R^{4a}$, or
$C_2$–$C_4$ alkynyl substituted with 0–1 $R^{4a}$;

$R^{4a}$, at each occurrence, is independently selected from
H, F, $CF_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^5$ is $C_1$–$C_4$ alkyl substituted with 0–1 $R^{5b}$;
$C_2$–$C_4$ alkenyl substituted with 0–1 $R^{5b}$;
$C_2$–$C_4$ alkynyl substituted with 0–1 $R^{5b}$;

$R^{5b}$, at each occurrence, is independently selected from:
H, methyl, ethyl, propyl, butyl, $CF_3$, $OR^{14}$, =O;
$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{11}$, at each occurrence, is independently selected from
H, =O, $NR^{18}R^{19}$, $CF_3$;
$C_1$–$C_4$ alkyl optionally substituted with 0–1 $R^{11a}$;
phenyl substituted with 0–3 $R^{11a}$;
$C_3$–$C_6$ carbocycle substituted with 0–3 $R^{11b}$; or
5 to 6 membered heterocycle containing 1 to 4 heteroatoms selected from nitrogen, oxygen, and sulphur, wherein said 5 to 6 membered heterocycle is substituted with 0–3 $R^{11a}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$, at each occurrence, is independently selected from H, $C_1$–$C_4$ alkyl, $OR^{14}$, F, Cl, =O, $NR^{15}R^{16}$, $CF_3$, or phenyl substituted with 0–3 $R^{11b}$;

$R^{11a}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

Z is $C_1$–$C_3$ alkyl substituted with 1–3 $R^{12}$;
$C_2$–$C_3$ alkenyl substituted with 1–3 $R^{12}$;
$C_2$–$C_3$ alkynyl substituted with 1–3 $R^{12}$;
$C_6$–$C_{10}$ aryl substituted with 0–4 $R^{12b}$;
$C_3$–$C_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12}$, at each occurrence, is independently selected from
$C_6$–$C_{10}$ aryl substituted with 0–4 $R^{12b}$;
$C_3$–$C_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

provided, when $R^{13}$ is H.

then Z is $C_2$–$C_3$ alkenyl substituted with 1–3 $R^{12}$; or
$C_2$–$C_3$ alkynyl substituted with 1–3 $R^{12}$.

[18] In another even further more preferred embodiment the present invention provides for a compound of Formula (Ie):

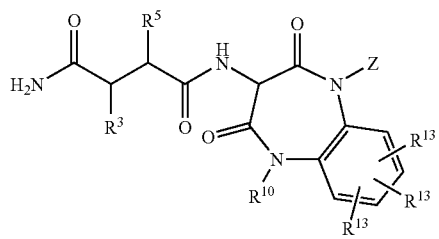

or a pharmaceutically acceptable salt or prodrug thereof wherein:

$R^3$ is $R^4$, $R^4$ is $C_1$–$C_4$ alkyl substituted with 0–1 $R^{4a}$,
$C_2$–$C_4$ alkenyl substituted with 0–1 $R^{4a}$, or
$C_2$–$C_4$ alkynyl substituted with 0–1 $R^{4a}$;

$R^{4a}$, at each occurrence, is independently selected from
H, F, $CF_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$–$C_2$ haloalkyl, and $C_1$–$C_2$ haloalkoxy;

$R^5$ is $C_1$–$C_4$ alkyl substituted with 0–1 $R^{5b}$;
$C_2$–$C_4$ alkenyl substituted with 0–1 $R^{5b}$;
$C_2$–$C_4$ alkynyl substituted with 0–1 $R^{5b}$;

$R^{5b}$, at each occurrence, is independently selected from:
H, methyl, ethyl, propyl, butyl, $CF_3$, $OR^{14}$, =O;
$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$–$C_2$ haloalkyl, and $C_1$–$C_2$ haloalkoxy;

$R^{10}$ is H, C(=O)$R^{17}$, C(=O)$OR^{17}$;
$C_1$–$C_4$ alkyl optionally substituted with 0–1 $R^{10a}$;
phenyl substituted with 0–4 $R^{10b}$;
$C_3$–$C_6$ carbocycle substituted with 0–3 $R^{10b}$; or
5 to 6 membered heterocycle containing 1 to 4 heteroatoms selected from nitrogen, oxygen, and sulphur, wherein said 5 to 6 membered heterocycle is substituted with 0–3 $R^{10b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{10a}$, at each occurrence, is independently selected from H, methyl, ethyl, propyl, butyl, $OR^{14}$, Cl, F, =O, $NR^{15}R^{16}$, $CF_3$, or phenyl substituted with 0–4 $R^{10b}$;

$R^{10b}$, at each occurrence, is independently selected from H, OH, methyl, ethyl, propyl, butyl, methoxy, ethoxy, propoxy, Cl, F, $NR^{15}R^{16}$, and $CF_3$;

Z is $C_1$–$C_3$ alkyl substituted with 1–3 $R^{12}$;
$C_2$–$C_3$ alkenyl substituted with 1–3 $R^{12}$;
$C_2$–$C_3$ alkynyl substituted with 1–3 $R^{12}$;
$C_6$–$C_{10}$ aryl substituted with 0–4 $R^{12b}$;
$C_3$–$C_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12}$, at each occurrence, is independently selected from
$C_6$–$C_{10}$ aryl substituted with 0–4 $R^{12b}$;
$C_3$–$C_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, $NR^{15}R^{16}$, $CF_3$, acetyl, $SCH_3$, S(=O)$CH_3$, S(=O)$_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{17}$ is H, methyl, ethyl, propyl, butyl, methoxymethyl, ethoxymethyl, methoxyethyl, ethoxyethyl, phenyl substituted by 0–3 $R^{17a}$, or —CH$_2$-phenyl substituted by 0–3 $R^{17a}$;

$R^{17a}$ is H, methyl, methoxy, —OH, F, Cl, CF$_3$, or OCF$_3$;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

provided, when $R^{13}$ is H, then Z is C$_2$–C$_3$ alkenyl substituted with 1–3 $R^{12}$; or
C$_2$–C$_3$ alkynyl substituted with 1–3 $R^{12}$.

[19] In another even further more preferred embodiment the present invention provides for a compound of Formula (If):

(If)

<chemical structure> or a pharmaceutically acceptable salt or prodrug thereof wherein:

$R^3$ is $R^4$, $R^4$ is C$_1$–C$_4$ alkyl substituted with 0–1 $R^{4a}$,
C$_2$–C$_4$ alkenyl substituted with 0–1 $R^{4a}$, or
C$_2$–C$_4$ alkynyl substituted with 0–1 $R^{4a}$;

$R^{4a}$, at each occurrence, is independently selected from
H, F, CF$_3$,
C$_3$–C$_6$ carbocycle substituted with 0–3 $R^{4b}$, phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^5$ is C$_1$–C$_4$ alkyl substituted with 0–1 $R^{5b}$;
C$_2$–C$_4$ alkenyl substituted with 0–1 $R^{5b}$;
C$_2$–C$_4$ alkynyl substituted with 0–1 $R^{5b}$;

$R^{5b}$, at each occurrence, is independently selected from:
H, methyl, ethyl, propyl, butyl, CF$_3$, OR$^{14}$, =O;
C$_3$–C$_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

Z is 0° C.—C$_3$ alkyl substituted with 1–3 $R^{12}$;
C$_2$–C$_3$ alkenyl substituted with 1–3 $R^{12}$;
C$_2$–C$_3$ alkynyl substituted with 1–3 $R^{12}$;
C$_6$–C$_{10}$ aryl substituted with 0–4 $R^{12b}$;
C$_3$–C$_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12}$, at each occurrence, is independently selected from
C$_6$–C$_{10}$ aryl substituted with 0–4 $R^{12b}$;
C$_3$–C$_6$ carbocycle substituted with 0–3 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, NR$^{15}$R$^{16}$, CF$_3$, acetyl, SCH$_3$, S(=O)CH$_3$, S(=O)$_2$CH$_3$, methyl, ethyl, propyl, butyl, methoxy, ethoxy, propoxy, C$_1$–C$_2$ haloalkyl, and C$_1$–C$_2$ haloalkoxy;

$R^{13}$, at each occurrence, is independently selected from H, OH, methyl, ethyl, propyl, butyl, methoxy, ethoxy, Cl, F, Br, CN, NR$^{15}$R$^{16}$, and CF$_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from –3H, methyl, and ethyl.

provided, when $R^{13}$ is H, then Z is C$_2$–C$_3$ alkenyl substituted with 1–3 $R^{12}$; or
C$_2$–C$_3$ alkynyl substituted with 1–3 $R^{12}$.

[20] In another even further more preferred embodiment the present invention provides for a compound of one of Formulas (Ic), (Id), (Ie), or (If), wherein:

$R^3$ is —CH$_3$, —CH$_2$CH$_3$, —CH$_2$CH$_2$CH$_3$, —CH$_2$CH$_2$CH$_2$CH$_3$, —CH$_2$(CH$_3$)$_2$, —CH(CH$_3$)CH$_2$CH$_3$, —CH$_2$CH(CH$_3$)$_2$, —CH$_2$C(CH$_3$)$_3$, —CF$_3$, —CH$_2$CF$_3$, —CH$_2$CH$_2$CF$_3$, —CH$_2$CH$_2$CH$_2$CF$_3$, —CH=CH$_2$, —CH$_2$CH=CH$_2$, —CH$_2$C(CH$_3$)=CH$_2$, —CH$_2$CH=C(CH$_3$)$_2$, —CH$_2$CH$_2$CH=CH$_2$, —CH$_2$CH$_2$C(CH$_3$)=CH$_2$, —CH$_2$CH$_2$CH=C(CH$_3$)$_2$, cis-CH$_2$CH=CH(CH$_3$), cis-CH$_2$CH$_2$CH=CH(CH$_3$), trans-CH$_2$CH=CH(CH$_3$), trans-CH$_2$CH$_2$CH=CH(CH$_3$); —C≡CH, —CH$_2$C≡CH, —CH$_2$C≡C(CH$_3$), cyclopropyl-CH$_2$—, cyclobutyl-CH$_2$—, cyclopentyl-CH$_2$—, cyclohexyl-CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, phenyl-CH$_2$—, (2-F-phenyl)CH$_2$—, (3-F- phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, or (3-F-5-Cl-phenyl)CH$_2$CH$_2$—, R$^5$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CF$_3$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, —CH=CH$_2$, —CH$_2$CH=CH$_2$, —CH=CHCH$_3$, cis-CH$_2$CH=CH(CH$_3$), trans-CH$_2$CH=CH(CH$_3$), trans-CH$_2$CH=CH(C$_6$H$_5$), —CH$_2$CH=C(CH$_3$)$_2$, cis-CH$_2$CH=CHCH$_2$CH$_3$, trans-CH$_2$CH=CHCH$_2$CH$_3$, cis-CH$_2$CH$_2$CH=CH(CH$_3$), trans-CH$_2$CH$_2$CH=CH(CH$_3$), trans-CH$_2$CH=CHCH$_2$(C$_6$H$_5$), —C—CH, —CH$_2$C—CH, —CH$_2$C—C(CH$_3$), —CH$_2$C≡C(C$_6$H$_5$) —CH$_2$CH$_2$C—CH, —CH$_2$CH$_2$C≡C(CH$_3$), —CH$_2$CH$_2$C≡C(C$_6$H$_5$) —CH$_2$CH$_2$CH$_2$C≡CH, —CH$_2$CH$_2$CH$_2$C≡C(CH$_3$), —CH$_2$CH$_2$CH$_2$C≡C(C$_6$H$_5$) cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, furanyl-CH$_2$—, thienyl-CH$_2$—, pyridyl-CH$_2$—, 1-imidazolyl-CH$_2$—, oxazolyl-CH$_2$—, isoxazolyl-CH$_2$—, phenyl-CH$_2$—, (2-F-phenyl)CH$_2$CH$_2$—, (3-F-phenyl)CH$_2$CH$_2$—, (4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—, Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, 1-benzimidazolyl, cyclopropyl, cyclobutyl, cyclopentyl, cyclohexyl, morpholino, N-piperinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, 4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (1-benzimidazolyl)CH$_2$—, (cyclopropyl)CH$_2$—, (cyclobutyl)CH$_2$—, (cyclopentyl)CH$_2$—, (cyclohexyl)CH$_2$—, (morpholino)CH$_2$—, (N-pipridinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-1-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$—, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (benzimidazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, (morpholino)CH$_2$CH$_2$—, or (N-pipridinyl)CH$_2$CH$_2$—;

R$^{10}$ is H, methyl, ethyl, phenyl, benzyl, phenethyl, 4-F-phenyl, (4-F-phenyl)CH$_2$—, (4-F-phenyl)CH$_2$CH$_2$—, 4-Cl-phenyl, (4-Cl-phenyl)CH$_2$—, (4-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 4-CF$_3$-phenyl, (4-CF$_3$-phenyl)CH$_2$—, or (4-CF$_3$-phenyl)CH$_2$CH$_2$—;

R$^{11}$, at each occurrence, is independently selected from H, =O, methyl, ethyl, phenyl, benzyl, phenethyl, L 4-F-phenyl, (4-F-phenyl)CH$_2$—, (4-F-phenyl)CH$_2$CH$_2$—, 3-F-phenyl, (3-F-phenyl)CH$_2$—, (3-F-phenyl)CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl)CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, pyrid-2-yl, pyrid-3-yl, or pyrid-4-yl, and $R^{13}$, at each occurrence, is independently selected from H, F, Cl, OH, —$CH_3$, —$CH_2CH_3$, —$OCH_3$, or —$CF_3$.

[21] In another embodiment the present invention provides for a method for the treatment of neurological disorders associated with β-amyloid production comprising administering to a host in need of such treatment a therapeutically effective amount of a compound of Formula (I):

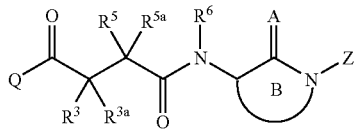

(I)

or a pharmaceutically acceptable salt or prodrug thereof, wherein:
A is O or S;
Q is —$NR^1R^2$;
$R^1$ is $OR^{14}$;
$R^2$ is independently selected from H, $C_1$–$C_6$ alkyl, $C_3$–$C_{10}$ carbocycle, $C_6$–$C_{10}$ aryl, and 5 to 10 membered heterocycle containing 1 to 4 heteroatoms selected from nitrogen, oxygen, and sulphur;
$R^3$ is —$(CR^7R^{7a})_n$—$R^4$,
—$(CR^7R^{7a})_n$—$S(CR^7R^{7a})_m$—$R^4$,
—$(CR^7R^{7a})_n$—O—$(CR^7R^{7a})_m$—$R^4$,
—$(CR^7R^{7a})_n$—$N(R^{7b})$—$(CR^7R^{7a})_m$—$R^4$,
—$(CR^7R^{7a})_n$—$S(=O)$—$(CR^7R^{7a})_m$—$R^4$,
—$(CR^7R^{7a})_n$—$S(=O)_2$—$(CR^7R^{7a})_m$—$R^4$,
—$(CR^7R^{7a})_n$—$C(=O)$—$(CR^7R^{7a})_m$—$R^4$,
—$(CR^7R^{7a})_n$—$N(R^{7b})C(=O)$—$(CR^7R^{7a})_m$—$R^4$,
—$(CR^7R^{7a})_n$—$C(=O)N(R^{7b})$—$(CR^7R^{7a})_m$—$R^4$,
—$(CR^7R^{7a})_n$—$N(R^{7b})S(=O)_2$—$(CR^7R^{7a})_m$—$R^4$, or
—$(CR^7R^{7a})_n$—$S(=O)_2N(R^{7b})$—$(CR^7R^{7a})_m$—$R^4$;
n is 0, 1, 2, or 3;
m is 0, 1, 2, or 3;
$R^{3a}$ is H, OH, $C_1$–$C_4$ alkyl, $C_1$–$C_4$ alkoxy, $C_2$–$C_4$ alkenyl or $C_2$–$C_4$ alkenyloxy;
$R^4$ is H, OH, $OR^{14a}$,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from is H, F, Cl, Br, I, $CF_3$,
$C_3$–$C_{10}$ carbocycle substituted with 0–3 $R^{4b}$,
$C_6$–$C_{10}$ aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl,
$C_1$–$C_4$ haloalkoxy, and $C_1$–$C_4$ halothioalkyl-S—;
$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H, OH, $C_1$–$C_4$ alkyl, $C_1$–$C_4$ alkoxy, $C_2$–$C_4$ alkenyl, or $C_2$–$C_4$ alkenyloxy;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
$C_6$–$C_{10}$ aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$,
$C_1$–$C_6$ alkyl, $C_1$–$C_4$ alkoxy, $C_1$–$C_4$ haloalkyl,
$C_1$–$C_4$ haloalkoxy, and $C_1$–$C_4$ halothioalkyl-S—;
$R^6$ is H;
$C_1$–$C_6$ alkyl substituted with 0–3 $R^{6a}$;
$C_3$–$C_{10}$ carbocycle substituted with 0–3 $R^{6b}$; or
$C_6$–$C_{10}$ aryl substituted with 0–3 $R^{6b}$;
$R^{6a}$, at each occurrence, is independently selected from H, $C_1$–$C_6$ alkyl, $OR^{14}$, Cl, F, Br, I, =O, CN, $NO_2$, $NR^{15}R^{16}$, aryl or $CF_3$;
$R^{6b}$, at each occurrence, is independently selected from H, OH, Cl, F, Br, I, CN, $NO_2$, $NR^{15}R^{16}$, $CF_3$, $C_1$–$C_6$ alkyl, $C_1$–$C_4$ alkoxy, $C_1$–$C_4$ haloalkyl, and $C_1$–$C_4$ haloalkoxy;
$R^7$, at each occurrence, is independently selected from H, OH, Cl, F, Br, I, CN, $NO_2$, $CF_3$, phenyl and $C_1$–$C_4$ alkyl;
$R^{7a}$, at each occurrence, is independently selected from H, OH, Cl, F, Br, I, CN, $NO_2$, $CF_3$, and $C_1$–$C_4$ alkyl;
$R^{7b}$ is independently selected from H and $C_1$–$C_4$ alkyl;
Ring B is a 7 membered lactam or thiolactam,
wherein the lactam or thiolactam is saturated, partially saturated or unsaturated;
wherein each additional lactam carbon or thiolactam carbon is substituted with 0–2 $R^{11}$; and,
optionally, the lactam or thiolactam contains a heteroatom selected from —O—, —S—, —S(=O)—, —S(=O)$_2$—, —N=, —NH—, and —N($R^{10}$)—;
additionally, two $R^{11}$ substituents on adjacent atoms may be combined to form a benzo fused radical; wherein said benzo fused radical is substituted with 0–4 $R^{13}$;
additionally, two $R^{11}$ substituents on adjacent atoms may be combined to form a 5 to 6 membered heteroaryl fused radical, wherein said 5 to 6 membered heteroaryl fused radical comprises 1 or 2 heteroatoms selected from N, O, and S; wherein said 5 to 6 membered heteroaryl fused radical is substituted with 0–3 $R^{13}$;
additionally, two $R^{11}$ substituents on the same or adjacent carbon atoms may be combined to form a $C_3$–$C_6$ carbocycle substituted with 0–3 $R^{13}$;
$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$–$C_6$ alkyl optionally substituted with 0–3 $R^{10a}$;
$C_6$–$C_{10}$ aryl substituted with 0–4 $R^{10b}$;
$C_3$–$C_{10}$ carbocycle substituted with 0–3 $R^{10b}$; or 5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or aryl substituted with 0–4 $R^{10b}$;

$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ haloalkyl-S—;

$R^{11}$, at each occurrence, is independently selected from H, $C_1$–$C_4$ alkoxy, Cl, F, Br, I, =O, CN, $NO_2$, $NR^{18}R^{19}$, C(=O)$R^{17}$, C(=O)O$R^{17}$, C(=O)$NR^{18}R^{19}$, S(=O)$_2$$NR^{18}R^{19}$, $CF_3$;

$C_1$–$C_6$ alkyl optionally substituted with 0–3 $R^{11a}$;

$C_6$–$C_{10}$ aryl substituted with 0–3 $R^{11b}$;

$C_3$–$C_{10}$ carbocycle substituted with 0–3 $R^{11b}$; or 5 to 10 membered heterocycle containing 1 to 4—heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$;

phenyl substituted with 0–3 $R^{11a}$;

$C_3$–$C_6$ cycloalkyl substituted with 0–3 $R^{11b}$; and 5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$,
$C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkyl-S—;

Z is H;

$C_1$–$C_8$ alkyl substituted with 1–3 $R^{12}$;

$C_2$–$C_4$ alkenyl substituted with 1–3 $R^{12}$;

$C_2$–$C_4$ alkynyl substituted with 1–3 $R^{12}$;

$C_1$–$C_8$ alkyl substituted with 0–3 $R^{12a}$;

$C_2$–$C_4$ alkenyl substituted with 0–3 $R^{12a}$;

$C_2$–$C_4$ alkynyl substituted with 0–3 $R^{12a}$;

$C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12}$ at each occurrence, is independently selected from $C_6$–$C_{10}$ aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12a}$, at each occurrence, is independently selected from H, OH, Cl, F, Br, I, CN, $NO_2$, $NR^{15}R^{16}$, —C(=O)$NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, or $C_1$–$C_4$ halothioalkyl-S—;

$R^{12b}$, at each occurrence, is independently selected from H, OH, Cl, F, Br, I, CN, $NO_2$, $NR^{15}R^{16}$, $CF_3$, acetyl, $SCH_3$, S(=O)$CH_3$, S(=O)$_2CH_3$, $C_1$–$C_6$ alkyl, $C_1$–$C_4$ alkoxy, $C_1$–$C_4$ haloalkyl, $C_1$–$C_4$ haloalkoxy, and $C_1$–$C_4$ halothioalkyl-S—;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, $C_2$–$C_6$ alkoxyalkyl, or $C_3$–$C_6$ cycloalkyl;

$R^{14a}$ is H, phenyl, benzyl, or $C_1$–$C_4$ alkyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, S(O)$CH_3$, $SO_2CH_3$, —$NH_2$, —N($CH_3$)$_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and $R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

provided, when $R^{13}$ is H, then Z is H;

$C_4$–$C_8$ alkyl substituted with 1–3 $R^{12}$;

$C_2$–$C_4$ alkenyl substituted with 1–3 $R^{12}$;

$C_2$–$C_4$ alkynyl substituted with 1–3 $R^{12}$;

$C_2$–$C_0$ alkyl substituted with 0–3 $R^{12a}$;

$C_2$–$C_4$ alkenyl substituted with 0–3 $R^{12a}$; or $C_2$–$C_4$ alkynyl substituted with 0–3 $R^{12a}$; and provided, when ring B is a 1,3,4,5-tetrahydro-1-(Z)-5-($R^{10}$)-6,6,7,7-tetra($R^{11}$)-2,4-dioxo-2H-1,5-diazepin-3-yl core, and $R^{13}$ is H; then $R^{10}$ is H, C(=O)$R^{17}$, C(=O)O$R^{17}$, C(=O)$NR^{18}R^{19}$, S(=O)$_2NR^{18}R^{19}$, S(=O)$_2R^{17}$; or $C_1$–$C_6$ alkyl optionally substituted with 0–3 $R^{10a}$;

$R^{10a}$ at each occurrence, is independently selected from H, $C_1$–$C_6$ alkyl, $OR^{14}$, Cl, F, Br, I, =O, CN, $NO_2$, —$NR^{15}R^{16}$, and $CF_3$.

In a more preferred embodiment of the present invention, Q is $NH_2$.

In a most preferred embodiment the total number of carbon atoms in $R^3$, $R^{3a}$, $R^5$, and $R^{5a}$ equals seven or more.

It is understood that any and all embodiments of the present invention may be taken in conjunction with any other embodiment to describe additional even more preferred embodiments of the present invention.

In a second embodiment, the present invention provides a pharmaceutical composition comprising a compound of Formula (I) and a pharmaceutically acceptable carrier.

In a third embodiment, the present invention provides a method for the treatment of neurological disorders associated with β-amyloid production comprising administering to a host in need of such treatment a therapeutically effective amount of a compound of Formula (I).

In a preferred embodiment the neurological disorder associated with β-amyloid production is Alzheimer's Disease.

In a fourth embodiment, the present invention provides a method for inhibiting γ-secretase activity for the treatment of a physiological disorder associated with inhibiting γ-secretase activity comprising administering to a host in need of such inhibition a therapeutically effective amount of a compound of Formula (I) that inhibits γ-secretase activity.

Thus, the present invention provides a method for inhibiting γ-secretase activity comprising administering to a host in need of such inhibition a therapeutically effective amount of a compound of Formula (I) that inhibits γ-secretase activity.

In a preferred embodiment the physiological disorder associated with inhibiting γ-secretase activity is Alzheimer's Disease.

In a fifth embodiment, the present invention provides a compound of Formula (I) for use in therapy.

In a preferred embodiment the present invention provides a compound of Formula (I) for use in therapy of Alzheimer's Disease.

In a sixth embodiment, the present invention provides for the use of a compound of Formula (I) for the manufacture of a medicament for the treatment of Alzheimer's Disease.

Definitions

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is:

```
1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr
```

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^{5b}$) occurs more than one time in any constituent or formula for a compound, its definition at each occurrence is independent of its definition at every other occurrence. Thus, for example, if a group is shown to be substituted with 0–2 $R^{5b}$, then said group may optionally be substituted with up to two $R^{5b}$ groups and $R^{5b}$ at each occurrence is selected independently from the definition of $R^{5b}$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$–$C_6$ alkyl" denotes alkyl having 1, 2, 3, 4, 5, or 6 carbon atoms. Examples of alkyl include, but are not limited to, methyl, ethyl, n-propyl, i-propyl, n-butyl, i-butyl, sec-butyl, t-butyl, pentyl, and hexyl. Preferred "alkyl" group, unless otherwise specified, is "$C_1$–$C_4$ alkyl". Additionally, unless otherwise specified, "propyl" denotes n-propyl or i-propyl; "butyl" denotes n-butyl, i-butyl, sec-butyl, or t-butyl.

As used herein, "alkenyl" or "alkenylene" is intended to include hydrocarbon chains of either a straight or branched configuration and one or more unsaturated carbon—carbon bonds which may occur in any stable point along the chain. Examples of "$C_2$–$C_6$ alkenyl" include, but are not limited to, ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein, "alkynyl" or "alkynylene" is intended to include hydrocarbon chains of either a straight or branched configuration and one or more carbon—carbon triple bonds which may occur in any stable point along the chain, such as ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy. Similarly, "alkylthio" or "thioalkoxy" is represents an alkyl group as defined above with the indicated number of carbon atoms attached through a sulphur bridge.

"Halo" or "halogen" as used herein refers to fluoro, chloro, bromo, and iodo. Unless otherwise specified, preferred halo is fluoro and chloro. "Counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, 2,2-difluoroethyl, heptafluoropropyl, and heptachloropropyl. "Haloalkoxy" is intended to mean a haloalkyl group as defined above with the indicated number of carbon atoms attached through an oxygen bridge; for example trifluoromethoxy, pentafluoroethoxy, 2,2,2-trifluoroethoxy, and the like. "Halothioalkoxy" is intended to mean a haloalkyl group as defined above with the indicated number of carbon atoms attached through a sulphur bridge.

"Cycloalkyl" is intended to include saturated ring groups, having the specified number of carbon atoms. For example, "$C_3$–$C_6$ cycloalkyl" denotes such as cyclopropyl, cyclobutyl, cyclopentyl, or cyclohexyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin). Preferred "carbocycle" are cyclopropyl, cyclobutyl, cyclopentyl, and cyclohexyl.

As used herein, the term "heterocycle" or "heterocyclic ring" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl. Preferred 5 to 10 membered heterocycles include, but are not limited to, pyridinyl, pyrimidinyl, triazinyl, furanyl, thienyl, thiazolyl, pyrrolyl, pyrazolyl, imidazolyl, oxazolyl, isoxazolyl, tetrazolyl, benzofuranyl, benzothiofuranyl, indolyl, benzimidazolyl, 1H-indazolyl, oxazolidinyl, isoxazolidinyl, benzotriazolyl, benzisoxazolyl, oxindolyl, benzoxazolinyl, quinolinyl, and isoquinolinyl. Preferred 5 to 6 membered heterocycles include, but are not limited to, pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, tetrazolyl; more preferred 5 to 6 membered heterocycles include, but are not limited to, pyridinyl, pyrimidinyl, triazinyl, furanyl, thienyl, thiazolyl, piperazinyl, piperidinyl, pyrazolyl, imidazolyl, and tetrazolyl. Also included are fused ring and spiro compounds containing, for example, the above heterocycles.

As used herein, the term "aryl", "$C_6$–$C_{10}$ aryl" or aromatic residue, is intended to mean an aromatic moiety containing the specified number of carbon atoms; for example phenyl, pyridinyl or naphthyl. Preferred "aryl" is phenyl. Unless otherwise specified, "aryl" may be unsubstituted or substituted with 0 to 3 groups selected from H, methyl, ethyl, propyl, butyl, methoxy, ethoxy, propoxy, butoxy, amino, hydroxy, Cl, F, Br, I, $CF_3$, $SCH_3$, $S(O)CH_3$, $SO_2CH_3$, —$N(CH_3)_2$, $N(CH_3)H$, CN, $NO_2$, $OCF_3$, $C(=O)CH_3$, $CO_2H$, $CO_2CH_3$, or $C_1$–$C_4$ haloalkyl.

The phrase "additional lactam or thiolactam carbons", as used herein, is intended to denote the number of optional carbon atoms in the lactam or thiolactam ring B of Formula (I). Formula (I''):

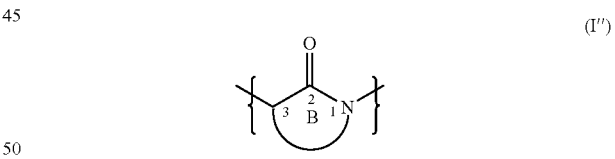

represents the lactam ring B of Formula (I). Additional lactam carbons are carbons in lactam ring B other than the carbons numbered 2 and 3 in the backbone of the formula. The same numbering applies to the carbons in the analogous thiolactam ring B. The additional lactam carbons may be optionally replaced by a heteroatom selected from oxygen, nitrogen and sulfur. Lactam ring B contains 1, 2, 3, 4, 5, 6 or 7 optional carbons, wherein one optional carbon may optionally be replaced by a heteroatom, such that the total number of members of lactam ring B, including atoms numbered 1, 2 and 3 in the backbone, does not exceed 10. It is preferred that the total number of atoms of lactam ring B is 6, 7 or 8; it is more preferred that the total number of atoms of lactam ring B is seven. It is further understood that lactam ring B may optionally be unsaturated or partially unsaturated (i.e. two adjacent atoms in the ring form a double bond) wherein the backbone of lactam ring B may contain one, two or three double bonds. Examples of lactam ring B include:

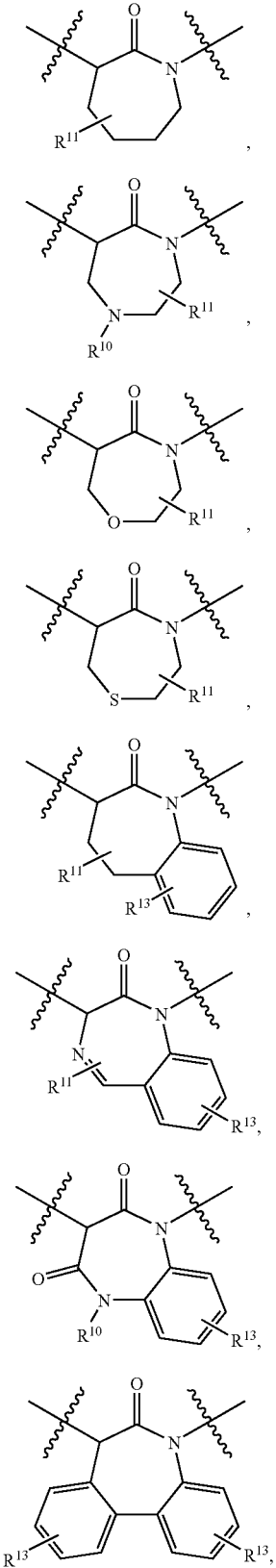

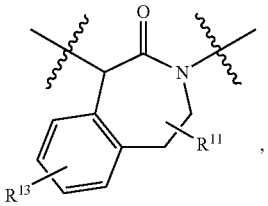

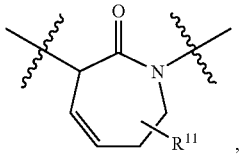

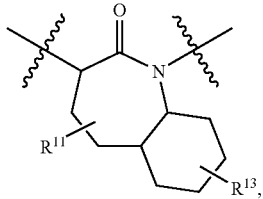

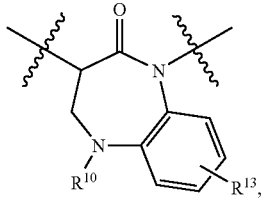

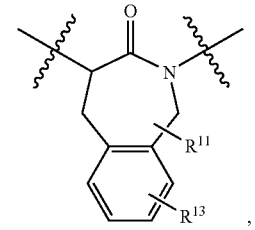

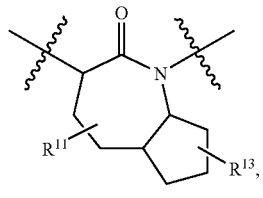

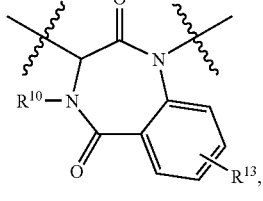

but are not intended to limit the invention. Preferred examples of lactam ring B are B1, B2, B5, B6, B8, B9, B13, and B16; more preferred examples of lactam ring B are B1, B6, B8, B9, and B13. Preferred examples of substituent $R^{10}$ or $R^{11}$ on lactam B are methyl, ethyl, phenyl, 4-fluorophenyl, 4-chlorophenyl, 4-trifluoromethylphenyl, (4-fluorophenyl)

methyl, (4-chlorophenyl)methyl, (4-trifluoromethylphenyl) methyl, and 2-, 3-, and 4-pyridinyl. Preferred examples of $R^{13}$ on lactam B are F, Cl, OH, methyl, ethyl, methoxy, and trifluoromethyl.

The compounds herein described may have asymmetric centers. One enantiomer of a compound of Formula (I) may display superior biological activity over the opposite enantiomer. For example carbon 3 of lactam ring B Formula (I") may exist in either an S or R configuration. Thus, an R or S configuration at carbon 3 in Formula (I") is considered part of the invention. An example of such configuration includes,

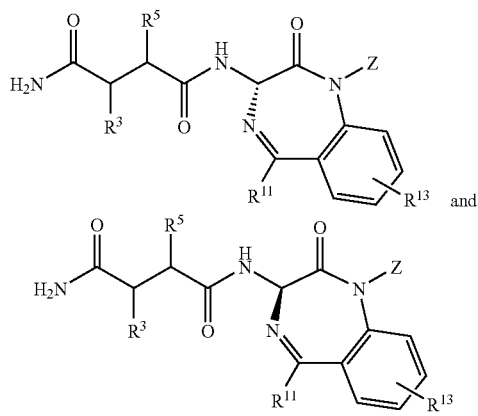

but is not intended to be limited to this example of ring B. When required, separation of the racemic material can be achieved by methods known in the art. Additionally, the carbon atoms to which $R^3$ and $R^5$ are attached may describe chiral carbons which may display superior biological activity over the opposite enantiomer. For example, where $R^3$ and $R^5$ are not H, then the configuration of the two centers may be described as (2R,3R), (2R,3S), (2S,3R), or (2S,3S). All configurations are considered part of the invention; however, the (2R,3S) and the (2S,3R) are preferred and the (2R,3S) is more preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to formula (I) in vivo when such prodrug is administered to a mammalian subject. Prodrugs of a compound of formula (I) are prepared by modifying functional groups present in the compound in such a way that the modifications are cleaved, either in routine manipulation or in vivo, to the parent compound. Prodrugs include compounds of formula (I) wherein a hydroxy, amino, or sulfhydryl group is bonded to any group that, when the prodrug or compound of formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

Methods for the synthesis of succinylamino lactams are known in the art and are disclosed in a number of references including PCT publication number WO 96/29313, which is hereby incorporated by reference.

Disubstituted succinate derivatives can be prepared by a number of known procedures. The procedure of Evans (D.

A. Evans et al, *Org. Synth.* 86, p 83 (1990)) is outlined in Scheme 1 where acylation of an oxazolidinone with an acylating agent such as an acid chloride provides structures 1. Alkylation to form 2 followed by cleavage of the chiral auxiliary and subsequent alkylation of the dianion of the carboxylic acid 3 provides a variety of disubstituted succinates which can be separated and incorporated into structures of formula (I) by those skilled in the art. Additional examples are found in P. Becket, M. J. Crimmin, M. H. Davis, Z. Spavold, Synlett, (1993), 137–138, incorporated herein by reference.

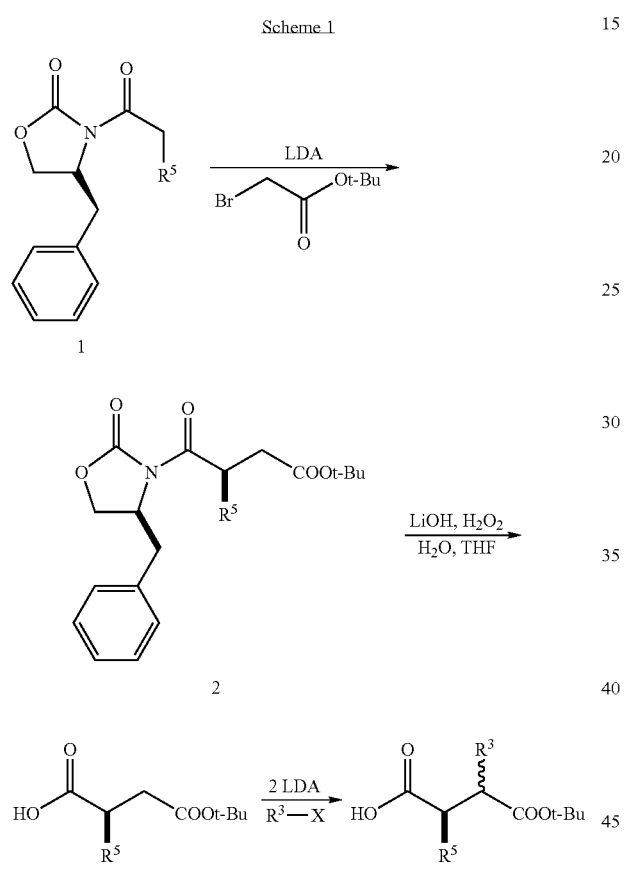

Diastereomerically pure succinate derivatives can be accessed using the chemistry outlined below, adapted from P. Becket, M. J. Crimmin, M. H. Davis, Z. Spavold, Synlett, (1993), 137–138 incorporated herein by reference. This reference provides the synthesis below to obtain compound 9, Scheme 2. Compound 11, Scheme 2, is used as an intermediate and is prepared from 9 by hydrogenation of the allyl group followed by coupling of 9-fluorenemethanol under standard conditions using DCC and DMAP in $CH_2Cl_2$. Deprotection of the tert-butyl ester is accomplished by treatment with 50% trifluoroacetic acid.

Additional methods useful for the preparation of succinate derivatives are known by those skilled in the art. Such references include, McClure and Axt, Bioorganic & Medicinal Chemistry Letters, 8 (1998) 143–146; Jacobson and Reddy, Tetrahedron Letters, Vol 37, No. 46, 8263–8266 (1996); Pratt et al., SYNLETT, May 1998, p. 531; WO 97/18207; and WO 98/51665. The synthetic disclosures of WO97/18207 and WO 98/51665 are hereby incorporated by reference.

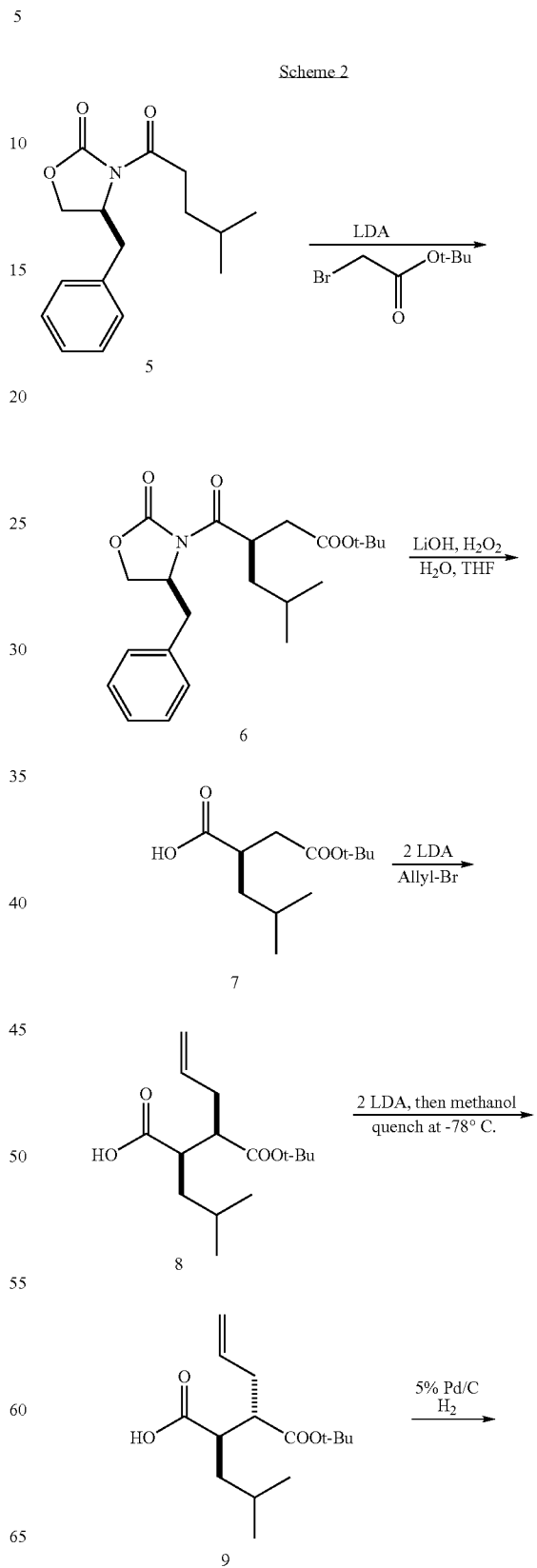

Scheme 3

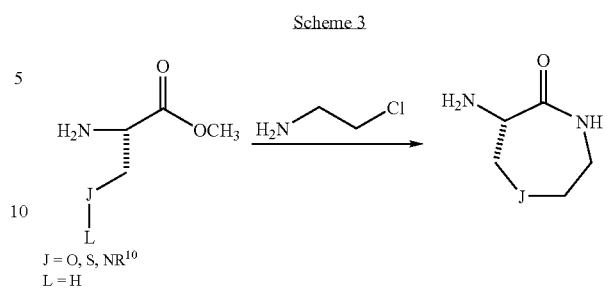

J = O, S, NR[10]
L = H

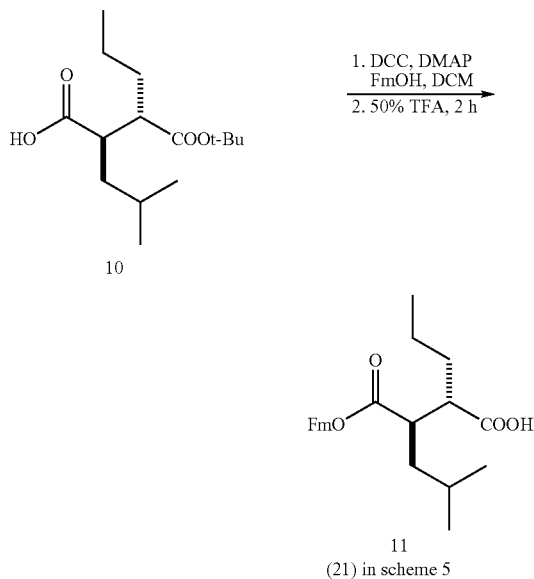

10

11
(21) in scheme 5

A variety of compounds of Formula (I) can be prepared by methods described in Scheme 4. The protected α-amine 3 of the α-amino-ε-caprolactam can be prepared by methods well known in the literature for amino protecting groups as discussed in Theodora W. Greene's book "Protective Groups in Organic Synthesis", like N-Boc using di-t-butyldicarbonate in an appropriate solvent like DMSO. A sulfur atom can be introduced into the ring providing L-α-amino-β-thio-ε-caprolactam according to the procedure in S. A. Ahmed et al, FEBS Letters, (1984), vol. 174, pages 76–9 (Scheme 3). One skilled in the art can extend this methodology to the synthesis of β-amino and oxygen containing rings by analogy. The sulfur-containing molecules can also be oxidized to the sulfoxide and sulfone by methods known to one skilled in the art.

The lactam nitrogen of compound 13 can be alkylated by generating the anion with bases such as LDA, lithium bis(trimethylsilyl)amide or sodium hydride in solvents like THF, with or without cosolvents such as DMPU or HMPA and reacting this with a variety of groups containing leaving groups (X″) like bromide, iodide, mesylate or tosylate. Alkylating agents such as α-bromo amides, ketones and acids can be prepared by a number of literature methods including halogenation of amino acids by diazotization or are commercially available. Other suitable alkylating agents such as alkyl, allylic and benzylic halides can be formed form a variety of precursors such as free-radical addition of halides or activation of alcohols, and other chemistries known to those skilled in the art. For discussion of these types of reactions, see Carey, F. A. and Sundberg, R. J., Advanced Organic Chemistry, Part A, New York: Plenum Press, 1990, pages 304–305, 342–347, 695–698.

The N-Boc protecting group can be removed by any number of methods well known in the literature like TFA in methylene chloride to give the compound 15. The amine 15 can be coupled to an appropriately substituted carboxylic acid or acid chloride by methods well described in the literature for making amide bonds, like TBTU in DMF with a base like NMM to give the elaborated compound 16. Compounds 16 can be alkylated using standard bases like LDA, NaH, or NaHMDS to deprotonate the amide followed by addition of an alkylating agent with an appropriate leaving group like halide, mesylate, or triflate in an appropriate solvent to provide compounds 17 with an R[6] substituent. The t-butyl ester is then removed by treatment with TFA in methylene chloride to give the carboxylic acid 17.

Scheme 4

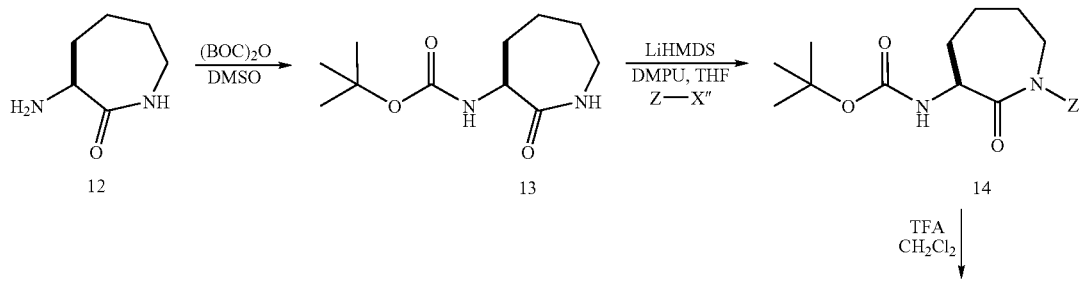

TFA
CH₂Cl₂

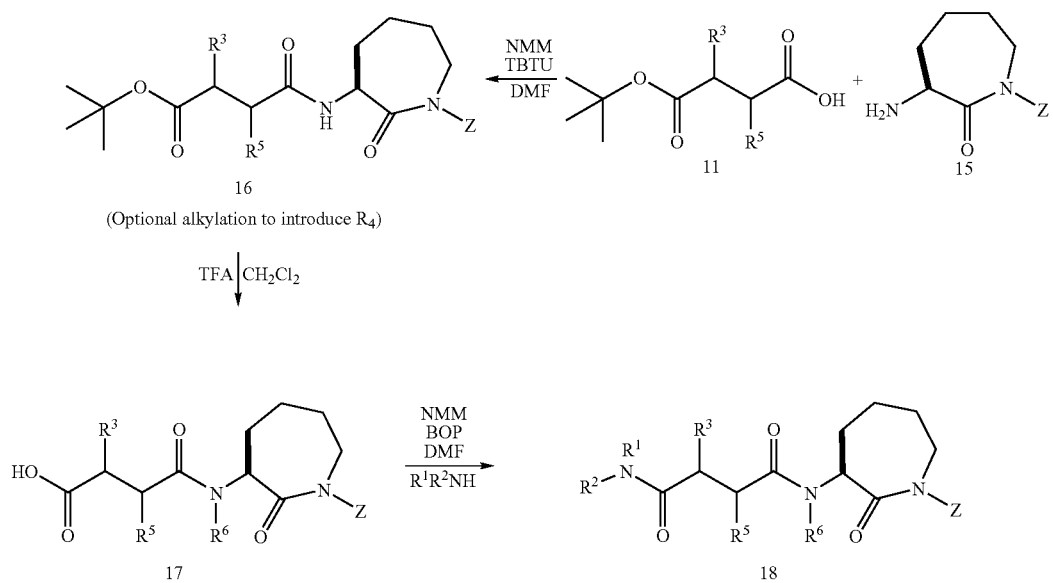

The final compounds 18 were prepared by treating the activated carboxylic acid of 17 with an appropriately substituted amine. For instance, activation of the carboxylic acid with HATU (O-(7-azabenzotriazol-1-yl)-1,1,3,3,-tetramethyluronium hexafluorophosphate) or PyBOP (benzotriazole-1-yl-oxy-tris-pyrrolidino-phosphonium hexafluorophosphate) or other coupling agents known to those skilled in the art allows condensation with ammonia to form primary amides. Similarly, condensation of the activated acid with hydroxylamine hydrochloride provides the hydroxamic acid, or reaction with a primary or secondary amine provides the substituted amine derivative. Activation of the acid with PyBrOP (bromo-tris-pyrrolidino-phosphonium hexafluorophosphate) followed by addition of an alcohol and 4-dimethylaminopyridine allows formation of the ester directly. For additional acylation reactions see for example Carey, F. A. and Sundberg, R. J., Advanced Organic Chemistry, Part A, New York: Plenum Press, 1990, pages 475479.

Additional intermediates in the synthesis of compounds of formula (I) can be prepared as shown in Scheme 5. A suitable resin for solid phase synthesis such as Fmoc (Fluorenylmethylcarbonyl)-protected hydroxylamine bound to polystyrene beads can be purchased from Novabiochem, Inc. Deprotection of the Fmoc group under standard conditions using 20% piperidine in DMF provides trityl-linked hydroxylamine resin. Coupling of a fluorenylmethyl-protected succinic acid derivative such as 20 with a coupling agent such as HATU in a suitable solvent like DMF or N-methylpyrrolidinone provides the support-bound hydroxamate 21. The Fluorenylmethyl ester can be removed using 20% piperidine in DMF to provide the free carboxylic acid which can be coupled to amines like the caprolactam 22 (which is available using chemistry outlined in Scheme 4) using PyBOP (benzotriazole-1-yl-oxy-tris-pyrrolidino-phosphonium hexafluorophosphate) and a suitable base like DIEA in DMF or NMP. The support-bound intermediate 23 can then be elaborated to biaryl structures of the type 24 using typical Suzuki coupling conditions employing a catalyst such as Palladium complexes like tetrakis(triphenylphosphine)-palladium with 2M aqueous sodium carbonate as a base in a suitable solvent like THF or DME and an excess of a boronic acid. The final compounds are liberated from the support employing dilute (5%) trifluoroacetic acid in $CH_2Cl_2$ and purified by conventional chromatography.

Scheme 5

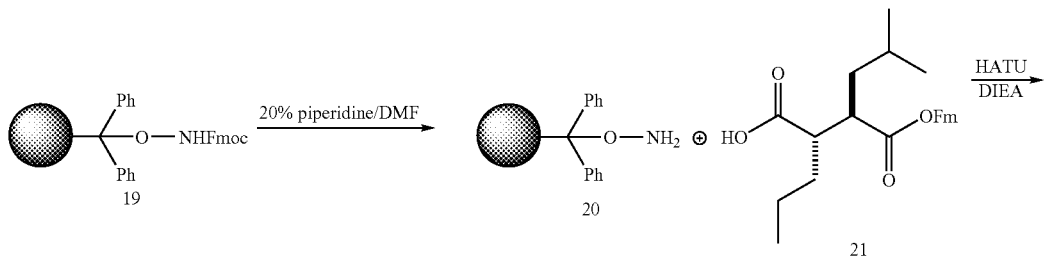

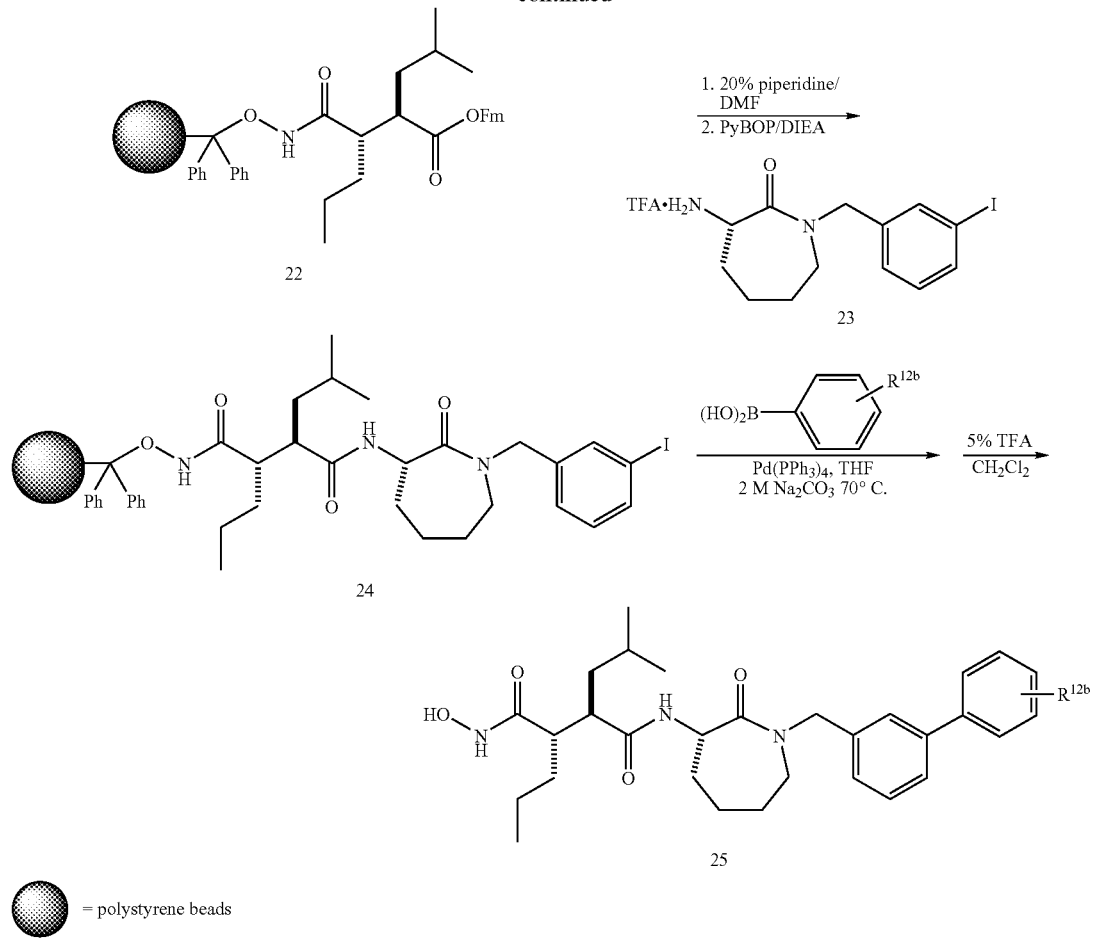

The compounds of formula (I) of the present invention can also be prepared from aminolactams and aminothiolactams (27) and succinic acid derivatives (11) using amide bond syntheses known in the art, including methods commonly used in peptide syntheses, such as HATU, TBTU, BOP, pyBOP, EDC, CDI, DCC, hydroxysuccinimide, mixed carboxylic anhydride, and phenyl ester mediated couplings, as illustrated in Scheme 6 for the synthesis of (Ia), a particular embodiment of (I). Depending on the structure of the final product, it will be appreciated by those skilled in the art that protecting groups or precursor functionality convertable to the desired groups may be desireable. Protecting groups and their use in synthesis are described in Green and Wuts, *Protective Groups in Organic Synthesis*, (Wiley 1991). This is further illustrated in Scheme 6a, in which the succinate half-ester (9) (Becket et al., Synlett 1993, 137–138) is coupled to the aminobenzodiazepine (30) (Sherrill and Sugg, J. Org. Chem. 1995, 60, 730–734; Bock et al., *J. Med. Chem.*, 1993, p 36, 4276–4292) to give ester (Ib), followed by conversion of the ester group to the primary amide (Ic).

The synthesis of the thiolactams of the present invention (Formula (I), A=S) can be carried out using thiolactam intermediates (27, A=S), using the methods described above. The thiolactam intermediates may be prepared from suitably protected aminolactams employing methods known to those skilled in the art, using, for example, Lawessson's reagent,

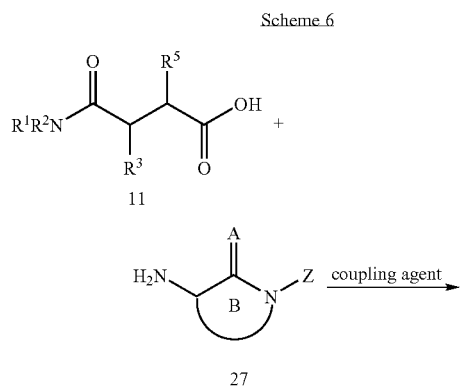

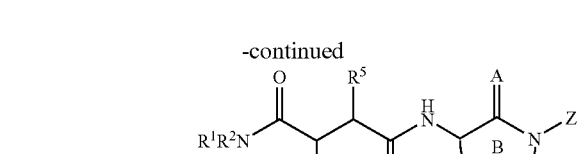

P4S10, or related methods (see Taylor et al., Bioorg. Med. Chem. Lett. 1997, 7 (4), 453–456; Schwarz et al., Tetrahedron, 1997, 53 (26), 87958806; Achour et al., Synth. Commun. 1994, 24 (20), 28992905; Buege et al., Arch. Pharm. 1994, 327 (2), 99–103; Levai, et al., Arch. Pharm. 1992 (325 (11), 721–726; Duhammel et al., Tetrahedron Asymmetry 1991, 2 (3), 203–206; Bodine et al., Synth. Commun. 1982, 12, 787). Deprotection of the amine, coupling to an appropriate succinate derivative and elaboration of the distal succinic acid derivative-provides the desired thiolactams of the present invention.

Scheme 6a

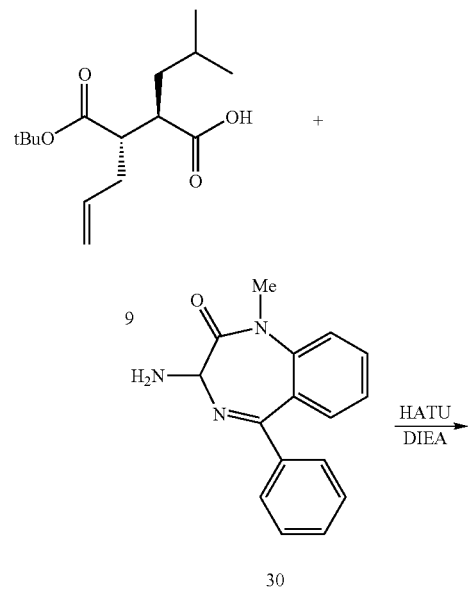

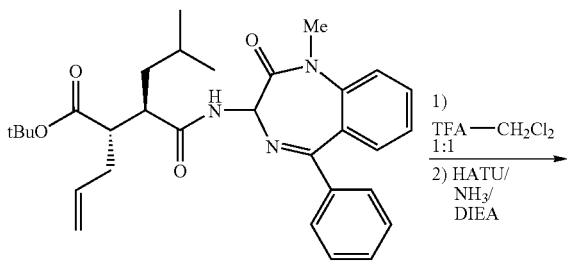

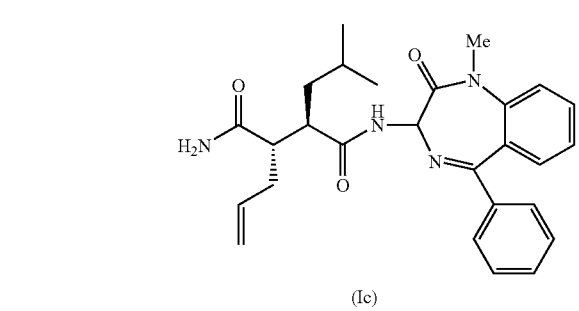

Methods for the synthesis of lactams, including amino benzodiazapines, are known in the art and are disclosed in a number of references including PCT publication number WO 98/28268, which is hereby incorporated by reference. Additional examples of the synthesis of ring B lactams within the scope of the invention are shown below in Schemes 7, 8, 9, and 10.

Scheme 7

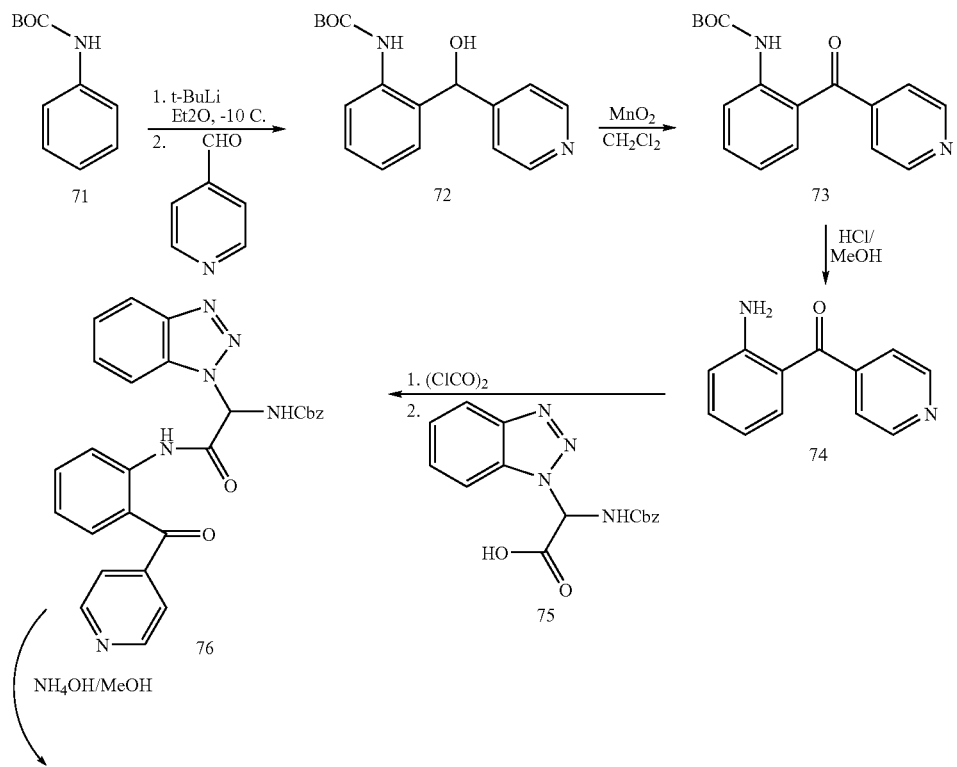

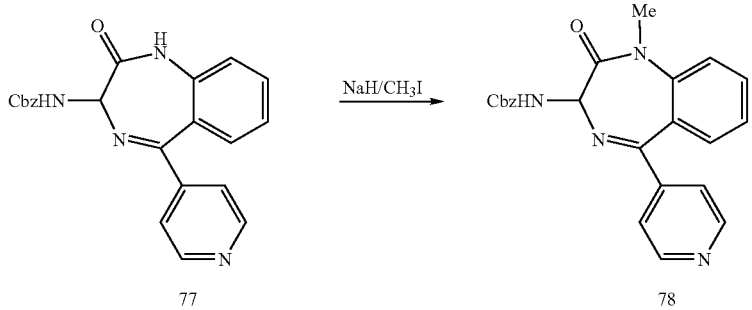

Step 1: Preparation of 72;

Following the literature procedures: Stanetty, P.; Koller, H.; mihovilovic, M. *J. Org. Chem.*, 1992, 57, 68336837; Muchowski, J. M.; Venuti, M. D. *J. Org. Chem.*, 1980, 57, 4798–4801.

A stirred mixture of 71 (13.0 g, 67.3 mmol) in diether ether (100 mL) under nitrogen was cooled to below –50° in a dry ice/acetone bath. A solution of t-butyllithium in hexanes (2.5 M, 90 mL) was added dropwise. The cooling bath was removed and the reaction allowed to warm to approximately –25° C. and then the temperature was maintained between –20° C. and –10° C. for 3.25 hours with a dry ice/ethylene glycol cooling bath. The reaction was cooled again to below –50° C. and 4-pyridine carboxaldehyde (8.3 mL, 87.5 mmol) was added and the reaction stirred at approximately –15° C. for 1.25 hours. The reaction was quenched with a saturated solution of ammonium chloride and the mixture stirred overnight. Hexanes (100 mL) was added. The reaction was filtered, washed with water and dried in vacuo to give 72° C. (15.0 g, 74% as a tan solid: $^1$HNMR (300 MHz, DMSO-d$_6$) δ 8.55 (s, 1H), 8.48 (d, 2H), 7.50 (d, 1H), 7.36 (d, 1H), 7.24 (d, 2H), 7.23 (m, 1H), 7.09 (t of d, 1H0, 6.68 (d, 1H), 5.93 (d, 1H), 1.38 (s, 9H; API MS m/z=301 [C$_{17}$H$_{20}$N$_2$O$_3$+H]$^+$.

Step 2: Preparation of 73;

To a vigorously stirred solution of 72 (1.21 g, 4.03 mmol) in methylene chloride (45 mL) was added manganese oxide (5.2 g, 59.8 mmol). After 5 hours the reaction was filtered over celite and the celite washed with methylene chloride. The filtrate was concentrated to an oil and triturated with hexanes. The hexanes were removed via pipette and the solid was dried in vacuo to give a 73 (1.01 g, 84%) as a tan solid: $^1$HNMR (300 MHz, CDCl$_3$) δ 10.25 (s, 1H), 8.80 (d, 2H), 8.50 (d, 1H), 7.48 (t, 1H), 7.47 (d, 2H), 7.43 (d, 1H), 7.00 (t, 1H), 1.53 (s, 9H); API MS m/z=299 [C$_{17}$H$_{18}$N$_2$O$_3$+H]$^+$.

Step 3: Preparation of 74;

Following the literature procedure; Nudelman, Ayetlet; Bechor, Y.; Falb, E.; Fischer, B.; Wexler, B. A.; Nudelman, Abraham; Syn. Com., 1998, 28(3), 471–474.

Acetyl chloride (57 mL, 801 mmol) was added to ice cold methanol (280 mL) with vigorous stirring. Solid 73 (9.0 g., 30.2 mmol) was added and the reaction stirred overnight. The methanol was evaporated in vacuo and the residue dissolved in water and cooled in an ice bath. The pH was adjusted to approximately 9 with 6N NaOH. The resulting yellow precipitate was collected by vacuum filtration and washed with water and dried in vacuo at 40° C. to give 74 (5.71 g, 95%) as a yellow solid: $^1$HNMR (300 MHz, CDCl$_3$) δ 8.77 (d; 2H), 7.43 (d, 2H), 7.33 (m, 2H), 6.74 (d, 1H), 6.49 (t, 1H), 6.30 (broad s, 2H); CI MS m/z=199 [C$_{12}$H$_{10}$N$_2$O$_1$+H]$^+$.

Step 4: Preparation of 76;

The benzotriazole acid 75 (13.6 g, 41.7 mmol) and a catalytic amount of DMF were dissolved in dry THF (130 mL.) The reaction was cooled in an ice/salt bath. Oxalyl chloride (3.6 mL, 41.2 mmol) was added dropwise over 1 hour. The reaction was stirred an additional 2.5 hours. A solution of 74 (5.5 g, 27.7 mmol) in THF (50 mL) was added dropwise forming a thick precipitate. Water and ether were added and the layers separated. The aqueous layer was extracted with methylene chloride. The combined organics were washed with saturated sodium bicarbonate, dried over magnesium sulfate and concentrated. The resulting oil was chromotographed over silica gel (1:1 methyl acetate/methylene chloride) to provide 76 (12.2 g, 86%) as a yellow solid: $^1$HNMR (300 MHz, CDCl$_3$) δ 11.62 (s, 1H), 8.78 (d, 2H), 8.63 (d, 1H), 8.08 (d, 1H), 7.71 (broad s, 1H), 7.63 (t, 1H), 7.54 (m, 1H), 7.44 (d, 1H), 7.40–7.19 (m, 11H), 7.17 (t, 1H), 7.02 (broad s, 1H), 5.24–5.07 (m, 2H); API MS m/z=5.07 [C$_{28}$H$_{22}$N$_6$O$_4$+H]$^+$.

Step 5: Preparation of 77;

Based on the literature procedures; Semple, G.; Ryder, H.; Ohta, M.; Satoh, M. *Syn. Comm.*, 1996, 26(4), 721–727. Semple, G.; Ryder, H.; Rooker, D. P.; Batt, A. R.; Kendrick, D. A.; Szelke, M.; Ohta, M.; Satoh, M.; Nishida, A.; Akuzawa, S.; Miyata, K. *J. Med. Chem.*, 1997, 40, 331–341.

To stirred ice cold methanol (40 mL) was added 76 (4.0 g, 7.9 mmol) and ammonium hydroxide (20 mL.) The reaction was stirred for 2.5 hours forming a heavy precipitate. The reaction mixture was added slowly to cold acetic acid (40 mL) and stirred overnight at room temperature. The reaction mixture was evaporated and water added. The solution was adjusted to pH 9 with concentrated ammonium hydroxide and stirred 0.5 hour. The resulting tan solid was collected by vacuum filtration and dried in vacuo. The solid was stirred in ethyl acetate (20 mL) and heated under reflux for 1 hour. The mixture was cooled in ice and filtered. The product was washed with cold ethyl acetate and dried in vacuo to give 77 (2.2 g, 72%) as a white solid: $^1$HNMR (300 MHz, DMSO-d$_6$) δ 10.94 (s, 1H), 8.68 (d, 2H), 8.51 (d, 1H), 7.57 (t, 1H), 7.43–7.25 (m, 10H), 5.10 (d, 2H); CI MS m/z=387 [C$_{22}$H$_{18}$N$_4$O$_3$+H]$^+$.

Step 6: Preparation of 78;

Following the literature procedures; Semple, G.; Ryder, H.; Ohta, M.; Satoh, M. *Syn. Comm.*, 1996, 26(4), 721–727. Semple, G.; Ryder, H.; Rooker, D. P.; Batt, A. R.; Kendrick, D. A.; Szelke, M.; Ohta, M.; Satoh, M.; Nishida, A.; Akuzawa, S.; Miyata, K. *J. Med. Chem.*, 1997, 40, 331341.

A stirred solution of 77 (1.0 g, 2.59 mmol) in DMF (10 mL) under nitrogen was cooled in ice. Sodium hydride (62 mg, 2.59 mmol) was added and the reaction stirred 2 hours. Methyl iodide (0.16 mL, 2.59 mmol) was added and the reaction stirred 2 hours at room temperature. The reaction was evaporated and chloroform and water were added. The layers were separated and the aqueous extracted with chloroform. The combined organics were washed with brine, dried over sodium sulfate, decanted, evaporated and dried in vacuo. The crude product was passed through a pad a silica gel (1:1 ethyl acetate/methylene chloride) and evaporated to give 78 (934 mg, 90%) was a tan solid: $^1$H NMR (300 MHz, CDCl$_3$) δ 8.59 (d, 2H), 7.62 (t, 1H), 7.52 (d, 1H), 7.42–7.25 (m, 9H), 6.72 (d, 1H), 5.38–5.30 (m, 1H), 5.15 (s, 2H), 3.48 (s, 3H); CI MS m/z=401 [C$_{23}$H$_{20}$N$_4$O$_3$+H]$^+$.

Using the procedures discribed in Scheme 7 the 3-pyridyl isomer can be prepared. The following data characterizes the individual intermediates.

Intermediate 82;
$^1$H NMR (300 MHz, DMSO-d$_6$) δ 8.61 (broad s, 1H), 8.49 (s, 1H), 8.42 (d, 1H), 7.61 (d, 1H), 7.49 (d, 1H), 7.40 (d, 1H), 7.34–7.21 (m, 2H), 7.40 (t, 1H), 6.51 (broad s, 1H), 6.00 (s, 1H), 1.39 (s, 9H).

Intermediate 83;
$^1$H NMR (300 MHz, CDCl$_3$) δ 10.11 (s, 1H), 8.92 (s, 1H), 8.80 (d, 1H), 8.48 (d, 1H), 8.02 (d, 1H), 7.59 (t, 1H), 7.52–7.42 (m, 2H), 7.05 (t, 1H), 1.54 (s, 9 h).

Intermediate 84;
$^1$H NMR (300 MHz, CDCl$_3$) δ 8.84 (s, 1H), 8.73 (d, 1H), 7.93 (d, 1H), 7.44–7.37 (m, 2H), 7.32 (t, 1H), 6.75 (d, 1H), 6.60 (t, 1H), 6.22 (broad s, 2H); CI MS m/z 199 [C$_{12}$H$_{10}$N$_2$O$_1$+H]$^+$.

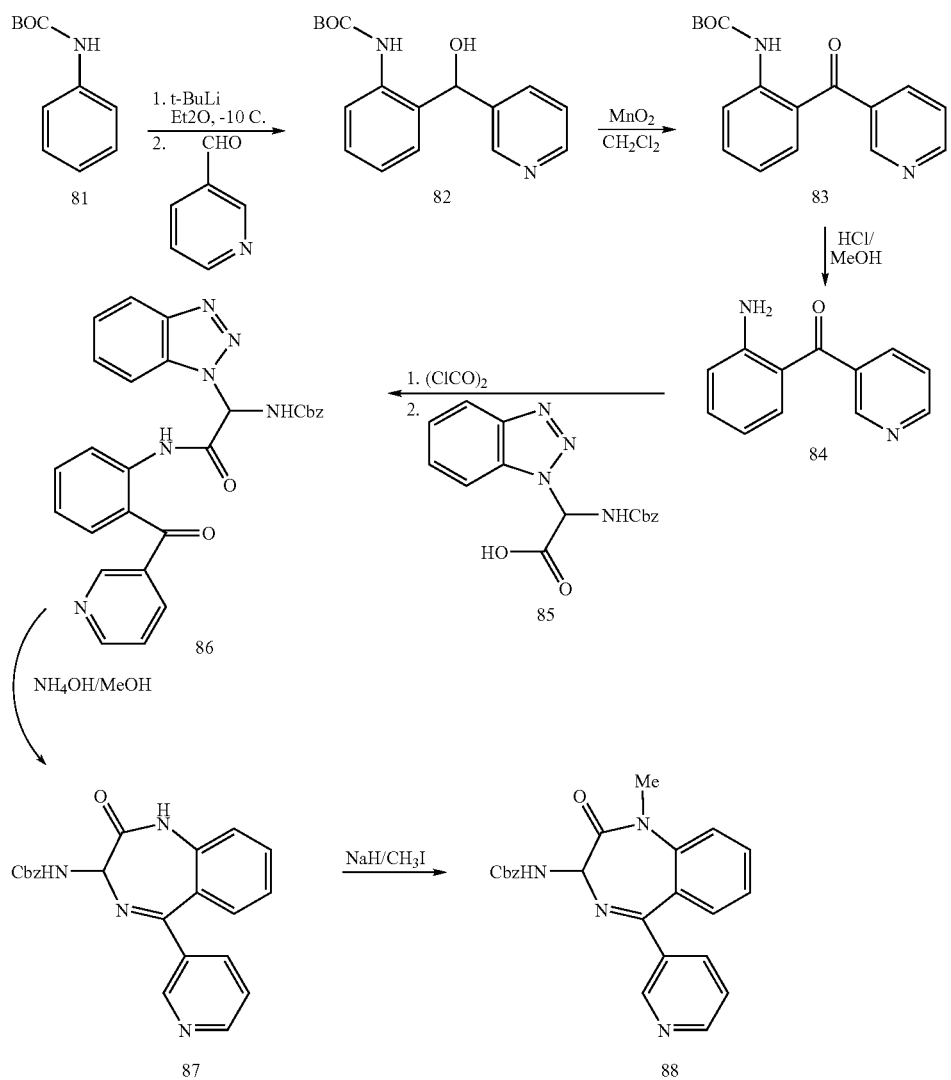

Scheme 8

Intermediate 86;
$^1$H NMR (300 MHz, CDCl$_3$) δ 11.51 (s, 1H), 8.81–8.75 (m, 2H), 8.60 (d, 1H), 8.07 (d, 1H), 7.89 (d of t, 1H), 7.80 (broad s, 1H), 7.63 (t, 1H), 7.52 (d, 2H), 7.42–7.15 (m, 9H), 6.94 (broad s, 1H), 5.22–5.02 (m, 2H); API MS m/z=507 [C$_{28}$H$_{22}$N$_6$O$_4$+H]$^+$.

Intermediate 87;
$^1$H NMR (300 MHz, CDCl$_3$) δ 8.69 (s, 2H), 8.24 (broad s, 1H), 7.98 (d, 1H), 8.48 (t, 1H), 7.42–7.25 (m, 8H), 7.17 (d, 1H), 6.60 (d, 1H), 5.47 (d, 1H), 5.18 (s, 2H); CIMS m/z=387 [C$_{22}$H$_{18}$N$_4$O$_3$+H]$^+$.

Intermediate 88;
$^1$H NMR (300 MHz, CDCl$_3$) δ 8.70 (d, 2H), 8.25 (d, 1H0, 7.62 (t, 1H), 7.40–7.24 (m, 9H), 6.68 (d, 1H), 5.33 (d, 1H), 5.14 (s, 2H), 3.46 (s, 3H).

extracts were washed with EtOAc (3×12 mL). The aqueous layer was made basic (pH>10) using 6N NaOH and extracted with CH$_2$Cl$_2$. The organic extracts were washed with sat. NaCl, dried over NaSO$_4$, filtered, and concentrated to give a crude mixture containing 93. The crude oil was purified by chromatography on silica to provide pure 93 (0.17 g, 14%) as a yellow oil; $^1$H NMR (500 MHz, DMSO-d$_6$) δ 7.40–7.43 (m, 1H), 7.27–7.30 (m, 1H), 7.07–7.17 (m, 4H), 6.86–6.88 (m, 1H), 6.49–6.52 (m, 1H), 3.81 (s, 3H); CI MS m/z=228 [C$_{14}$H$_{13}$NO$_2$+H]$^+$.

Step 2: Preparation of 95;
Based on the literature procedures; Semple, G.; Ryder, H.; Ohta, M.; Satoh, M. *Syn. Comm.*, 1996, 26(4), 721–727. Semple, G.; Ryder, H.; Rooker, D. P.; Batt, A. R.; Kendrick,

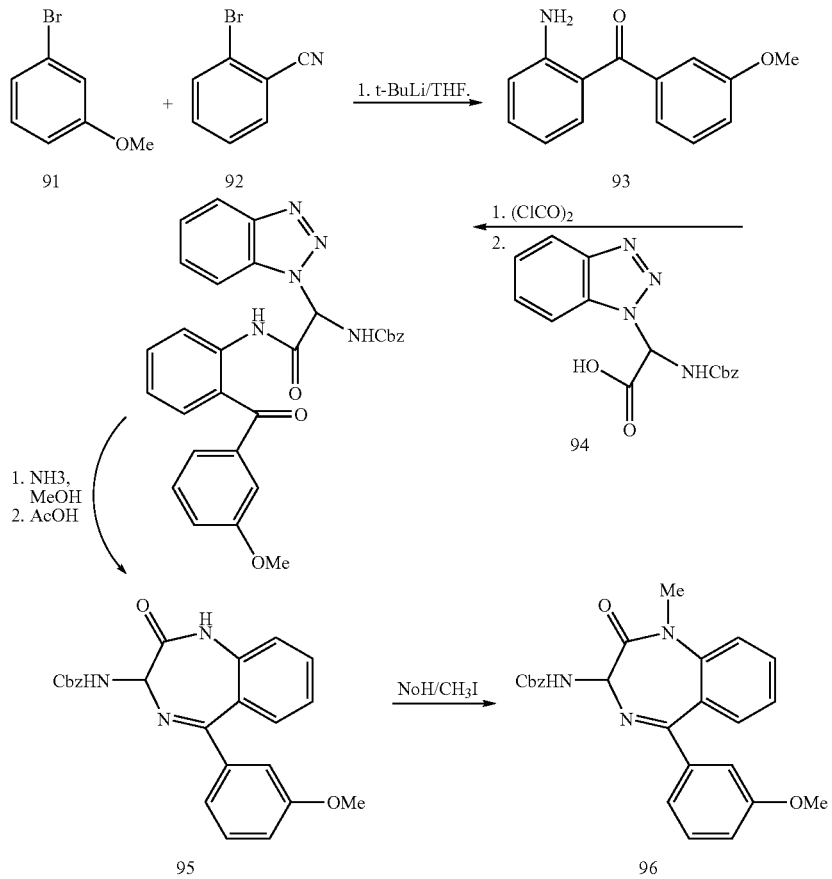

Scheme 9

Step 1: Preparation of 2-Amino-3'-methoxybenzophenone 93;

Following the literature precedent: Walsh, D. A. Synthesis, 1980, 677–688.

To a solution of bromoanisole 91 (1.38 mL, 10.7 mmol) in THF (5 mL) at 78° C. and under nitrogen atmosphere, was added 1.2 M t-BuLi in pentane (18.2 mL, 21.9 mmol) dropwise. After stirring for 20 min, anthranilonitrile 92 (0.63 g, 5.3 mmol) was added. The reaction was warmed to rt and stirred overnight. The reaction was cooled to 0° C. and quenched with 3N HCl. After stirring 30 min at rt, the acidic D. A.; Szelke, M.; Ohta, M.; Satoh, M.; Nishida, A.; Akuzawa, S.; Miyata, K. *J. Med. Chem.*, 1997, 40, 331–341.

To a solution of benzotriazole acid 94 (16.47 g, 50.5 mmol) in THF (101 mL) at 0° C. under a nitrogen atmosphere was added oxalyl chloride (4.84 mL, 55.5 mmol) and a catalytic amount of DMF (1.0 mL). After stirring for 1 h, a solution of 93 (11.47 g, 50.5 mmol) and N-methylmorpholine (12.25 mL, 111 mmol) in THF (51 mL) was added dropwise via dropping funnel. The reaction was allowed to warm to rt and stirred overnight. The solids were removed by filtration. The filtrate was diluted with MeOH (62 mL), and NH₃ gas was condensed into the solution for 15 min, the reaction vessel was sealed and stirred at rt for 2 h. After concentration, the crude oil was dissolved in EtOAc, washed with 3N NaOH (3×20 mL). The organic extracts were dried over Na₂SO₄, filtered and concentrated. The resultant crude oil was dissolved in AcOH (121 mL), and NH₄OAc (7.17 g) was added. After stirring at rt overnight (16 h), the reaction was concentrated and diluted with water and made basic with 50% NaOH. The basic aqueous solution was extracted with EtOAc (3×150 mL). The combined organic extracts were washed with sat. NaCl, dried over Na₂SO₄, filtered, and concentrated. The crude product was purified by chromatography on silica to provide 95 (6.96 g, 33%) as a solid; ¹H NMR (500 MHz, CDCl₃) δ 7.50 (t, 1H0, 7.10–7.40 (m, 9H), 7.05 (d, 1H), 6.97 (dd, 1H0, 6.63 (d, 1H0, 5.30 (d, 1H), 5.20 (s, 2H0, 3.77 (s, 3H).

dried in a vacuum oven at 55° C. to provide 96 (1.5 g, 3.5 mmol) as a red solid; ¹H NMR (300 MHz, CDCl₃) δ 7.58 (t, 1H), 7.19–7.42 (m, 9H), 7.07 (d, 1H0, 7.00 (dd, 1H), 6.69 (d, 1H), 5.32 (d, 1H0, 5.15 (s, 2H0, 3.83 (s, 3H0, 3.45 (s, 3H).

Step 3: Preparation of 97; Cbz deprotection to free amine.

To protected amine 96 (2.13 g, 4.9 mmol) was added 30% HBr in AcOH (50 mL). This was stirred at rt for 1 h. The reaction was poured into water (200 mL) and washed with ETOAc (200 mL). The aqueous layer was made basic with 50% NaOH and extracted with EtOAc (2×200 mL). The extracts were concentrated to give crude 97 (1.14 g, 78%) as a yellow solid; ¹H NMR (300 MHz, CDCl₃) δ 7.58 (t, 1H), 7.17–7.40 (m, 5H), 7.12 (d, 1H0, 7.00 (dd, 1H) 3.83 (s, 3H), 3.48 (s, 3H); CI MS m/z=296 $[C_{17}H_{17}N_3O_2+H]^+$.

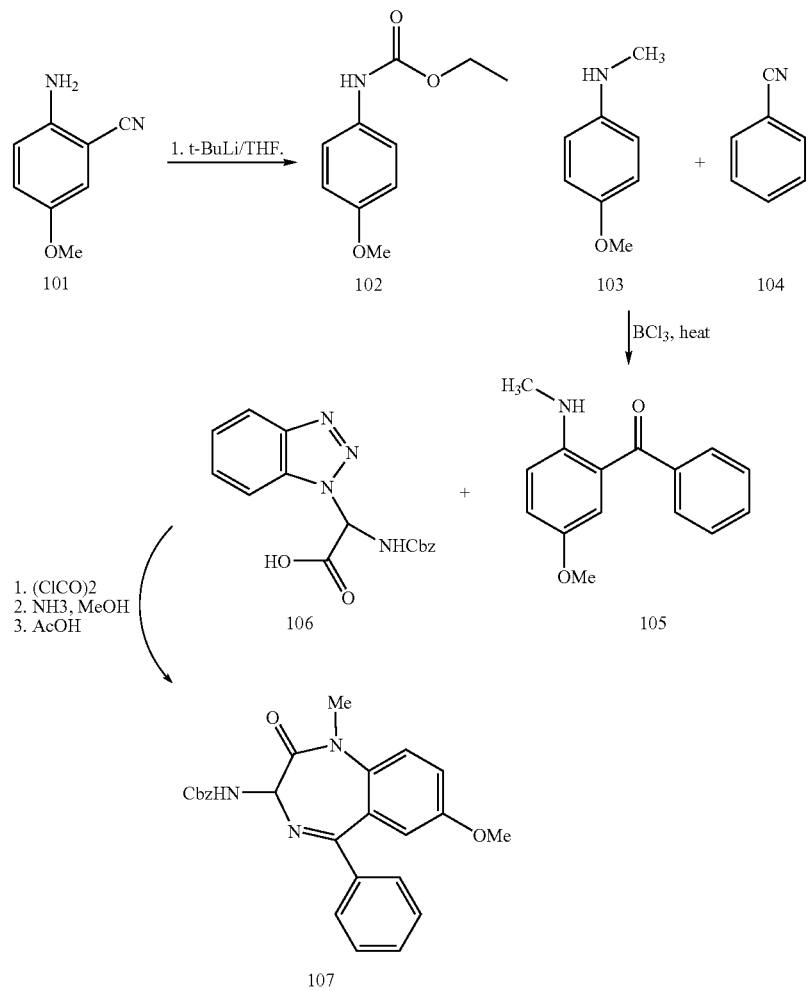

Scheme 10

Step 3: Preparation of 96;

To a solution of 95 (2.07 g, 5.4 mmol) and K₂CO₃ (3.71 g, 26.8 mmol) in DMF (9.7 mL), was added MeI (0.50 mL, 8.1 mmol). After stirring 1 h at rt, the reaction was poured into water (100 mL) and stirred overnight. The solid was collected by filtration, rinsed with water and Et₂O. This was Step 1: Preparation of 102;

To a stirred mixture of p-anisidine (6 g, 48.7 mmol) in methylene chloride (170 mL) under nitrogen was added DMAP (5.0 mg, mmol) and triethylamine (13.9 mL, 99.7 mmol.) Ethyl chloroformate (4.85 mL, 50.7 mmol) was added and the reaction stirred for 2.5 hours. Dilute phosphoric acid (0.5 N) was added and the mixture stirred for 15 minutes. The aqueous layer was neutralized with sodium bicarbonate and then extracted with methylene chloride. The methylene chloride solution was dried over sodium sulfate, filtered and concentrated. Purification by column chromatography (gradient ethyl acetate/hexanes) provided 102 (7.2 g, 75%) as a solid: $^1$H NMR (300 MHz, CDCl$_3$) δ 7.27 (d, 2H), 6.82 (d, 2H0, 6.45 (broad s, 1H), 4.20 (q, 2H), 3.77 (s, 3H0, 1.31 (t, 3H).

Step 2: Preparation of 103;

To a stirred suspension of lithium aluminum hydride (1.8 g, 47.4 mmol) in THF (95 mL) was added 102 (3.0 g, 15.4 mmol.) The reaction was heated at reflux for 2 hours. The reaction was cooled and quenched with ethyl acetate (150 mL). Solid sodium sulfate was added and the mixture filtered. The clear solution was evaporated and dried to give 103 (2.1 g, 100%); $^1$H NMR (300 MHz, CDCl$_3$) δ 6.79 (d, 2H), 6.56 (d, 2H), 3.74 (s, 3H), 2.78 (s, 3H).

Step 3: Preparation of 105;

Based on the following literature references: Sugasawa, T., Toyoda, T.; Adachi, M.; Sasakura, K. *J. Chem. Soc.*, 1978, 100, 4842–4852. Houpis, I. N.; Moline, A.; Douglas, A. W.; Xavier, L.; Lynch, J.; Volante, R. P.; Reider, P. J. *Tet. Lett.*, 1994, 35, 6811–6814. Adachi, M.; Sasukura, K.; Sugasawa, T. Chem. *Pharm. Bull.*, 1985, 33, 1826–1835. Sugasawa, T.; Adachi, M.; Sasakura, K.; Kitagawa, A. *J. Org. Chem.*, 1979, 44, 578–586.

To a stirred solution of boron trichloride (1 M in CH$_2$CL$_2$, 29.9 mL) at 0° C. was added toluene (15 mL.) A solution of 103 (3.42 g, 24.9 mmol) in toluene (40 mL) was added dropwise over 0.5 h. The reaction was stirred at 0° C. for 20 minutes and then heated under reflux for 1 h. Anthranilonitrile (25.7 g, 249 mmol) was added and the reaction heated under reflux for 6.5 h. 2N HCl (1.5 mL) was added and the reaction heated at 80° C. for 0.5 h. Water was added and the reaction was neutralized with solid sodium carbonate and extracted with methylene chloride. The combined organics were dried over magnesium sulfate, filtered and concentrated. Purification by column chromatography gave 105 (1.3 g, 33%) as a yellow solid. $^1$H NMR (300 MHz, CDCl$_3$) δ 9.98 (broad s, 1H), 7.61 (d, 2H0, 7.55–7.4 (m, 3H0, 7.1 (d of d, 1H), 7.02 (d, 1H), 6.72 (d, 1H0, 3.64 (s, 3H), 2.93 (d, 3H)

Step 4: Preparation of 107;

Based on the following literature references: Semple, G.; Ryder, H.; Ohta, M.; Satoh, M. *Syn. Comm.*, 1996, 26(4), 721–727. Semple, G.; Ryder, H.; Rooker, D. P.; Batt, A. R.; Kendrick, D. A.; Szelke, M.; Ohta, M.; Satoh, M.; Nishida, A.; Akuzawa, S.; Miyata, K. *J. Med. Chem.*, 1997, 40, 331-341.

To a stirred solution of benzotriazole acid 106 in THF (3 mL) at 0° C. was added oxalyl chloride (0.95 mL, 1.1 mmol) and a catalytic amount of DMF and the reaction stirred 1 h. A solution of 105 (240 mg, 1 mmol) and N-methyl morpholine (0.24 mL, 2.2 mmol) in THF 1.5 mL) was added dropwise. The reaction was stirred overnight at room temperature. The solution was filtered and concentrated. Methanol (3 mL) was added ammonia gas was bubbled into the reaction for 25 minutes. The reaction was stirred at room temperature for 1.5 h and then evaporated in vacuo and diluted with ethyl acetate. The solution was washed with 1 N NaOH. The aqueous layer was extracted with ethyl acetate and the combined organics were dried over magnesium sulfate and concentrated. The residue was dissolved in acetic acid (2.4 mL) and ammonium acetate (140 mg) was added and the reaction stirred for 16 h. The reaction was concentrated in vacuo and diluted with 1 N NaOH and extracted with ethyl acetate. The organic layer was dried over sodium sulfate, filtered and concentrated. The residue was chromatographed on silica gel (ethyl acetate/hexanes) to give 107 (98 mg, 45%) as a yellow solid; $^1$H NMR (500 MHz, CDCl$_3$) δ 7.63 (d, 2H0, 7.45 (t, 1H0, 7.34–7.23 (m, 8H), 7.13 (d, 1H), 6.79 (s, 1H), 6.67 (d, 1H), 5.34 (d, 1H), 5.14 (q, 2H), 3.73 (s, 3H0, 3.40 (s, 3H0; API MS m/z=430 [C$_{25}$H$_{23}$N$_3$O$_4$+H]$^+$; mp. 71–73° C.; IR (thin film) 3410, 1724, 1678, 1498, 1289, 1231, 1039, 699 cm$^{-1}$.

EXAMPLES

Chemical abbreviations used in the Examples are defined as follows: "DMPU" for 1,3-dimethyl-3,4,5,6-tetrahydro-2 (1H)-pyrimidone, "TBTU" for O-(1H-benzotriazol-1-yl)-N, N,N',N'-tetramethyluronium tetrafluoroborate, "BOP" for benzotriazol-1-yloxytris-(dimethylamino)-phosphonium hexafluorophosphate, and "HATU" for O-(7-azabenzotriazol-1-yl)-N,N,N',N'-tetramethyluronium hexafluorophosphate. "HPLC" is an abbreviation used herein for high pressure liquid chromatography. Reverse-phase HPLC was carried out using a Vydac C-18 column with gradient elution from 10% to 100% buffer B in buffer A (buffer A: water containing 0.1% trifluoroacetic acid, buffer B: 10% water, 90% acetonitrile containing 0.1% trifluoroacetic acid). Alternatively, reverse-phase HPLC was carried out using a Vydac C-18 column with gradient elution from 10% to 90% acetonitrile in water.

Example 1

(2R,3S) N1-[1,3-dihydro-1-methyl-2-oxo-5-phenyl-2H-1,4-benzodiazepin-3-yl]-2-(2-methylpropyl)-3-allyl-butanediamide

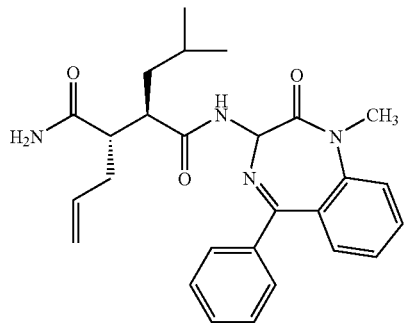

Step 1

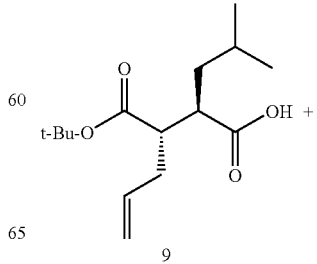

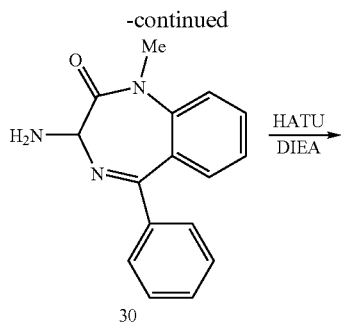

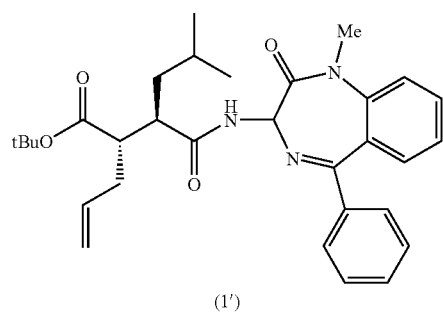

A solution of tert-butyl succinate ester (9) (1.0 eq.) in DMF (0.25 M) under N₂ at 0° C. was added HATU (1.1 eq.), then Hunig's base (4.0 eq.). The mixture was stirred at 0° C. for 10 mins. A solution of 1,3-dihydro-1-methyl-3-amino-5-phenyl-2H-1,4-benzodiazepin-2-one (30) in DMF (0.8 M) (1.0 eq.) was added to this solution. The reaction mixture was stirred overnight at room temperature and then transfered to a separatory funnel containing water. 30% n-Hexane in ethyl acetate was added which gave a clear organic layer. The aqueous solution was extracted twice with 30% n-hexane in ethyl acetate. The combined organic layers were washed with water and brine, dried over magnesium sulfate, and concentrated in vacuo. The residue was purified by chromatography on flash grade silica gel using 20–30% ethyl acetate in n-hexane; preferably 30% ethyl acetate in n-hexane. Compound, 1', was isolated as an amorphous white solid (85%). Rf=0.25 (7:3 n-hexane:ethyl acetate).

¹H-NMR: (CDCl₃): δ7.61–7.21 (m, 10H); 5.77–5.73 (m, 1H); 5.57–5.54 (d, 1H); 5.20–4.97 (m, 2H); 3.47 (s, 3H); 2.63–2.33 (m, 4H); 1.80–1.76 (m, 2H); 1.47–1.46 (d, 9H); 1.43–1.11 (m, 1H); 1.01–0.86 (m, 6H).

MS: $C_{31}H_{39}N_3O_4$ (M+H) 518.3 (M+Na) 540.3.

Step 2

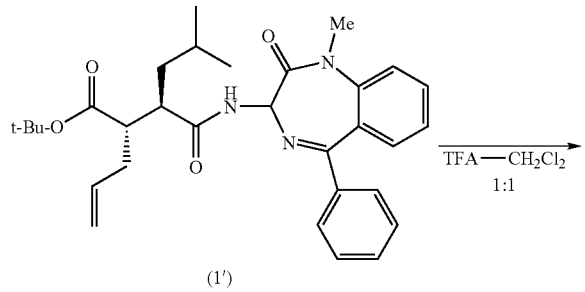

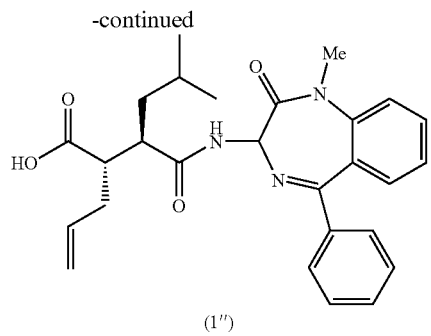

A solution of (1') in 50% TFA in methylene chloride (0.15M) was stirred at room temperature overnight. The solution was concentrated in vacuo, washed and concentrated four times with toluene in vacuo to give compound (1") as an amorphous solid (95%). Rf=0.64 (9.5:0.5 methylene chloride:methanol). MS: $C_{27}H_{31}N_3O_4$ (M+H) 462.

Step 3

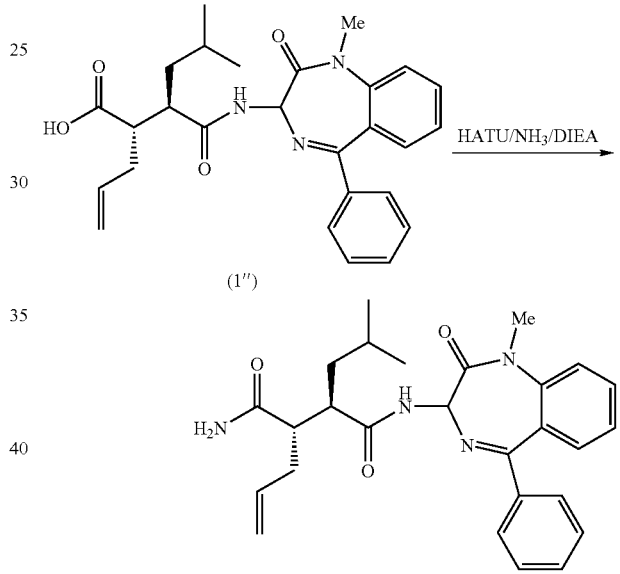

To a solution of (1") (1.0 eq.) in DMF (0.25 M) under N₂ at 0° C. was added HATU (1.1 eq.), and then Hunig's base (4.0 eq.). The mixture was stirred at 0° C. for 10 mins, and then anhydrous ammonia bubbled through the solution for two minutes. The reaction mixture was stirred overnight at room temperature and then transfered to a separatory funnel containing water and diluted with 30% n-hexane in ethyl. The aqueous solution was extracted twice with 30% n-hexane in ethyl acetate. The combined organic layers were washed with water and brine, dried over magnesium sulfate, and concentrated in vacuo. The residue was purified by chromatography on flash grade silica gel using 4% methanol in methylene chloride. The title compound, Example 1, was isolated as an amorphous white solid (87%). Rf=0.43 (9:1 methylene chloride:methanol).

¹H NMR: (CDCl₃): δ 7.63–7.22 (m, 10H); 6.25–6.13 (d, 1H) 5.88–5.73 (m, 1H); 5.53–5.51 (dd, 1H); 5.44–5.41 (d, 1H); 5.22–5.04 (m, 2H); 3.47–3.46 (d, 3H); 2.74–2.31 (m, 4H); 1.81–1.61 (m, 2H); 1.34–1.22 (m, 1H); 0.99–0.87 (m, 6H).

MS: $C_{27}H_{32}N_4O_3$ (M+H) 461.

Example 2

(2R,3S) N1-[1,3-dihydro-1-methyl-2-oxo-5-phenyl-2H-1,4-benzodiazepin-3-yl]-2-(2-methylpropyl)-3-allyl-N-4-[3,5-difluorobenzyl]-butanediamide

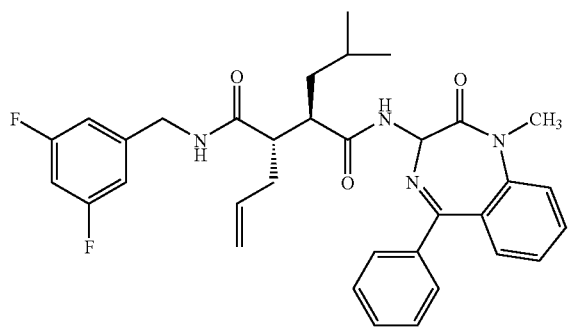

Following a procedure analogous to the preparation of Example 1 using 3,5-difluorobenzylamine in place of ammonia in Step 3, the title compound was prepared. MS (M+H)+=587.

Example 3

(2R,3S) N1-[1,3-dihydro-1-methyl-2-oxo-5-phenyl-2H-1,4-benzodiazepin-3-yl]-2-(2-methylpropyl)-3-propyl-butanediamide

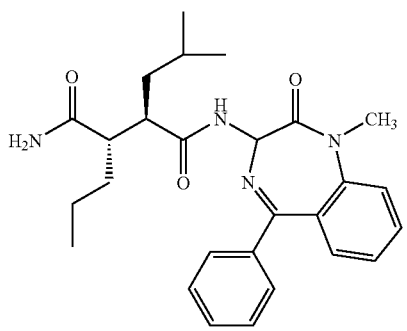

Following a procedure analogous to the preparation of Example 1 using succinate ester (10) (Scheme 2) in place of succinate ester (9) in Step 1, as well as reagents known to one skilled in the art, the title compound was prepared. MS (M+H)+=463.0.

Example 4a (2R,3S) N1-[(3S)-1,3-dihydro-1-methyl-2-oxo-5-(2-fluorophenyl)-2H-1,4-benzodiazepin-3-yl]-2-(2-methylpropyl)-3-allyl-butanediamide

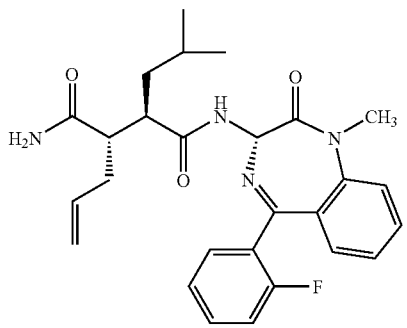

Following a procedure analogous to the preparation of Example 1 using 1,3-dihydro-1-methyl-3-amino-5-(2-fluorophenyl)-2H-1,4-benzodiazepine-2-one in place of (30) in Step 1, the mixture of benzodiazepine diastereomers of the title compound was prepared. The isomers were separated using reverse phase chromatography (C-18 column, isocratic eluent composed of 65% 90:10 water:acetonitrile and 35% 10:90 water:acetonitrile). The first eluting isomer was assigned the (S)-benzodiazepine configuration using the H-NMR method described for Example 12a. The required aminobenzodiazepine was prepared using the method of Sherrill and Sugg (J. Org. Chem. 1995, 60, 730–734). MS (M+H)+=479.4; (M+Na)+=501.4.

Example 4b (2R,3S) N1-[(3R)-1,3-dihydro-1-methyl-2-oxo-5-(2-fluorophenyl)-2H-1,4-benzodiazepin-3-yl]-2-(2-methylpropyl)-3-allyl-butanediamide Following the procedure of Example 4a, the second eluting isomer was isolated and assigned the (R)-benzodiazepine configuration using the H-NMR method described for Example 12b. MS (M+H)+=479.4; (M+Na)+=501.4.

Example 5

(2R,3S) N1-[(3S)-1,3-dihydro-1-methyl-2-oxo-5-phenyl-2H-1,4-benzodiazepin-3-yl]-2-(2-methylpropyl)-3-allyl-butanediamide

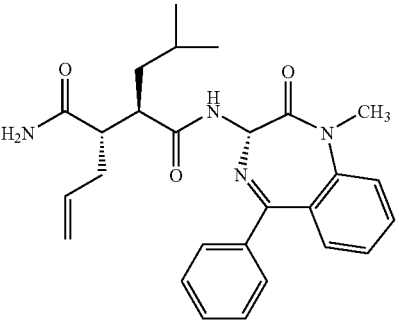

Following a procedure analogous to the preparation of Example 1 using (S) isomer of benzodiazepinone (30) in Step 1 in place of racemic benzodiazepinone (30), and reducing the amount of Hunig's base in Step 1 to 2.2 eq., the title compound was prepared.

$^1$H-NMR for product of Step 1: (CDCl$_3$): 7.61–7.21 (m, 10H); 5.77–5.73 (m, 1H); 5.57–5.54 (d, 1H); 5.20–5.00 (m, 2H); 3.46 (s, 3H); 2.63–2.33 (m, 4H); 1.80–1.76 (m, 2H); 1.46 (s, 9H); 1.43–1.11 (m, 1H); 0.97–0.95 (d, 3H); 0.88–0.85 (d, 3H).

$^1$H-NMR for product of Step 3: (CDCl$_3$): 7.65–7.00 (m, 10H); 6.10–6.00 (s, 1H); 5.85–5.65 (m, 1H); 5.54–5.52 (d, 1H); 5.40–5.30 (s, 1H); 5.23–5.00 (m, 2H); 3.47 (s, 3H); 2.80–2.20 (m, 4H); 1.85–1.60 (m, 2H); 1.40–1.20 (m, 1H), 0.98–0.95 (d, 3H); 0.90–0.87 (d, 3H). MS (M+H)+=461.3; MS (M+H)+=483.3.

Example 6

(2R,3S) N1-[(3R)-1,3-dihydro-1-methyl-2-oxo-5-phenyl-2H-1,4-benzodiazepin-3-yl]-2-(2-methylpropyl)-3-allyl-butanediamide

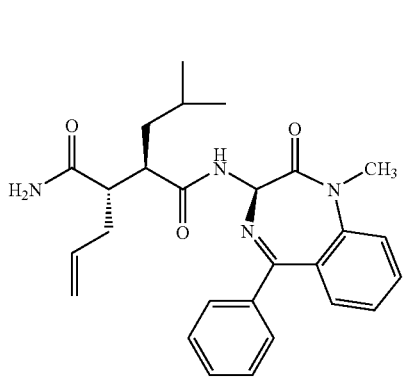

Using the method of Example 5, but replacing the (S) isomer of benzodiazepinone (30) with (R) isomer of benzodiazepinone (30) in Step 1, the title compound was prepared. Alternatively, the (R)- and (S)-benzodiazepine diastereomers may be separated using a Chiralpack AD column, eluting with 0.1% diethylamine in 1:1 n-hexane/i-propanol. Under these conditions, the compound of Example 6 [(R)-benzodiazepine diastereomer] elutes first.

$^1$H-NMR: (CDCl$_3$): 7.65–7.00 (m, 10H); 6.10–6.00 (s, 1H); 5.85–5.65 (m, 1H); 5.54–5.52 (d, 1H); 5.40–5.30 (s, 1H); 5.23–5.00 (m, 2H); 3.47 (s, 3H); 2.80–2.20 (m, 4H); 1.85–1.60 (m, 2H); 1.40–1.20 (m, 1H), 0.99–0.95 (apparent t, 6H). MS (M+H)$^+$=461.3; MS (M+Na)$^+$=483.3.

Example 7

(2R,3S) N1-[(3R)-1,3-dihydro-1-methyl-2-oxo-5-phenyl-2H-1,4-benzodiazepin-3-yl]-2-(2-methylpropyl)-3-propyl-butanediamide

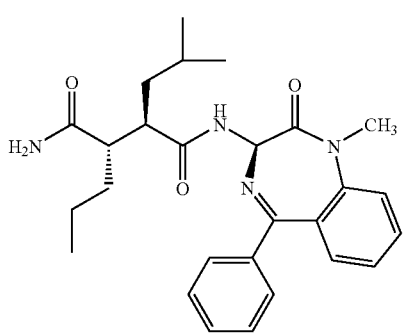

The product of Example 6 was hydrogenated by dissolution in methanol (0.25M), addition of an equal amount by weight of Pearlman's catalyst [Pd(OH)$_2$/C (20% Wt, Water %≦50)] and 30 eq. of 1,4-cyclohexadiene at room temperature. The solution was heated to reflux for 1 hr, then cooled to room temperature. Removal of volatiles and purification by flash chromatography using 4% methanol in CH$_2$Cl$_2$ gave the title compound. MS (M+H)$^+$=463.3; MS (M+Na)$^+$=485.3.

Example 8

(2R,3S) N1-[(3S)-1,3-dihydro-1-methyl-2-oxo-5-phenyl-2H-1,4-benzodiazepin-3-yl]-2-(2-methylpropyl)-3-propyl-butanediamide

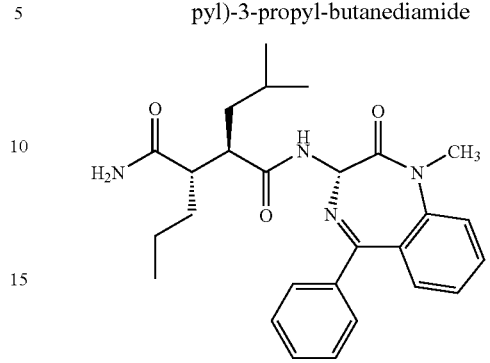

Using the product of Example 5 as starting material, and following the method of Example 7, the title compound was prepared. MS (M+H)$^+$=463.3; MS (M+Na)$^+$=485.3.

Example 9a (2R,3S) N1-[(3S)-1,3-dihydro-1-methyl-2-oxo-5-phenyl-2H-1,4-benzodiazepin-3-yl]-2-methyl-3-allyl-butanediamide

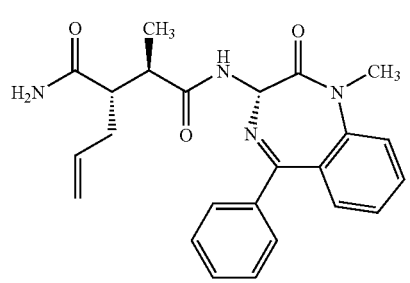

Following a procedure analogous to the preparation of Example 5, coupling the appropriate succinate ester, prepared using the method disclosed in PCT publication WO 98/51665, in place of (9), with (S)isomer of benzodiazepinone-(30) in Step 1, the title compound was prepared. MS (M+H)$^+$=419.1; (M+Na)$^+$=441.1.

Example 10

(2R) N1-[1,3-dihydro-1-methyl-2-oxo-5-phenyl-2H-1,4-benzodiazepin-3-yl]-2-methyl-butanediamide

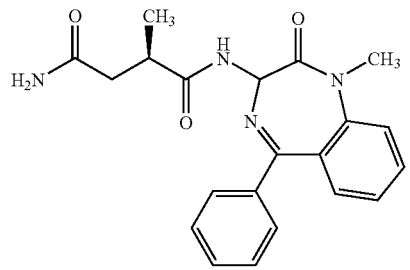

Following a procedure analogous to the preparation of Example 1 using the appropriate succinate ester (prepared by methods disclosed in Becket et al. (Synlett, 1993, pp.

137–138) and shown in Scheme 1), in place of ester (9) in Step 1, the title compound was prepared. MS (M+H)⁺=379.0

Example 11

(2R,3S) N1-[1,3-dihydro-2-oxo-5-phenyl-2H-1,4-benzodiazepin-3-yl]-2-(2-methylpropyl)-3-allyl-butanediamide

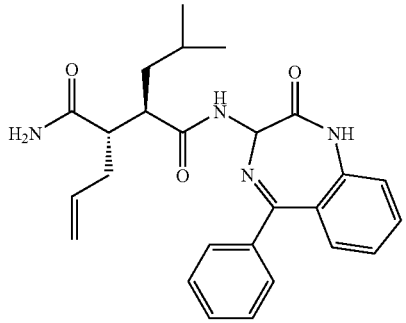

Following a procedure analogous to the preparation of Example 1 using 1,3-dihydro-3-amino-5-phenyl-2H-1,4-benzodiazepine-2-one in place of (30) in Step 1, the title compound was prepared. MS (M+H)⁺=447.2.

Example 12

(2R,3S) N1-[1,3-dihydro-1-methyl-2-oxo-5-phenyl-7-chloro-2H-1,4-benzodiazepin-3-yl]-2-(2-methyl-propyl)-3-allyl-butanediamide

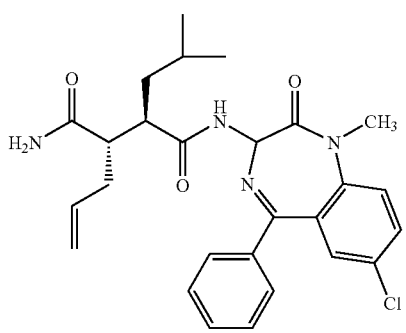

Following a procedure analogous to the preparation of Example 1 using 1,3-dihydro-1-methyl-3-amino-5-phenyl-7-chloro-2H-1,4-benzodiazepine-2-one in place of (30) in Step 1, the title compound was prepared. MS (M+H)⁺=495.0.

Example 12a (2R,3S) N1-[(3S)-1,3-dihydro-1-methyl-2-oxo-5-phenyl-7-chloro-2H-1,4-benzodiazepin-3-yl]-2-(2-methylpropyl)-3-allyl-butanediamide

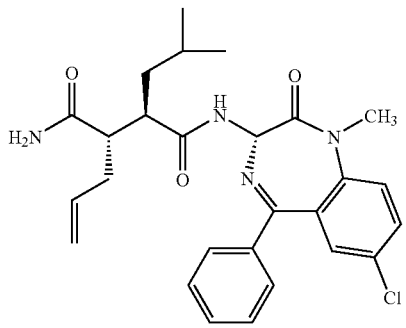

The product of Example 12 was separated into the (S)- and (R)-benzodiazepine diastereomers using a Chiralpack AD column, eluting with 1:1 n-hexane-i-propanol. The diastereomers were assigned on the basis of the elution order ((S)-diastereomer elutes second under these conditions), and the i-butyl signals in the H-NMR spectra, consistent with the elution order and H-NMR spectra of the products of Examples 5 and 6. In CDCl₃ the (S)-diastereomer shows two doublets (6H total) above 1 ppm and the (R)-diastereomer shows an apparent triplet (6H) above 1 ppm. MS (M+H)⁺=495.2; MS (M+Na)⁺=517.1.

Example 12b (2R,3S) N1-[(3R)-1,3-dihydro-1-methyl-2-oxo-5-phenyl-7-chloro-2H-1,4-benzodiazepin-3-yl]-2-(2-methylpropyl)-3-allyl-butanediamide

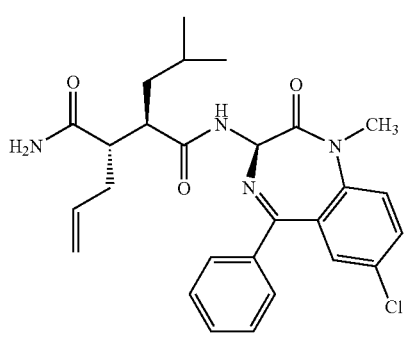

As described for Example 12a, the product of Example 12 was separated into the (S)- and (R)-benzodiazepine diastereomers using a Chiralpack AD column, eluting with 1:1 n-hexane-i-propanol, with the (R)-diastereomer eluting first under these conditions. In CDCl₃ the i-butyl signals for the (R)-diastereomer appear as an apparent triplet (6H) above 1 ppm. MS (M+H)⁺=495.2; MS (M+Na)⁺=517.1.

Example 13

(2R,3S) N1-[1,3-dihydro-1-methyl-2-oxo-5-(2-fluorophenyl)-7-chloro-2H-1,4-benzodiazepin-3-yl]-2-(2-methylpropyl)-3-allyl-butanediamide

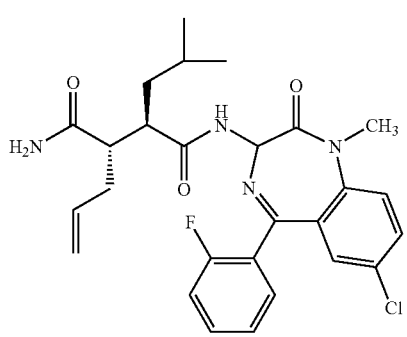

Following a procedure analogous to the preparation of Example 1 using 1,3-dihydro-1-methyl-3-amino-5-(2-fluorophenyl)-7-chloro-2H-1,4-benzodiazepine-2-one, prepared by methods known by one skilled in the art, in place of (30) in Step 1, the title compound was prepared. MS (M+H)⁺=513.3; MS (M+Na)⁺=535.2.

Example 13a (2R,3S) N1-[(3S)-1,3-dihydro-1-methyl-2-oxo-5-(2-fluorophenyl)-7-chloro-2H-1,4-benzodiazepin-3-yl]-2-(2-methylpropyl)-3-allyl-butanediamide

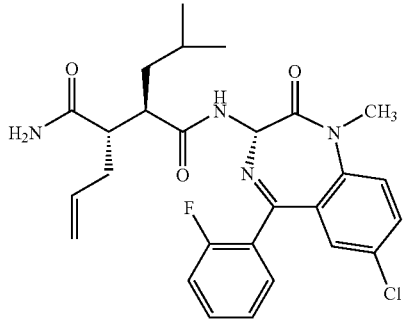

Following a procedure analogous to the preparation of Examples 12a and 12b, the (S)-benzodiazepine diastereomer of Example 13 was isolated. MS (M+H)$^+$=513.3; MS (M+Na)$^+$=535.2.

Example 13b (2R,3S) N1-[(3R)-1,3-dihydro-1-methyl-2-oxo-5-(2-fluorophenyl)-7-chloro-2H-1,4-benzodiazepin-3-yl]-2-(2-methylpropyl)-3-allyl-butanediamide

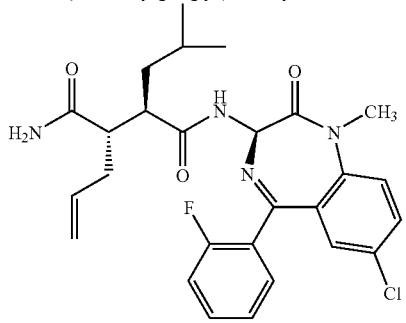

Following a procedure analogous to the preparation of Examples 12a and 12b, the (R)-benzodiazepine diastereomer of Example 13 was isolated. MS (M+H)$^+$=513.3; MS (M+Na)$^+$=535.2.

Example 14

(2S,3S) N1-[1,3-dihydro-1-methyl-2-oxo-5-phenyl-2H-1,4-benzodiazepin-3-yl]-2-(2-methylpropyl)-3-allyl-butanediamide

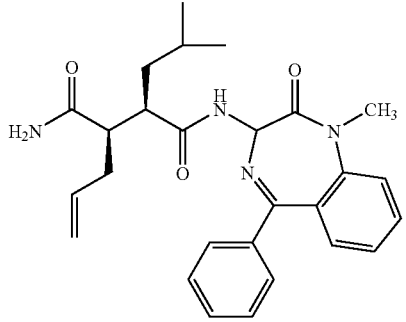

Following a procedure analogous to the preparation of Example 1 using the appropriate syn-succinate ester (prepared by methods disclosed in Becket et al. (Synlett, 1993, pp. 137–138) and shown in Scheme 1), in place of ester (9) in Step 1, the title compound was prepared. MS (M+H)$^+$=461.4; (M+Na)$^+$=483.4.

Example 15

(2R,3S) N1-[(3S)-1,3-dihydro-1-methyl-2-oxo-5-phenyl-7-chloro-2H-1,4-benzodiazepin-3-yl]-2-(2-methylpropyl)-3-propyl-butanediamide

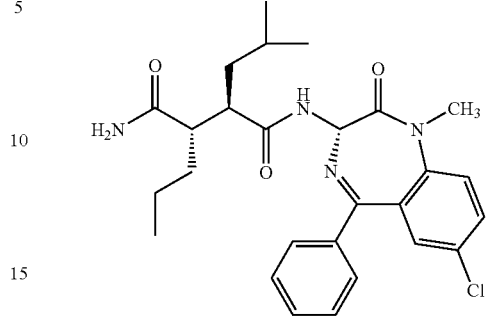

Using the product of Example 12a as starting material, and following the reduction procedure of Example 7, the title compound was prepared. MS (M+H)$^+$=497.2; MS (M+Na)$^+$=519.1

Example 16

(2R,3S) N1-[(3S)-1,3-dihydro-1-methyl-2-oxo-5-(2-fluorophenyl)-7-chloro-2H-1,4-benzodiazepin-3-yl]-2-(2-methylpropyl)-3-propyl-butanediamide

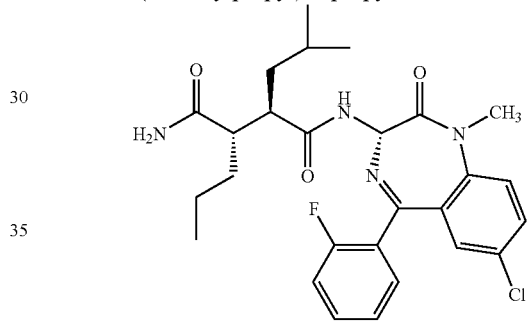

Using the product of Example 13a as starting material, and following the reduction procedure of Example 7, the title compound was prepared. MS (M+H)$^+$=515.3; MS (M+Na)$^+$=537.2

Example 17

(2R,3S) N1-[1,3-dihydro-1-methyl-2-oxo-5-(4-fluorophenyl)-2H-1,4-benzodiazepin-3-yl]-2-(2-methylpropyl)-3-allyl-butanediamide

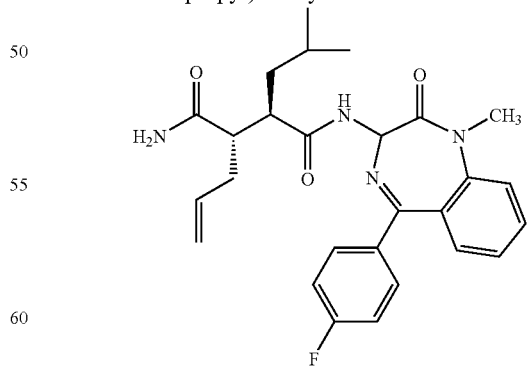

Following a procedure analogous to the preparation of Example 1 using 1,3-dihydro-1-methyl-3-amino-5-(4-fluorophenyl)-2H-1,4-benzodiazepine-2-one, prepared by methods known to one skilled in the art, in place of (30) in Step 1, the title compound was prepared. MS (M+H)$^+$=479.3.

Example 17a (2R,3S) N1-[(3S)-1,3-dihydro-1-methyl-2-oxo-5-(4-fluorophenyl)-2H-1,4-benzodiazepin-3-yl]-2-(2-methylpropyl)-3-allyl-butanediamide

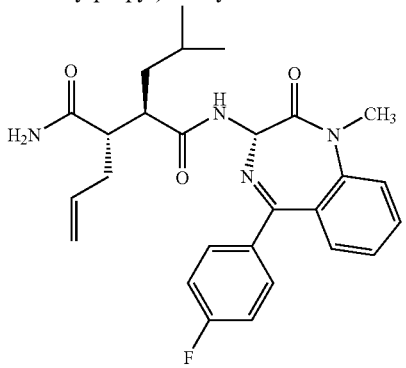

Following a procedure analogous to the preparation of Examples 12a and 12b, the (S)-benzodiazepine diastereomer of Example 13 was isolated. MS (M+H)$^+$=479.3; MS (M+Na)$^+$=501.2.

Example 17b (2R,3S) N1-[(3R)-1,3-dihydro-1-methyl-2-oxo-5-(4-fluorophenyl)-2H-1,4-benzodiazepin-3-yl]-2-(2-methylpropyl)-3-allyl-butanediamide

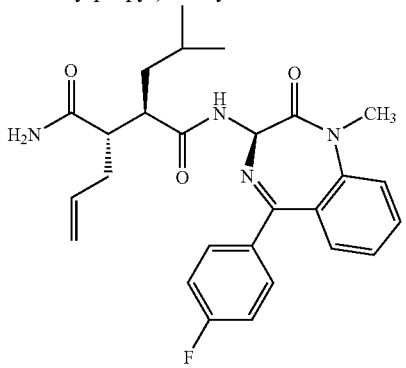

Following a procedure analogous to the preparation of Examples 12a and 12b, the (R)-benzodiazepine diastereomer of Example 13 was isolated. MS (M+H)$^+$=479.3; MS (M+Na)$^+$=501.2.

Example 18

(2R,3S) N1-[1,3-dihydro-1-methyl-2-oxo-5-(pyrid-2-yl)-2H-1,4-benzodiazepin-3-yl]-2-(2-methylpropyl)-3-allyl-butanediamide

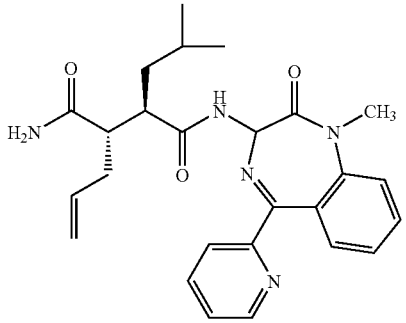

Following a procedure analogous to the preparation of Example 1 using 1,3-dihydro-1-methyl-3-amino-5-(pyrid-2-yl)-2H-1,4-benzodiazepine-2-one, prepared by methods known to one skilled in the art, in place of (30) in Step 1, the title compound was prepared. MS (2M+Na)$^+$=945.6.

Example 19

(2R,3S) N1-[1,3-dihydro-1-methyl-2-oxo-5-(N-morpholino)-2H-1,4-benzodiazepin-3-yl]-2-(2-methylpropyl)-3-allyl-butanediamide

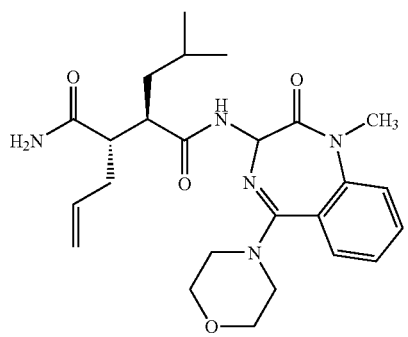

Following a procedure analogous to the preparation of Example 1 using 1,3-dihydro-1-methyl-3-amino-5-(N-morpholinyl)-2H-1,4-benzodiazepine-2-one, prepared by methods known to one skilled in the art, in place of (30) in Step 1, the title compound was prepared. Mp 145–151° C.; MS (M+H)$^+$=470.

Example 20

(2R,3S) N1-[1,3-dihydro-1-methyl-2-oxo-5-(dimethylamino)-2H-1,4-benzodiazepin-3-yl]-2-(2-methylpropyl)-3-allyl-butanediamide

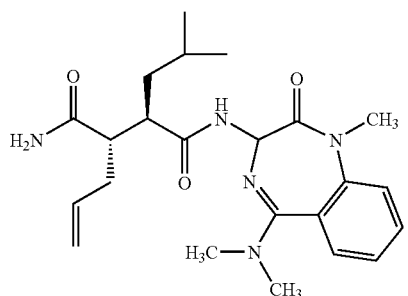

Following a procedure analogous to the preparation of Example 1 using 1,3-dihydro-1-methyl-3-amino-5-(dimethylamino)-2H-1,4-benzodiazepine-2-one, prepared by methods known to one skilled in the art, in place of (30) in Step 1, the title compound was prepared. Mp 230–232° C.; MS (M+H)$^+$=428.

Example 21

(2R,3S) N1-[1,3-dihydro-1-methyl-2-oxo-5-(N-methyl-N-phenylamino)-2H-1,4-benzodiazepin-3-yl]-2-(2-methylpropyl)-3-allyl-butanediamide

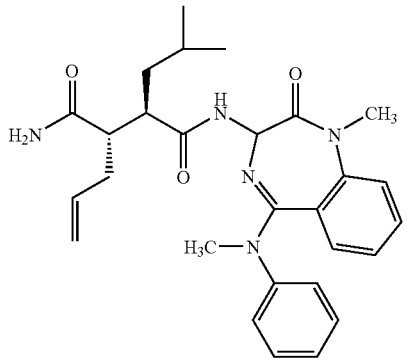

Following a procedure analogous to the preparation of Example 1 using 1,3-dihydro-1-methyl-3-amino-5-(N-methyl-N-phenylamino)-2H-1,4-benzodiazepine-2-one, prepared by methods known to one skilled in the art, in place of (30) in Step 1, the title compound was prepared. melting point 266.6–267.8° C.; MS (M+H)$^+$=490.

Example 22

(2R,3S) N1-[1,3-dihydro-1-methyl-2-oxo-5-(N-piperidinyl)-2H-1,4-benzodiazepin-3-yl]-2-(2-methylpropyl)-3-allyl-butanediamide

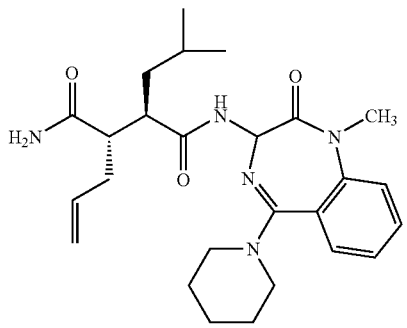

Following a procedure analogous to the preparation of Example 1 using 1,3-dihydro-1-methyl-3-amino-5-(N-piperidinyl)-2H-1,4-benzodiazepine-2-one, prepared by methods known to one skilled in the art, in place of (30) in Step 1, the title compound was prepared. melting point 231–238° C.; MS (M+H)$^+$=468.

Example 23

(2R,3S) N1-[1,3-dihydro-1-methyl-2-oxo-5-(N-homopiperidinyl)-2H-1,4-benzodiazepin-3-yl]-2-(2-methylpropyl)-3-allyl-butanediamide

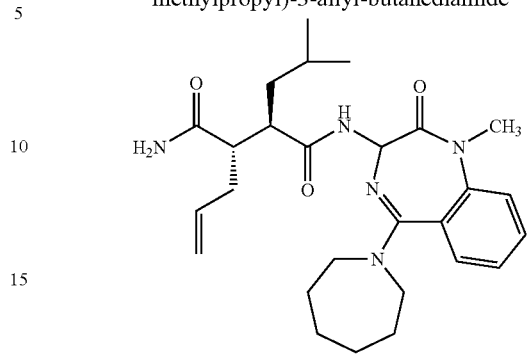

Following a procedure analogous to the preparation of Example 1 using 1,3-dihydro-1-methyl-3-amino-5-(N-homopiperidinyl)-2H-1,4-benzodiazepine-2-one, prepared by methods known to one skilled in the art, in place of (30) in Step 1, the title compound was prepared. melting point 232–237° C.; MS (M+H)$^+$=482.

Example 24

(2R,3S) N1-[1,3-dihydro-1-methyl-2-oxo-5-(3-methoxyphenyl)-2H-1,4-benzodiazepin-3-yl]-2-(2-methylpropyl)-3-allyl-butanediamide

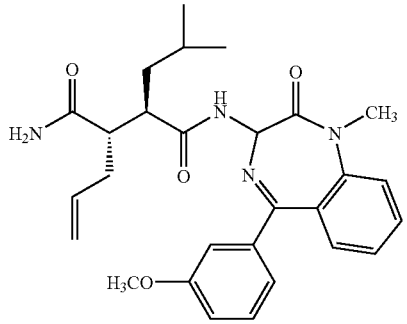

Following a procedure analogous to the preparation of Example 1 using 1,3-dihydro-1-methyl-3-amino-5-(3-methoxyphenyl)-2H-1,4-benzodiazepine-2-one, prepared by methods known to one skilled in the art, in place of (30) in Step 1, the title compound was prepared. melting point 225–230° C.; MS (M+H)$^+$=491.

Step 1: Preparation of 24';

This was prepared using the standard HATU coupling conditions with 97 (1.03 g, 3.5 mmol) to give 24' (0.48 g, 25%) as a colorless oil (mixture of diastereomers): $^1$H NMR (500 MHz, CDCl$_3$) δ 7.63 (t, 1H), 7.33–7.38 (m, 2H0, 7.24–7.30 (m, 2H), 7.05 (d, 1H), 7.00 (dd, 1H), 5.65–5.8 (m, 1H), 5.57 (d, 1H), 4.92–5.20 (m, 2H0, 3.80 (s, 3H), 3.77 (s, 3H), 3.48 (s, 3H) 2.27–2.67 (m, 3H), 1.75–1.80 (m, 1H0, 1.60–1.63 (m, 1H), 1.48 (s, 9H), 1.46 (s, 9H), 1.22–1.26 (m, 1H0, 0.88–1.00 (m, 3H), 0.80 (d, 3H).

Step 2: Preparation of 24";

This was prepared using the standard t-Bu ester deprotection with TFA. The acid intermediate 24" is a mixture of diastereomers: $^1$H NMR (500 MHz, CDCl$_3$) 9.75 (bs, 1H), 7.75–7.85 (m, 1H), 7.00–7.51 (m, 7H), 5.70–5.80 (m, 2H), 5.05–5.15 (m, 2H), 3.80 (s, 3H), 3.53, 3.50 (s, 3H), 5.74–2.93 (m, 1H0, 2.25–2.53 (m, 1H), 1.53–1.80 (m, 1H), 1.25–1.30 (m, 1H0, 0.93 (d, 3H), 0.89 (d, 3H); API MS m/z=492 [$C_{28}H_{33}N_3O_5$+H]$^+$.

Step 3: Preparation of Example 24;

This was prepared using the HATU mediated amide formation.

mp 225–230° C.; $^1$H NMR (500 MHz, CD$_3$OD) δ 7.55–7.70 (m, 2H), 7.27–7.33 (m, 3H), 7.24 (s, 1H), 7.0–7.07 (m, 2H) 5.70–5.77 (m, 1H), 5.45 (d, 1H), 4.93–5.10 (m, 2H0, 3.78, 3.76 (s, 3H0, 3.48 (m, 3H), 2.75–2.85 (m, 1H), 2.27–2.50 (m, 2H), 1.53–1.71 (m, 2H), 1.10–1.25 (m, 1H), 0.80–1.00 (m, 6H); IR (KBr) 3423, 2956, 1655, 1601, 1326 cm$^{-1}$; API MS m/z=491 [$C_{28}H_{34}N_4O_4$+H]$^+$; Anal. Calcd. For $C_{28}H_{34}N_4O_4$-0.5 H$_2$O: C, 67.3; H, 7.06; N, 11.21. Found: C, 67.52; H, 6.85; N, 11.21.

Example 25

(2R,3S) N1-[1,3-dihydro-1-methyl-2-oxo-5-(pyrid-4-yl)-2H-1,4-benzodiazepin-3-yl]-2-(2-methylpropyl)-3-allyl-butanediamide

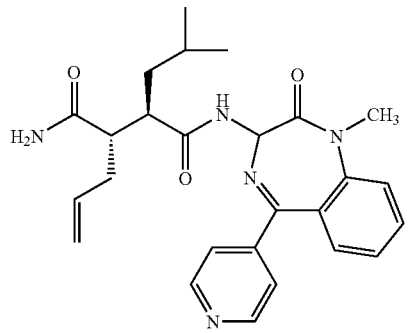

Following a procedure analogous to the preparation of Example 1 using methods known to one skilled in the art, the title compound was prepared. MS (M+H)$^+$=462.

Example 26

(2R,3S) N1-[1,3-dihydro-1-methyl-2-oxo-5-phenyl-7-methoxy-2H-1,4-benzodiazepin-3-yl]-2-(2-methyl-propyl)-3-allyl-butanediamide

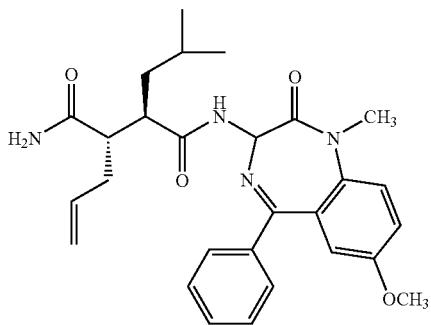

Following a procedure analogous to the preparation of Example 1 using reagents known to one skilled in the art, the title compound was prepared. m.pt. 244–255° C.; MS (M+H)$^+$=491.

Example 27

(2R,3S) N1-[1,3-dihydro-1-methyl-2-oxo-5-(pyrid-3-yl)-2H-1,4-benzodiazepin-3-yl]-2-(2-methylpropyl)-3-allyl butanediamide

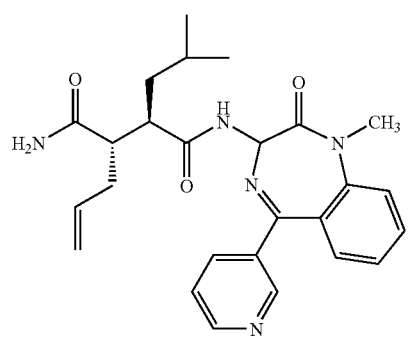

Following a procedure analogous to the preparation of Example 1 using reagents known to one skilled in the art, the title compound was prepared. m.pt. 251–253° C.; MS (M+H)$^+$=462.

Example 28a (2R,3S) N1-[(3S)-1,3-dihydro-1-methyl-2-oxo-5-phenyl-2H-1,4-benzodiazepin-3-yl]-2-(2-methylpropyl)-3-(cyclopropylmethyl)-butanediamide

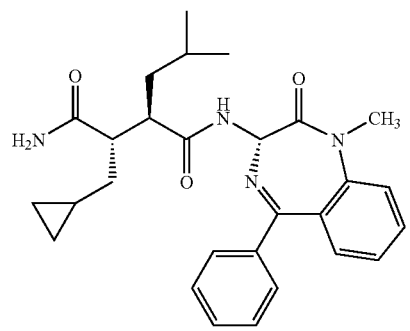

A procedure analogous to the preparation of Example 5 was followed. The appropriate succinate ester was prepared using the method disclosed in PCT publication WO 98/51665, using cyclopropylmethyl iodide for reagent R$^3$—X in place of allyl bromide (see Scheme 2). This succinate half-ester, a mixture of syn- and anti-isomers, was coupled to the (S) benzodiazepinone-(30) using the procedures of Example 1, Step 1. After Steps 2 and 3, the mixture of butanediamide isomers was separated using silica gel chromatography to provide Example 28a. MS (M+H)$^+$=475.

Example 28b (2R,3R)N1-[(3S)-1,3-dihydro-1-methyl-2-oxo-5-phenyl-2H-1,4-benzodiazepin-3-yl]-2-(2-methylpropyl)-3-(cyclopropylmethyl)-butanediamide

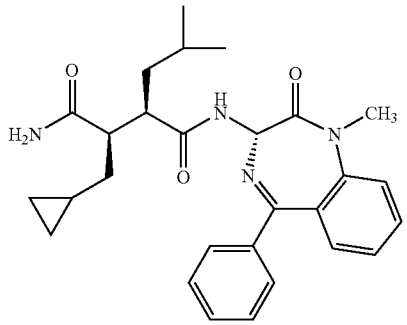

From the product of Step 3 of Example 28a, the other succinate isomer, Example 28b, was isolated. Mp 146–148° C.; MS (M+H)$^+$=475.

Example 29

(2R,3S) N1-[1,3-dihydro-1-methyl-2-oxo-5-(3-fluorophenyl)-2H-1,4-benzodiazepin-3-yl]-2-(2-methylpropyl)-3-allyl-butanediamide

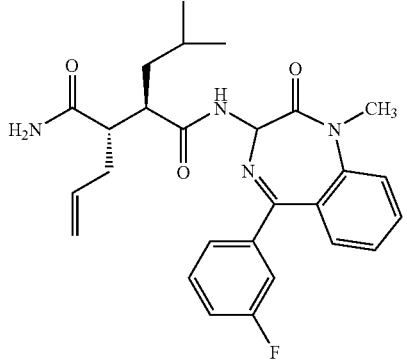

Following a procedure analogous to the preparation of Example 1 using 1,3-dihydro-1-methyl-3-amino-5-(3-fluorophenyl)-2H-1,4-benzodiazepine-2-one, prepared by methods known to one skilled in the art, in place of (30) in Step 1, the title compound was prepared. MS (M+H)$^+$=479.3.; (M+Na)$^+$=501.3.

Example 29a (2R,3S) N1-[(3S)-1,3-dihydro-1-methyl-2-oxo-5-(3-fluorophenyl)-2H-1,4-benzodiazepin-3-yl]-2-(2-methylpropyl)-3-allyl-butanediamide

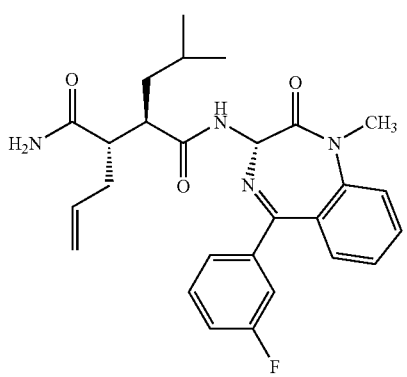

Following a procedure analogous to the preparation of Examples 12a and 12b, the (S)-benzodiazepine diastereomer of Example 29 was isolated. MS (M+H)$^+$=479.3.

Example 29b (2R,3S) N1-[(3R)-1,3-dihydro-1-methyl-2-oxo-5-(3-fluorophenyl)-2H-1,4-benzodiazepin-3-yl]-2-(2-methylpropyl)-3-allyl-butanediamide

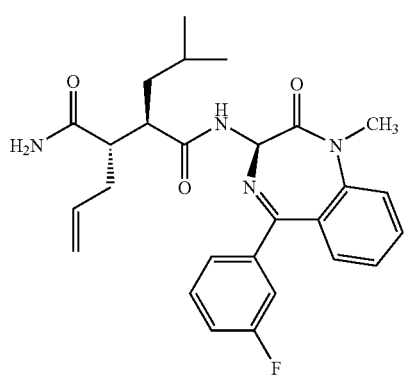

Following a procedure analogous to the preparation of Examples 12a and 12b, the (R)-benzodiazepine diastereomer of Example 29 was isolated. MS (M+H)$^+$=479.3.

Example 30

(2R,3S) N1-[(3S)-1,3-dihydro-1-methyl-2-oxo-5-phenyl-2H-1,4-benzodiazepin-3-yl]-2-(2-methylpropyl)-3-(3-buten-1-yl)-butanediamide

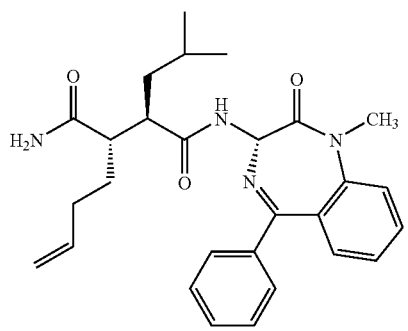

A procedure analogous to the preparation of Example 5 was followed. The appropriate succinate ester was prepared using the method disclosed in PCT publication WO 98/51665), using 3-butenyl bromide for R$^3$—X in place allyl bromide (see Scheme 2). The anti-succinate half-ester was coupled to (S)-isomer benzodiazepine (30) using the procedures of Step 1. After Steps 2 and 3, the title compound was isolated. MS (M+H)$^+$=475.3; (M+Na)$^+$=497.3.

Example 31

(2R,3S) N1-[(3S)-1,3-dihydro-1-methyl-2-oxo-5-phenyl-2H-1,4-benzodiazepin-3-yl]-2-(2-methylpropyl)-3-(cyclopentylethyl)-butanediamide

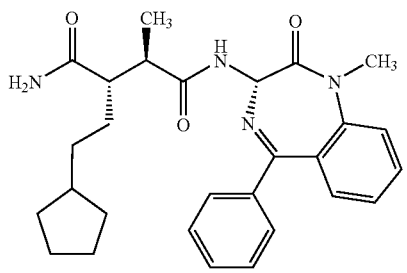

A procedure analogous to the preparation of Example 5 was followed. The appropriate succinate ester was prepared using the method disclosed in PCT publication WO 98/51665, using 2-(cyclopentyl)ethyl iodide for $R^3$—X in place of allyl bromide (see Scheme 2). The anti-succinate half-ester was coupled to (S)-isomer benzodiazepine (30) using the procedures of Step 1. After Steps 2 and 3, the title compound was isolated. MS $(M+H)^+=475$; $(M+Na)^+=497.2$.

Example 32a (2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-(3-buten-1-yl)-butanediamide

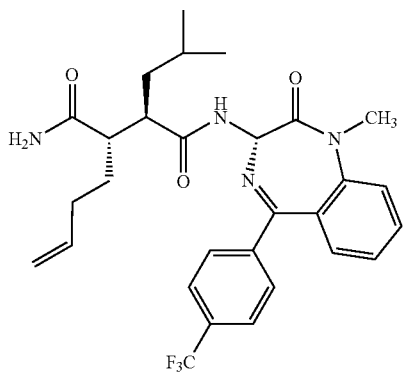

A procedure analogous to the preparation of Example 5 was followed. The succinate ester of Example 30 was employed. The anti-succinate half-ester was coupled to (S)-1,3-dihydro-1-methyl-3-amino-S-(4-trifluoromethylphenyl)-2H-1,4-benzodiazepine-2-one using the procedures of Step 1. The required (S)-3-aminobenzodiazepine was prepared by HBr deprotection of the corresponding benzyloxycarbonyl derivative, which was separated from the (R)-isomer using chiral chromatography. The racemic Cbz-aminobenzodiazepine was prepared using the method of Sherrill and Sugg (J. Org. Chem. 1995, 60, 730–734). After Steps 2 and 3, the title compound was isolated. The stereochemical assignment of Examples 32a and 32b was performed following the H-NMR method of Examples 12a and 12b. MS $(M+H)^+=543.2$; $(M+Na)^+=565.3$.

Example 32b (2R,3S) N1-[(3R)-1,3-dihydro-1-methyl-2-oxo-5-(4-trifluoromethylphenyl)-2H-1,4-benzodiazepin-3-yl]-2-(2-methylpropyl)-3-(3-buten-1-yl)-butanediamide

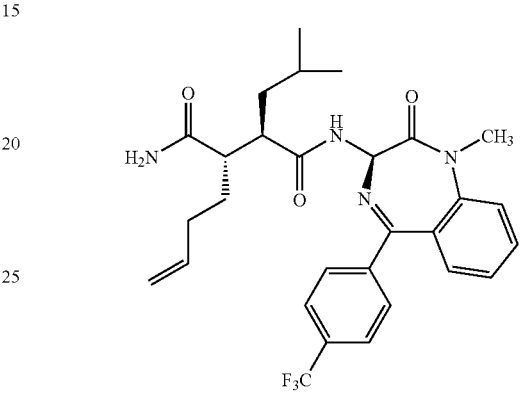

A procedure analogous to the preparation of Example 32a was followed using (R)-1,3-dihydro-1-methyl-3-amino-5-(4-trifluoromethylphenyl)-2H-1,4-benzodiazepine-2-one in Step 1. MS $(M+H)^+=543.2$; $(M+Na)^+=565.3$.

Example 33

(2R,3S) N1-[1,3-dihydro-1-methyl-2-oxo-5-(4-trifluoromethylphenyl)-2H-1,4-benzodiazepin-3-yl]-2-(2-methylpropyl)-3-allyl-butanediamide

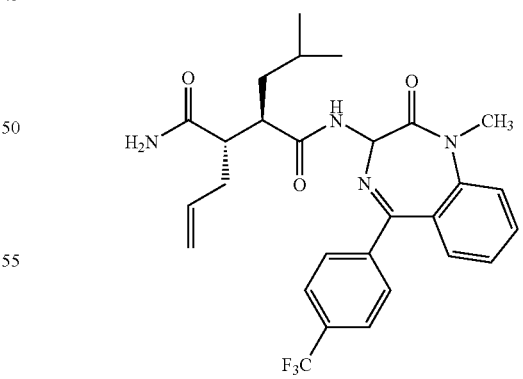

Following a procedure analogous to the preparation of Example 1 using 1,3-dihydro-1-methyl-3-amino-5-(4-fluoromethylphenyl)-2H-1,4-benzodiazepine-2-one, prepared by methods known to one skilled in the art, in place of (30) in Step 1, the title compound was prepared. MS $(M+H)^+=529.2$.

Example 33a (2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-allyl-butanediamide

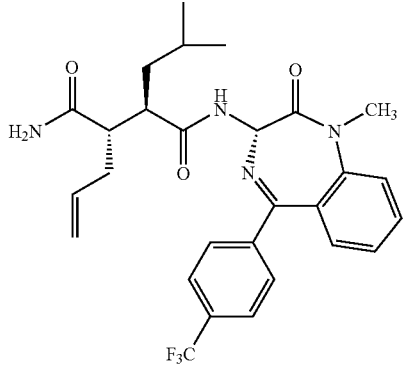

Following a procedure analogous to the preparation of Examples 12a and 12b, the (S)-benzodiazepine diastereomer of Example 33 was isolated. MS (M+H)$^+$=529.2.

Example 33b (2R,3S) N1-[(3R)-1,3-dihydro-1-methyl-2-oxo-5-(4-trifluoromethylphenyl)-2H-1,4-benzodiazepin-3-yl]-2-(2-methylpropyl)-3-allyl-butanediamide

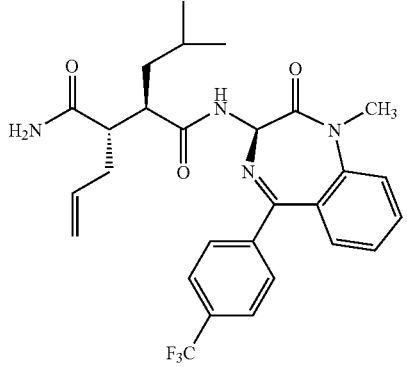

Following a procedure analogous to the preparation of Examples 12a and 12b, the (S)-benzodiazepine diastereomer of Example 33 was isolated. MS (M+H)$^+$=529.2; (M+Na)$^+$=551.2.

Example 34

(2R,3S) N1-[(3S)-1,3-dihydro-1-methyl-2-oxo-5-phenyl-2H-1,4-benzodiazepin-3-yl]-2-(2-methylpropyl)-3,3-diallyl-butanediamide

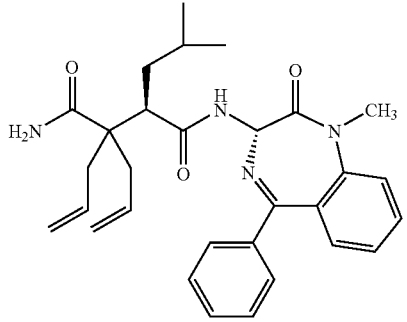

A procedure analogous to the preparation of Example 5 was followed. The diallyl succinate ester was prepared using the method of Curtin et al. (Biorg. Med. Chem. Lett., 8, 1998, 1443–8). The succinate half-ester was coupled to the (S)isomer of benzodiazepinone (30) using the procedures of Step 1. After Steps 2 and 3, the title compound was isolated. MS (M+Na)$^+$=523.2.

Example 35a (2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-n-butyl-butanediamide

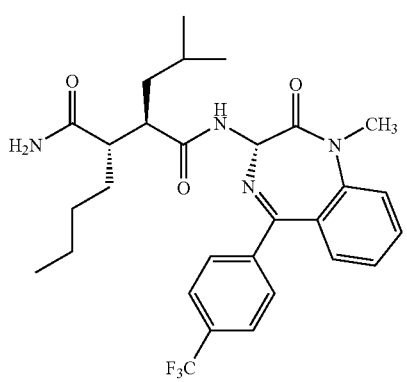

Following the reduction procedure of Example 7, the product of Example 32a was converted to the title compound. MS (M+H)$^+$=545.2; (M+Na)$^+$=567.3.

Example 36

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-propyl-butanediamide

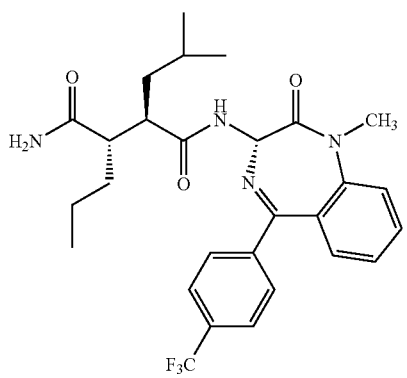

Following the reduction procedure of Example 7, the product of Example 33a was converted to the title compound. MS (M+H)$^+$=531.2; (M+Na)$^+$=553.2.

Example 37

(2R,3S) N1-[(3S)-1,3-dihydro-1-methyl-2-oxo-5-(4-chlorophenyl)-2H-1,4-benzodiazepin-3-yl]-2-(2-methylpropyl)-3-(3-buten-1-yl)-butanediamide

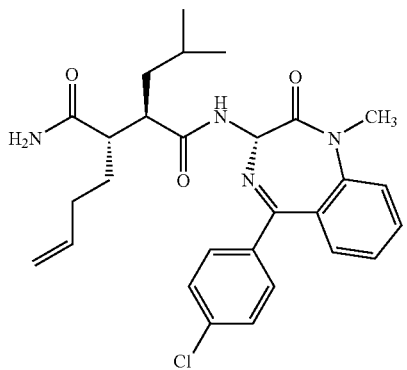

A procedure analogous to the preparation of Example 5 was followed. The succinate ester of Example 30 was employed and was coupled to (S)-2,3-dihydro-1-methyl-3-amino-5-(4-chlorophenyl)-1H-1,4-benzodiazepine-2-one using the procedures of Step 1. The required (S)-3-aminobenzodiazepine was prepared by HBr deprotection of the corresponding benzyloxycarbonyl derivative, which was separated from the (R)-isomer using chiral chromatography. The racemic Cbz-aminobenzodiazepine was prepared using the method of Sherrill and Sugg (J. Org. Chem. 1995, 60, 730–734). After Steps 2 and 3, the title compound was isolated. The stereochemical assignment was performed following the H-NMR method of Example 12a. MS (M+H)$^+$=509.2.

Example 38

(2R,3S) N1-[(3S)-1,3-dihydro-1-methyl-2-oxo-5-(4-chlorophenyl)-2H-1,4-benzodiazepin-3-yl]-2-(2-methylpropyl)-3-n-butyl-butanediamide

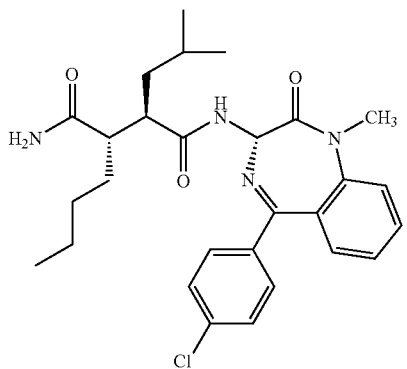

The product of Example 37 was taken up in ethanol (0.25M) together with 10% by weight Wilkinson's catalyst (chlorotris(triphenylphosphine) rhodium (I)). The mixture was shaken under 50 psi hydrogen overnight. The reaction mixture was filtered through a layer of celite and the solvent was evaporated. The residue was purified by flash chromatography on silica gel using 4% methanol in CH$_2$Cl$_2$ to provide the title compound. MS (M+H)$^+$=511.2; (M+Na)$^+$=533.2.

Example 39

(2R,3S) N1-[(3S)-1,3-dihydro-1-methyl-2-oxo-5-phenyl-2H-1,4-benzodiazepin-3-yl]-2-(2-methylpropyl)-3-allyl-N4-[benzyl]-butanediamide

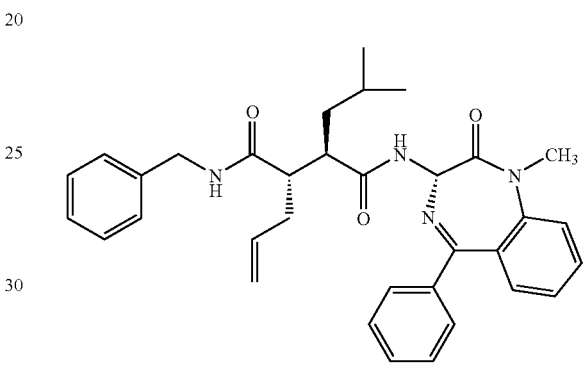

Following a procedure analogous to the preparation of Example 5 using benzylamine in place of ammonia in Step 3, the title compound was prepared. MS (M+H)$^+$=551.2; (M+Na)$^+$=565.3.

Example 40

(2R,3S) N1-[1,3-dihydro-1-methyl-2-oxo-5-methyl-2H-1,4-benzodiazepin-3-yl]-2-(2-methylpropyl)-3-allyl-butanediamide

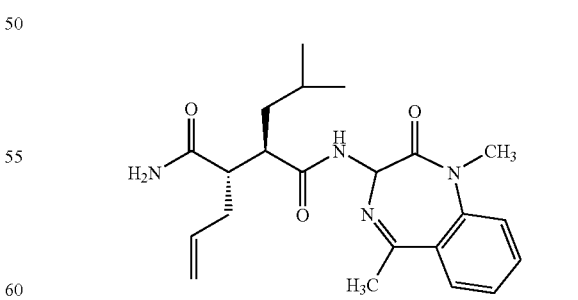

Following a procedure analogous to the preparation of Example 1 using 1,3-dihydro-1-methyl-3-amino-5-methyl-2H-1,4-benzodiazepine-2-one in place of (30) in Step 1, the title compound was prepared. MS (M+H)$^+$=399.1.

Example 41

(2R,3S) N1-[1,3-dihydro-1-methyl-2-oxo-5-n-butyl-2H-1,4-benzodiazepin-3-yl]-2-(2-methylpropyl)-3-allyl-butanediamide

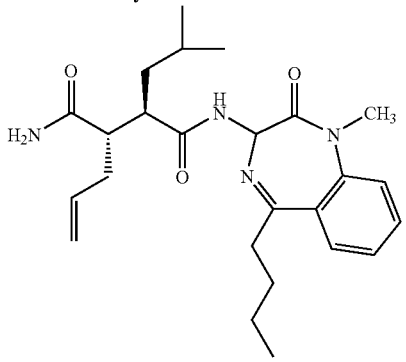

Following a procedure analogous to the preparation of Example 1 using 1,3-dihydro-1-methyl-3-amino-5-(n-butyl)-2H-1,4-benzodiazepine-2-one in place of (30) in Step 1, the title compound was prepared. The benzodiazepine diastereomers, Example 41a (3S) isomer and 41b (3R) isomer, were separated by silica gel chromatography. MS (M+H)$^+$=441.2.

Example 42

(2R,3S) N1-[1,3-dihydro-1-methyl-2-oxo-5-(2-methylpropyl)-2H-1,4-benzodiazepin-3-yl]-2-(2-methylpropyl)-3-allyl-butanediamide

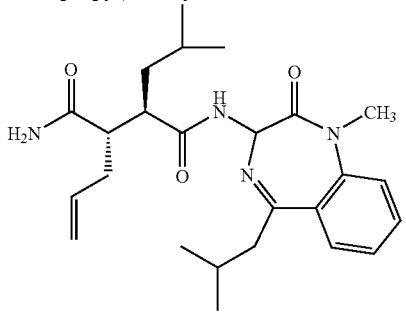

Following a procedure analogous to the preparation of Example 1 using 1,3-dihydro-1-methyl-3-amino-5-(i-butyl)-2H-1,4-benzodiazepine-2-one in place of (30) in Step 1, the title compound was prepared. MS (M+H)$^+$=441.2.

Example 43a (2R,3S) N1-[(3S)-1,3-dihydro-1-methyl-2-oxo-5-(4-chlorophenyl)-2H-1,4-benzodiazepin-3-yl]-2-(2-methylpropyl)-3-allyl-butanediamide

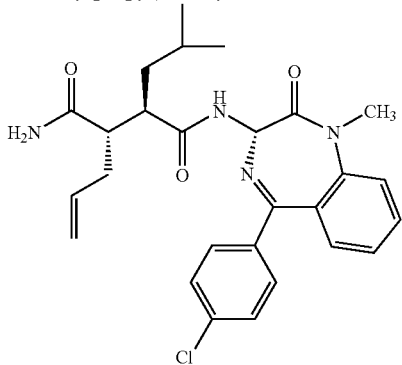

Following a procedure analogous to the preparation of Example 1 using 1,3-dihydro-1-methyl-3-amino-5-(4-chlorophenyl)-2H-1,4-benzodiazepine-2-one in place of (30) in Step 1, the mixture of benzodiazepine diastereomers of the title compound was prepared. The isomers were separated using reverse phase chromatography (C-18 column, isocratic eluent composed of 65% 90:10 water:acetonitrile and 35% 10:90 water:acetonitrile). The first eluting isomer was assigned the (S)-benzodiazepine configuration using the H-NMR method described for Example 12a. The required aminobenzodiazepine was prepared using the method of Sherrill and Sugg (J. Org. Chem. 1995, 60, 730–734). MS (M+H)$^+$=495.

Example 44a (2R,3S) N1-[(3S)-1,3-dihydro-1-ethyl-2-oxo-5-phenyl-2H-1,4-benzodiazepin-3-yl]-2-(2-methylpropyl)-3-allyl-butanediamide

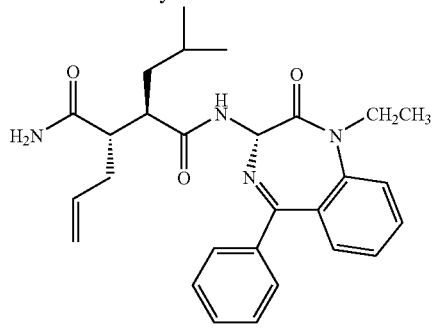

Following a procedure analogous to the preparation of Example 1 using 1,3-dihydro-1-ethyl-3-amino-5-phenyl-2H-1,4-benzodiazepine-2-one in place of (30) in Step 1, the title compound was prepared. The required aminobenzodiazepine was prepared using the method of Sherrill and Sugg (J. Org. Chem. 1995, 60, 730–734). The benzodiazepine diastereomers of the product were separated using reverse phase HPLC as described for Example 43a. The first eluting isomer was assigned the (S)-benzodiazepine configuration using the H-NMR method described for Example 12a. MS (M+H)$^+$=475.

Example 45a (2R,3S) N1-[(3S)-1,3-dihydro-1-propyl-2-oxo-5-phenyl-2H-1,4-benzodiazepin-3-yl]-2-(2-methylpropyl)-3-allyl-butanediamide

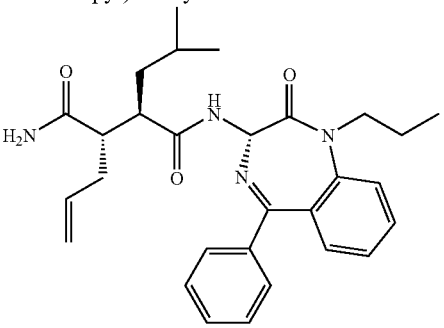

Following a procedure analogous to the preparation of Example 1 using 1,3-dihydro-1-(n-propyl)-3-amino-5-phenyl-2H-1,4-benzodiazepine-2-one in place of (30) in Step 1, the title compound was prepared as a mixture of benzodiazepine diastereomers, which were separated using reverse phase HPLC as described for Example 43a. The first eluting isomer was assigned the (S)-benzodiazepine configuration using the H-NMR method described for Example 12a. The required aminobenzodiazepine was prepared using the method of Sherrill and Sugg (J. Org. Chem. 1995, 60, 730–734. MS (M+H)+=489.

Example 45b (2R,3S) N1-[(3R)-1,3-dihydro-1-propyl-2-oxo-5-phenyl-2H-1,4-benzodiazepin-3-yl]-2-(2-methylpropyl)-3-allyl-butanediamide Following the procedure of Example 45a, the second eluting isomer was isolated and assigned the (R)benzodiazepine configuration using the H-NMR method described for Example 12b. MS (M+H)+=489.

Example 46

(2R,3S) N1-[1,3-dihydro-1-(isopropyl)-2-oxo-5-phenyl-2H-1,4-benzodiazepin-3-yl]-2-(2-methylpropyl)-3-allyl-butanediamide

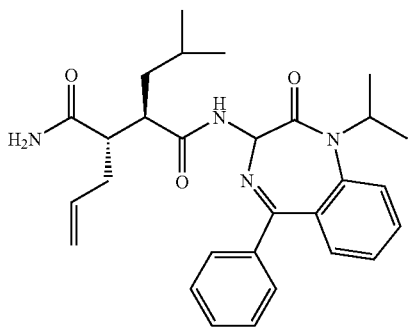

Following a procedure analogous to the preparation of Example 1 using 1,3-dihydro-1-(i-propyl)-3-amino-5-phenyl-2H-1,4-benzodiazepine-2-one in place of (30) in Step 1, the title compound was prepared. The required aminobenzodiazepine was prepared using the method of Sherrill and Sugg (J. Org. Chem. 1995, 60, 730–734). MS (M+H)+=489.

Example 47

(2R,3S) N1-[6,7-dihydro-5-methyl-6-oxo-5H-dibenz[b,d]azepin-7-yl]-2-(2-methylpropyl)-3-allyl-butanediamide Step 1: Preparation of Compound 47';

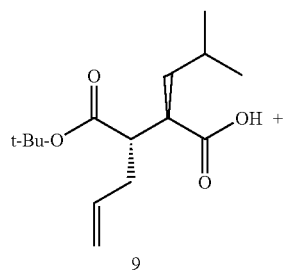

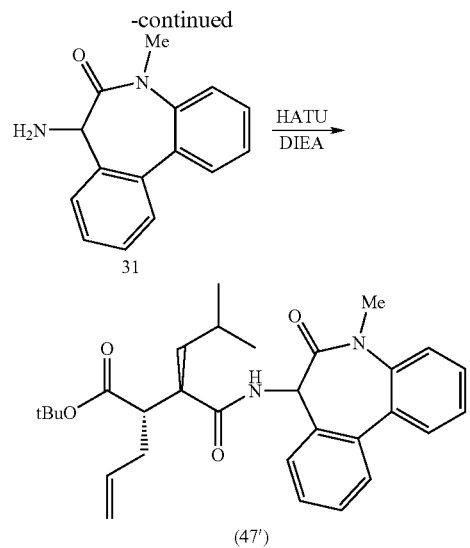

To a solution of amine 31, (for preparation see Audia, J. E., PCT patent application WO 99/32453) (0.42 g, 1.76 mmol), succinate 9, (0.52 g, 1.94 mmol), and DMF (50 mL) at 0° C. was added HATU (0.87 g, 2.29 mmol), and finally DIPEA (1.23 mL, 7.05 mmol). The solution was allowed to warm to room temperature while stirring for 18 h. The DMF was removed under reduced pressure and the residue was dissolved in ethyl acetate (200 mL), washed with 0.1 N HCl (2×100 mL), 5% aqueous NaHCO$_3$ (2×100 mL), dried over anhydrous Na$_2$SO$_4$, and concentrated to yield a brown oil. The crude material was further purified via silica gel column chromatography (1% MeOH, 99% CH$_2$Cl$_2$) to yield 47' (0.61 g, 70.5%) as a pale yellow solid.

$^1$H NMR (300 MHz, CDCl$_3$) δ0.87–1.42 (m, 9H), 1.48 (d, 9H), 2.21–2.79 (m, 4H), 3.38 (s, 3H), 4.92–5.11 (m, 3H), 5.41 (d, 1H), 5.72 (m, 1H), 7.29–7.65 (m, 8H) CI MS m/z=491 [C$_{30}$H$_{38}$N$_2$O$_4$+H]+.

Step 2: Preparation of Compound 47";

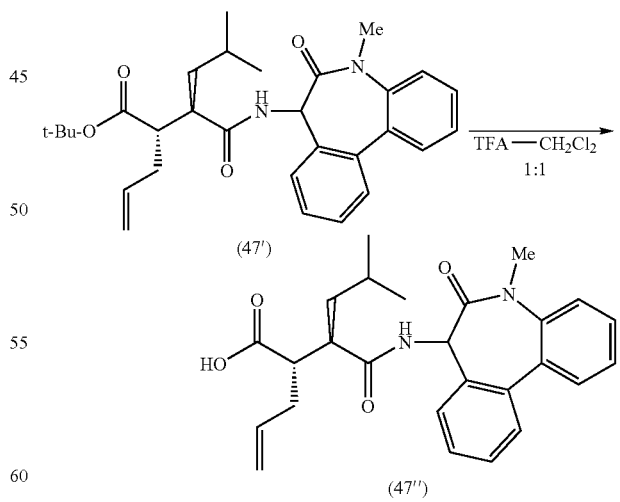

t-Butyl ester 47' (0.61 g, 1.24 mmol) was dissolved in TFA (15 mL) and stirred for 4 h at room temperature under N$_2$. The TFA was removed under reduced pressure, the residue was dissolved in ethyl acetate (50 mL), washed with a saturated solution of aqueous NaHCO$_3$ (2×50 mL), dried over anhydrous Na₂SO₄, and concentrated to yield 47″ (0.38 g, 71%) as a pale yellow foam.

$^1$H NMR (500 MHz, CD₃OD) δ 0.8–1.82 (m, 9H), 2.25–2.55 (m, 4H), 3.28 (s, 3H), 4.91–5.20 (m, 3H), 5.48 (s, 1H), 5.75.9 (m, 1H), 7.35–7.76 (m, 8H).

Step 3: Preparation of Example 47;

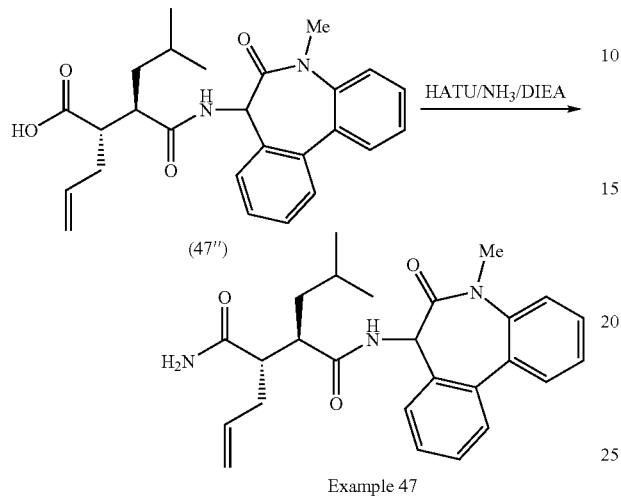

Ammonia gas was bubbled through as a solution of 47″ (0.38 g, 0.88 mmol), DMF (15 mL), HATU (0.4 g, 1.1 mmol), and DIPEA (4.3 mmol, 0.76 mL) at 000 for 10 min. The solution was allowed to warm to room temperature while stirring for 18 h. The DMF was removed under reduced pressure and the resulting residue was dissolved in ethyl acetate (200 mL), washed with 0.1 N HCl (2×100 mL), brine (2×100 mL), dried over anhydrous Na₂SO₄, and concentrated to yield a light brown oil. The crude material was further purified via silica gel chromatography (2% MeOH, 98% CH₂Cl₂) to yield the title compound, Example 47, as an off-white solid (0.21 g, 55%): mp 137–145° C.

$^1$H NMR (500 MHz, CDCl₃) δ 0.82–1.08 (m, 6H), 1.22–1.79 (m, 3H) 2.13–2.82 (m, 4H) 3.35 (s, 3H) 4.94–5.12 (m, 3H), 5.36 (d, 1H), 5.52 (d, 1H), 5.67–5.81 (m, 1H), 7.30–7.63 (m, 8H); IR (KBr) 3334, 2955, 1654, 1498, 1386 cm$^{-1}$; CI MS m/z=434 [C₂₆H₃₁N₃O₃+H]⁺; HPLC 95.4% tr=17.65 min. Anal. Calcd. for C₂₆H₃₁N₃O₃ 0.25 H₂O: C, 72.29; H, 7.25; N 9.59, Found: C, 71.22; H, 7.13; N, 9.32.

Example 48

(2R,3S) N1-[1,3,4,5-tetrahydro-1,5-dimethyl-2,4-dioxo-2H-1,5-benzodiazepin-3-yl]-2-(2-methylpropyl)-3-allyl-butanediamide

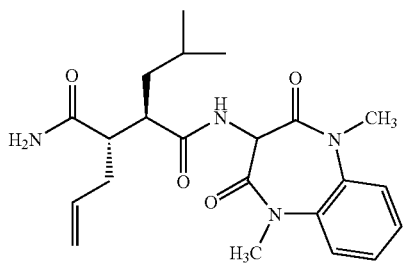

Step 1: Preparation of Compound 48';

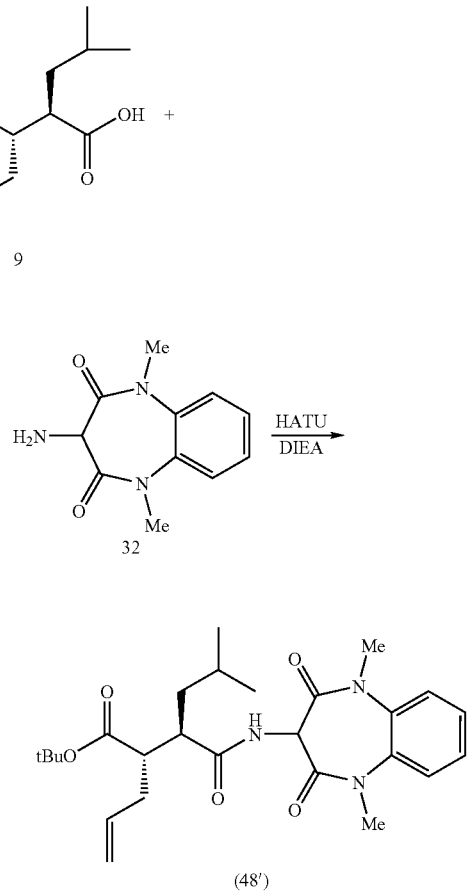

To a solution of tert-butyl succinate ester (9) (1.0 eq) in DMF (0.25 M) at zero degrees was added HATU (1.1 eq), then Hunig's base (4.0 eq). The mixture was stirred at zero degrees for 10 mins. A solution of 3 amino-1,3,4,5-tetrahydro-1,5-dimethyl-2H-1,5-benzodiazepin-2,4-dione (32) in DMF (0.8 M) (1.0 eq) was added to this solution. The reaction mixture was stirred overnight at RT and then transferred to a separatory funnel containing water. 30% N-hexane in ethyl acetate was added which gave a clear organic layer. The aqueous solution was extracted twice with 30% n-hexane in ethyl acetate. The combined organic layers were washed with water and brine, dried over magnesium sulfate, and concentrated in vacuo. The residue was purified by chromatography on flash grade silica gel using 30% ethyl acetate in n-hexane. Compound 48' was isolated as an amorphous white solid (92%). Rf=0.15 (7:3 n-hexane:ethyl acetate).

$^1$H-NMR (CDCl₁₃): δ 7.34 (s, 4H); 6.97–6.94 (d, 1H); 5.80–5.60 (m, 1H); 5.15–4.95 (m, 3H); 3.45 (s, 6H); 2.65–2.20 (m, 4H); 1.80–1.50 (m, 2H); 1.18–1.00 (m, 1H); 0.95–0.92 (d, 3H); 0.87–0.84 (d, 3H); MS (M+H)+ 472.2.

Step 2: Preparation of Compound 48";

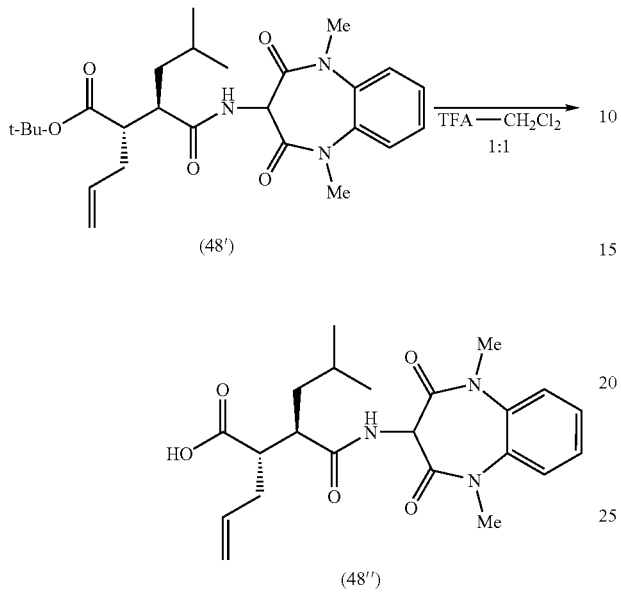

(48')

(48")

Following a procedure analogous to the procedure of Step 2 in Example 1, compound 48" was prepared.

Step 3: Preparation of Example 48;

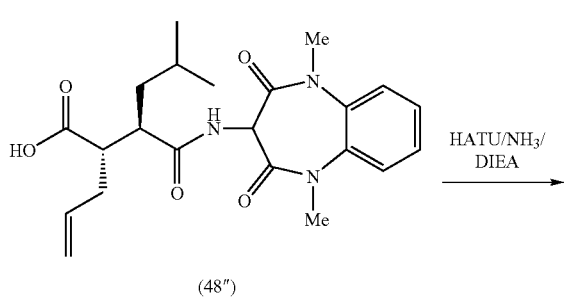

(48''')

Example 48

Following a procedure analogous to the procedure of Step 3 in Example 1, the title compound, Example 48, was prepared.

$^1$H-NMR (CDCl$_3$): δ8.36 (s, 4H); 7.10–7.00 (d, 1H); 6.44 (s, 1H); 5.85–5.75 (m, 1H); 5.40 (m, 1H); 5.19–5.00 (m, 3H); 3.50–3.45 (d, 6H); 2.70–2.33 (m, 4H); 1.60–1.40 (m, 2H); 1.30–1.20 (m, 1H); 0.90–0.85 (q, 6H). MS (M+H)+ =415.4 (M+Na)+=437.4.

Example 49

(2R,3S) N1-[1,3,4,5-tetrahydro-1-methyl-2-oxo-2H-benzoazepin-3-yl]-2-(2-methylpropyl)-3-allyl-butanediamide

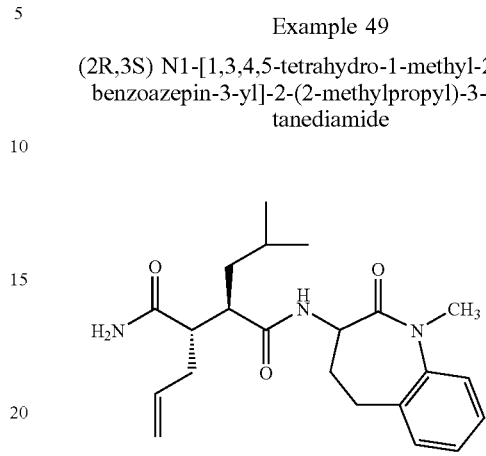

Following a procedure analogous to the preparation of Example 1 using 3-amino-1,3,4,5-tetrahydro-1-methyl-2-2H-benzoazepine-2-one, prepared by methods known to one skilled in the art, in place of (30) in step 1, the title compound was prepared. MS (M+H)$^+$=408.3.

Example 50

(2R,3S) N1-[(3S)-1,3-dihydro-1-methyl-2-oxo-5-phenyl-2H-1,4-benzodiazepin-3-yl]-2-methyl-3-propyl-butanediamide

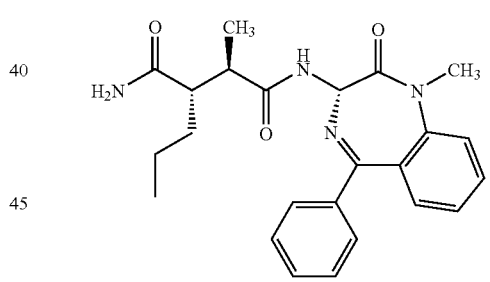

Using the product of Example 9a as starting material, and following the reduction procedure of Example 7, the title compound was prepared. MS (M+Na)$^+$=443.2.

Table 2 demonstrates representative compounds envisaged within the scope of the present invention. Each formulae at the start of Table 2 are intended to be paired with each entry in the table which follows.

For example the compound (2R,3S) N1-[6,7-dihydro-5-methyl-6-oxo-5H-dibenz[b,d]azepin-7-yl]-2-(2-methylpropyl)-3-(allyl)-butanediamide is represented by Example #500-B-j, which comprises the core B, succinate j, and entry #500.

For example the compound (2R,3S) N1-[(3S)-1,3-dihydro-1-methyl-2-oxo-5-phenyl-7-chloro-2H-1,4-benzodiazepin-3-yl]-2-(2-methylpropyl)-3-(butyl)-butanediamide, is represented by Example #502-D-ab, which comprises the core D, succinate ab, and entry #502.

TABLE 2
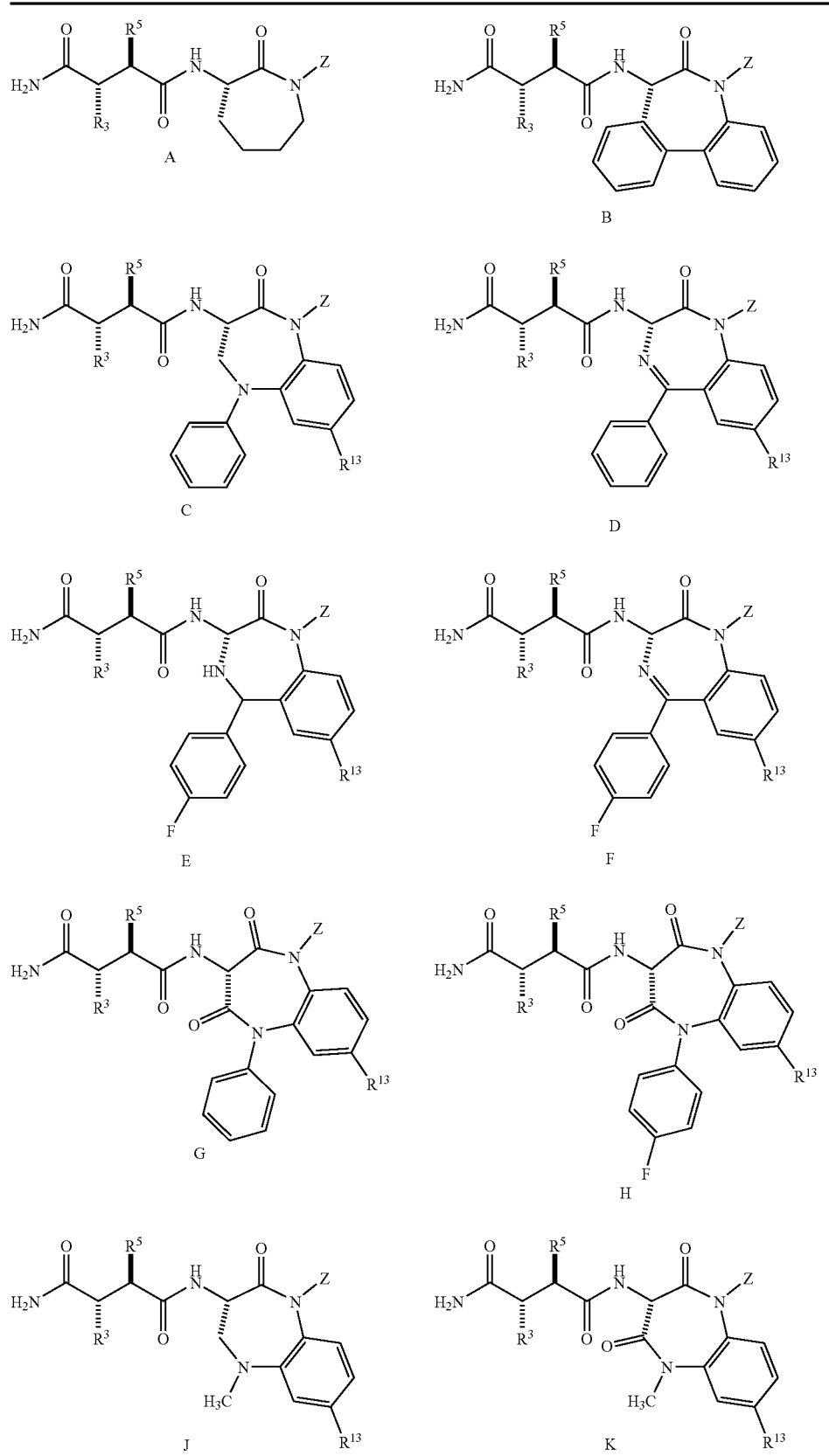

TABLE 2-continued
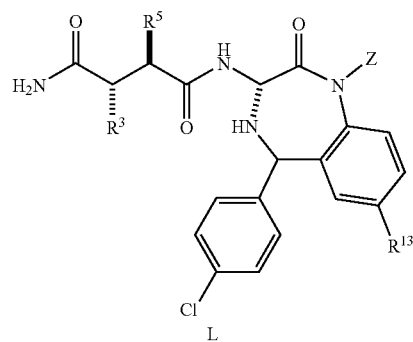
L
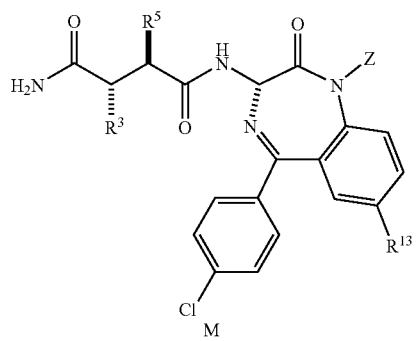
M
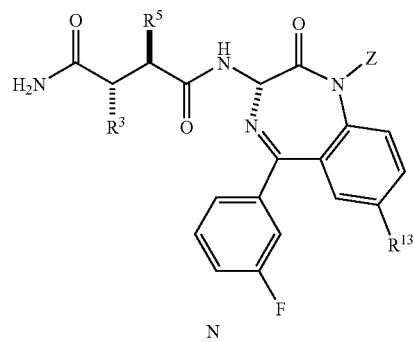
N
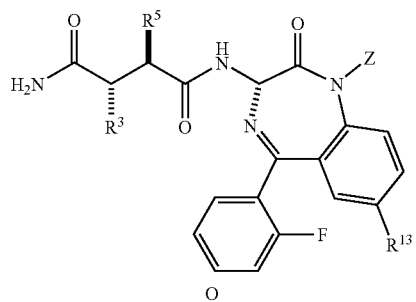
O
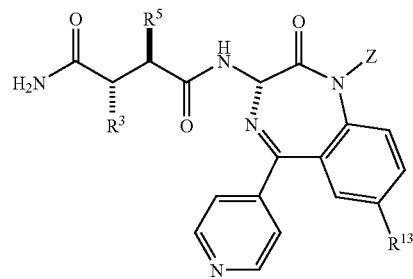
P
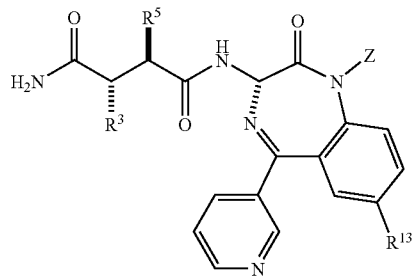
Q
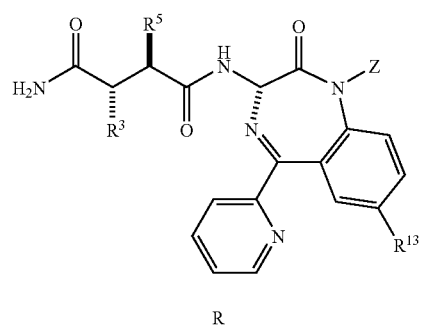
R
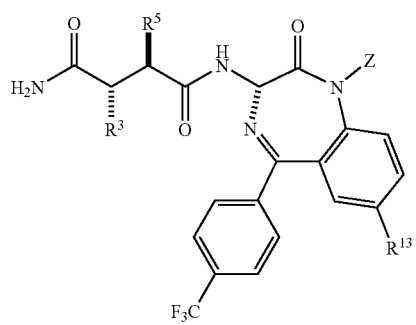
S TABLE 2-continued
wherein R³ and R⁵ are:
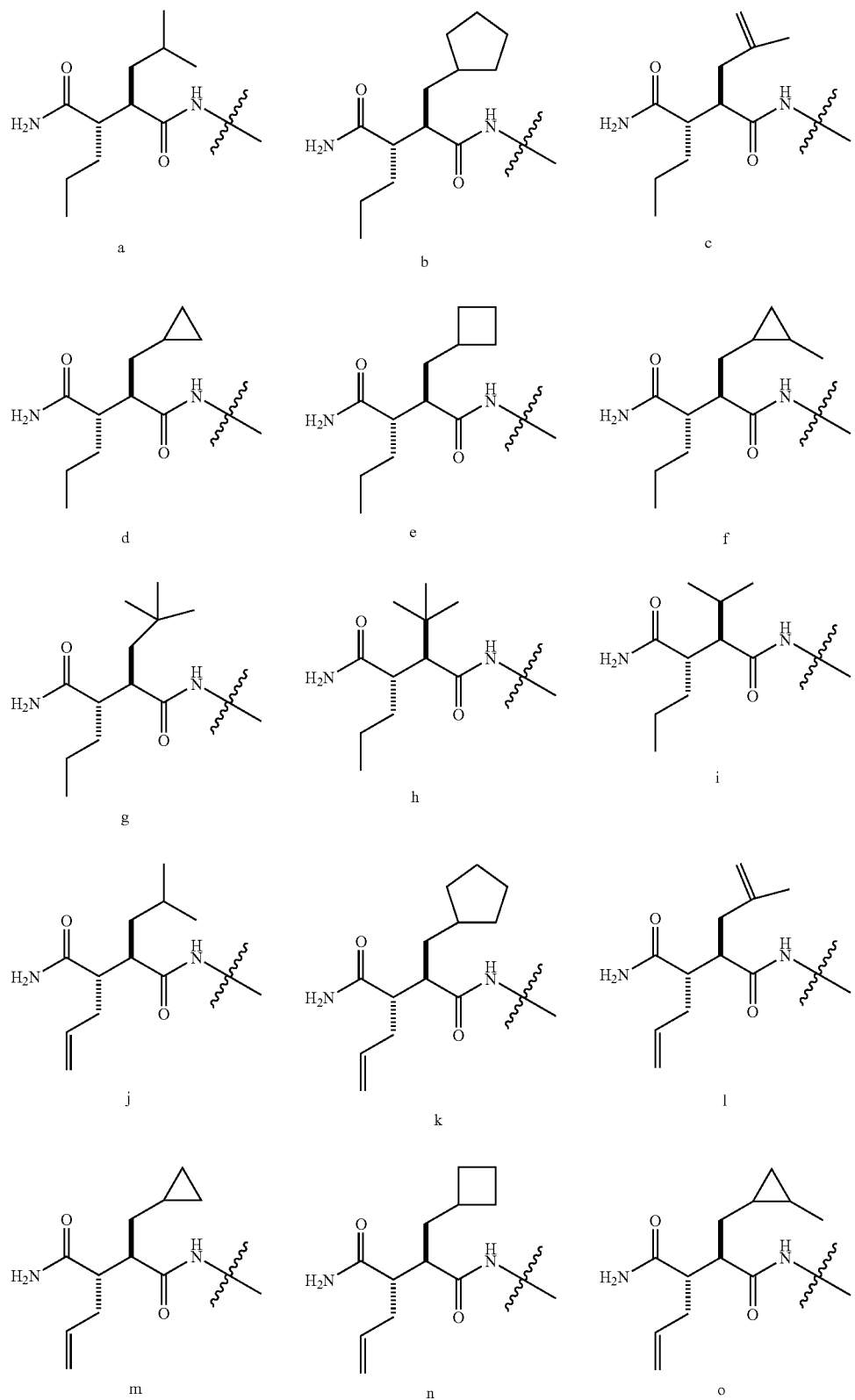

TABLE 2-continued
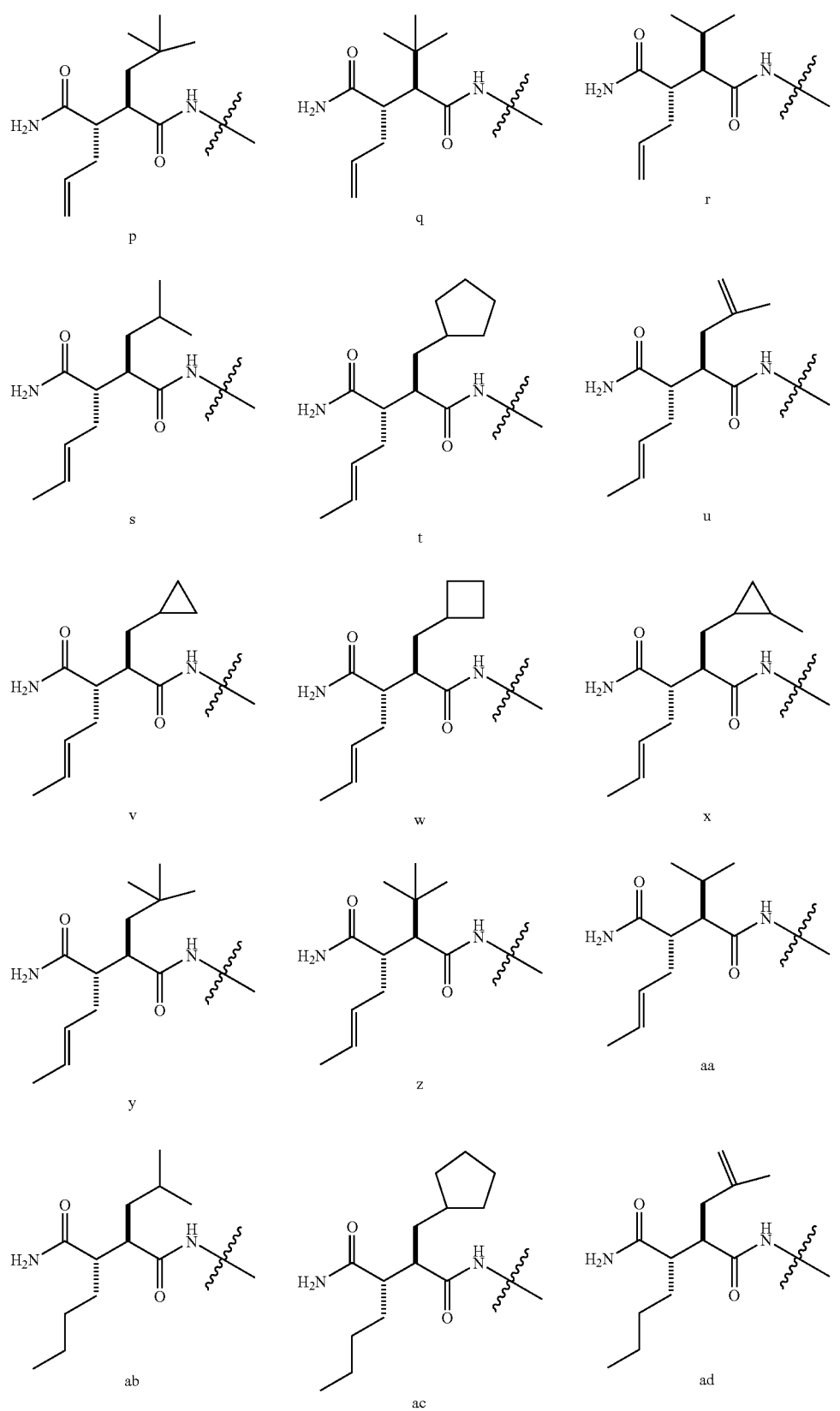

TABLE 2-continued
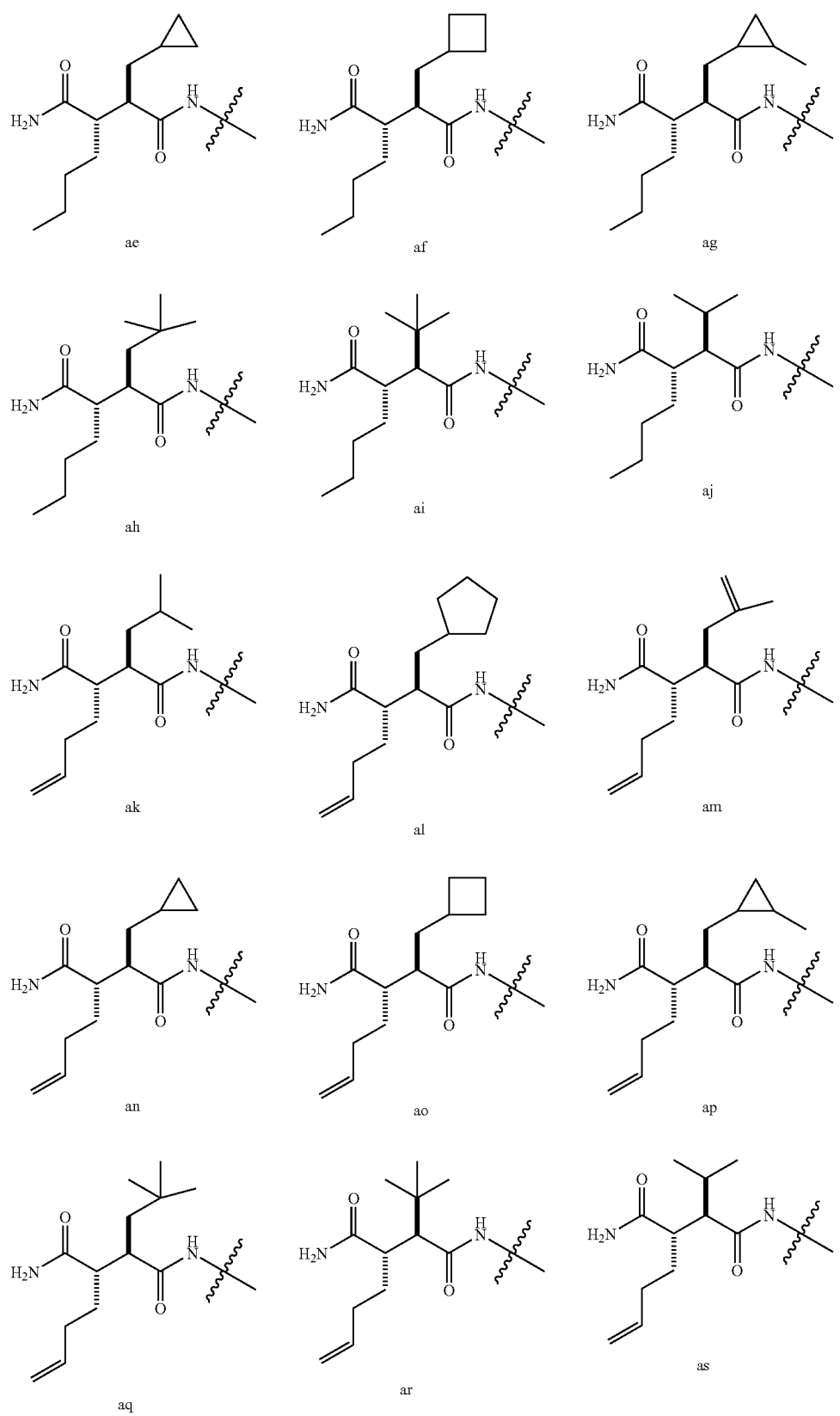

TABLE 2-continued
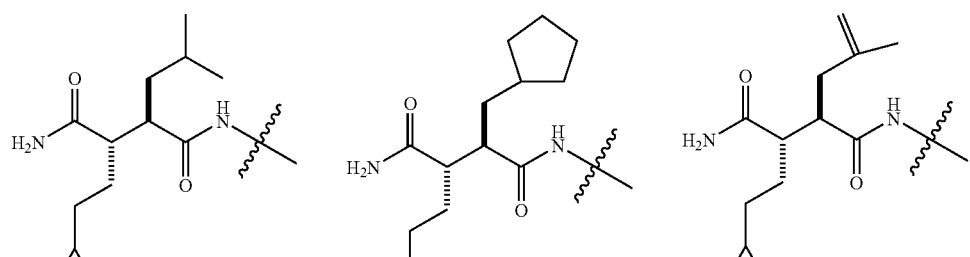
at
au
av
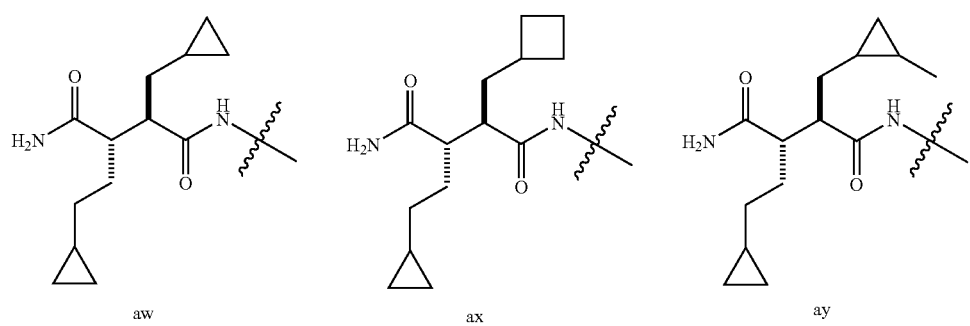
aw
ax
ay
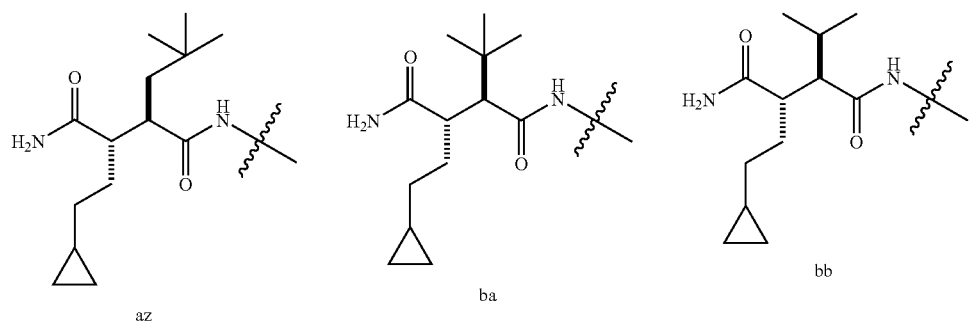
az
ba
bb
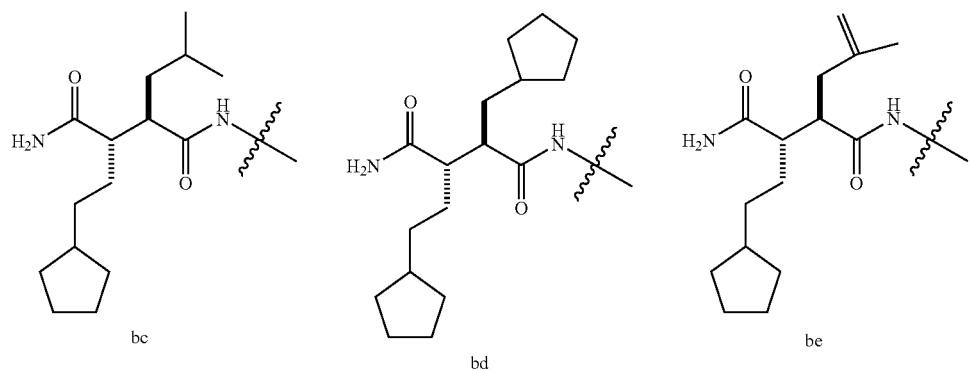
bc
bd
be TABLE 2-continued
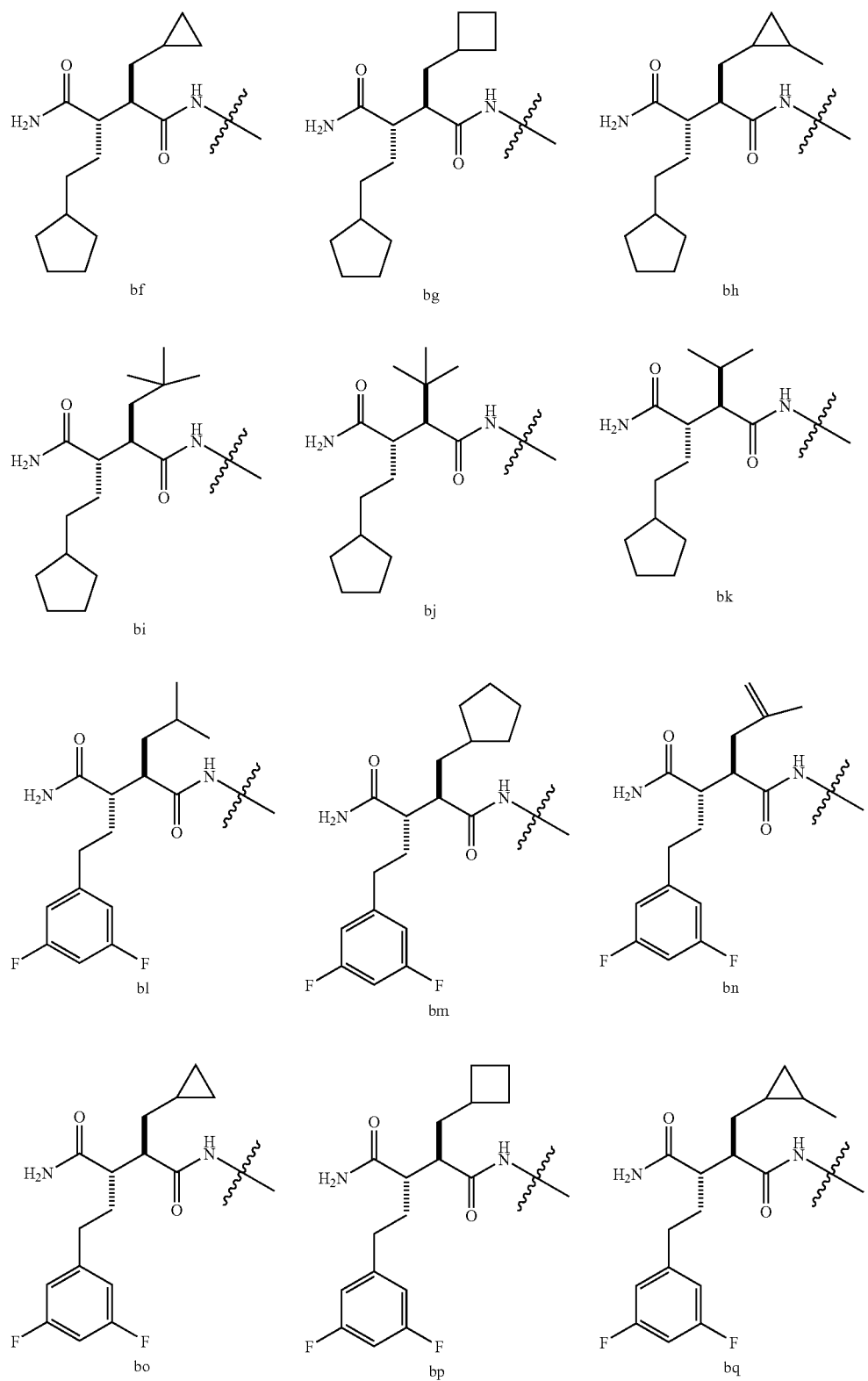

TABLE 2-continued

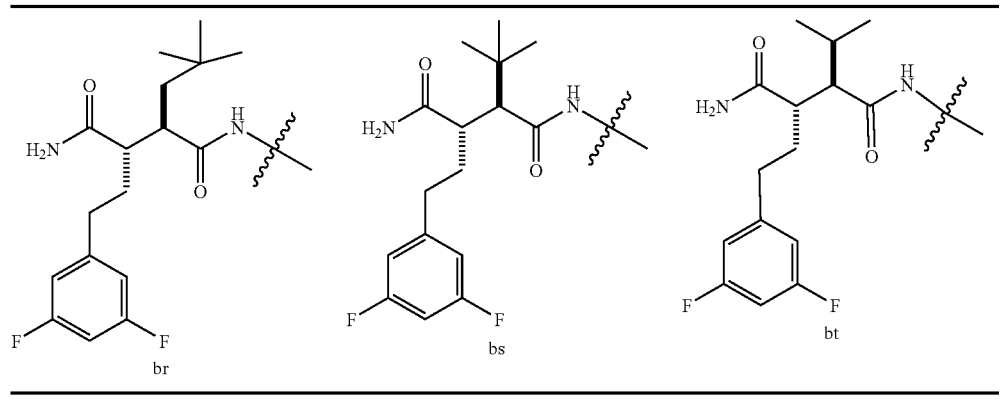

| Ex # | core | R3/R5 | R13 | Z |
|---|---|---|---|---|
| 500 | A–S | a–bt | H | methyl |
| 501 | A–S | a–bt | F | methyl |
| 502 | A–S | a–bt | Cl | methyl |
| 503 | A–S | a–bt | OH | methyl |
| 504 | A–S | a–bt | —CH₃ | methyl |
| 505 | A–S | a–bt | —CH₂CH₃ | methyl |
| 506 | A–S | a–bt | —OCH₃ | methyl |
| 507 | A–S | a–bt | —CF₃ | methyl |
| 508 | A–S | a–bt | H | ethyl |
| 509 | A–S | a–bt | F | ethyl |
| 510 | A–S | a–bt | Cl | ethyl |
| 511 | A–S | a–bt | OH | ethyl |
| 512 | A–S | a–bt | —CH₃ | ethyl |
| 513 | A–S | a–bt | —CH₂CH₃ | ethyl |
| 514 | A–S | a–bt | —OCH₃ | ethyl |
| 515 | A–S | a–bt | —CF₃ | ethyl |
| 516 | A–S | a–bt | H | i-propyl |
| 517 | A–S | a–bt | F | i-propyl |
| 518 | A–S | a–bt | Cl | i-propyl |
| 519 | A–S | a–bt | OH | i-propyl |
| 520 | A–S | a–bt | —CH₃ | i-propyl |
| 521 | A–S | a–bt | —CH₂CH₃ | i-propyl |
| 522 | A–S | a–bt | —OCH₃ | i-propyl |
| 523 | A–S | a–bt | —CF₃ | i-propyl |
| 524 | A–S | a–bt | H | n-propyl |
| 525 | A–S | a–bt | F | n-propyl |
| 526 | A–S | a–bt | Cl | n-propyl |
| 527 | A–S | a–bt | OH | n-propyl |
| 528 | A–S | a–bt | —CH₃ | n-propyl |
| 529 | A–S | a–bt | —CH₂CH₃ | n-propyl |
| 530 | A–S | a–bt | —OCH₃ | n-propyl |
| 531 | A–S | a–bt | —CF₃ | n-propyl |
| 532 | A–S | a–bt | H | n-butyl |
| 533 | A–S | a–bt | F | n-butyl |
| 534 | A–S | a–bt | Cl | n-butyl |
| 535 | A–S | a–bt | OH | n-butyl |
| 536 | A–S | a–bt | —CH₃ | n-butyl |
| 537 | A–S | a–bt | —CH₂CH₃ | n-butyl |
| 538 | A–S | a–bt | —OCH₃ | n-butyl |
| 539 | A–S | a–bt | —CF₃ | n-butyl |
| 540 | A–S | a–bt | H | i-butyl |
| 541 | A–S | a–bt | F | i-butyl |
| 542 | A–S | a–bt | Cl | i-butyl |
| 543 | A–S | a–bt | OH | i-butyl |
| 544 | A–S | a–bt | —CH₃ | i-butyl |
| 545 | A–S | a–bt | —CH₂CH₃ | i-butyl |
| 546 | A–S | a–bt | —OCH₃ | i-butyl |
| 547 | A–S | a–bt | —CF₃ | i-butyl |
| 548 | A–S | a–bt | H | s-butyl |
| 549 | A–S | a–bt | F | s-butyl |
| 550 | A–S | a–bt | Cl | s-butyl |
| 551 | A–S | a–bt | OH | s-butyl |
| 552 | A–S | a–bt | —CH₃ | s-butyl |
| 553 | A–S | a–bt | —CH₂CH₃ | s-butyl |
| 554 | A–S | a–bt | —OCH₃ | s-butyl |
| 555 | A–S | a–bt | —CF₃ | s-butyl |
| 556 | A–S | a–bt | H | t-butyl |
| 557 | A–S | a–bt | F | t-butyl |

TABLE 2-continued

| | | | | |
|---|---|---|---|---|
| 558 | A–S | a–bt | Cl | t-butyl |
| 559 | A–S | a–bt | OH | t-butyl |
| 560 | A–S | a–bt | —CH$_3$ | t-butyl |
| 561 | A–S | a–bt | —CH$_2$CH$_3$ | t-butyl |
| 562 | A–S | a–bt | —OCH$_3$ | t-butyl |
| 563 | A–S | a–bt | —CF$_3$ | t-butyl |
| 564 | A–S | a–bt | H | allyl |
| 565 | A–S | a–bt | F | allyl |
| 566 | A–S | a–bt | Cl | allyl |
| 567 | A–S | a–bt | OH | allyl |
| 568 | A–S | a–bt | —CH$_3$ | allyl |
| 569 | A–S | a–bt | —CH$_2$CH$_3$ | allyl |
| 570 | A–S | a–bt | —OCH$_3$ | allyl |
| 571 | A–S | a–bt | —CF$_3$ | allyl |
| 572 | A–S | a–bt | H | cyclopropyl |
| 573 | A–S | a–bt | F | cyclopropyl |
| 574 | A–S | a–bt | Cl | cyclopropyl |
| 575 | A–S | a–bt | OH | cyclopropyl |
| 576 | A–S | a–bt | —CH$_3$ | cyclopropyl |
| 577 | A–S | a–bt | —CH$_2$CH$_3$ | cyclopropyl |
| 578 | A–S | a–bt | —OCH$_3$ | cyclopropyl |
| 579 | A–S | a–bt | —CF$_3$ | cyclopropyl |
| 580 | A–S | a–bt | —CF$_3$ | cyclopropyl |
| 581 | A–S | a–bt | H | cyclopropyl-CH$_2$— |
| 582 | A–S | a–bt | F | cyclopropyl-CH$_2$— |
| 583 | A–S | a–bt | Cl | cyclopropyl-CH$_2$— |
| 584 | A–S | a–bt | OH | cyclopropyl-CH$_2$— |
| 585 | A–S | a–bt | —CH$_3$ | cyclopropyl-CH$_2$— |
| 586 | A–S | a–bt | —CH$_2$CH$_3$ | cyclopropyl-CH$_2$— |
| 587 | A–S | a–bt | —OCH$_3$ | cyclopropyl-CH$_2$— |
| 588 | A–S | a–bt | —CF$_3$ | cyclopropyl-CH$_2$— |
| 589 | A–S | a–bt | H | cyclobutyl |
| 590 | A–S | a–bt | F | cyclobutyl |
| 591 | A–S | a–bt | Cl | cyclobutyl |
| 592 | A–S | a–bt | OH | cyclobutyl |
| 593 | A–S | a–bt | —CH$_3$ | cyclobutyl |
| 594 | A–S | a–bt | —CH$_2$CH$_3$ | cyclobutyl |
| 595 | A–S | a–bt | —OCH$_3$ | cyclobutyl |
| 596 | A–S | a–bt | —CF$_3$ | cyclobutyl |
| 597 | A–S | a–bt | H | cyclobutyl-CH$_2$— |
| 598 | A–S | a–bt | F | cyclobutyl-CH$_2$— |
| 599 | A–S | a–bt | Cl | cyclobutyl-CH$_2$— |
| 600 | A–S | a–bt | OH | cyclobutyl-CH$_2$— |
| 601 | A–S | a–bt | —CH$_3$ | cyclobutyl-CH$_2$— |
| 602 | A–S | a–bt | —CH$_2$CH$_3$ | cyclobutyl-CH$_2$— |
| 603 | A–S | a–bt | —OCH$_3$ | cyclobutyl-CH$_2$— |
| 604 | A–S | a–bt | —CF$_3$ | cyclobutyl-CH$_2$— |
| 605 | A–S | a–bt | H | cyclopentyl |
| 606 | A–S | a–bt | F | cyclopentyl |
| 607 | A–S | a–bt | Cl | cyclopentyl |
| 608 | A–S | a–bt | OH | cyclopentyl |
| 609 | A–S | a–bt | —CH$_3$ | cyclopentyl |
| 610 | A–S | a–bt | —CH$_2$CH$_3$ | cyclopentyl |
| 611 | A–S | a–bt | —OCH$_3$ | cyclopentyl |
| 612 | A–S | a–bt | —CF$_3$ | cyclopentyl |
| 613 | A–S | a–bt | H | cyclopentyl-CH$_2$— |
| 614 | A–S | a–bt | F | cyclopentyl-CH$_2$— |
| 615 | A–S | a–bt | Cl | cyclopentyl-CH$_2$— |
| 616 | A–S | a–bt | OH | cyclopentyl-CH$_2$— |
| 617 | A–S | a–bt | —CH$_3$ | cyclopentyl-CH$_2$— |
| 618 | A–S | a–bt | —CH$_2$CH$_3$ | cyclopentyl-CH$_2$— |
| 619 | A–S | a–bt | —OCH$_3$ | cyclopentyl-CH$_2$— |
| 620 | A–S | a–bt | —CF$_3$ | cyclopentyl-CH$_2$— |
| 621 | A–S | a–bt | H | cyclohexyl |
| 622 | A–S | a–bt | F | cyclohexyl |
| 623 | A–S | a–bt | Cl | cyclohexyl |
| 624 | A–S | a–bt | OH | cyclohexyl |
| 625 | A–S | a–bt | —CH$_3$ | cyclohexyl |
| 626 | A–S | a–bt | —CH$_2$CH$_3$ | cyclohexyl |
| 627 | A–S | a–bt | —OCH$_3$ | cyclohexyl |
| 628 | A–S | a–bt | —CF$_3$ | cyclohexyl |
| 629 | A–S | a–bt | H | cyclohexyl-CH$_2$— |
| 630 | A–S | a–bt | F | cyclohexyl-CH$_2$— |
| 631 | A–S | a–bt | Cl | cyclohexyl-CH$_2$— |
| 632 | A–S | a–bt | OH | cyclohexyl-CH$_2$— |
| 633 | A–S | a–bt | —CH$_3$ | cyclohexyl-CH$_2$— |
| 634 | A–S | a–bt | —CH$_2$CH$_3$ | cyclohexyl-CH$_2$— |
| 635 | A–S | a–bt | —OCH$_3$ | cyclohexyl-CH$_2$— |
| 636 | A–S | a–bt | —CF$_3$ | cyclohexyl-CH$_2$— |

TABLE 2-continued

| | | | | |
|---|---|---|---|---|
| 637 | A–S | a–bt | H | phenyl |
| 638 | A–S | a–bt | F | phenyl |
| 639 | A–S | a–bt | Cl | phenyl |
| 640 | A–S | a–bt | OH | phenyl |
| 641 | A–S | a–bt | —CH$_3$ | phenyl |
| 642 | A–S | a–bt | —CH$_2$CH$_3$ | phenyl |
| 643 | A–S | a–bt | —OCH$_3$ | phenyl |
| 644 | A–S | a–bt | —CF$_3$ | phenyl |
| 645 | A–S | a–bt | H | 2-F-phenyl |
| 646 | A–S | a–bt | F | 2-F-phenyl |
| 647 | A–S | a–bt | Cl | 2-F-phenyl |
| 648 | A–S | a–bt | OH | 2-F-phenyl |
| 649 | A–S | a–bt | —CH$_3$ | 2-F-phenyl |
| 650 | A–S | a–bt | —CH$_2$CH$_3$ | 2-F-phenyl |
| 651 | A–S | a–bt | —OCH$_3$ | 2-F-phenyl |
| 652 | A–S | a–bt | —CF$_3$ | 2-F-phenyl |
| 653 | A–S | a–bt | H | 3-F-phenyl |
| 654 | A–S | a–bt | F | 3-F-phenyl |
| 655 | A–S | a–bt | Cl | 3-F-phenyl |
| 656 | A–S | a–bt | OH | 3-F-phenyl |
| 657 | A–S | a–bt | —CH$_3$ | 3-F-phenyl |
| 658 | A–S | a–bt | —CH$_2$CH$_3$ | 3-F-phenyl |
| 659 | A–S | a–bt | —OCH$_3$ | 3-F-phenyl |
| 660 | A–S | a–bt | —CF$_3$ | 3-F-phenyl |
| 661 | A–S | a–bt | H | 4-F-phenyl |
| 662 | A–S | a–bt | F | 4-F-phenyl |
| 663 | A–S | a–bt | Cl | 4-F-phenyl |
| 664 | A–S | a–bt | OH | 4-F-phenyl |
| 665 | A–S | a–bt | —CH$_3$ | 4-F-phenyl |
| 666 | A–S | a–bt | —CH$_2$CH$_3$ | 4-F-phenyl |
| 667 | A–S | a–bt | —OCH$_3$ | 4-F-phenyl |
| 668 | A–S | a–bt | —CF$_3$ | 4-F-phenyl |
| 669 | A–S | a–bt | H | 3-Cl-phenyl |
| 670 | A–S | a–bt | F | 3-Cl-phenyl |
| 671 | A–S | a–bt | Cl | 3-Cl-phenyl |
| 672 | A–S | a–bt | OH | 3-Cl-phenyl |
| 673 | A–S | a–bt | —CH$_3$ | 3-Cl-phenyl |
| 674 | A–S | a–bt | —CH$_2$CH$_3$ | 3-Cl-phenyl |
| 675 | A–S | a–bt | —OCH$_3$ | 3-Cl-phenyl |
| 676 | A–S | a–bt | —CF$_3$ | 3-Cl-phenyl |
| 677 | A–S | a–bt | H | 4-Cl-phenyl |
| 678 | A–S | a–bt | F | 4-Cl-phenyl |
| 679 | A–S | a–bt | Cl | 4-Cl-phenyl |
| 680 | A–S | a–bt | OH | 4-Cl-phenyl |
| 681 | A–S | a–bt | —CH$_3$ | 4-Cl-phenyl |
| 682 | A–S | a–bt | —CH$_2$CH$_3$ | 4-Cl-phenyl |
| 683 | A–S | a–bt | —OCH$_3$ | 4-Cl-phenyl |
| 684 | A–S | a–bt | —CF$_3$ | 4-Cl-phenyl |
| 685 | A–S | a–bt | H | 3-Me-phenyl |
| 686 | A–S | a–bt | F | 3-Me-phenyl |
| 687 | A–S | a–bt | Cl | 3-Me-phenyl |
| 688 | A–S | a–bt | OH | 3-Me-phenyl |
| 689 | A–S | a–bt | —CH$_3$ | 3-Me-phenyl |
| 690 | A–S | a–bt | —CH$_2$CH$_3$ | 3-Me-phenyl |
| 691 | A–S | a–bt | —OCH$_3$ | 3-Me-phenyl |
| 692 | A–S | a–bt | —CF$_3$ | 3-Me-phenyl |
| 693 | A–S | a–bt | H | 4-Me-phenyl |
| 694 | A–S | a–bt | F | 4-Me-phenyl |
| 695 | A–S | a–bt | Cl | 4-Me-phenyl |
| 696 | A–S | a–bt | OH | 4-Me-phenyl |
| 697 | A–S | a–bt | —CH$_3$ | 4-Me-phenyl |
| 698 | A–S | a–bt | —CH$_2$CH$_3$ | 4-Me-phenyl |
| 699 | A–S | a–bt | —OCH$_3$ | 4-Me-phenyl |
| 700 | A–S | a–bt | —CF$_3$ | 4-Me-phenyl |
| 701 | A–S | a–bt | H | 3-MeO-phenyl |
| 702 | A–S | a–bt | F | 3-MeO-phenyl |
| 703 | A–S | a–bt | Cl | 3-MeO-phenyl |
| 704 | A–S | a–bt | OH | 3-MeO-phenyl |
| 705 | A–S | a–bt | —CH$_3$ | 3-MeO-phenyl |
| 706 | A–S | a–bt | —CH$_2$CH$_3$ | 3-MeO-phenyl |
| 707 | A–S | a–bt | —OCH$_3$ | 3-MeO-phenyl |
| 708 | A–S | a–bt | —CF$_3$ | 3-MeO-phenyl |
| 709 | A–S | a–bt | H | 4-MeO-phenyl |
| 710 | A–S | a–bt | F | 4-MeO-phenyl |
| 711 | A–S | a–bt | Cl | 4-MeO-phenyl |
| 712 | A–S | a–bt | OH | 4-MeO-phenyl |
| 713 | A–S | a–bt | —CH$_3$ | 4-MeO-phenyl |
| 714 | A–S | a–bt | —CH$_2$CH$_3$ | 4-MeO-phenyl |
| 715 | A–S | a–bt | —OCH$_3$ | 4-MeO-phenyl |

TABLE 2-continued

| | | | | |
|---|---|---|---|---|
| 716 | A–S | a–bt | —CF$_3$ | 4-MeO-phenyl |
| 717 | A–S | a–bt | H | 3-F$_3$C-phenyl |
| 718 | A–S | a–bt | F | 3-F$_3$C-phenyl |
| 719 | A–S | a–bt | Cl | 3-F$_3$C-phenyl |
| 720 | A–S | a–bt | OH | 3-F$_3$C-phenyl |
| 721 | A–S | a–bt | —CH$_3$ | 3-F$_3$C-phenyl |
| 722 | A–S | a–bt | —CH$_2$CH$_3$ | 3-F$_3$C-phenyl |
| 723 | A–S | a–bt | —OCH$_3$ | 3-F$_3$C-phenyl |
| 724 | A–S | a–bt | —CF$_3$ | 3-F$_3$C-phenyl |
| 725 | A–S | a–bt | H | 4-F$_3$C-phenyl |
| 726 | A–S | a–bt | F | 4-F$_3$C-phenyl |
| 727 | A–S | a–bt | Cl | 4-F$_3$C-phenyl |
| 728 | A–S | a–bt | OH | 4-F$_3$C-phenyl |
| 729 | A–S | a–bt | —CH$_3$ | 4-F$_3$C-phenyl |
| 730 | A–S | a–bt | —CH$_2$CH$_3$ | 4-F$_3$C-phenyl |
| 731 | A–S | a–bt | —OCH$_3$ | 4-F$_3$C-phenyl |
| 732 | A–S | a–bt | —CF$_3$ | 4-F$_3$C-phenyl |

Utility

Aβ production has been implicated in the pathology of Alzheimer's Disease (AD). The compounds of the present invention have utility for the prevention and treatment of AD by inhibiting Aβ production. Methods of treatment target formation of Aβ production through the enzymes involved in the proteolytic processing of β amyloid precursor protein. Compounds that inhibit β or γ secretase activity, either directly or indirectly, control the production of Aβ. Such inhibition of β or γ secretases reduces production of Aβ, and is expected to reduce or prevent the neurological disorders associated with Aβ protein, such as Alzheimer's Disease.

Cellular screening methods for inhibitors of Aβ production, testing methods for the in vivo suppression of Aβ production, and assays for the detection of secretase activity are known in the art and have been disclosed in numerous publications, including PCT publication number WO 98/22493, EPO publication number 0652009, U.S. Pat. No. 5,703,129 and U.S. Pat. No. 5,593,846; all hereby incorporated by reference.

The compounds of the present invention have utility for the prevention and treatment of disorders involving Aβ production, such as cerebrovascular disorders.

Compounds of the present invention have been shown to inhibit Aβ production, as determined by the secretase inhibition assay described below.

Compounds of the present invention have been shown to inhibit Aβ production, utilizing the C-terminus β amyloid precursor protein accumulation assay described below.

Compounds of Formula (I) are expected to possess γ-secretase inhibitory activity. The γ-secretase inhibitory activity of the compounds of the present invention is demonstrated using assays for such activity, for example, using the assay described below. Compounds of the present invention have been shown to inhibit the activity of γ-secretase, as determined by the Aβ immunoprecipitation assay.

Compounds provided by this invention should also be useful as standards and reagents in determining the ability of a potential pharmaceutical to inhibit Aβ production. These would be provided in commercial kits comprising a compound of this invention.

As used herein "μg" denotes microgram, "mg" denotes milligram, "g" denotes gram, "μL" denotes microliter, "mL" denotes milliliter, "L" denotes liter, "nM" denotes nanomolar, "μM" denotes micromolar, "mM" denotes millimolar, "M" denotes molar, "nm" denotes nanometer, "SDS" denotes sodium dodecyl sulfate, and "DMSO" denotes dimethyl sulfoxide, and "EDTA" denotes ethylenediaminetetraacetato.

A compound is considered to be active if it has an IC$_{50}$ or K$_i$ value of less than about 100 μM for the inhibition of Aβ production.

β Amyloid Precursor Protein Accumulation Assay

A novel assay to evaluate the accumulation of Aβ protein was developed to detect potential inhibitors of secretase. The assay uses the N 9 cell line, characterized for expression of exogenous APP by immunoblotting and immunoprecipitation.

The effect of test compounds on the accumulation of Aβ in the conditioned medium is tested by immunoprecipitation. Briefly, N 9 cells are grown to confluency in 6-well plates and washed twice with 1×Hank's buffered salt solution. The cells are starved in methionine/cysteine deficient media for 30 min, followed by replacement with fresh deficient media containing 150 uCi S35 Translabel (Amersham). Test compounds dissolved in DMSO (final concentration 1%) are added together with the addition of radiolabel. The cells are incubated for 4 h at 37° C. in a tissue culture incubator.

At the end of the incubation period, the conditioned medium is harvested and pre-cleared by the addition of 5 μl normal mouse serum and 50 ul of protein A Sepharose (Pharmacia), mixed by end-over-end rotation for 30 minutes at 4° C., followed by a brief centrifugation in a microfuge. The supernatant is then harvested and transferred to fresh tubes containing 5 ug of a monoclonal antibody (clone 1101.1; directed against an internal peptide sequence in Aβ) and 50 μl protein A Sepharose. After incubation overnight at 4° C., the samples are washed three times with high salt washing buffer (50 mM Tris, pH 7.5, 500 mM NaCl, 5 mM EDTA, 0.5% Nonidet P-40), three times with low salt wash buffer (50 mM Tris, pH 7.5, 150 mM NaCl, 5 mM EDTA, 0.5% Nonidet P-40), and three times with 10 mM Tris, pH 7.5. The pellet after the last wash is resuspended in SDS sample buffer (Laemmli, 1970) and boiled for 3 minutes. The supernatant is then fractionated on either 10–20% Tris/Tricine SDS gels or on 16.5% Tris/Tricine SDS gels. The gels are dried and exposed to X-ray film or analyzed by phosphorimaging. The resulting image is analyzed for the presence of Aβ polypeptides. The steady-state level of Aβ in the presence of a test compound is compared to wells treated with DMSO (1%) alone. A typical test compound blocks Aβ accumulation in the conditioned medium, and is therefore considered active, with an IC$_{50}$ less than 100 μM.

C-Terminus β Amyloid Precursor Protein Accumulation Assay

The effect of test compounds on the accumulation of C-terminal fragments is determined by immunoprecipitation of APP and fragments thereof from cell lysates. N 9 cells are metabolically labeled as above in the presence or absence of test compounds. At the end of the incubation period, the conditioned medium are harvested and cells lysed in RIPA buffer (10 mM Tris, pH 8.0 containing 1% Triton X-100, 1% deoxycholate, 0.1% SDS, 150 mM NaCl, 0.125% $NaN_3$). Again, lysates are precleared with 5 ul normal rabbit serum/50 ul protein A Sepharose, followed by the addition of BC-1 antiserum (15 μl) and 50 μl protein A Sepharose for 16 hours at 4° C. The immunoprecipitates are washed as above, bound proteins eluted by boiling in SDS sample buffer and fractionated by Tris/Tricine SDS-PAGE. After exposure to X-ray film or phosphorimager, the resulting images are analyzed for the presence of C-terminal APP fragments. The steady-state level of C-terminal APP fragments is compared to wells treated with DMSO (1%) alone. A typical test compound stimulates C-terminal fragment accumulation in the cell lysates, and is therefore considered active, with an $IC_{50}$ less than 100 μM.

Aβ Immunoprecipitation Assay

This immunoprecipitation assay is specific for γ secretase (i.e., proteolytic activity required to generate the C-terminal end of Aβ either by direct cleavage or generating a C-terminal extended species which is subsequently further proteolyzed). N 9 cells are pulse labeled in the presence of a reported γ secretase inhibitor (MDL 28170) for 1 h, followed by washing to remove radiolabel and MDL 28170. The media is replaced and test compounds are added. The cells are chased for increasing periods of times and A β is isolated from the conditioned medium and C-terminal fragments from cell lysates (see above). The test compounds are characterized whether a stabilization of C-terminal fragments is observed and whether Aβ is generated from these accumulated precursor. A typical test compound prevents the generation of Aβ out of accumulated C-terminal fragments and is considered active with an $IC_{50}$ less than 100 μM.

Dosage and Formulation

The compounds of the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present invention can be administered in such oral dosage forms as tablets, capsules (each of which includes sustained release or timed release formulations), pills, powders, granules, elixirs, tinctures, suspensions, syrups, and emulsions. Likewise, Len they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present invention may be administered in a single daily dose, or the total daily dosage may be administered in divided doses of two, three, or four times daily.

The compounds for the present invention can be administered in intranasal form via topical use of suitable intranasal vehicles, or via transdermal routes, using those forms of transdermal skin patches wall known to those of ordinary skill in that art. To be administered in the form of a transdermal delivery system, the dosage administration will, of course, be continuous rather than intermittant throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators as include, without limitation, starch, methyl cellulose, agar, bentonite, xanthan gum, and the like.

The compounds of the present invention can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:

1. A compound of Formula (I):

(I)

or a pharmaceutically acceptable salt thereof, wherein:

A is O or S;
Q is —NR$^1$R$^2$;
R$^1$ is selected from: H and C$_1$–C$_6$ alkyl;
R$^2$ is independently selected from H and C$_1$–C$_6$ alkyl;
R$^3$ is {CR$^7$R$^{7a}$)$_n$—R$^4$,
—(CR$^7$R$^{7a}$)$_n$—S—CR$^7$R$^{7a}$)$_m$—R$^4$
—(CR$^7$R$^{7a}$)$_n$—O—(CR$^7$R$^{7a}$)$_m$—R$^4$,
—(CR$^7$R$^{7a}$)$_n$—S(O)—(CR$^7$R$^{7a}$)$_m$—R$^4$,
—(CR$^7$R$^{7a}$)$_n$—S(=O)$_2$—(CR$^7$R$^{7a}$)$_m$—R$^4$,
—(CR$^7$R$^{7a}$)$_n$—C(=O)(CR$^7$R$^{7a}$)$_m$—R$^4$,
—(CR$^7$R$^{7a}$)$_n$—N(R$^{7b}$)C(=O)—(CR$^7$R$^{7a}$)$_m$—R$^4$,
—(CR$^7$R$^{7a}$)$_n$—C(=O)N(R$^{7b}$)(CR$^7$R$^{7a}$)$_m$—R$^4$,
—(CR$^7$R$^{7a}$)$_n$—N(R$^{7b}$)S(=O)$_2$—(CR$^7$R$^{7a}$)$_m$—R$^4$, or
—(CR$^7$R$^{7a}$)$_n$—S(=O)$_2$N(R$^{7b}$)—(CR$^7$R$^{7a}$)$_m$—R$^4$;

n is 0, 1, 2, or 3;
m is 0, 1, 2, or 3;
R$^{3a}$ is H, OH, C$_1$–C$_4$ alkyl, C$_1$–C$_4$ alkoxy, C$_2$–C$_4$ alkenyl or C$_2$–C$_4$ alkenyloxy;
R$^4$ is H, OH, OR$^{14a}$,
  C$_1$–C$_6$ alkyl substituted with 0–3 R$^{4a}$,
  C$_2$–C$_6$ alkenyl substituted with 0–3 R$^{4a}$,
  C$_2$–C$_6$ alkynyl substituted with 0–3 R$^{4a}$,
  C$_3$–C$_{10}$ carbocycle substituted with 0–3 R$^{4b}$,
  aryl substituted with 0–3 R$^{4b}$, or
  5 to 10 membered heterocycle containing 1 to 4 heteroatoms selected from nitrogen, oxygen, and sulphur, wherein said 5 to 10 membered heterocycle is substituted with 0–3 R$^{4b}$;
R$^{4a}$, at each occurrence, is independently selected from H, F, Cl, Br, I, CF$_3$,
  C$_3$–C$_{10}$ carbocycle substituted with 0–3 R$^{4b}$,
  aryl substituted with 0–3 R$^{4b}$, or
  5 to 10 membered heterocycle containing 1 to 4 heteroatoms selected from nitrogen, oxygen, and sulphur, wherein said 5 to 10 membered heterocycle is substituted with 0–3 R$^{4b}$;
R$^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
  C$_1$–C$_6$ alkyl, C$_1$–C$_4$ alkoxy, C$_1$–C$_4$ haloalkyl,
  C$_1$–C$_4$ haloalkoxy, and C$_1$–C$_4$ haloalkyl-S—;
R$^5$ is H, OR$^{14}$;
  C$_1$–C$_6$ alkyl substituted with 0–3 R$^{5b}$;
  C$_1$–C$_6$ alkoxy substituted with 0–3 R$^{5b}$;
  C$_2$–C$_6$ alkenyl substituted with 0–3 R$^{5b}$;
  C$_2$–C$_6$ alkynyl substituted with 0–3 R$^{5b}$;
  C$_3$–C$_{10}$ carbocycle substituted with 0–3 R$^{5c}$;
  aryl substituted with 0–3 R$^{5c}$; or
  5 to 10 membered heterocycle containing 1 to 4 heteroatoms selected from nitrogen, oxygen, and sulphur, wherein said 5 to 10 membered heterocycle is substituted with 0–3 R$^{5c}$;
R$^{5a}$ is H, OH, C$_1$–C$_4$ alkyl, C$_1$–C$_4$ alkoxy, C$_2$–C$_4$ alkenyl, or C$_2$–C$_4$ alkenyloxy;
R$^{5b}$, at each occurrence, is independently selected from:
  H, C$_1$–C$_6$ alkyl, CF$_3$, OR$^{14}$, Cl, F, Br, I, =O, CN, NO$_2$, NR$^{15}$R$^{16}$;
  C$_3$–C$_{10}$ carbocycle substituted with 0–3 R$^{5c}$;
  aryl substituted with 0–3 R$^{5c}$; or
  5 to 10 membered heterocycle containing 1 to 4 heteroatoms selected from nitrogen, oxygen, and sulphur, wherein said 5 to 10 membered heterocycle is substituted with 0–3 R$^{5c}$;
R$^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$,
  C$_1$–C$_6$ alkyl, C$_1$–C$_4$ alkoxy, C$_1$–C$_4$ haloalkyl,
  C$_1$–C$_4$ haloalkoxy, and C$_1$–C$_4$ haloalkyl-S—;
R$^6$ is H;
  C$_1$–C$_6$ alkyl substituted with 0–3 R$^{6a}$;
  C$_3$–C$_{10}$ carbocycle substituted with 0–3 R$^{6b}$; or
  aryl substituted with 0–3 R$^{6b}$;
R$^{6a}$, at each occurrence, is independently selected from H, C$_1$–C$_6$ alkyl, OR$^{14}$, Cl, F, Br, I, =O, CN, NO$_2$, NR$^{15}$R$^{16}$, aryl or CF$_3$;

$R^{6b}$, at each occurrence, is independently selected from H, OH, Cl, F, Br, I, CN, NO$_2$, NR$^{15}$R$^{16}$, CF$_3$, C$_1$–C$_6$ alkyl, C$_1$–C$_4$ alkoxy, C$_1$–C$_4$ haloalkyl, and C$_1$–C$_4$ haloalkoxy;

$R^7$, at each occurrence, is independently selected from H, OH, Cl, F, Br, I, CN, NO$_2$, CF$_3$, phenyl and C$_1$–C$_4$ alkyl;

$R^{7a}$, at each occurrence, is independently selected from 14, OH, Cl, F, Br, I, CN, NO$_2$, CF$_3$, and C$_1$–C$_4$ alkyl;

$R^{7b}$ is independently selected from H and C$_1$–C$_4$ alkyl;

Ring B is a 7 membered lactam or thiolactam,
  wherein the lactam is 2-oxo-azepinyl or thiolactam is 2-thioxo-azepinyl;
    wherein each additional lactam carbon or thiolactam carbon is substituted with 0–2 R$^{11}$;
      provided two R$^{11}$ substituents are present on adjacent atoms and are combined to form a benzo fused radical; wherein said benzo fused radical is substituted with 0–4 R$^{13}$; and,
    wherein the lactam or thiolactam contains a heteroatom selected from —N=, —NH—, and —N(R$^{10}$)—;

$R^{10}$ is H, C(=O)R$^{17}$, C(=O)OR$^{17}$, C(=O)NR$^{18}$R$^{19}$, S(=O)$_2$NR$^{18}$R$^{19}$, S(=O)$_2$R$^{17}$;
  C$_1$–C$_6$ alkyl optionally substituted with 0–3 R$^{10a}$;
  aryl substituted with 0–4 R$^{10b}$;
  C$_3$–C$_{10}$ carbocycle substituted with 0–3 R$^{10b}$; Or
  5 to 10 membered heterocycle containing 1 to 4 heteroatoms selected from nitrogen, oxygen, and sulphur, wherein said 5 to 10 membered heterocycle is substituted with 0–3 R$^{10b}$;

$R^{10a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$, or aryl substituted with 0–4 R$^{10b}$;

$R^{10b}$, at each occurrence, is independently selected from H, OH, C$_1$–C$_6$ allyl, C$_1$–C$_4$ alkoxy, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

$R^{11}$, at each occurrence, is independently selected from H, C$_1$–C$_4$ alkoxy, Cl, F, Br, I, CN, NO$_2$, NR$^{18}$R$^{19}$, C(=O)R$^{17}$, C(=O)OR$^{17}$, C(=O)NR$^{18}$R$^{19}$, S(=O)$_2$NR$^{18}$R$^{19}$, CF$_3$;
  C$_1$–C$_6$ alkyl optionally substituted with 0–3 R$^{11a}$;
  aryl substituted with 0–3 R$^{11b}$;
  C$_3$–C$_{10}$ carbocycle substituted with 0–3 R$^{11b}$; or
  5 to 10 membered heterocycle containing 1 to 4 heteroatoms selected from nitrogen, oxygen, and sulphur, wherein said 5 to 10 membered heterocycle is substituted with 0–3 R$^{11b}$;

$R^{11a}$, at each occurrence, is independently selected from H, C$_1$–C$_6$ alkyl, OR$^{14}$, Cl, F, Br, I, =O, CN, NO$_2$, NR$^{15}$R$^{16}$, CF$_3$;
  phenyl substituted with 0–3 R$^{11b}$;
  C$_3$–C$_6$ cycloalkyl substituted with 0–3 R$^{11b}$; and
  5 to 6 membered heterocycle containing 1 to 4 heteroatoms selected from nitrogen, oxygen, and sulphur, wherein said 5 to 6 membered heterocycle is substituted with 0–3 R$^{11b}$;

$R^{11b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

Z is H;
  C$_1$–C$_8$ alkyl substituted with 1–3 R$^{12}$;
  C$_2$–C$_4$ alkenyl substituted with 1–3 R$^{12}$;
  C$_2$–C$_4$ alkynyl substituted with 1–3 R$^{12}$;
  C$_1$–C$_8$ alkyl substituted with 0–3 R$^{12a}$;
  C$_2$–C$_4$ alkenyl substituted with 0–3 R$^{12a}$;
  C$_2$–C$_4$ alkynyl substituted with 0–3 R$^{12a}$;
  aryl substituted with 0–4 R$^{12b}$;
  C$_1$–C$_{10}$ carbocycle substituted with 0–4 R$^{12b}$; or
  5 to 10 membered heterocycle containing 1 to 4 heteroatoms selected from nitrogen, oxygen, and sulphur, wherein said 5 to 10 membered heterocycle is substituted with 0–3 R$^{12b}$;

$R^{12}$, at each occurrence, is independently selected from
  aryl substituted with 0–4 R$^{12b}$;
  C$_3$–C$_{10}$ carbocycle substituted with 0–4 R$^{12b}$; or
  5 to 10 membered heterocycle containing 1 to 4 heteroatoms selected from nitrogen, oxygen, and sulphur, wherein said 5 to 10 membered heterocycle is substituted with 0–3 R$^{12b}$;

$R^{12a}$, at each occurrence, is independently selected from H, OH, Cl, F, Br, I, CN, NO$_2$, NR$^{15}$R$^{16}$, —C(=O)NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, or C$_1$–C$_4$ haloalkyl-S—;

$R^{12b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, C$_1$–C$_6$ alkyl, C$_1$–C$_4$ alkoxy, C$_1$–C$_4$ haloalkyl, C$_1$–C$_4$ haloalkoxy, and C$_1$–C$_4$ haloalkyl-S—;

$R^{13}$, at each occurrence, is independently selected from H, OH, C$_1$–C$_6$ alkyl, C$_1$–C$_4$ alkoxy, Cl, F, Br, I, CN, NO$_2$, NR$^{15}$R$^{16}$, and CF$_3$;

$R^{14}$ is H, phenyl, benzyl, C$_1$–C$_6$ alkyl, C$_2$–C$_6$ alkoxyalkyl, or C$_3$–C$_6$ cycloalkyl;

$R^{14a}$ is H, phenyl, benzyl, or C$_1$–C$_4$ alkyl;

$R^{15}$, at each occurrence, is independently selected from H, C$_1$–C$_6$ alkyl, benzyl, phenethyl, (C$_1$–C$_6$ alkyl)-C(=O)—, and (C$_1$–C$_6$ alkyl)-S(=O)$_2$—;

$R^{16}$, at each occurrence, is independently selected from H, OH, C$_1$–C$_6$ alkyl, benzyl, phenethyl, (C$_1$–C$_6$ alkyl)-C(=O)—, and (C$_1$–C$_6$ alkyl)-S(=O)$_2$—;

$R^{17}$ is H, C$_1$–C$_6$ alkyl, C$_2$–C$_6$ alkoxyalkyl,
  aryl substituted by 0–4 R$^{17a}$, or
  —CH$_2$-aryl substituted by 0–4 R$^{17a}$;

$R^{17a}$ is H, methyl, ethyl, propyl, butyl, methoxy, ethoxy, propoxy, butoxy, —OK, F, Cl, Br, I, CF$_3$, OCF$_3$, SCH$_3$, S(O)CH$_3$, SO$_2$CH$_3$, —NH$_2$, —N(CH$_3$)$_2$, or C$_1$–C$_4$ haloalkyl;

$R^{18}$, at each occurrence, is independently selected from H, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—; and $R^{19}$, at each occurrence, is independently selected from H, OH, C$_1$–C$_6$ alkyl, phenyl, benzyl, phenethyl, (C$_1$–C$_6$ alkyl)-C(=O)—, and (C$_1$–C$_6$ alkyl)-S(=O)$_2$—;

provided, when R$^{13}$ is H,
then Z is H;
  C$_4$–C$_8$ alkyl substituted with 1–3 R$^{12}$;
  C$_2$–C$_4$ alkenyl substituted with 1–3 R$^{12}$;
  C$_2$–C$_4$ alkynyl substituted with 1–3 R$^{12}$;
  C$_1$–C$_8$ alkyl substituted with 0–3 R$^{12a}$;
  C$_2$–C$_4$ alkenyl substituted with 0–3 R$^{12a}$; or
  C$_2$–C$_4$ alkynyl substituted with 0–3 R$^{12a}$.

2. A compound, according to claim 1, of Formula (Ia):

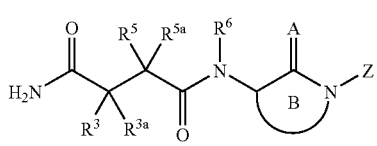

(Ia)

or a pharmaceutically acceptable salt thereof,
wherein:
Z is H;
$C_1$–$C_8$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$.

3. A compound according to claim 2 of Formula (Ia)

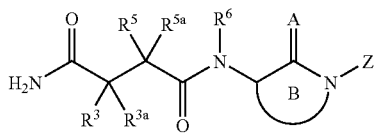

(Ia)

or a pharmaceutically acceptable salt thereof,
wherein:
$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—N($R^{7b}$)—$(CR^7R^{7a})_m$—$R^4$;
n is 0, 1, or 2;
m is 0, 1, or 2;
$R^{3a}$ is H. OH, methyl, ethyl, propyl, butyl, methoxy, ethoxy, propoxy, butoxy, allyl, or 3-buten-1-yl,
$R^4$ is H, OH, $OR^{14a}$,
  $C_1$–$C_6$ alkyl substituted with 0–3 $R^{4a}$,
  $C_2$–$C_6$ alkenyl substituted with 0–3 $R^{4a}$,
  $C_2$–$C_6$ alkynyl substituted with 0–3 $R^{4a}$,
  $C_3$–$C_{10}$ carbocycle substituted with 0–3 $R^{4b}$,
  aryl substituted with 0–3 $R^{4b}$, or
  5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from H, F, Cl, Br, I, $CF_3$,
  $C_3$–$C_{10}$ carbocycle substituted with 0–3 $R^{4b}$,
  aryl substituted with 0–3 $R^{4b}$, or
  5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^5$ is H, $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H or $C_1$–$C_4$ alkyl;
$R^{5b}$, at each occurrence, is independently selected from:
  H, $C_1$–$C_6$ alkyl, $CF_3$, $OR^{14}$, Cl, F, Br, I, =O, CN, NQ, $NR^{15}R^{16}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2C_1$–$C_6$, $C_1$–$C_6$ alkyl, $C_1$–$C_4$ alkoxy, $C_1$–$C_4$ haloalkyl, and $C_1$–$C_4$ haloalkoxy;
$R^6$ is H, methyl, or ethyl;
$R^7$, at each occurrence, is independently selected from H, OH, Cl, F, Br, I, CN, $NO_2$, $CF_3$, phenyl and $C_1$–$C_4$ alkyl;
$R^{7a}$, at each occurrence, is independently selected from H, OH, Cl, F, Br, T, CN, $NO_2$, $CF_3$, and $C_1$–$C_4$ alkyl;
$R^{7b}$ is independently selected from H, methyl, ethyl, propyl, and butyl;
Ring B is selected from

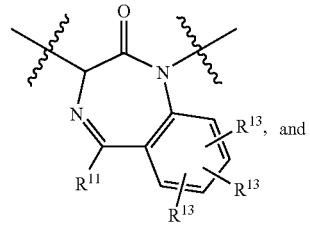

$R^{13}$, and

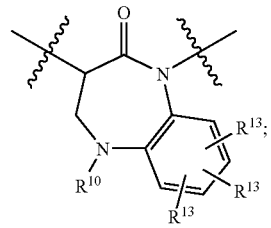

$R^{10}$ is H, $C(=O)R^{17}$, $C(=O)OR^{17}$, $C(=O)NR^{18}R^{19}$, $S(=O)_2NR^{18}R^{19}$, $S(=O)R^{17}$;
  $C_1$–$C_6$ alkyl optionally substituted with 0–2 $R^{10a}$;
  aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$, at each occurrence, is independently selected from H, $C_1$–$C_6$ alkyl, $OR^{14}$, Cl, F, Br, I, =O, CN, $NO_2$, $NR^5R^{16}$, $CF_3$, or phenyl substituted with 0–4 $R^{10b}$;
$R^{10b}$, at each occurrence, is independently selected from H, OH, $C_1$–$C_4$ alkyl, $C_1$–$C_4$ alkoxy, Cl, F, Br, I, CN, $NO_2$, $NR^{15}R^{16}$, or $CF_3$;
$R^{11}$, at each occurrence, is independently selected from H, $C_1$–$C_4$ alkoxy, Cl, F, Br, I, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;

$C_1-C_6$ alkyl optionally substituted with 0–3 $R^{11a}$;
aryl substituted with 0–3 $R^{11b}$;
$C_3-C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;

$R^{11a}$, at each occurrence, is independently selected from H, $C_1-C_6$ alkyl, $OR^{14}$, Cl, F, Br, I, =O, CN, $NO_2$, $NR^{15}R^{16}$, $CF_3$, or phenyl substituted with 0–3 $R^{11b}$;

$R^{11b}$, at each occurrence, is independently selected from H, OH, Cl, F, Br, I, CN, $NO_2$, $NR^{15}R^{116}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, and $C_1-C_4$ haloalkoxy;

Z is H;
$C_1-C_6$ alkyl substituted with 0–3 $R^{12a}$;
$C_2-C_4$ alkenyl substituted with 0–3 $R^{12a}$; or
$C_2-C_4$ alkynyl substituted with 0–3 $R^{12a}$;

$R^{12a}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_6$ alkyl, $C_1-C_4$ alkoxy, $C_1-C_4$ haloalkyl, and $C_1-C_4$ haloalkoxy;

$R^{13}$, at each occurrence, is independently selected from H, OH, $C_1-C_6$ alkyl, $C_1-C_4$ alkoxy, Cl, F, Br, I, CN, $NO_2$, $NR^{15}R^{16}$, and $CF_3$;

$R^{14}$ is H, phenyl, benzyl, $C_1-C_6$ alkyl, or $C_2-C_6$ alkoxyalkyl;

$R^{14a}$ is H, phenyl, benzyl, methyl, ethyl, propyl, or butyl;

$R^{15}$, at each occurrence, is independently selected from H, $C_1-C_6$ alkyl, benzyl, phenethyl, $(C_1-C_6$ alkyl)-C(=O)—, and $(C_1-C_6$ alkyl)-$S(=O)_2$—;

$R^{16}$, at each occurrence, is independently selected from H, OH, $C_1-C_6$ alkyl, benzyl, phenethyl, $(C_1-C_6$ alkyl)-C(=O)—, and $(C_1-C_6$ alkyl)-$S(=O)_2$—;

$R^{17}$ is H, $C_1-C_6$ alkyl, $C_2-C_6$ alkoxyalkyl,
aryl substituted by 0–4 $R^{17a}$, or
—$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1-C_4$ haloalkyl;

$R^{18}$, at each occurrence, is independently selected from H, $C_1-C_6$ alkyl, phenyl, benzyl, phenethyl, $(C_1-C_6$ alkyl)-C(=O)—, and $(C_1-C_6$ alkyl)-$S(=O)_2$—; and $R^{19}$, at each occurrence, is independently selected from H, OH, $C_1-C_6$ alkyl, phenyl, benzyl, phenethyl, $(C_1-C_6$ alkyl)-C(=O)—, and $(C_1-C_6$ alkyl)-$S(=O)_2$—.

4. A compound according to claim 3 of Formula (Ia)

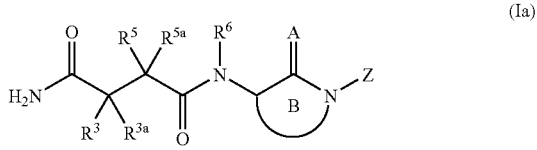

(Ia)

or a pharmaceutically acceptable salt thereof,
wherein;
$R^3$ is —$(CHR^7)_x$—$R^4$,
n is 0 or 1;

$R^{3a}$ is H, OH, methyl, ethyl, propyl, butyl, methoxy, ethoxy, propoxy, butoxy, allyl, or 3-buten-1-yl;

$R^4$ is H, OH, $OR^{14a}$,
$C_1-C_4$ alkyl substituted with 0–2 $R^{4a}$,
$C_2-C_4$ alkenyl substituted with 0–2 $R^{4a}$,
$C_2-C_4$ alkynyl substituted with 0–1 $R^{4a}$,
$C_3-C_6$ carbocycle substituted with 0–3 $R^{4b}$,
aryl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4a}$, at each occurrence, is independently selected from H, F, Cl, Br, I, $CF_3$,
$C_3-C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_4$ alkyl, $C_1-C_3$ alkoxy, $C_1-C_2$ haloalkyl, and $C_1-C_2$ haloalkoxy;

$R^5$ is H, $OR^{14}$;
$C_1-C_4$ alkyl substituted with 0–3 $R^{5b}$;
$C_2-C_4$ alkenyl substituted with 0–3 $R^{5b}$;
$C_2-C_4$ alkynyl substituted with 0–3 $R^{5b}$;

$R^{5a}$ is H, methyl, ethyl, propyl, or butyl;

$R^{5b}$, at each occurrence, is independently selected from:
H, methyl, ethyl, propyl, butyl, $CF_3$, $OR^{14}$, Cl, F, Br, I, =O;
$C_3-C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1-C_4$ alkyl, $C_1-C_3$ alkoxy, $C_1-C_2$ haloalkyl, and $C_1-C_2$ haloalkoxy;

$R^6$ is H;

$R^7$, at each occurrence, is independently selected from H, F, $CF_3$, methyl, and ethyl;

Ring B is selected from

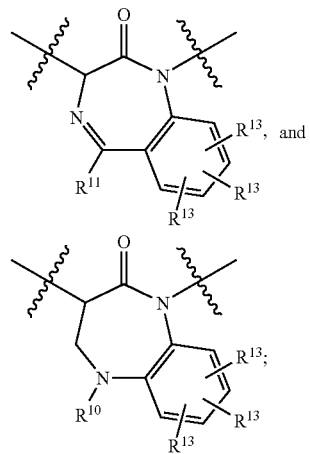

$R^{10}$ is H, C(=O)$R^{17}$, C(=O)O$R^{17}$;
  $C_1$–$C_4$ alkyl optionally substituted with 0–1 $R^{10a}$;
  phenyl substituted with 0–4 $R^{10b}$;
  $C_3$–$C_6$ carbocycle substituted with 0–3 $R^{10b}$; or
  5 to 6 membered heterocycle containing 1 to 4 heteroatoms selected from nitrogen, oxygen, and sulphur, wherein said 5 to 6 membered heterocycle is substituted with 0–3 $R^{10b}$;

$R^{10a}$ is selected from H, $C_1$–$C_4$ alkyl, O$R^{14}$, Cl, F, Br, I, =O, CN, NO$_2$, N$R^5R^{16}$, CF$_3$, or phenyl substituted with 0–4 $R^{10b}$;

$R^{10b}$, at each occurrence, is independently selected from H, OH, $C_1$–$C_4$ alkyl, $C_1$–$C_3$ alkoxy, Cl, F, Br, I, CN, NO$_2$, N$R^{15}R^{16}$, or CF$_3$;

$R^{11}$ is selected from
  H, $C_1$–$C_4$ alkoxy, Cl, F, N$R^{18}R^{19}$, C(=O)$R^{17}$, C(=O)O$R^{17}$, CF$_3$;
  $C_1$–$C_6$ alkyl optionally substituted with 0–3 $R^{11a}$;
  aryl substituted with 0–3 $R^{11b}$;
  $C_3$–$C_6$ carbocycle substituted with 0–3 $R^{11b}$; or
  5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11a}$, at each occurrence, is independently selected from H, $C_1$–$C_4$ alkyl, O$R^{14}$, F, =O, N$R^{15}R^{16}$, CF$_3$, or phenyl substituted with 0–3 $R^{11b}$;

$R^{11b}$, at each occurrence, is independently selected from H, OH, Cl, F, N$R^{15}R^{16}$, CF$_3$, $C_1$–$C_4$ alkyl, $C_1$–$C_3$ alkoxy, $C_1$–$C_2$ haloalkyl, and $C_1$–$C_2$ haloalkoxy;

Z is 14;
  $C_1$–$C_4$ alkyl substituted with 0–3 $R^{12a}$;
  $C_2$–$C_4$ alkenyl substituted with 0–3 $R^{12a}$; or
  $C_2$–$C_4$ alkynyl substituted with 0–3 $R^{12a}$;

$R^{12a}$, at each occurrence, is independently selected from H, OH, Cl, F, N$R^{15}R^{16}$, CF$_3$, acetyl, SCH$_3$, S(=O)CH$_3$, S(=O)$_2$CH$_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, NO$_2$N$R^{15}R^{16}$, and CF$_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{17}$ is H, methyl, ethyl, propyl, butyl, methoxymethyl, ethoxymethyl, methoxyethyl,
  ethoxyethyl,
  phenyl substituted by 0–3 $R^{17a}$, or
  —CH$_2$-phenyl substituted by 0–3 $R^{17a}$;

$R^{17a}$ is 1H, methyl, methoxy, —OH, F, Cl, CF$_3$, or OCF$_3$;

$R^{18}$, at each occurrence, is independently selected from
  H, methyl, ethyl, propyl, butyl, phenyl, benzyl, and phenethyl; and $R^{19}$, at each occurrence, is independently selected from
  H, methyl, and ethyl.

5. A compound according to claim 4 of Formula (Ic)

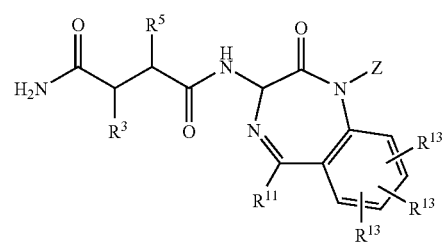

(Ic)

or a pharmaceutically acceptable salt thereof
wherein
  $R^3$ is $R^4$,
  $R^4$ is $C_1$–$C_4$ alkyl substituted with 0–1 $R^{4a}$,
    $C_2$–$C_4$ alkenyl substituted with 0–1 $R^{4a}$, or
    $C_2$–$C_4$ alkynyl substituted with 0–1 $R^{4a}$;
  $R^{4a}$ is selected from
    H, F, CF$_3$,
    $C_3$–$C_6$ carbocycle substituted with 0–3 $R^{4b}$,
    phenyl substituted with 0–3 $R^{4b}$, or
    5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
  $R^{4b}$, at each occurrence, is independently selected from H, OH, Cl, F, N$R^{15}R^{16}$, CF$_3$, acetyl, SCH$_3$, S(=O)CH$_3$, S(=O)$_2$CH$_3$, methyl, ethyl, propyl, butyl, methoxy, ethoxy, propoxy, $C_1$–$C_2$ haloalkyl, and $C_1$–$C_2$ haloalkoxy;
  $R^5$ is $C_1$–$C_4$ alkyl substituted with 0–1 $R^{5b}$;
    $C_2$–$C_4$ alkenyl substituted with 0–1 $R^{5b}$;
    $C_2$–$C_4$ alkynyl substituted with 0–1 $R^{5b}$;
  $R^{5b}$ is selected from:
    H, methyl, ethyl, propyl, butyl, CF$_3$, O$R^{14}$, =O;
    $C_3$–$C_6$ carbocycle substituted with 0–2 $R^{5c}$;
    phenyl substituted with 0–3 $R^{5c}$; or
    5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
  $R^{5c}$, at each occurrence, is independently selected from H, OH, Cl, F, N$R^{15}R^{16}$, CF$_3$, acetyl, SCH$_3$, S(=O)CH$_3$, S(=O)$_2$CH$_3$, methyl, ethyl, propyl, butyl, methoxy, ethoxy, propoxy, $C_1$–$C_2$ haloalkyl, and $C_1$–$C_2$ haloalkoxy;
  $R^{11}$ is selected from
    H, N$R^{18}R^{19}$, CF$_3$;
    $C_1$–$C_4$ alkyl optionally substituted with 0–1 $R^{11a}$;
    phenyl substituted with 0–3 $R^{11b}$;
    $C_3$–$C_6$ carbocycle substituted with 0–3 $R^{11b}$; and
    5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{11a}$ is selected from H, $C_1$–$C_4$ alkyl, $OR^{14}$, F, =O, $NR^{15}R^{16}$ $CF_3$, or phenyl substituted with 0–3 $R^{11b}$;

$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;

Z is H;
  $C_1$–$C_4$ alkyl substituted with 0–3 $R^{12a}$;
  $C_2$–$C_4$ alkenyl substituted with 0–3 $R^{12a}$; or
  $C_2$–$C_4$ alkynyl substituted with 0–3 $R^{12a}$;

$R^{12a}$, at each occurrence, is independently selected from H, OH, Cl, F, $NR^{15}R^{16}$, $CF_3$, acetyl, $SCH_3$, S(=O) $CH_3$, S(=O)$_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $NR^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$, at each occurrence, is independently selected from H, OH, methyl, ethyl, propyl, butyl, benzyl, phenethyl, methyl-C(=O), ethyl-C(=O)—, methyl-S(=O)$_2$—, and ethyl-S(=O)$_2$—;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl.

6. A compound, according to claim 5, wherein:

$R^3$ is —$CH_3$, —$CH_2CH_3$, —$CH_2CH_2CH_3$, —$CH_2CH_2CH_2CH_3$, —$CH(CH_3)_2$, —$CH(CH_3)CH_2CH_3$, —$CH_2CH(CH_3)_2$, —$CH_2CF_3$, —$CH_2CH_2CF_3$, —$CH_2CH_2CH_2CF_3$, —CH=$CH_2$, —$CH_2C_4$=$CH_2$, —$CH_2C(CH_3)$=$CH_2$, —$CH_2CH_2CH$—$CH_2$, cis-$CH_2CH$=CH($CH_3$), trans-$CH_2CH$≡CH($CH_3$), —C≡CH, —$CH_2C$≡CH, —$CH_2C$≡C($CH_3$), cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-$CH_2CH_2$—, cyclohexyl-$CH_2CH_2$—, phenyl-$CH_2$—, (2-F-phenyl)$CH_2$—, (3-F-phenyl)$CH_2$—, (4-F-phenyl)$CH_2$—, (2-Cl-phenyl)$CH_2$—, (3-Cl-phenyl)$CH_2$—, (4-Cl-phenyl)$CH_2$—, (2,3-diF-phenyl)$CH_2$—, (2,4-diF-phenyl)$CH_2$—, (2,5-diF-phenyl)$CH_2$—, (2,6-diF-phenyl)$CH_2$—, (3,4-diF-phenyl)$CH_2$—, (3,5-diF-phenyl)$CH_2$—, (2,3-diCl-phenyl)$CH_2$—, (2,4-diCl-phenyl)$CH_2$—, (2,5-diCl-phenyl)$CH_2$—, (2,6-diCl-phenyl)$CH_2$—, (3,4-diCl-phenyl)$CH_2$—, (3,5-diCl-phenyl)$CH_2$—, (3-F-4-Cl-phenyl)$CH_2$—, (3-F-5-Cl-phenyl)$CH_2$—, (3-Cl-4-F-phenyl)$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, (2-Cl-phenyl)$CH_2CH_2$—, (3-Cl-phenyl)$CH_2CH_2$—, (4-Cl-phenyl)$CH_2CH_2$—, (2,3-diF-phenyl)$CH_2CH_2$—, (2,4-diF-phenyl)$CH_2CH_2$—, (2,5-diF-phenyl)$CH_2CH_2$—, (2,6-diF-phenyl)$CH_2CH_2$—, (3,4-diF-phenyl)$CH_2CH_2$—, (3,5-diF-phenyl)$CH_2CH_2$—, (2,3-diCl-phenyl)$CH_2CH_2$—, (2,4-diCl-phenyl)$CH_2CH_2$—, (2,5-diCl-phenyl)$CH_2CH_2$—, (2,6-diCl-phenyl)$CH_2CH_2$—, (3,4-diCl-phenyl)$CH_2CH_2$—, (3,5-diCl-phenyl)$CH_2CH_2$—, (3-F-4-Cl-phenyl)$CH_2CH_2$—, or (3-F-5-Cl-phenyl)$CH_2CH_2$—, $R^5$ is —$CH_3$, —$CH_2CH_3$, —$CH_2CH_2CH_3$, —$CH(CH_3)_2$, $CH_2CH_2CH_2CH_3$, —$CH(CH_3)CH_2CH_3$, —$CH_2CH(CH_3)_2$, —$CH_2C(CH_3)_3$, —$CH_2CH_2CH_2CH_2CH_3$, —$CH(CH_3)CH_2CH_2CH_3$, —$CH_2CH(CH_3)CH_2CH_3$, —$CH_2CH_2CH(CH_3)_2$, —$CH((CH_2CH_3)_2$, —$CH_2CF_3$, —$CH_2CH_2CF_3$, —$CH_2CH_2CH_2CF_3$, —$CH_2CH_2CH_2CH_2CF_3$, —CH=$CH_2$, —$CH_2CH$=$CH_2$, —CH=$CHCH_3$, cis-$CH_2CHCH$($CH_3$), trans-$CH_2CH$=CH($CH_3$), trans-$CH_2CH$≡CH($C_6H_5$), —$CH_2CH$=C($CH_3$)$_2$, cis-$CH_2CH$=$CHCH_2CH_3$, trans-$CH_2CH$=$CHCH_2CH_3$, cis-$CH_2CH_2CH$=CH($CH_3$), trans-$CH_2CH_2CHCH$($CH_3$), trans-$CH_2CH$=$CHCH_2$($C_6H_5$), —C—CH, —$CH_2C$=CH, —$CH_2C$=C($CH_3$), —$CH_2C$=C($C_6H_5$), —$CH_2CH_2C$—CH, —$CHR^2CH_2C$≡C($CH_3$), —$CH_2CH_2CC$($C_6H_5$), cyclopropyl-$CH_2$—, cyclobutyl-$CH_2$—, cyclopentyl-$CH_2$—, cyclohexyl-$CH_2$—, (2-$CH_3$-cyclopropyl)$CH_2$—, (3-$CH_3$-cyclobutyl)$CH_2$—, cyclopropyl-$CH_2CH_2$—, cyclobutyl-$CH_2CH_2$—, cyclopentyl-$CH_2CH_2$—, cyclohexyl-$CH_2CH_2$—, (2-$CH_3$-cyclopropyl)$CH_2CH_2$—, (3-$CH_3$-cyclobutyl)$CH_2CH_2$—, phenyl-$CH_2$—, (2-F-phenyl)$CH_2$—, (3-F-phenyl)$CH_2$—, (4-F-phenyl)$CH_2$—, furanyl-$CH_2$—, phenyl-$CH_2$—, pyridyl-$CH_2CH_2$—, 1-imidazolyl-$CH_2$—, oxazolyl-$CH_2$—, isoxazolyl-$CH_2$—, phenyl-$CH_2CH_2$—, (2-F-phenyl)$CH_2CH_2$—, (3-F-phenyl)$CH_2CH_2$—, (4-F-phenyl)$CH_2CH_2$—, furanyl-$CH_2CH_2$—, thienyl-$CH_2CH_2$—, pyridyl-$CH_2CH_2$—, 1-imidazolyl-$CH_2CH_2$—, oxazolyl-$CH_2CH_2$—, isoxazolyl-$CH_2CH_2$—;

Z is methyl, ethyl, i-propyl, n-propyl, n-butyl, i-butyl, s-butyl, t-butyl, or allyl, $R^{11}$, at each occurrence, is independently selected from H, methyl, ethyl, phenyl, benzyl, phenethyl,
  4-F-phenyl, (4-F-phenyl)$CH_2$—, (4-F-phenyl)$CH_2CH_2$—,
  3-F-phenyl, (3-F-phenyl)$CH_2$—, (3-F-phenyl)$CH_2CH_2$—,
  2-F-phenyl, (2-F-phenyl)$CH_2$—, (2-F-phenyl)$CH_2CH_2$—,
  4-Cl-phenyl, (4-Cl-phenyl)$CH_2$—, (4-Cl-phenyl)$CH_2CH_2$—,
  3-Cl-phenyl, (3-Cl-phenyl)$CH_2$—, (3-Cl-phenyl)$CH_2CH_2$—,
  4-$CH_3$-phenyl, (4-$CH_3$-phenyl)$CH_2$—, (4-$CH_3$-phenyl)$CH_2CH_2$—,
  3-$CH_3$-phenyl, (3-$CH_3$-phenyl)$CH_2$—, (3-$CH_3$-phenyl)$CH_2CH_2$—,
  4-$CF_3$-phenyl, (4-$CF_3$-phenyl)$CH_2$—, (4-$CF_3$-phenyl)$CH_2CH_2$—,
  pyrid-2-yl, pyrid-3-yl, or pyrid-4-yl, and $R^{13}$, at each occurrence, is independently selected from H, F, Cl, OH, $CH_3$, —$CH_2CH_3$, —$OCH_3$, or —$CF_3$.

7. A compound according to claim 2 selected from:

(2R,3S) N1-[1,3-dihydro-1-methyl-2-oxo-5-phenyl-2H-1,4-benzodiazepin-3-yl]-2-(2-methylpropyl)-3-allyl-butanediamide;

(2R,3S) N1-[1,3-dihydro-1-methyl-2-oxo-5-phenyl-2H-1,4-benzodiazepin-3-yl]-2-(2-methylpropyl)-3-propyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-allyl-butanediamide;

(2R,3S) N1-[(3R)-1,3-dihydro-1-methyl-2-oxo-5-phenyl-2H-1,4-benzodiazepin-3-yl]-2-(2-methylpropyl)-3-allyl-butanediamide;

(2R,3S) N1-[(3R)-1,3-dihydro-1-methyl-2-oxo-5-phenyl-2H-1,4-benzodiazepin-3-yl]-2-(2-methylpropyl)-3-propyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-propyl-butanediamide;

(2R,3S) N1-[1,3-dihydro-1-methyl-2-oxo-5-phenyl-2H-1,4-benzodiazepin-3-yl]-2-ethyl-3-allyl-butanediamide;

(2R,3S) N1-[(3S)-1,3-dihydro-1-methyl-2-oxo-5-phenyl-2H-1,4-benzodiazepin-3-yl]-2-methyl-3-allyl-butanediamide;

(2R,3S) N1-[(3S)-1,3-dihydro-1-methyl-2-oxo-5-phenyl-2H-1,4-benzodiazepin-3-yl]-2-methyl-3-propyl-butanediamide;

(2R) N1-[1,3-dihydro-1-methyl-2-oxo-5-phenyl-2H-1,4-benzodiazepin-3-yl]-2-methyl-butanediamide;

(2R,3S) N1-[1,3-dihydro-2-oxo-5-phenyl-2H-1,4-benzodiazepin-3-yl]-2-(2-methylpropyl)-3-allyl-butanediamide;

(2R,3S) N1-[1,3-dihydro-1-methyl-2-oxo-5-phenyl-7-chloro-2H-1,4-benzodiazepin-3-yl]-2-(2-methylpropyl)-3-allyl-butanediamide;

(2R,3S) N1-[(3S)-1,3-dihydro-1-methyl-2-oxo-5-phenyl-7-chloro-2H-1,4-benzodiazepin-3-yl]-2-(2-methylpropyl)-3-allyl-butanediamide;

(2R,3S) N1-[(3R)-1,3-dihydro-1-methyl-2-oxo-5-phenyl-7-chloro-2H-1,4-benzodiazepin-3-yl]-2-(2-methylpropyl)-3-allyl-butanediamide;

(2R,3S) N1-[1,3-dihydro-1-methyl-2-oxo-5-(2-fluorophenyl)₇-chloro-2H-1,4-benzodiazepin-3-yl]-2-(2-methylpropyl)-3-allyl-butanediamide;

(2R,3S) N1-[(3S)-1,3-dihydro-1-methyl-2-oxo-5-(2-fluorophenyl)-7-chloro-2H-1,4-benzodiazepin-3-yl]-2-(2-methylpropyl)-3-allyl-butanediamide;

(2R,3S) N1-[(3R)-1,3-dihydro-1-methyl-2-oxo-5-(2-fluorophenyl)-7-chloro-2H-1,4-benzodiazepin-3-yl]-2-(2-methylpropyl)-3-allyl-butanediamide;

(2S,3S) N1-[1,3-dihydro-1-methyl-2-oxo-5-phenyl-2H-1,4-benzodiazepin-3-yl]-2-(2-methylpropyl)-3-allyl-butanediamide;

(2R,3S) N1-[(3S)-1,3-dihydro-methyl-2-oxo-5-phenyl-7-chloro-2H-1,4-benzodiazepin-3-yl]-2-(2-methylpropyl)-3-propyl-butanediamide;

(2R,3S) N1-[(3S)-1,3-dihydro-1-methyl-2-oxo-5-(2-fluorophenyl)-7-chloro-2H-1,4-benzodiazepin-3-yl]-2-(2-methylpropyl)-3-propyl-butanediamide;

(2R,3S) N1-[1,3-dihydro-1-methyl-2-oxo-5-(4-fluorophenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-fluorophenyl)-2H-1,4-benzodiazepin-3-yl]-2-(2-methylpropyl)-3-allyl-butanediamide;

(2R,3S) N1-[(3R)-1,3-dihydro-1-methyl-2-oxo-5-(4-fluorophenyl)-2H-1,4-benzodiazepin-3-yl]-2-(2-methylpropyl)-3-allyl-butanediamide;

(2R,3S) N1-[1,3-dihydro-1-methyl-2-oxo-5-(pyrid-2-yl)-2H-1,4-benzodiazepin-3-yl]-2-(2-methylpropyl)-3-allyl-butanediamide;

(2R,3S) N1-[1,3-dihydro-1-methyl-2-oxo-5-(N-morpholino)-2H-1,4-benzodiazepin-3-yl]-2-(2-methylpropyl)-3-allyl-butanediamide;

(2R,3S) N1-[1,3-dihydro-1-methyl-2-oxo-5-(dimethylamino)-2H-1,4-benzodiazepin-3-yl]-2-(2-methylpropyl)-3-allyl-butanediamide;

(2R,3S) N1-[1,3-dihydro-1-methyl-2-oxo-5-(N-methyl-N-phenylamino)-2H-1,4-benzodiazepin-3-yl]-2-(2-methylpropyl)-3-allyl-butanediamide;

(2R,3S) N1-[1,3-dihydro-1-methyl-2-oxo-5-(N-piperidinyl)-2H-1,4-benzodiazepin-3-yl]-2-(2-methylpropyl)-3-allyl-butanediamide;

(2R,3S) N1-[1,3-dihydro-1-methyl-2-oxo-5-(N-homopiperidinyl)-2H-1,4-benzodiazepin-3-yl]-2-(2-methylpropyl)-3-allyl-butanediamide;

(2R,3S) N1-[1,3-dihydro-1-methyl-2-oxo-5-(3-methoxyphenyl)-2H-1,4-benzodiazepin-3-yl]-2-(2-methylpropyl)-3-allyl-butanediamide;

(2R,3S) N1-[1,3-dihydro-1-methyl-2-oxo-5-(pyrid-4-yl)-2H-1,4-benzodiazepin-3-yl]-2-(2-methylpropyl)-3-allyl-butanediamide;

(2R,3S) N1-[1,3-dihydro-1-methyl-2-oxo-5-phenyl-7-methoxy-2H-1,4-benzodiazepin-3-yl]-2-(2-methylpropyl)-3-allyl-butanediamide;

(2R,3S) N1-[1,3-dihydro-1-methyl-2-oxo-5-(pyrid-3-yl)-2H-1,4-benzodiazepin-3-yl]-2-(2-methylpropyl)-3-allyl-butanediamide;

(2R,3S) N1-[1,3-dihydro-1-methyl-2-oxo-5-phenyl-2H-1,4-benzodiazepin-3-yl]-2-(2-methylpropyl)-3-(cyclopropylmethyl)-butanediamide;

(2R,3S) N1-[1,3-dihydro-1-methyl-2-oxo-5-(3-fluorophenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(3-fluorophenyl)-2H-1,4-benzodiazepin-3-yl]-2-(2-methylpropyl)-3-allyl-butanediamide;

(2R,3S) N1-[(3R)-1,3-dihydro-1-methyl-2-oxo-5-(3-fluorophenyl}2H-1,4-benzodiazepin-3-yl]-2-(2-methylpropyl)-3-allyl-butanediamide;

(2R,3S) N1-[(3S)-1,3-dihydro-1-diethyl-2-oxo-5-phenyl-2H-1,4-benzodiazepin-3-yl]-2-(2-methylpropyl) 3-(3-buten-1-yl)-butanediamide;

(2R,3S) N1-[(3S)-1,3-dihydro-1-methyl-2-oxo-5-phenyl-2H-1,4-benzodiazepin-3-yl]-2-(2-methylpropyl)-3-(cyclopentylethyl)-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-(3-buten-1-yl)-butanediamide;

(2R,3S) N1-[(3R)-1,3-dihydro-1-methyl-2-oxo-5-(4-trifluoromethylphenyl)-2H-1,4-benzodiazepin-3-yl]-2-(2-methylpropyl)-3-(3-buten-1-yl)-butanediamide;

(2R,3S) N1-[1,3-dihydro-1-methyl-2-oxo-5-(4-trifluoromethylphenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-allyl-butanediamide;

(2R,3S) N1-[(3R)-1,3-dihydro-1-methyl-2-oxo-5-(4-trifluoromethylphenyl)-2H-1,4-benzodiazepin-3-yl]-2-(2-methylpropyl)-3-allyl-butanediamide;

(2R,3S) N1-[(3S)-1,3-dihydro-1-methyl-2-oxo-5-(4-trifluoromethylphenyl)-2H-1,4-benzodiazepin-3-yl]-2-(2-methylpropyl)-3-n-butyl-butanediamide;

(2R,3S) N1-[(3-S)-1,3-dihydro-1-methyl-2-oxo-5-(4-trifluoromethylphenyl)-2H-1,4-benzodiazepin-3-yl]-2-(2-methylpropyl)-3-propyl-butanediamide;

(2R,3S) N1-[(3S)-1,3-dihydro-1-methyl-2-oxo-5-(4-chlorophenyl)-2H-1,4-benzodiazepin-3-yl]-2-(2-methylpropyl)-3-(3-buten-1-yl)-butanediamide;

(2R,3S) N1-[(3S)-1,3-dihydro-1-methyl-2-oxo-5-(4-chlorophenyl)-2H-1,4-benzodiazepin-3-yl]-2-(2-methylpropyl)-3-n-butyl-butanediamide;

(2R,3S) N1-[(3S)-1,3-dihydro-1-methyl-2-oxo-5-phenyl-2H-1,4-benzodiazepin-3-yl]-2-(2-methylpropyl)-3-allyl-N-4-[benzyl]-butanediamide;

(2R,3S) N1-[1,3-dihydro-1-methyl-2-oxo-5-methyl-2H-1,4-benzodiazepin-3-yl]-2-(2-methylpropyl)-3-allyl-butanediamide;

(2R,3S) N1-[1,3-dihydro-1-methyl-2-oxo-5-n-butyl-2H-1,4-benzodiazepin-3-yl]-2-(2-methylpropyl)-allyl-butanediamide;

(2R,3S) N1-[1,3-hydro-1-methyl-2-oxo-5-(2-methylpropyl)-2H-1,4-benzodiazepin-3-yl]-2-(2-methylpropyl)-3-allyl-butanediamide;

(2R,3S) N1-[1,3-dihydro-1-methyl-2-oxo-5-(4-chlorophenyl)-2H-1,4-benzodiazepin-3-yl]-2-(2-methylpropyl)-3-allyl-butanediamide;

(2R,3S) N1-[1,3-dihydro-1-ethyl-2-oxo-5-phenyl-2H-1,4-benzodiazepin-3-yl]-2-(2-methylpropyl)-3-allyl-butanediamide;

(2R,3S) N1-[1,3-dihydro-1-propyl-2-oxo-5-phenyl-2H-1,4-benzodiazepin-3-yl]-2-(2-methylpropyl)-3-allyl-butanediamide;

(2R,3S) N1-[1,3-dihydro-1-(isopropyl)-2-oxo-5-phenyl-2H-1,4-benzodiazepin-3-yl]-2-(2-methylpropyl)-3-allyl-butanediamide; and (2R,3S) N1-[(3S)-1,3-dihydro-1-methyl-2-oxo-5-phenyl-2H-1,4-benzodiazepin-3-yl]-2-(2-methylpropyl)-3,3-diallyl-butanediamide.

8. A compound, according to claim 1, of Formula (Ia''):

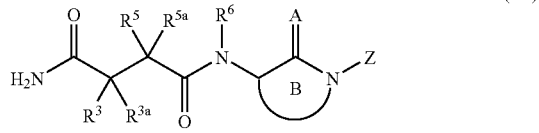

or a pharmaceutically acceptable salt thereof, wherein:

Z is $C_1$–$C_8$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$, provided, when $R^{13}$ is H,
then Z is $C_4$–$C_8$ alkyl substituted with 1–3 $R^{12}$;
$C_2$–$C_4$ alkenyl substituted with 1–3 $R^{12}$; or
$C_2$–$C_4$ alkynyl substituted with 1–3 $R^{12}$.

9. A compound according to claim 8 of Formula (Ia'')

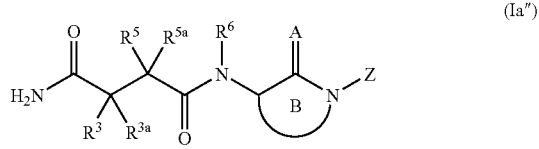

or a pharmaceutically acceptable salt thereof, wherein:

$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—N($R^{7b}$)—$(CR^7R^{7a})_m$—$R^4$;
n is 0, 1, or 2;

m is 0, 1, or 2;

$R^{3a}$ is H, OH, methyl, ethyl, propyl, butyl, methoxy, ethoxy, propoxy, butoxy, allyl, or 3-buten-1-yl;

$R^4$ is H, OH, OR$^{14a}$,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, F, Cl, Br, I, CF$_3$,
$C_3$–$C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, and $C_1$–$C_4$ haloalkoxy;

$R^5$ is H, OR$^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H or $C_1$–$C_4$ alkyl;

$R^{5b}$, at each occurrence, is independently selected from:
H, $C_1$–$C_6$ alkyl, CF$_3$, OR$^{14}$, Cl, F, Br, I, =O, CN, NO$_2$, NR$^{15}$R$^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, NO$_2$, NR$^{15}$R$^{16}$, CF$_3$, acetyl, SCH$_3$, S(=O)CH$_3$, S(=O)$_2$CH$_3$, $C_1$–$C_6$ alkyl, $C_1$–$C_4$ alkoxy, $C_1$–$C_4$ haloalkyl, and $C_1$–$C_4$ haloalkoxy;

$R^6$ is H, methyl, or ethyl;

$R^7$, at each occurrence, is independently selected from H, OH, Cl, F, Br, I, CN, NO$_2$, CF$_3$, phenyl, and $C_1$–$C_4$ alkyl;

$R^{7a}$, at each occurrence, is independently selected from H, OH, Cl, F, Br, I, CN, NO$_2$, CF$_3$, and $C_1$–$C_4$ alkyl;

$R^{7b}$ is independently selected from H, methyl, ethyl, propyl, and butyl;

Ring B is selected from

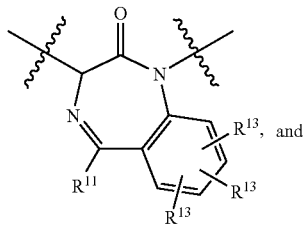

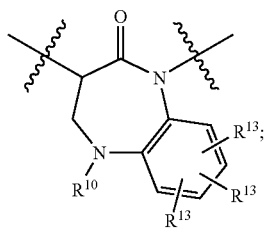

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$–$C_6$ alkyl optionally substituted with 0–2 $R^{10a}$;
aryl substituted with 0–4 $R^{10b}$;
$C_3$–$C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–4 $R^{10b}$;
$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
$R^{11}$, at each occurrence, is independently selected from H, $C_1$–$C_4$ alkoxy, Cl, F, Br, I, CN, $NO_2$, $NR^{18}R^{19}$, $C(=O)R^{17}$, $C(=O)OR^{17}$, $C(=O)NR^{18}R^{19}$, $S(=O)_2NR^{18}R^{19}$, $CF_3$;
$C_1$–$C_6$ alkyl optionally substituted with 0–3 $R^{11a}$;
aryl substituted with 0–3 $R^{11b}$;
$C_3$–$C_{10}$ carbocycle substituted with 0–3 $R^{11b}$; or
5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;
$R^{11b}$, at each occurrence, is independently selected from 1, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
Z is $C_1$–$C_6$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12}$, at each occurrence, is independently selected from aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_{13}$, $C_1$–$C_6$ alkyl, $C_1$–$C_4$ alkoxy, $C_1$–$C_4$ haloalkyl, and $C_1$–$C_4$ haloalkoxy;
$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;
$R^{14}$ is H, phenyl, benzyl, $C_1$–$C_6$ alkyl, or $C_2$–$C_6$ alkoxyalkyl;
$R^{14a}$ is H, phenyl, benzyl, methyl, ethyl, propyl, or butyl;
$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{17}$ is H, $C_1$–$C_6$ alkyl, $C_2$–$C_6$ alkoxyalkyl,
aryl substituted by 0–4 $R^{17a}$, or
—$CH_2$-aryl substituted by 0–4 $R^{17a}$,
$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;
$R^{18}$, at each occurrence, is independently selected from H, $C_1$–$C_6$ alkyl, phenyl, benzyl, phenethyl, ($C_1$–$C_6$ alkyl)-C(=O), and ($C_1$–$C_6$ alkyl)-S(=O)$_2$—; and
$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;
provided, when $R^{13}$ is H,
then Z is $C_4$–$C_6$ alkyl substituted with 1–3 $R^{12}$;
$C_2$–$C_4$ alkenyl substituted with 1–3 $R^{12}$; or
$C_2$–$C_4$ alkynyl substituted with 1–3 $R^{12}$.

10. A compound according to claim 9 of Formula (Ia″)

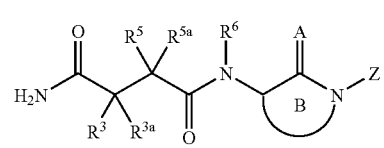

(Ia″)

or a pharmaceutically acceptable salt thereof,
wherein:
$R^3$ is —$(CHR^7)_n$—$R^4$,
n is 0 or 1;
$R^{3a}$ is H, OH, methyl, ethyl, propyl, butyl, methoxy, ethoxy, propoxy, butoxy, allyl, or 3-buten-1-yl;
$R^4$ is H, OH, $OR^{14a}$,
$C_1$–$C_4$ alkyl substituted with 0–2 $R^{4a}$,
$C_2$–$C_4$ alkenyl substituted with 0–2 $R^{4a}$,
$C_2$–$C_4$ alkynyl substituted with 0–1 $R^{4a}$,
$C_3$–$C_6$ carbocycle substituted with 0–3 $R^{4b}$,
aryl substituted with 0–3 $R^{4b}$, or 5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4a}$, at each occurrence, is independently selected from H, F, Cl, Br, I, $CF_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^5$ is H, $OR^{14}$;
$C_1$–$C_4$ alkyl substituted with 0–3 $R^{5b}$;
$C_2$–$C_4$ alkenyl substituted with 0–3 $R^{5b}$;
$C_2$–$C_4$ alkynyl substituted with 0–3 $R^{5b}$;
$R^{5a}$ is H, methyl, ethyl, propyl, or butyl;
$R^{5b}$, at each occurrence, is independently selected from:
H, methyl, ethyl, propyl, butyl, $CF_3$, $OR^{14}$, Cl, F, Br, I, =O;
$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^6$ is H;
$R^7$, at each occurrence, is independently selected from H, F, $CF_3$, methyl, and ethyl;
Ring B is selected from

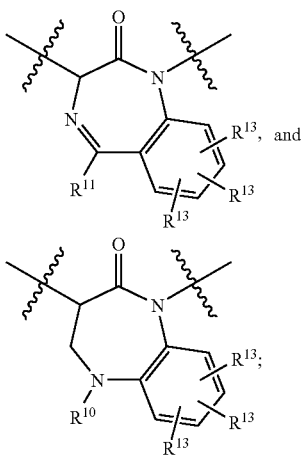

$R^{10}$ is H, $C(=O)R^{17}$, $C(=O)OR^{17}$;
$C_1$–$C_4$ alkyl optionally substituted with 0–1 $R^{10a}$.
phenyl substituted with 0–4 $R^{10b}$;
$C_3$–$C_6$ carbocycle substituted with 0–3 $R^{10b}$; or
5 to 6 membered heterocycle containing 1 to 4 heteroatoms selected from nitrogen, oxygen, and sulphur, wherein said 5 to 6 membered heterocycle is substituted with 0–3 $R^{10b}$;

$R^{10a}$ is selected from H, $C_1$–$C_4$ alky), $OR^{14}$, Cl, F, Br, I, =O. CN, $NO_2$, $NR^{15}R^{16}$. $CF_3$, or phenyl substituted with 0–4 $R^{10b}$;

$R^{10b}$, at each occurrence, is independently selected from H, OH, $C_1$–$C_4$ alkyl, $C_1$–$C_3$ alkoxy, Cl, F, Br, I, CN, $NO_2$, $NR^{15}R^{16}$, or $CF_3$;

$R^{11}$ is selected from
H, $C_1$–$C_4$ alkoxy, Cl, F, $NR^{18}R^{19}$, $C(=O)R^{17}$, $C(=O)OR^{17}$, $CF_3$;
$C_1$–$C_6$ alkyl optionally substituted with 0–3 $R^{11a}$;
aryl substituted with 0–3 $R^{11b}$;
$C_3$–$C_6$ carbocycle substituted with 0–3 $R^{11b}$; or
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11a}$, at each occurrence, is independently selected from H, $C_1$–$C_4$ alkyl, $OR^{14}$, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Z is $C_1$–$C_4$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
aryl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 6 membered heterocycle is substituted with 0–3 $R^{12b}$;

$R^{12}$, at each occurrence, is independently selected from
aryl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_4$ alkyl, benzyl, phenethyl, ($C_1$–$C_4$ alkyl)-C(=O), and ($C_1$–$C_4$ alkyl)-S(=O)$_2$—;

$R^{17}$ is H, methyl, ethyl, propyl, butyl, methoxymethyl, ethoxymethyl, methoxyethyl,
ethoxyethyl,
phenyl substituted by 0–3 $R^{17a}$, or
—$CH_2$-phenyl substituted by 0–3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;

provided, when $R^{13}$ is H,
then Z is butyl substituted with 1–3 $R^{12}$;
$C_2$–$C_4$ alkenyl substituted with 1–3 $R^{12}$; or
$C_2$–$C_4$ alkynyl substituted with 1–3 $R^{12}$.

11. A compound according to claim 10 of Formula (Ic):

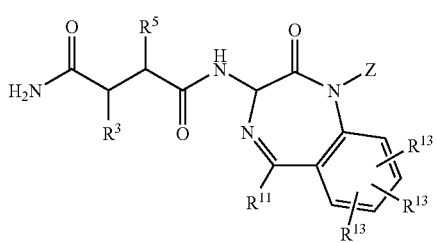

(Ic)

or a pharmaceutically acceptable salt thereof
wherein
$R^3$ is $R^4$,
$R^4$ is $C_1$–$C_4$ alkyl substituted with 0–1 $R^{4a}$,
  $C_2$–$C_4$ alkenyl substituted with 0–1 $R^{4a}$, or
  $C_2$–$C_4$ alkynyl substituted with 0–1 $R^{4a}$;
$R^{4a}$ is selected from
  H, F, $CF_3$,
  $C_3$–$C_6$ carbocycle substituted with 0–3 $R^{4b}$,
  phenyl substituted with 0–3 $R^{4b}$, or
  5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{4b}$, at each occurrence, is independently selected from H. OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;
$R^5$ is $C_1$–$C_4$ alkyl substituted with 0–1 $R^{5b}$;
  $C_2$–$C_4$ alkenyl substituted with 0–1 $R^{5b}$;
  $C_2$–$C_4$ alkynyl substituted with 0–1 $R^{5b}$;
$R^{5b}$ is selected from:
  H, methyl, ethyl, propyl, butyl, $CF_3$, $OR^{14}$, =O;
  $C_3$–$C_6$ carbocycle substituted with 0–2 $R^{5c}$;
  phenyl substituted with 0–3 $R^{5c}$; or
  5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;
$R^{11}$ is, selected from
  H, $NR^{18}R^{19}$, $CF_3$;
  $C_1$–$C_4$ alkyl optionally substituted with 0–1 $R^{11a}$;
  phenyl substituted with 0–3 $R^{11b}$;
  $C_3$–$C_6$ carbocycle substituted with 0–3 $R^{11b}$; or
  5 to 6 membered heterocycle containing 1 to 4 heteroatoms selected from nitrogen, oxygen, and sulphur, wherein said 5 to 6 membered heterocycle is substituted with 0–3 $R^{11b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{11a}$ is selected from H, $C_1$–$C_4$ alkyl, $OR^{14}$, F, =O, $NR^{15}R^6$, $CF_3$, or phenyl substituted with 0–3 $R^{11b}$;
$R^{11b}$, at each occurrence, is independently selected from H, OH, Cl, F, $NR^{15}R^{16}$, $CF_3$, methyl, ethyl, propyl, butyl, methoxy, ethoxy, propoxy, $C_1$–$C_2$ haloalkyl, and $C_1$–$C_2$ haloalkoxy;
Z is $C_1$–$C_3$ alkyl substituted with 1–3 $R^{12}$;
  $C_2$–$C_3$ alkenyl substituted with 1–3 $R^{12}$;
  $C_2$–$C_3$ alkynyl substituted with 1–3 $R^{12}$;
  aryl substituted with 0–4 $R^{12b}$;
  $C_3$–$C_6$ carbocycle substituted with 0–3 $R^{12b}$; or
  5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{12}$, at each occurrence, is independently selected from
  aryl substituted with 0–4 $R^{12b}$;
  $C_3$–$C_6$ carbocycle substituted with 0–3 $R^{12b}$; or
  5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{12b}$, at each occurrence, is independently selected from H, OH, Cl, F, $NR^{15}R^{16}$, $CF_3$, acetyl, $SCH_3$, $S(=O)CH_3$, $S(=O)_2C_{13}$, methyl, ethyl, propyl, butyl, methoxy, ethoxy, propoxy, $C_1$–$C_2$ haloalkyl, and $C_1$–$C_2$ haloalkoxy;
$R^{13}$, at each occurrence, is independently selected from H, OH, methyl, ethyl, propyl, butyl, methoxy, ethoxy, Cl, F, Br, CN, $NR^{15}R^{16}$, and $CF_3$;
$R^{14}$ is H, phenyl, benzyl, methyl, ethyl, propyl, or butyl;
$R^{15}$, at each occurrence, is independently selected from H, methyl, ethyl, propyl, and butyl;
$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;
$R^{18}$, at each occurrence, is independently selected from H, methyl, ethyl, propyl, butyl, phenyl, benzyl, and phenethyl; and
$R^{19}$, at each occurrence, is independently selected from H, methyl, and ethyl;
provided, when $R^{13}$ is H,
then Z is $C_2$–$C_3$ alkenyl substituted with 1–3 $R^{12}$; or
  $C_2$–$C_3$ alkynyl substituted with 1–3 $R^{12}$.

12. A compound according to claim 11, wherein:
$R^3$ is —$CH_3$, —$CH_2CH_3$, —$CH_2CH_2CH_3$, —$CH_2CH_2CH_2CH_3$, —$CH(CH_3)_2$, —$CH(CH_3)CH_2CH_3$, —$CH_2CH(CH_3)_2$, —$CH_2CF_3$, —$CH_2CH_2CF_3$, —$CH_2CH_2CH_2CF_3$, —CH=$CH_2$, —$CH_2CH$=$CH_2$, —$CH_2C(CH_3)$=$CH_2$, —$CH_2CH_2CH$=$CH_2$, cis-$CH_2CH$—$CH(CH_3)$, trans-$CH_2C_{14}$=$CH(CH_3)$, —C≡CH, —$CH_2C$—CH, —$CH_2C$≡$C(CH_3)$, cyclopropyl-$CH_2$—, cyclobutyl-$CH_2$—, cyclopentyl-$CH_2$—, cyclohexyl-$CH_2$—, cyclopropyl-$CH_2CH_2$—, cyclobutyl-$CH_2CH_2$—, cyclopentyl-CH$_2$CH$_2$—, cyclohexyl-CH$_2$CH$_2$—, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-Cl-phenyl)CH$_2$—, (3-Cl-4-F-phenyl)CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, or (3-F-5-Cl-phenyl)CH$_2$CH$_2$—, $R^5$ is —CH$_3$, —CH$_2$CH$_3$, —CH$_2$CH$_2$CH$_3$, —CH(CH$_3$)$_2$, —CH$_2$CH$_2$CH$_2$CH$_3$, —CH(CH$_3$)CH$_2$CH$_3$, —CH$_2$CH(CH$_3$)$_2$, —CH$_2$C(CH$_3$)$_3$, —CH$_2$CH$_2$CH$_2$CH$_2$CH$_3$, —CH(CH$_3$)CH$_2$CH$_2$CH$_3$, —CH$_2$CH(CH$_3$)CH$_2$CH$_3$, —CH$_2$CH$_2$CH(CH$_3$)$_2$, —CH(CH$_2$CH$_3$)$_2$, —CH$_2$CF$_3$, —CH$_2$CH$_2$CF$_3$, —CH$_2$CH$_2$CH$_2$CF$_3$, —CH$_2$CH$_2$CH$_2$CH$_2$CF$_3$, —CH=CH$_2$, —CH$_2$CH=CH$_2$, —CH=CH$_2$CH$_3$, cis-CH$_2$CH=CH(CH$_3$), trans-CH$_2$CH=CH(CH$_3$), trans-CH$_2$CH=CH(C$_6$H$_5$), —CH$_2$CH=C(CH$_3$)$_2$, cis-CH$_2$CH=CHCH$_2$CH$_3$, trans-CH$_2$CH=CHCH$_2$CH$_3$, cis-CH$_2$CH$_2$CH=CH(CH$_3$), trans-CH$_2$CH$_2$CH=CH(CH$_3$), trans-CH$_2$CH=CHCH$_2$(C$_6$H$_5$), —C≡CH, —CH$_2$C≡CH, —CH$_2$C≡C(CH$_3$), —CH$_2$(C$_6$H$_5$), —CH$_2$CH$_2$C≡CH, —CH$_2$CH$_2$C≡C(CH$_3$), —CH$_2$CH$_2$C≡C(C$_6$H$_5$), cyclopropyl-CH$_2$—, cyclobutyl-CH$_2$—, cyclopentyl-CH$_2$—, cyclohexyl-CH$_2$—, (2-CH$_3$-cyclopropyl)CH$_2$—, (3-CH$_3$-cyclobutyl)CH$_2$—, cyclopropyl-CH$_2$CH$_2$—, cyclobutyl-CH$_2$CH$_2$—, cyclopentyl-CH$_2$CH$_2$—, cyclohexyl-CH$_2$CH$_2$—, (2-CH$_3$-cyclopropyl)CH$_2$CH$_2$—, (3-CH$_3$-cyclobutyl)CH$_2$CH$_2$—, phenyl-CH$_2$—, (2-F-phenyl)CH$_2$—, (3-F-phenyl)CH$_2$—, (4-F-phenyl)CH$_2$—, furanyl-CH$_2$—, thienyl-CH$_2$—, pyridyl-H$_2$—, 1-imidazolyl-CH$_2$—, oxazolyl-CH$_2$—, isoxazolyl-CH$_2$—, phenyl-CH$_2$CH$_2$—, (2-F-phenyl)CH$_2$CH$_2$—, (3-F-phenyl)CH$_2$CH$_2$—, (4-F-phenyl)CH$_2$CH$_2$—, furanyl-CH$_2$CH$_2$—, thienyl-CH$_2$CH$_2$—, pyridyl-CH$_2$CH$_2$—, 1-imidazolyl-CH$_2$CH$_2$—, oxazolyl-CH$_2$CH$_2$—, isoxazolyl-CH$_2$CH$_2$—;

Z is phenyl, 2-F-phenyl, 3-F-phenyl, 4-F-phenyl, 2-Cl-phenyl, 3-Cl-phenyl, 4-Cl-phenyl, 2,3-diF-phenyl, 2,4-diF-phenyl, 2,5-diF-phenyl, 2,6-diF-phenyl, 3,4-diF-phenyl, 3,5-diF-phenyl, 2,3-diCl-phenyl, 2,4-diCl-phenyl, 2,5-diCl-phenyl, 2,6-diCl-phenyl, 3,4-diCl-phenyl, 3,5-diCl-phenyl, 3-F-4-Cl-phenyl, 3-F-5-Cl-phenyl, 3-Cl-4-F-phenyl, 2-MeO-phenyl, 3-MeO-phenyl, 4-MeO-phenyl, 2-Me-phenyl, 3-Me-phenyl, 4-Me-phenyl, 2-MeS-phenyl, 3-MeS-phenyl, 4-MeS-phenyl, 2-CF$_3$O-phenyl, 3-CF$_3$O-phenyl, 4-CF$_3$O-phenyl, furanyl, thienyl, pyridyl, 2-Me-pyridyl, 3-Me-pyridyl, 4-Me-pyridyl, 1-imidazolyl, oxazolyl, isoxazolyl, cyclopropyl, cyclobutyl, cyclopentyl, cyclohexyl, N-piperidinyl, phenyl-CH$_2$—, (2-F-phenyl)CH$_2$—, (3-F-phenyl)CH$_2$—, (4-F-phenyl)CH$_2$—, (2-Cl-phenyl)CH$_2$—, (3-Cl-phenyl)CH$_2$—, (4-Cl-phenyl)CH$_2$—, (2,3-diF-phenyl)CH$_2$—, (2,4-diF-phenyl)CH$_2$—, (2,5-diF-phenyl)CH$_2$—, (2,6-diF-phenyl)CH$_2$—, (3,4-diF-phenyl)CH$_2$—, (3,5-diF-phenyl)CH$_2$—, (2,3-diCl-phenyl)CH$_2$—, (2,4-diCl-phenyl)CH$_2$—, (2,5-diCl-phenyl)CH$_2$—, (2,6-diCl-phenyl)CH$_2$—, (3,4-diCl-phenyl)CH$_2$—, (3,5-diCl-phenyl)CH$_2$—, (3-F-4-Cl-phenyl)CH$_2$—, (3-F-5-C-phenyl)CH$_2$—, (3-Cl-4-F-phenyl)CH$_2$—, (2-MeO-phenyl)CH$_2$—, (3-MeO-phenyl)CH$_2$—, (4-MeO-phenyl)CH$_2$—, (2-Me-phenyl)CH$_2$—, (3-Me-phenyl)CH$_2$—, (4-Me-phenyl)CH$_2$—, (2-MeS-phenyl)CH$_2$—, (3-MeS-phenyl)CH$_2$—, (4-MeS-phenyl)CH$_2$—, (2-CF$_3$O-phenyl)CH$_2$—, (3-CF$_3$O-phenyl)CH$_2$—, (4-CF$_3$O-phenyl)CH$_2$—, (furanyl)CH$_2$—, (thienyl)CH$_2$—, (pyridyl)CH$_2$—, (2-Me-pyridyl)CH$_2$—, (3-Me-pyridyl)CH$_2$—, (4-Me-pyridyl)CH$_2$—, (1-imidazolyl)CH$_2$—, (oxazolyl)CH$_2$—, (isoxazolyl)CH$_2$—, (cyclopropyl)CH$_2$—, (cyclobutyl)CH$_2$—, (cyclopentyl)CH$_2$—, (cyclohexyl)CH$_2$—, (N-piperidinyl)CH$_2$—, phenyl-CH$_2$CH$_2$—, (phenyl)$_2$CHCH$_2$—, (2-F-phenyl)CH$_2$CH$_2$—, (3-F-phenyl)CH$_2$CH$_2$—, (4-F-phenyl)CH$_2$CH$_2$—, (2-Cl-phenyl)CH$_2$CH$_2$—, (3-Cl-phenyl)CH$_2$CH$_2$—, (4-Cl-phenyl)CH$_2$CH$_2$—, (2,3-diF-phenyl)CH$_2$CH$_2$—, (2,4-diF-phenyl)CH$_2$CH$_2$—, (2,5-diF-phenyl)CH$_2$CH$_2$—, (2,6-diF-phenyl)CH$_2$CH$_2$—, (3,4-diF-phenyl)CH$_2$CH$_2$—, (3,5-diF-phenyl)CH$_2$CH$_2$—, (2,3-diCl-phenyl)CH$_2$CH$_2$—, (2,4-diCl-phenyl)CH$_2$CH$_2$—, (2,5-diCl-phenyl)CH$_2$CH$_2$—, (2,6-diCl-phenyl)CH$_2$CH$_2$—, (3,4-diCl-phenyl)CH$_2$CH$_2$—, (3,5-diCl-phenyl)CH$_2$CH$_2$—, (3-F-4-Cl-phenyl)CH$_2$CH$_2$—, (3-F-5-Cl-phenyl)CH$_2$CH$_2$—, (3-Cl-4-F-phenyl)CH$_2$CH$_2$—, (2-MeO-phenyl)CH$_2$CH$_2$—, (3-MeO-phenyl)CH$_2$CH$_2$—, (4-MeO-phenyl)CH$_2$CH$_2$—, (2-Me-phenyl)CH$_2$CH$_2$—, (3-Me-phenyl)CH$_2$CH$_2$—, (4-Me-phenyl)CH$_2$CH$_2$—, (2-MeS-phenyl)CH$_2$CH$_2$—, (3-MeS-phenyl)CH$_2$CH$_2$—, (4-MeS-phenyl)CH$_2$CH$_2$—, (2-CF$_3$O-phenyl)CH$_2$CH$_2$—, (3-CF$_3$O-phenyl)CH$_2$CH$_2$—, (4-CF$_3$O-phenyl)CH$_2$CH$_2$—, (furanyl)CH$_2$CH$_2$, (thienyl)CH$_2$CH$_2$—, (pyridyl)CH$_2$CH$_2$—, (2-Me-pyridyl)CH$_2$CH$_2$—, (3-Me-pyridyl)CH$_2$CH$_2$—, (4-Me-pyridyl)CH$_2$CH$_2$—, (imidazolyl)CH$_2$CH$_2$—, (oxazolyl)CH$_2$CH$_2$—, (isoxazolyl)CH$_2$CH$_2$—, (cyclopropyl)CH$_2$CH$_2$—, (cyclobutyl)CH$_2$CH$_2$—, (cyclopentyl)CH$_2$CH$_2$—, (cyclohexyl)CH$_2$CH$_2$—, or (N-piperidinyl)CH$_2$CH$_2$—;

$R^{11}$, at each occurrence, is independently selected from H, methyl, ethyl, phenyl, benzyl, phenethyl, 4-F-phenyl, (4-F-phenyl)CH$_2$—, (4-F-phenyl)CH$_2$CH$_2$—, 3-F-phenyl, (3-F-phenyl)CH$_2$—, (3-F-phenyl)CH$_2$CH$_2$—, 2-F-phenyl, (2-F-phenyl)CH$_2$—, (2-F-phenyl)CH$_2$CH$_2$—, 4-Cl-phenyl, (4-Cl-phenyl)CH$_2$—, (4-Cl-phenyl)CH$_2$CH$_2$—, 3-Cl-phenyl, (3-Cl-phenyl)CH$_2$—, (3-Cl-phenyl)CH$_2$CH$_2$—, 4-CH$_3$-phenyl, (4-CH$_3$-phenyl)CH$_2$—, (4-CH$_3$-phenyl)CH$_2$CH$_2$—, 3-CH$_3$-phenyl, (3-CH$_3$-phenyl)CH$_2$—, (3-CH$_3$-phenyl)CH$_2$CH$_2$—, 4-CF$_3$-phenyl, (4-CF$_3$-phenyl)CH$_2$—, (4-CF$_3$-phenyl)CH$_2$CH$_2$—, pyrid-2-yl, pyrid-3-yl, or pyrid-4-yl, and $R^{13}$, at each occurrence, is independently selected from H, F, Cl, OH, —CH$_3$, —CH$_2$CH$_3$, —OCH$_3$, or —CF$_3$.

13. A compound according to claim 4 of Formula (Ig):

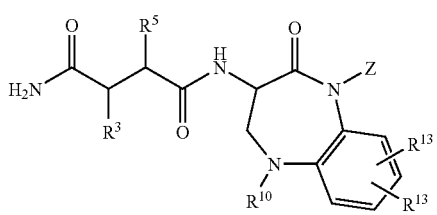

(Ig)

or a pharmaceutically acceptable salt thereof wherein:
$R^3$ is $R^4$,
$R^4$ is $C_1-C_4$ alkyl substituted with 0–1 $R^{4a}$,
  $C_2-C_4$ alkenyl substituted with 0–1 $R^{4a}$, or
  $C_2-C_4$ alkynyl substituted with 0–1 $R^{4a}$;
$R^{4a}$, at each occurrence, is independently selected from
  H, F, $CF_3$,
  $C_3-C_6$ carbocycle substituted with 0–3 $R^{4b}$,
  phenyl substituted with 0–3 $R^{4b}$, or
  5 to 6 membered heterocycle containing 1 to 4 heteroatoms selected from nitrogen, oxygen, and sulphur, wherein said 5 to 6 membered heterocycle is substituted with 0–3 $R^{4b}$, wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1-C_2$ haloalkyl, and $C_1-C_2$ haloalkoxy;
$R^5$ is $C_1-C_4$ alkyl substituted with 0–1 $R^{5b}$;
  $C_2-C_4$ alkenyl substituted with 0–1 $R^{5b}$;
  $C_2-C_4$ alkynyl substituted with 0–1 $R^{5b}$;
$R^{5b}$ is selected from:
  H, methyl, ethyl, propyl, butyl, $CF_3$, $OR^{14}$, $=O$;
  $C_3-C_6$ carbocycle substituted with 0–2 $R^{5c}$;
  phenyl substituted with 0–3 $R^{5c}$; or
  5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;
$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1-C_2$ haloalkyl, and $C_1-C_2$ haloalkoxy;
$R^{10}$ is H, $C(=O)R^{17}$, $C(=O)OR^{17}$;
  $C_1-C_4$ alkyl optionally substituted with 0–1 $R^{10a}$;
  phenyl substituted with 0–4 $R^{10b}$;
  $C_3-C_6$ carbocycle substituted with 0–3 $R^{10b}$; or
  5 to 6 membered heterocycle containing 1 to 4 heteroatoms selected from nitrogen, oxygen, and sulphur, wherein said 5 to 6 membered heterocycle is substituted with 0–3 $R^{10b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{10a}$ is selected from H, methyl, ethyl, propyl, butyl, $OR^{14}$, Cl, F, $=O$, $NR^{15}R^{16}$, $CF_3$, or phenyl substituted with 0–4 $R^{10b}$;
$R^{10b}$, at each occurrence, is independently selected from H, OH, methyl, ethyl, propyl, butyl, methoxy, ethoxy, propoxy, Cl, F, $NR^{15}R^{16}$, and $CF_3$;
Z is H;
  $C_1-C_4$ alkyl substituted with 0–3 $R^{12a}$;
  $C_2-C_4$ alkenyl substituted with 0–3 $R^{12a}$; or
  $C_2-C_4$ alkynyl substituted with 0–3 $R^{12a}$;
$R^{12a}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1-C_2$ haloalkyl, and $C_1-C_2$ haloalkoxy;
$R^{13}$, at each occurrence, is independently selected from H, OH, methyl, ethyl, propyl, butyl, methoxy, ethoxy, Cl, F, Br, CN, $NR^{15}R^{16}$, and $CF_3$;
$R^{14}$ is H, phenyl, benzyl, methyl, ethyl, propyl, or butyl;
$R^{15}$, at each occurrence, is independently selected from H, methyl, ethyl, propyl, and butyl;
$R^{16}$, at each occurrence, is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;
$R^{17}$ is H, methyl, ethyl, propyl, butyl, methoxymethyl, ethoxymethyl, methoxyethyl, ethoxyethyl,
  phenyl substituted by 0–3 $R^{17a}$, or
  —$CH_2$-phenyl substituted by 0–3 $R^{17a}$;
$R^{17a}$ is H, methyl, methoxy, —OH, F, Cl, $CF_3$, or —$OCF_3$;
$R^{18}$, at each occurrence, is independently selected from H, methyl, ethyl, propyl, butyl, phenyl, benzyl, and phenethyl; and
$R^{19}$, at each occurrence, is independently selected from H, methyl, and ethyl.

14. A compound according to claim 10 of Formula (Ig):

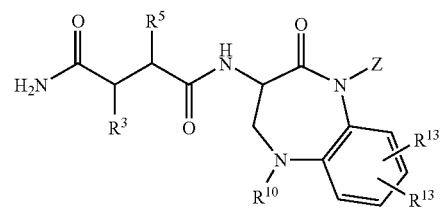

(Ig)

or a pharmaceutically acceptable salt thereof wherein:
$R^3$ is $R^4$,
$R^4$ is $C_1-C_4$ alkyl substituted with 0–1 $R^{4a}$,
  $C_2-C_4$ alkenyl substituted with 0–1 $R^{4a}$, or
  $C_2-C_4$ alkynyl substituted with 0–1 $R^{4a}$;
$R^{4a}$ is selected from
  H, F, $CF_3$,
  $C_3-C_6$ carbocycle substituted with 0–3 $R^{4b}$,
  phenyl substituted with 0–3 $R^{4b}$, or
  5 to 6 membered heterocycle containing 1 to 4 heteroatoms selected from nitrogen, oxygen, and sulphur, wherein said 5 to 6 membered heterocycle is substituted with 0–3 $R^{4b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{4b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^5$ is $C_1$–$C_4$ alkyl substituted with 0–1 $R^{5b}$;
$C_2$–$C_4$ alkenyl substituted with 0–1 $R^{5b}$;
$C_2$–$C_4$ alkynyl substituted with 0–1 $R^{5b}$;

$R^{5b}$ is selected from:
H, methyl, ethyl, propyl, butyl, $CF_3$, $OR^{14}$, =O;
$C_3$–$C_6$ carbocycle substituted with 0–2 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{5c}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{10}$ is H, $C(=O)R^{17}$, $C(=O)OR^{17}$;
$C_1$–$C_4$ alkyl optionally substituted with 0–1 $R^{10a}$;
phenyl substituted with 0–4 $R^{10b}$;
$C_3$–$C_6$ carbocycle substituted with 0–3 $R^{10b}$; or
5 to 6 membered heterocycle containing 1 to 4 heteroatoms selected from nitrogen, oxygen, and sulphur, wherein said 5 to 6 membered heterocycle is substituted with 0–3 $R^{10b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{10a}$ is selected from H, methyl, ethyl, propyl, butyl, $OR^{14}$, Cl, F, =O, $NR^{15}R^{16}$, $CF_3$, or phenyl substituted with 0–4 $R^{10b}$;

$R^{10b}$, at each occurrence, is independently selected from H, OH, methyl, ethyl, propyl, butyl, methoxy, ethoxy, propoxy, Cl, F, $NR^{15}R^{16}$, and $CF_3$;

Z is $C_1$–$C_3$ alkyl substituted with 1–3 $R^{12}$,
$C_2$–$C_3$ alkenyl substituted with 1–3 $R^{12}$;
$C_2$–$C_3$ alkynyl substituted with 1–3 $R^{12}$;
aryl substituted with 0–4 $R^{12b}$;
$C_3$–$C_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12}$, at each occurrence, is independently selected from aryl substituted with 0–4 $R^{12b}$;
$C_3$–$C_6$ carbocycle substituted with 0–3 $R^{12b}$; or
5 to 6 membered heterocycle containing 1 to 4 heteroatoms selected from nitrogen, oxygen, and sulphur, wherein said 5 to 6 membered heterocycle is substituted with 0–3 $R^{12b}$; wherein said 5 to 6 membered heterocycle is selected from pyridinyl, pyrimidinyl, triazinyl, furanyl, thienyl, thiazolyl, pyrrolyl, piperazinyl, piperidinyl, pyrazolyl, imidazolyl, oxazolyl, isoxazolyl, and tetrazolyl;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, methyl, ethyl, propyl, butyl, methoxy, ethoxy, propoxy, $C_1$–$C_2$ haloalkyl, and $C_1$–$C_2$ haloalkoxy;

$R^{13}$, at each occurrence, is independently selected from H, OH, methyl, ethyl, propyl, butyl, methoxy, ethoxy, Cl, F, Br, CN, $N^{15}R^{16}$, and $CF_3$;

$R^{14}$ is H, phenyl, benzyl, methyl, ethyl, propyl, or butyl;

$R^{15}$, at each occurrence, is independently selected from H, methyl, ethyl, propyl, and butyl;

$R^{16}$ at each occurrence is independently selected from H, OH, methyl, ethyl, propyl, butyl, benzyl, phenethyl, methyl-C(=O)—, ethyl-C(=O)—, methyl-S(=O)$_2$—, and ethyl-S(=O)$_2$—;

$R^{17}$ is H, methyl, ethyl, propyl, butyl, methoxymethyl, ethoxymethyl, methoxyethyl,
ethoxyethyl,
phenyl substituted by 0–3 $R^{17a}$, or
—CH$_2$-phenyl substituted by 0–3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;

provided, when $R^{13}$ is H,
then Z is $C_2$–$C_3$ alkenyl substituted with 1–3 $R^{12}$; or
$C_2$–$C_3$ alkynyl substituted with 1–3 $R^{12}$.

15. A compound according to claim 2 of Formula (Ia)

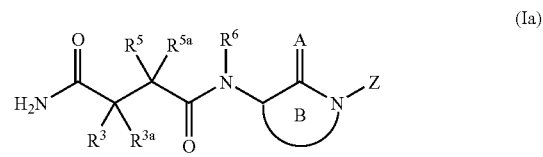

(Ia)

or a pharmaceutically acceptable salt thereof,
wherein:
$R^3$ is —$(CR^7R^{7a})_n$—$R^4$,
—$CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—N($R^{7b}$)—$(CR^7R^{7a})_m$—$R^4$;
n is 0, 1, or 2;
m is 0, 1, or 2;
$R^{3a}$ is H, OH, methyl, ethyl, propyl, butyl, methoxy, ethoxy, propoxy, butoxy, allyl, or 3-buten-1-yl;
$R^4$ is H, OH, $OR^{14a}$,
$C_1$–$C_6$ alkyl substituted with 0–3 $R^{4a}$,
$C_2$–$C_6$ alkenyl substituted with 0–3 $R^{4a}$,
$C_2$–$C_6$ alkynyl substituted with 0–3 $R^{4a}$,
$C_3$–$C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, F, Cl, Br, I, $CF_3$,
$C_3$–$C_{10}$ carbocycle substituted with 0–3 $R^{4b}$,
aryl substituted with 0–3 $R^{4b}$, or

155

5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, T, CN, $NO_2$, $NR^{15}R^{16}$, $CF_3$, acetyl, $SCH_3$, $S(=O)CH_3$, $S(=O)_2CH_3$, $C_1$–$C_6$ alkyl, Cl-C alkoxy, $C_1$–$C_4$ haloalkyl, and $C_1$–$C_4$ haloalkoxy;

$R^5$ is H, $OR^{14}$;
- $C_1$–$C_6$ alkyl substituted with 0–3 $R^{5b}$;
- $C_1$–$C_6$ alkoxy substituted with 0–3 $R^{5b}$;
- $C_2$–$C_6$ alkenyl substituted with 0–3 $R^{5b}$;
- $C_2$–$C_6$ alkynyl substituted with 0–3 $R^{5b}$;
- $C_3$–$C_{10}$ carbocycle substituted with 0–3 $R^{5c}$;
- aryl substituted with 0–3 $R^{5c}$; or
- 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H or $C_1$–$C_4$ alkyl;

$R^{5b}$, at each occurrence, is independently selected from:
- H, $C_1$–$C_6$ alkyl, $CF_3$, $OR^{14}$, Cl, F, Br, I, =O, CN, $NO_2$, $NR^{15}R^{16}$;
- $C_3$–$C_{10}$ carbocycle substituted with 0–3 $R^{5c}$;
- aryl substituted with 0–3 $R^{5c}$; or
- 5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^6$ is H, methyl, or ethyl;

$R^7$, at each occurrence, is independently selected from K, OH, Cl, F, Br, I, CN, $NO_2$, $CF_3$, phenyl and $C_1$–$C_4$ alkyl;

$R^{7a}$, at each occurrence, is independently selected from H, OH, Cl, F, Br, I, CN, $NO_2$, $CF_3$, and $C_1$–$C_4$ alkyl;

$R^{7b}$ is independently selected from K, methyl, ethyl, propyl, and butyl;

Ring B is $R^{11}$, at each occurrence, is independently selected from H, $C_1$–$C_4$ alkoxy, Cl, F, Br, I, CN, $NO_2$, $NR^{18}R_{19}$, $C(=O)R^{17}$, $C(=O)OR^{17}$, $C(=O)NR^{18}R^{19}$, $S(=O)_2NR^{18}R^{19}$, $CF_3$;
- $C_1$–$C_6$ alkyl optionally substituted with 0–3 $R^{11a}$;
- aryl substituted with 0–3 $R^{11b}$;
- $C_3$–$C_{10}$ carbocycle substituted with 0–3 $R^{11b}$; or
- 5 to 10 membered heterocycle containing 1 to 4 heteroatoms selected from nitrogen, oxygen, and sulphur, wherein said 5 to 10 membered heterocycle is substituted with 0–3 $R^{11b}$;

156

$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;

$R^{11b}$, at each occurrence, is independently selected from H, OH, Cl, P, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

Z is H;
- $C_1$–$C_6$ alkyl substituted with 0–3 $R^{12a}$;
- $C_2$–$C_4$ alkenyl substituted with 0–3 $R^{12a}$; or
- $C_2$–$C_4$ alkynyl substituted with 0–3 $R^{12a}$;

$R^{12a}$ at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, or $C_2$–$C_6$ alkoxyalkyl;

$R^{14a}$ is H, phenyl, benzyl, methyl, ethyl, propyl, or butyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O), and ($C_1$–$C_6$ alkyl)-S(=O)$_2$—;

$R^{17}$ is H, $C_1$–$C_6$ alkyl, $C_2$–$C_6$ alkoxyalkyl,
- aryl substituted by 0–4 $R^{17a}$, or
- —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(C_1$–$C_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O), and ($C_1$–$C_6$ alkyl)-S(=O)$_2$—; and $R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—.

16. A compound according to claim 2 of Formula (Ia)

(Ia)

or a pharmaceutically acceptable salt thereof, wherein:

$R^3$ is —$(CR^7R^{7a})_n$—$R^4$,
- —$(CR^7R^{7a})_n$—S—$(CR^7R^{7a})_m$—$R^4$,
- —$(CR^7R^{7a})_n$—O—$(CR^7R^{7a})_m$—$R^4$, or
- —$(CR^7R^{7a})_n$—N($R^{7b}$)—$(CR^7R^{7a})_m$—$R^4$;

n is 0, 1, or 2;

m is 0, 1, or 2;

$R^{3a}$ is H, OH, methyl, ethyl, propyl, butyl, methoxy, ethoxy, propoxy, butoxy, allyl, or 3-buten-1-yl;

$R^4$ is H OH, $OR^{14a}$,
- $C_1$–$C_6$ alkyl substituted with 0–3 $R^{4a}$, $C_2$–$C_6$ alkenyl substituted with 0–3 $R^{4a}$,
$C_2$–$C_6$ alkynyl substituted with 0–3 $R^{4a}$,
$C_3$–$C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4a}$, at each occurrence, is independently selected from H, F, Cl, Br, I, $CF_3$,
$C_3$–$C_{10}$ carbocycle substituted with 0–3 $R^{4b}$,
aryl substituted with 0–3 $R^{4b}$, or
5 to 10 membered heterocycle containing 1 to 4 heteroatoms selected from nitrogen, oxygen, and sulphur, wherein said 5 to 10 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^5$ is H, $OR^{14}$;
$C_1$–$C_6$ alkyl substituted with 0–3 $R^{5b}$;
$C_1$–$C_6$ alkoxy substituted with 0–3 $R^{5b}$;
$C_2$–$C_6$ alkenyl substituted with 0–3 $R^{5b}$;
$C_2$–$C_6$ alkynyl substituted with 0–3 $R^{5b}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5a}$ is H or $C_1$–$C_4$ alkyl;
$R^{5b}$, at each occurrence, is independently selected from:
H, $C_1$–$C_6$ alkyl, $CF_3$, $OR^{14}$, Cl, F, Br, I, =O, CN, $NO_2$, $NR^{15}R^{16}$;
$C_3$–$C_{10}$ carbocycle substituted with 0–3 $R^{5c}$;
aryl substituted with 0–3 $R^{5c}$; or
5 to 10 membered heterocycle containing 1 to 4 heteroatoms selected from nitrogen, oxygen, and sulphur, wherein said 5 to 10 membered heterocycle is substituted with 0–3 $R^{5c}$;

$R^{5c}$, at each occurrence, is independently selected from H, OH, Cl, F, Br, T, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^6$ is H, methyl, or;
$R^7$, at each occurrence, is independently selected from H, OH, Cl, F, Br, L, CN, $NO_2$, $CF_3$, phenyl and $C_1$–$C_4$ alkyl;
$R^{7a}$, at each occurrence, is independently selected from H, OH, Cl, F, Br, I, CN, $NO_2$, $CF_3$, and $C_1$–$C_4$ alkyl;
$R^{7b}$ is independently selected from H, methyl, ethyl, propyl, and butyl;

Ring R is

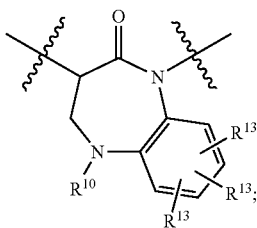

$R^{10}$ is H, $C(=O)R^{17}$, $C(=O)OR^{17}$, $C(=O)NR^{18}R^{19}$, $S(=O)_2NR^{18}R^{19}$, $S(=O)_2R^{17}$;
$C_1$–$C_6$ alkyl optionally substituted with 0–2 $R^{10a}$;
aryl substituted with 0–4 $R^{10b}$;
$C_3$–$C_{10}$ carbocycle substituted with 0–3 $R^{10b}$; or
5 to 10 membered heterocycle containing 1 to 4 heteroatoms selected from nitrogen, oxygen, and sulphur, wherein said 5 to 10 membered heterocycle is substituted with 0–3 $R^{10b}$;

$R^{10a}$, at each occurrence, is independently selected from H, $C_{01}$–$C_6$ alkyl, $OR^{14}$, Cl, F, Br r, =O, CN, $NO_2$, $NR^{15}R^{16}$, $CF_3$, or phenyl substituted with 0–4 $R^{10b}$,
$R^{10b}$, at each occurrence, is independently selected from H. OH, $C_1$–$C_6$ alkyl, $C_1$–$C_4$ alkoxy, Cl, F, Br, I, CN, $NO_2$, $NR^5R^{16}$, or $CF_3$;

Z is H;
$C_1$–$C_6$ alkyl substituted with 0–3 $R^{12a}$;
$C_2$–$C_4$ alkenyl substituted with 0–3 $R^{12a}$; or
$C_2$–$C_4$ alkynyl substituted with 0–3 $R^{12a}$;

$R^{12a}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^{13}$, at each occurrence, is independently selected from H, OH, $C_1$–$C_6$ alkyl, $C_1$–$C_4$ alkoxy, Cl, F, I, CN, $NO_2$, $NR^{15}R^{16}$, and $CF_3$;

$R^{14}$ is H, phenyl, benzyl, $C_1$–$C_6$ alkyl, or $C_2$–$C_6$ alkoxyalkyl;
$R^{14a}$ is H, phenyl, benzyl, methyl, ethyl, propyl, or butyl;
$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{17}$ is H, $C_1$–$C_6$ alkyl, $C_2$–$C_6$ alkoxyalkyl,
aryl substituted by 0–4 $R^{17a}$, or
—$CH_2$-aryl substituted by 0–4 $R^{17a}$;
$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;
$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and
$R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$.

17. A compound according to claim 8 of Formula (Ia″)

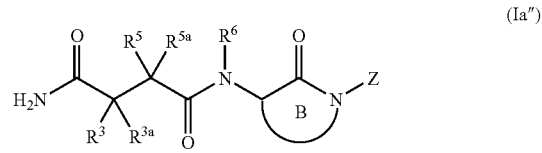

(Ia″)

or a pharmaceutically acceptable salt thereof,
wherein:
$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—N($R^{7b}$)—$(CR^7R^{7a})_m$—$R^4$;

n is 0, 1, or 2;
m is 0, 1, or 2;
$R^{3a}$ is H, OH, methyl, ethyl, propyl, butyl, methoxy, ethoxy, propoxy, butoxy, allyl, or 3-buten-1-yl;
$R^4$ is H, OH, $OR^{14a}$,
  $C_1$–$C_6$ alkyl substituted with 0–3 $R^{4a}$,
  $C_2$–$C_6$ alkenyl substituted with 0–3 $R^{4a}$,
  $C_2$–$C_6$ alkynyl substituted with 0–3 $R^{4a}$,
  $C_3$–$C_{10}$ carbocycle substituted with 0–3 $R^{4b}$,
  aryl substituted with 0–3 $R^{4b}$, or
  5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from H. T. Cl, Br, I, $CF_3$,
  $C_3$–$C_{10}$ carbocycle substituted with 0–3 $R^{4b}$,
  aryl substituted with 0–3 $R^{4b}$, or
  5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4b}$, at each occurrence, is independently selected from H, OH, Cl, F, Br, T, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^5$ is H, $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H or $C_1$–$C_4$ alkyl;
$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5'}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^6$ is H, methyl, or ethyl;
$R^7$, at each occurrence, is independently selected from H, OH, Cl, F, Br, I, CN, $NO_2$, $CF_3$, phenyl, and $C_1$–$C_4$ alkyl;
$R^{7a}$, at each occurrence, is independently selected from H, OH, Cl, F, Br, I, CN, $NO_2$, $CF_3$, and $C_1$–$C_4$ alkyl;
$R^{7b}$ is independently selected from H, methyl, ethyl, propyl, and butyl;
Ring B is

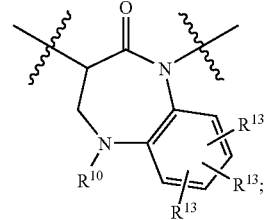

$R^{10}$ is H, $C(=O)R^{17}$, $C(=O)OR^{17}$, $C(=O)NR^{18}R^{19}$, $S(O)_2NR^{18}R^{19}$, $S(=O)_2R^{17}$;
  $C_1$–$C_6$ alkyl optionally substituted with 0–2 $R^{10a}$;
  aryl substituted with 0–4 $R^{10b}$;
  $C_3$–$C_{10}$ carbocycle substituted with 0–3 $R^{10b}$; or
  5 to 10 membered heterocycle containing 1 to 4 heteroatoms selected from nitrogen, oxygen, and sulphur, wherein said 5 to 10 membered heterocycle is substituted with 0–3 $R^{10b}$;
$R^{10a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–4 $R^{10b}$;
$R^{10b}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, or $CF_3$;
Z is $C_1$–$C_6$ alkyl substituted with 1–3 $R^{12}$;
  $C_2$–$C_4$ alkenyl substituted with 1–3 $R^{12}$;
  $C_2$–$C_4$ alkynyl substituted with 1–3 $R^{12}$;
  aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12}$, at each occurrence, is independently selected from
  aryl substituted with 0–4 $R^{12b}$;
  $C_3$–$C_{10}$ carbocycle substituted with 0–4 $R^{12b}$; or
  5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;
$R^{14}$ is H, phenyl, benzyl, $C_1$–$C_6$ alkyl, or $C_2$–$C_6$ alkoxyalkyl;
$R^{14a}$ is 1H, phenyl, benzyl, methyl, ethyl, propyl, or butyl;
$R^{15}$, at each occurrence, is independently selected from H, $C_1$–$C_6$ alkyl, benzyl, phenethyl, ($C_1$–$C_6$ alkyl)-C(=O—, and ($C_1$–$C_6$ alkyl)-S(=O)$_2$—;
$R^{16}$, at each occurrence, is independently selected from H, OH, $C_1$–$C_6$ alkyl, benzyl, phenethyl, ($C_1$–$C_6$ alkyl)-C(=O)—, and ($C_1$–$C_6$ alkyl)-S(=O)$_2$—;
$R^{17}$ is H, $C_1$–$C_6$ alkyl, $C_2$–$C_6$ alkoxyalkyl,
  aryl substituted by 0–4 $R^{17a}$, or
  —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O), and ($C_1$–$C_6$ alkyl)-S(=O)$_2$—, and $R^{19}$, at each occurrence, is independently selected from H, OH, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—;

provided, when $R^{13}$ is H, then Z is $C_4$–$C_6$ alkyl substituted with 1–3 $R^{12}$;
$C_2$–$C_4$ alkenyl substituted with 1–3 $R^{12}$; or
$C_2$–$C_4$ alkynyl substituted with 1–3 $R^{12}$.

18. A compound according to claim 8 of Formula (Ia″)

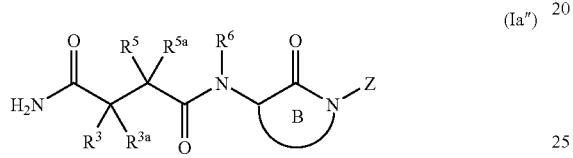

(Ia″)

or a pharmaceutically acceptable salt thereof,
wherein:
$R^3$ is —$(CR^7R^{7a})_n$—$R^4$,
—$(CR^7R^{7a})_n$—S—$(CR^7R^{7a})_m$—$R^4$,
—$(CR^7R^{7a})_n$—O—$(CR^7R^{7a})_m$—$R^4$, or
—$(CR^7R^{7a})_n$—N($R^{7b}$)$(CR^7R^{7a})_m$—$R^4$;
n is 0, 1, or 2;
m is 0, 1, or 2;
$R^{3a}$ is H, OH, methyl, ethyl, propyl, butyl, methoxy, ethoxy, propoxy, butoxy, allyl, or 3-buten-1-yl;
$R^4$ is H, OH, $OR^{14a}$,
  $C_1$–$C_6$ alkyl substituted with 0–3 $R^{4a}$,
  $C_2$–$C_6$ alkenyl substituted with 0–3 $R^{4a}$,
  $C_2$–$C_6$ alkynyl substituted with 0–3 $R^{4a}$,
  $C_3$–$C_{10}$ carbocycle substituted with 0–3 $R^{4b}$,
  aryl substituted with 0–3 $R^{4b}$, or
  5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4a}$, at each occurrence, is independently selected from H, F, Cl, Br, I, $CF_3$,
  $C_3$–$C_{10}$ carbocycle substituted with 0–3 $R^{4b}$,
  $C_6$–$C_{10}$ aryl substituted with 0–3 $R^{4b}$, or
  5 to 10 membered heterocycle containing 1 to 4 heteroatoms selected from nitrogen, oxygen, and sulphur, wherein said 5 to 10 membered heterocycle is substituted with 0–3 $R^{4b}$;
$R^{4b}$, at each occurrence, is independently selected from H, OH, Cl, F, Br, I, CN, $NO_2$, $NR^{15}R^{16}$, $CF_3$, acetyl, $SCH_3$, S(O)CH—, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^5$ is H, $OR^{14}$;
  $C_1$–$C_6$ alkyl substituted with 0–3 $R^{5b}$;
  $C_1$–$C_6$ alkoxy substituted with 0–3 $R^{5b}$;
  $C_2$–$C_6$ alkenyl substituted with 0–3 $R^{5b}$;
  $C_2$–$C_6$ alkynyl substituted with 0–3 $R^{5b}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5a}$ is H or $C_1$–$C_4$ alkyl;
$R^{5b}$, at each occurrence, is independently selected from:
  H, $C_1$–$C_6$ alkyl, $CF_3$, $OR^{14}$, Cl, F, Br, I, =O, CN, $NO_2$, $NR^{15}R^{16}$;
  $C_3$–$C_{10}$ carbocycle substituted with 0–3 $R^{5c}$;
  aryl substituted with 0–3 $R^{5c}$; or
  5 to 10 membered heterocycle containing 1 to 4 heteroatoms selected from nitrogen, oxygen, and sulphur, wherein said 5 to 10 membered heterocycle is substituted with 0–3 $R^{5c}$;
$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
$R^6$ is H, methyl, or ethyl;
$R^7$, at each occurrence, is independently selected from H, OH, Cl, F, Br, I, CN, $NO_2$, $CF_3$, phenyl, and $C_1$–$C_4$ alkyl;
$R^{7a}$, at each occurrence, is independently selected from H, OH, Cl, F, Br, I, CN, $NO_2$, $CF_3$, and $C_1$–$C_4$ alkyl;
$R^{7b}$ is independently selected from H, methyl, ethyl, propyl, and butyl;
Ring B is

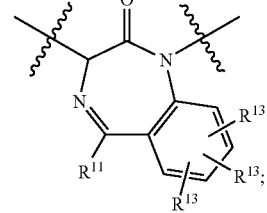

$R^{11}$, at each occurrence, is independently selected from H, $C_1$–$C_4$ alkoxy, Cl, F, Br, I, CN, $NO_2$, $NR^{18}R^{19}$, C(=O)$R^{17}$, C(=O)$OR^{17}$, C(=O)$NR^{18}R^{19}$, $S(=O)_2NR^{18}R^{19}$, $CF_3$;
  $C_1$–$C_6$ alkyl optionally substituted with 0–3 $R^{11a}$;
  aryl substituted with 0–3 $R^{11b}$;
  $C_3$–$C_{10}$ carbocycle substituted with 0–3 $R^{11b}$; or
  5 to 10 membered heterocycle containing 1 to 4 heteroatoms selected from nitrogen, oxygen, and sulphur, wherein said 5 to 10 membered heterocycle is substituted with 0–3 $R^{11b}$;
$R^{11a}$, at each occurrence, is independently selected from H, $C_1$–$C_6$ alkyl, $OR^{14}$, Cl, F, Br, I, =O, CN, $NO_2$, $NR^{15}R^{16}$, $CF_3$, or phenyl substituted with 0–3 $R^{11b}$;
$R^{11a}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;
Z is $C_1$–$C_6$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
aryl substituted with 0–4 $R^{12b}$;
$C_3$–$C_{10}$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;
$R^{12}$, at each occurrence, is independently selected aryl substituted with 0–4 $R^{12b}$;

$C_3$–$C_{10}$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, Br, I, CN, $NO_2$, $NR^{15}R^{16}$, $CF_3$, acetyl, $SCH_3$, $S(=O)H_3$, $S(=O)_2CH_3$, $C_1$–$C_6$ alkyl, $C_1$–$C_4$ alkoxy, $C_1$–$C_4$ haloalkyl, and $C_1$–$C_4$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_6$ alkyl, or $C_2$–$C_6$ alkoxyalkyl;

$R^{14a}$ is H, phenyl, benzyl, methyl, ethyl, propyl, or butyl;

$R^{15}$, at each occurrence, is independently selected from H, $C_1$–$C_6$ alkyl, benzyl, phenethyl, ($C_1$–$C_6$ alkyl)-C(=O)—, and ($C_1$–$C_6$ alkyl)-S(=O)$_2$—;

$R^{16}$, at each occurrence, is independently selected from H, OH, $C_1$–$C_6$ alkyl, benzyl, phenethyl, ($C_1$–$C_6$ alkyl)-C(=O), and ($C_1$–$C_6$ alkyl)-S(=O)$_2$—;

$R^{17}$ is H, $C_1$–$C_6$ alkyl, $C_2$–$C_6$ alkoxyalkyl, aryl substituted by 0–4 $R^{17a}$, or —$CH_2$-aryl substituted by 0–4 $R^{17a}$;

$R^{17a}$ is H, methyl, ethyl, propyl, butyl, methoxy, ethoxy, propoxy, butoxy, —OH, F, Cl, Br, I, $CF_3$, $OCF_3$, $SCH_3$, $S(O)CH_3$, $SO_2CH_3$, —$NH_2$, —$N(CH_3)_2$, or $C_1$–$C_4$ haloalkyl;

$R^{18}$, at each occurrence, is independently selected from H, $C_1$–$C_6$ alkyl, phenyl, benzyl, phenethyl, ($C_1$–$C_6$ alkyl)-C(=O)—, and ($C_1$–$C_6$ alkyl)-S(=O)$_2$—; and $R^{19}$, at each occurrence, is independently selected from H, OH, $C_1$–$C_6$ alkyl, phenyl, benzyl, phenethyl, ($C_1$–$C_6$ alkyl)-C(=O), and ($C_1$–$C_6$ alkyl)-S(=O)$_2$—;

provided, when $R^{13}$ is H, then Z is $C_4$–$C_6$ alkyl substituted with 1–3 $R^{12}$;

$C_2$–$C_4$ alkenyl substituted with 1–3 $R^{12}$; or $C_2$–$C_4$ alkynyl substituted with 1–3 $R^{12}$.

19. A compound according to claim 9 of Formula (Ia″)

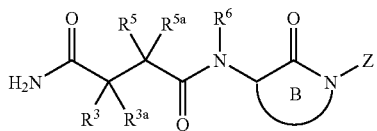

(Ia″)

or a pharmaceutically acceptable salt thereof, wherein:

$R^3$ is —$(CHR^7)_n$—$R^4$, n is 0 or 1;

$R^{3a}$ is H, OH, methyl, ethyl, propyl, butyl, methoxy, ethoxy, propoxy, butoxy, allyl, or 3-buten-1-yl;

$R^4$ is H, OH, $OR^{14a}$, $C_1$–$C_4$ alkyl substituted with 0–2 $R^{4a}$, $C_2$–$C_4$ alkenyl substituted with 0–2 $R^4$—, $C_2$–$C_4$ alkynyl substituted with 0–1 $R^{4a}$, $C_3$–$C_6$ carbocycle substituted with 0–3 $R^{4b}$, aryl substituted with 0–3 $R^{4b}$, or 5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4a}$, at each occurrence, is independently selected from H, F, Cl, Br, I, $CF_3$, $C_3$–$C_6$ carbocycle substituted with 0–3 $R^{4b}$, phenyl substituted with 0–3 $R^{4b}$, or 5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^5$ is H, $OR^{14}$;

$C_1$–$C_4$ alkyl substituted with 0–3 $R^{5b}$;

$C_2$–$C_4$ alkenyl substituted with 0–3 $R^{5b}$;

$C_2$–$C_4$ alkynyl substituted with 0–3 $R^{5b}$;

$R^{5a}$ is H, methyl, ethyl, propyl, or butyl;

$R^{5b}$, at each occurrence, is independently selected from, H, methyl, ethyl, propyl, butyl, $CF_3$, $OR^{14}$, Cl, F, Br, I, =O;

$C_3$–$C_6$ carbocycle substituted with 0–3 $R^{5c}$;

phenyl substituted with 0–3 $R^{5c}$; or 5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^6$ is H;

$R^7$, at each occurrence, is independently selected from H. F, $CF_3$, methyl, and ethyl;

Ring B is

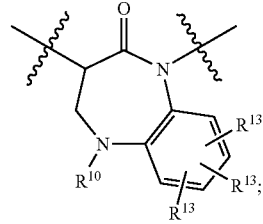

$R^{10}$ is H, C(=O)$R^{17}$, C(=O)$OR^{17}$.

$C_1$–$C_4$ alkyl optionally substituted with 0–1 $R^{10a}$;

phenyl substituted with 0–4 $R^{10b}$;

$C_3$–$C_6$ carbocycle substituted with 0–3 $R^{10b}$; or 5 to 6 membered heterocycle containing 1 to 4 heteroatoms selected from nitrogen, oxygen, and sulphur, wherein said 5 to 6 membered heterocycle is substituted with 0–3 $R^{10b}$;

$R^{10a}$ is selected from H, $C_1$–$C_4$ alkyl, $OR^{14}$, C, F, Br, I, =O, CN, $NO_2$, $NR^{15}R^{16}$, $CF_3$, or phenyl substituted with 0–4 $R^{10b}$;

$R^{10b}$, at each occurrence, is independently selected from H, OH, $C_1$–$C_4$ alkyl, $C_1$–$C_3$ alkoxy, Cl, F, Br, I, CN, $NO_2$, $NR^{15}R^{16}$, or $CF_3$;

Z is $C_1$–$C_4$ alkyl substituted with 1–3 $R^{12}$;

$C_2$–$C_4$ alkenyl substituted with 1–3 $R^{12}$;

$C_2$–$C_4$ alkynyl substituted with 1–3 $R^{12}$;

aryl substituted with 0–4 $R^{12b}$;

$C_3$–$C_6$ carbocycle substituted with 0–4 $R^{12b}$; or 5 to 10 membered heterocycle containing 1 to 4 heteroatoms selected from nitrogen, oxygen, and sulphur, wherein said 5 to 6 membered heterocycle is substituted with 0–3 $R^{12b}$;

$R^{12}$, at each occurrence, is independently selected from
aryl substituted with 0–4 $R^{12b}$;
$C_3$–$C_6$ carbocycle substituted with 0–4 $R^{12b}$; or
5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy, $R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{17}$ is H, methyl, ethyl, propyl, butyl, methoxymethyl, ethoxymethyl, methoxyethyl,
ethoxyethyl,
phenyl substituted by 0–3 $R^{17a}$, or
—$CH_2$-phenyl substituted by 0–3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;
provided, when $R^{13}$ is H,
then Z is butyl substituted with 1–3 $R^{12}$;
$C_2$–$C_4$ alkenyl substituted with 1–3 $R^{12}$; or
$C_2$–$C_4$ alkynyl substituted with 1–3 $R^{12}$.

20. A compound according to claim 9 of Formula (Ia″)

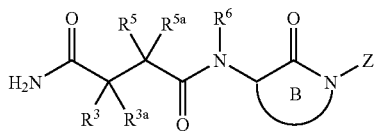

or a pharmaceutically acceptable salt thereof,
wherein:
$R^3$ is —(CHR$^7$)$_n$—$R^4$,
n is 0 or 1;
$R^{3a}$ is H, OH, methyl, ethyl, propyl, butyl, methoxy, ethoxy, propoxy, butoxy, allyl, or 3-buten-1-yl;
$R^4$ is H, OH, $OR^{14a}$,
$C_1$–$C_4$ alkyl substituted with 0–2 $R^{4a}$,
$C_2$–$C_4$ alkenyl substituted with 0–2 $R^{4a}$,
$C_2$–$C_4$ alkynyl substituted with 0–1 $R^{4a}$,
$C_3$–$C_6$ carbocycle substituted with 0–3 $R^{4b}$,
aryl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4a}$, at each occurrence, is independently selected from H, F, Cl, Br, I, $CF_3$,
$C_3$–$C_6$ carbocycle substituted with 0–3 $R^{4b}$,
phenyl substituted with 0–3 $R^{4b}$, or
5 to 6 membered heterocycle containing 1 to 4 heteroatoms selected from nitrogen, oxygen, and sulphur, wherein said 5 to 6 membered heterocycle is substituted with 0–3 $R^{4b}$;

$R^{4b}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^5$ is H, $OR^{14}$;
$C_1$–$C_4$ alkyl substituted with 0–3 $R^{5b}$;
$C_2$–$C_4$ alkenyl substituted with 0–3 $R^{5b}$;
$C_2$–$C_4$ alkynyl substituted with 0–3 $R^{5b}$;

$R^{5a}$ is H, methyl, ethyl, propyl, or butyl, $R^{5b}$, at each occurrence, is independently selected from:
H, methyl, ethyl, propyl, butyl, $CF_3$, $OR^{14}$, Cl, F, Br, I, =O;
$C_3$–$C_6$ carbocycle substituted with 0–3 $R^{5c}$;
phenyl substituted with 0–3 $R^{5c}$; or
5 to 6 membered heterocycle containing 1 to 4 heteroatoms selected from nitrogen, oxygen, and sulphur, wherein said 5 to 6 membered heterocycle is substituted with 0–3 $R^{5c}$;

$R^{5c}$, at each occurrence, is independently selected from H, OH, Cl, F, Br, I, CN, $NO_2$, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^6$ is H;

$R^7$, at each occurrence, is independently selected from H, F, $CF_3$, methyl, and ethyl;

Ring B is

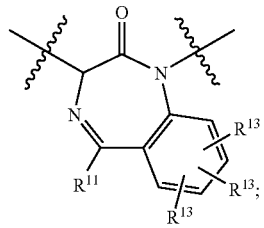

$R^{11}$ is selected from
H, $C_1$–$C_4$ alkoxy, Cl, F, $NR^{18}R^{19}$, $C(=O)R^{17}$, $C(=O)OR^{17}$, $CF_3$;
$C_1$–$C_6$ alkyl optionally substituted with 0–3 $R^{11a}$;
aryl substituted with 0–3 $R^{11b}$.
$C_3$–$C_6$ carbocycle substituted with 0–3 $R^{11b}$; or
5 to 6 membered heterocycle containing 1 to 4 heteroatoms selected from nitrogen, oxygen, and sulphur, wherein said 5 to 6 membered heterocycle is substituted with 0–3 $R^{11b}$;

$R^{11a}$, at each occurrence, is independently selected from H, $C_1$–$C_4$ alkyl, $OR^{14}$, F, =O, $NR^{15}R^{16}$, $CF_3$, or phenyl substituted with 0–3 $R^{11b}$;

$R^{11b}$, at each occurrence, is independently selected from H, OH, Cl, F, $NR^{15}R^{16}$, $CF_3$, $C_1$–$C_4$ alkyl, $C_1$–$C_3$ alkoxy, $C_1$–$C_2$ haloalkyl, and $C_1$–$C_2$ haloalkoxy;

Z is $C_1$–$C_4$ alkyl substituted with 1–3 $R^{12}$;
$C_2$–$C_4$ alkenyl substituted with 1–3 $R^{12}$;
$C_2$–$C_4$ alkynyl substituted with 1–3 $R^{12}$;
aryl substituted with 0–4 $R^{12b}$;
$C_3$–$C_6$ carbocycle substituted with 0–4 $R^{12b}$; or 5 to 10 membered heterocycle containing 1 to 4 heteroatoms selected from nitrogen, oxygen, and sulphur, wherein said 5 to 6 membered heterocycle is substituted with 0–3 $R^{12b}$;

$R^{12}$, at each occurrence, is independently selected from aryl substituted with 0–4 $R^{12b}$;

$C_3$–$C_6$ carbocycle substituted with 0–4 $R^{12b}$; or 5 to 10 membered heterocycle containing 1 to 4 heteroatoms selected from nitrogen, oxygen, and sulphur, wherein said 5 to 10 membered heterocycle is substituted with 0–3 $R^{12b}$;

$R^{12b}$, at each occurrence, is independently selected from H, OH, Cl, F, $NR^{15}R^{16}$, $CF_3$, acetyl, $SCH_3$, $S(=O)CH_3$, $S(=O)_2CH_3$, $C_1$–$C_4$ alkyl, $C_1$–$C_3$ alkoxy, $C_1$–$C_2$ haloalkyl, and $C_1$–$C_2$ haloalkoxy;

$R^{13}$, at each occurrence, is independently selected from H, OH, $C_1$–$C_6$ alkyl, $C_1$–$C_4$ alkoxy, Cl, F, Br, I, CN, $NO_2$, $NR^{15}R^{16}$, and $CF_3$;

$R^{14}$ is H, phenyl, benzyl, $C_1$–$C_4$ alkyl, or $C_2$–$C_4$ alkoxyalkyl;

$R^{15}$, at each occurrence, is independently selected from H, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{16}$, at each occurrence, is independently selected from H, OH, $C_1$–$C_4$ alkyl, benzyl, phenethyl, ($C_1$–$C_4$ alkyl)-C(=O)—, and ($C_1$–$C_4$ alkyl)-S(=O)$_2$—;

$R^{17}$ is H, methyl, ethyl, propyl, butyl, methoxymethyl, ethoxymethyl, methoxyethyl, ethoxyethyl, phenyl substituted by 0–3 $R^{17a}$, or —$CH_2$-phenyl substituted by 0–3 $R^{17a}$;

$R^{17a}$ is H, methyl, methoxy, —OH, F, Cl, $CF_3$, or $OCF_3$;

$R^{18}$, at each occurrence, is independently selected from H, methyl, ethyl, propyl, butyl, phenyl, benzyl, and phenethyl; and $R^{19}$, at each occurrence, is independently selected from H, methyl, and ethyl;

provided, when $R^{13}$ is H, then Z is butyl substituted with 1–3 $R^{12}$;

$C_2$–$C_4$ alkenyl substituted with 1–3 $R^{12}$; or $C_2$–$C_4$ alkynyl substituted with 1–3 $R^{12}$.

21. A pharmaceutical composition comprising a compound of claim 1; and a pharmaceutically acceptable carrier.

22. A pharmaceutical composition comprising a compound according to claim 2 and a pharmaceutically acceptable carrier.

23. A pharmaceutical composition comprising a compound according to claim 3 and a pharmaceutically acceptable carrier.

24. A pharmaceutical composition comprising a compound according to claim 4 and a pharmaceutically acceptable carrier.

25. A pharmaceutical composition comprising a compound according to claim 6 and a pharmaceutically acceptable carrier.

26. A pharmaceutical composition comprising a compound according to claim 7 and a pharmaceutically acceptable carrier.

27. A pharmaceutical composition comprising a compound according to claim 9 and a pharmaceutically acceptable carrier.

28. A pharmaceutical composition comprising a compound according to claim 10 and a pharmaceutically acceptable carrier.

29. A pharmaceutical composition comprising a compound according to claim 11 and a pharmaceutically acceptable carrier.

30. A pharmaceutical composition comprising a compound according to claim 12 and a pharmaceutically acceptable carrier.

31. A pharmaceutical composition comprising a compound according to claim 13 and a pharmaceutically acceptable carrier.

32. A pharmaceutical composition comprising a compound according to claim 14 and a pharmaceutically acceptable carrier.

33. A pharmaceutical composition comprising a compound according to claim 15 and a pharmaceutically acceptable carrier.

34. A pharmaceutical composition comprising a compound according to claim 16 and a pharmaceutically acceptable carrier.

35. A pharmaceutical composition comprising a compound according to claim 17 and a pharmaceutically acceptable carrier.

36. A pharmaceutical composition comprising a compound according to claim 18 and a pharmaceutically acceptable carrier.

37. A pharmaceutical composition comprising a compound according to claim 19 and a pharmaceutically acceptable carrier.

38. A pharmaceutical composition comprising a compound according to claim 20 and a pharmaceutically acceptable carrier.

39. A method for the treatment of Alzheimer's Disease comprising administering to a host in need of such treatment a therapeutically effective amount of a compound of claim 1.

40. A method for the treatment of Alzheimer's Disease comprising administering to a host in need of such treatment a therapeutically effective amount of a compound of claim 2.

41. A method for the treatment of Alzheimer's Disease comprising administering to a host in need of such treatment a therapeutically effective amount of a compound of claim 3.

42. A method for the treatment of Alzheimer's Disease comprising administering to a host in need of such treatment a therapeutically effective amount of a compound of claim 4.

43. A method for the treatment of Alzheimer's Disease comprising administering to a host in need of such treatment a therapeutically effective amount of a compound of claim 5.

44. A method for the treatment of Alzheimer's Disease comprising administering to a host in need of such treatment a therapeutically effective amount of a compound of claim 7.

45. A method for the treatment of Alzheimer's Disease comprising administering to a host in need of such treatment a therapeutically effective amount of a compound of claim 9.

46. A method for the treatment of Alzheimer's Disease comprising administering to a host in need of such treatment a therapeutically effective amount of a compound of claim 10.

47. A method for the treatment of Alzheimer's Disease comprising administering to a host in need of such treatment a therapeutically effective amount of a compound of claim 11.

48. A method for the treatment of Alzheimer's Disease comprising administering to a host in need of such treatment a therapeutically effective amount of a compound of claim 12.

49. A method for the treatment of Alzheimer's Disease comprising administering to a host in need of such treatment a therapeutically effective amount of a compound of claim 13.

50. A method for the treatment of Alzheimer's Disease comprising administering to a host in need of such treatment a therapeutically effective amount of a compound of claim 14.

51. A method for the treatment of Alzheimer's Disease comprising administering to a host in need of such treatment a therapeutically effective amount of a compound of claim 15.

52. A method for the treatment of Alzheimer's Disease comprising administering to a host in need of such treatment a therapeutically effective amount of a compound of claim 16.

53. A method for the treatment of Alzheimer's Disease comprising administering to a host in need of such treatment a therapeutically effective amount of a compound of claim 17.

54. A method for the treatment of Alzheimer's Disease comprising administering to a host in need of such treatment a therapeutically effective amount of a compound of claim 18.

55. A method for the treatment of Alzheimer's Disease comprising administering to a host in need of such treatment a therapeutically effective amount of a compound of claim 19.

56. A method for the treatment of Alzheimer's Disease comprising administering to a host in need of such treatment a therapeutically effective amount of a compound of claim 20.

* * * * *